US010731221B2

(12) United States Patent
Joy et al.

(10) Patent No.: US 10,731,221 B2
(45) Date of Patent: Aug. 4, 2020

(54) DIAGNOSING IDH1 RELATED SUBGROUPS AND TREATMENT OF CANCER

(71) Applicant: Dignity Health, Phoenix, AZ (US)

(72) Inventors: Anna Joy, Phoenix, AZ (US); Burt G. Feuerstein, Phoenix, AZ (US); Ivan Smirnov, Greenbrae, CA (US)

(73) Assignee: Dignity Health, Phoenix, AZ (US)

( * ) Notice: Subject to any disclaimer, the term of this patent is extended or adjusted under 35 U.S.C. 154(b) by 437 days.

(21) Appl. No.: 14/826,578

(22) Filed: Aug. 14, 2015

(65) Prior Publication Data

US 2015/0354012 A1 Dec. 10, 2015

Related U.S. Application Data

(63) Continuation-in-part of application No. 13/515,494, filed as application No. PCT/US2010/059953 on Dec. 10, 2010, now abandoned, application No. 14/826,578, which is a continuation-in-part of application No. PCT/US2014/067168, filed on Nov. 24, 2014.

(60) Provisional application No. 61/285,936, filed on Dec. 11, 2009, provisional application No. 61/907,987, filed on Nov. 22, 2013.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57407* (2013.01); *G01N 33/57484* (2013.01); *C12Q 2600/112* (2013.01); *C12Q 2600/158* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 5,830,648 | A | 11/1998 | Glowman | |
| 2007/0141066 | A1* | 6/2007 | Phillips | A61K 45/06 424/155.1 |
| 2008/0176229 | A1 | 7/2008 | Agus et al. | |
| 2008/0234264 | A1 | 9/2008 | Bell et al. | |
| 2008/0261829 | A1 | 10/2008 | Harvey et al. | |
| 2012/0252856 | A1 | 10/2012 | Joy et al. | |

FOREIGN PATENT DOCUMENTS

| | | | |
|---|---|---|---|
| CA | 2781886 | A1 | 6/2011 |
| CA | 2923672 | A1 | 2/2015 |
| WO | 2006/116016 | A2 | 11/2006 |
| WO | 2011/072258 | A1 | 6/2011 |
| WO | 2015/077725 | A1 | 5/2015 |

OTHER PUBLICATIONS

Sponzo (Cancer) vol. 31, pp. 1154-1159).*
Philips (Cancer Cell(2006) volume) , pp. 157-173).*
American Cancer Society "Second Cancers Caused by Cancer Treatment" p. Jan. 30, 2012).*
Cheung et al (Nature Genetics, 2003, vol. 33, pp. 422-425).*
Saito-Hisaminato et al. (DNA research (2002) vol. 9, pp. 35-45).*
Greenbaum et al (Genome Biology 2003, vol. 4, article 117, pp. 1-8).*
Joy (PLOS one (Jul. 2014) vol. 9, e100827, pp. 1-12).*
Burris ( Cancer Chemother Pharmacology (2013) vol. 71, pp. 829-842).*
Takahashi (Science (1989) vol. 246, pp. 491-494).*
International Search Report and Written Opinion for PCT/US2010/059953 dated Feb. 9, 2011, 6 pages.
International Preliminary Report on Patentability for PCT/US2010/059953 dated Jun. 12, 2012, 5 pages.
International Search Report and Written Opinion for PCT/US2014/067168 dated Feb. 26, 2015, 9 pages.
International Preliminary Report on Patentability for PCT/US2014/067168 dated May 24, 2016, 7 pages.
Alessi et al., Molecular Basis for the Substrate Specificity of Protein Kinase B; Comparison with MAPKAP Kinase-1 and p70 S6 Kinase, FEBS Lett, 1996, vol. 399(3), pp. 333-338.
Altomare et al., Perturbations of the AKT Signaling Pathway in Human Cancer, Oncogene, 2005, vol. 24(50), pp. 7455-7464.
Androutsellis-Theotokis et al., Notch Signaling Regulates Stem Cell Numbers in Vitro and in vivo. Nature, 2006, vol. 442(7104): pp. 823-826.
Baggerly et al., Deriving Chemosensetivity from Cell Lines: Forensic Bioinformatics and Reproducible Research in High-Throughout Biology, The Annals of Applied Sciences, 2009, vol. 3, pp. 1309-1334.
Bellecosa et al., Activation of AKT Kinases in Cancer: Implications for Therapeutic Targeting, Adv Cancer Res, 2005, vol. 94, pp. 29-86.
Benner et al., Evolution, Language and Analogy in Functional Genomics, TRENDS in Genetics, 2001, vol. 17(7), pp. 414-418.

(Continued)

*Primary Examiner* — Steven Pohnert
(74) *Attorney, Agent, or Firm* — Linda B. Huber; Nixon Peabody LLP

(57) ABSTRACT

The invention relates to classification, diagnosis and treatment of cancers. In one embodiment, the present invention provides methods and kits that classify cancers into various subtypes based on expression patterns of AKT pathway components. In another embodiment, the present invention provides methods and kits that diagnose cancer subtypes by evaluating expression patterns of AKT pathway components. In still another embodiment, the present invention provides methods and kits that treat a cancer subtype by administering an alkylating agent or a PI3K/AKT/mTOR inhibitor to a patient. Cancers suitable with various embodiments of the invention include but are not limited to brain tumors, gliomas and GBM.

4 Claims, 38 Drawing Sheets
(17 of 38 Drawing Sheet(s) Filed in Color)
Specification includes a Sequence Listing.

(56) References Cited

OTHER PUBLICATIONS

Cheng et al., The Akt/PKB Pathway: Molecular Target for Cancer Drug Discovery, Oncogene, 2005, vol. 24(50), pp. 7482-7492.
Cheung et al., Natural Variation in Human Gene Expression Assessed in Lymphoblastoid Cells, Nature Genetics, 2003, vol. 33, pp. 422-425.
Couzin-Frankel, As Questions Grow, Duke Halts Trials, Launches Investigation, Science Magazine, 2010, vol. 329, pp. 614-615.
Dresemann et al., Imatinib and Hydroxyurea in Pretreated Progressive Glioblastoma Multiforme: a patien series, Annals Oncology, 2005, vol. 16, pp. 1708-1708.
Franke, T.F., PI3K/Akt: Getting it Right Matters, Oncogene, 2008, vol. 27(50), pp. 6473-6488.
Garcia-Echeverria et al., Drug Discovery Approaches Targeting the PI3K/Akt Pathway in Cancer, Oncogene, 2008, vol. 27(41), pp. 5511-5526.
Giannini et al., Patient Tumor EGFR and PDGFRA Gene Amplifications Retained in an Invasive Intracranial Kenograft Model of Glioblastoma Multiforme, Neuro-Oncology, 2006, vol. 7, pp. 164-176.
Granville et al., Handicapping the Race to Develop Inhibitors of the Phosphoinositide 3-kinase/Akt/mammalian Target of Rapamycin Pathway, Clin Cancer Res, 2006, vol. 12(3 Pt 1), pp. 679-689.
Greenbaum et al., Comparing Protein Abundance and mRNA Expression Levels on a Genomic Scale, Genome Biology, 2003, vol. 4(117) pp. 1-8.
Haas-Kogan et al., Protein Kinase B (PKB/Akt) Activity is Elevated in Glioblastoma Cells due to Mutation of the Tumor Suppressor PTEN/MMAC, Curr Biol, 1998, vol. 8(21), pp. 1195-1198.
Hennessy, B.T., et al., Exploiting the PI3K/AKT pathway for cancer drug discovery. Nat Rev Drug Discov, 2005. 4(12): p. 988-1004.
Holland et al., Combined Activation of Ras and Akt in Neural Progenitors Induces Glioblastoma Formation in Mice, Nat Genet, 2000, vol. 25(1), pp. 55-57.
Joy et al., AKT Pathway Genes Define 5 Prognostic Subgroups in Glioblastoma, Plos One, 2014, vol. 9(7), pp. 1-7.
Lai et al., Evidence for Sequenced Molecular Evolution of IDH1 Mutant Glioblastoma From a Distinct Cell of Origin, Journal of Clinical Oncology, 2011, vol. 29, pp. 4482-4490.
Manning et al., AKT/PKB Signaling: Navigating Downstream, Cell, 2007, vol. 129, pp. 1261-1274.
May et al., How Many Species Are There on Earth?, Science, 1988, vol. 241, p. 1441.
Mischel et al., Identification of Molecular Subtypes of Glioblastoma by Gene Expression Profiling, Oncogene, 2003, vol. 22(15), pp. 2361-2373.
Puputti, Amplifications of KIT, PDGFRA, VEGFR2 and EGFR in Gliomas, Mole Cancer Research, 2006, vol. 4, pp. 927-934.
Saito-Hisaminato et al., Genome-Wide Profiling of Gene Expression in 29 Normal Human Tissues with a cDNA Microarray, DNA Research, 2002, vol. 9, pp. 35-45.
Sinor et al., Akt-1 Expression Level Regulates CNS Precursors, J Neurosci, 2004, vol. 24(39), pp. 8531-8541.
Stupp et al., Concomitant and Adjuvant Temozolomide (TMZ) and Radiotherapy (RT) for newly Diagnosed Glioblastoma Multiforme (GBM). Conclusive Results of a Randomized Phase III trial by the EORTC Brain and RT Groups and NCIC Clinical Trials Group, Journal of Clinical Oncology, 2004, vol. 22(14S), p. 2.
Testa et al., AKT Signaling in Normal and Malignant Cells, Oncogene, 2005, vol. 24(50), pp. 7391-7393.
Tokunaga et al., Deregulation of the Akt Pathway in Human Cancer, Curr Cancer Drug Targets, 2008, vol. 8(1), pp. 27-36.
Wu, Analysing Gene Expression Data from DNA Microarrays to Identify Candidate Genes, Journal of Pathology, 2001, vol. 195, pp. 53-65.

* cited by examiner

Fig. 2A
Discovery Set (GBM195)
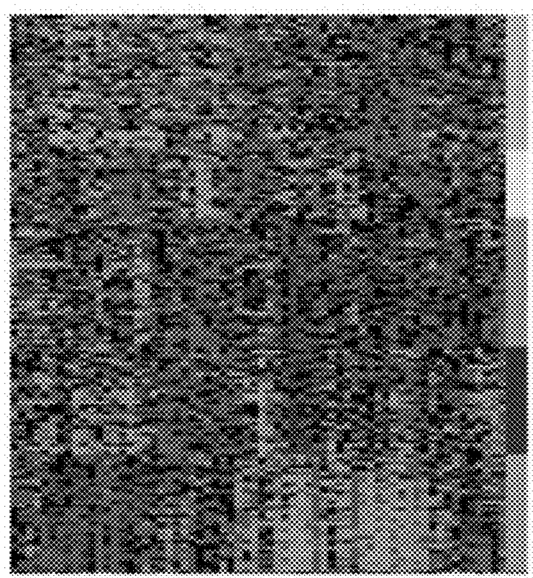
Fig. 2B
Validation Set (TCGA)
PN MES CLAS SL PROLIF
Fig. 2C
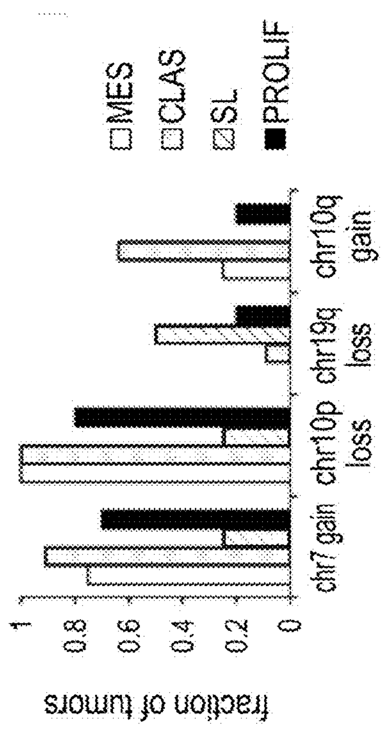
Fig. 2D
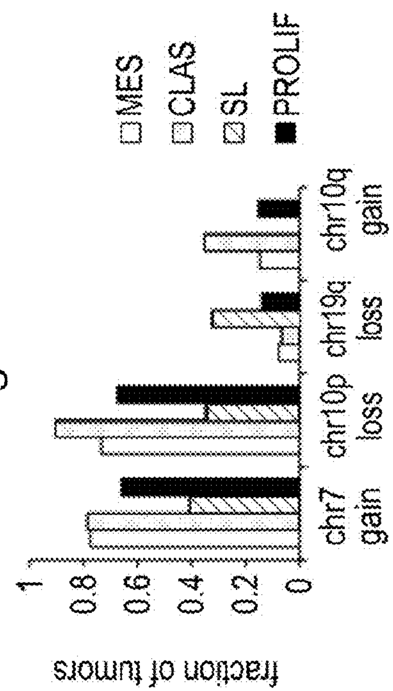

Fig. 8A

| AKT subgroup | C1 | Pro-Neural | Mesenchymal | Classical | Secondary-like | Proliferative |
|---|---|---|---|---|---|---|
| Phillips subgroups | Prolif | PN | Mes | Mes | PN | Prolif/PN |
| TCGA subgroups | ND | mixed | Mes | Clas | PN | PN |
| G-CIMP tumor | ND | NO | NO | NO | YES | YES |
| clinical | older | older, short survival, contained all non-neoplastic samples | older, short survival | older, short survival necrosis and angiogenesis | younger, longest survival less necrosis endothelial proliferation | older, short survival, enriched in recurrent tumors |
| molecular | ND | CDKN2A | NF1/RB1/MET | EGFR/CDKN2A | G-CIMP/IDH1/TP53 | PDGFRA/TP53 |
| unique broad DNA CNA | ND | | | 19 & 20 gain, 6q loss | 19q loss | 14 loss |
| unique focal DNA CNA | ND | amp: SOX, CCND2 | amp: FAM19A2 | amp: PRDM2, PDPN | amp: PIK3CA, CCND3, TARP CACNA1C,GLT1D1 | amp: MYCN, SLC38A4 del: CDKN2C, BAGE5 |
| cell of origin based on GO terms | ND | committed neural progenitor | NCS or early progenitor with microglia infiltration | committed neural progenitor | NSC or early progenitor | expanding NSC or early progenitor |

Fig. 8B

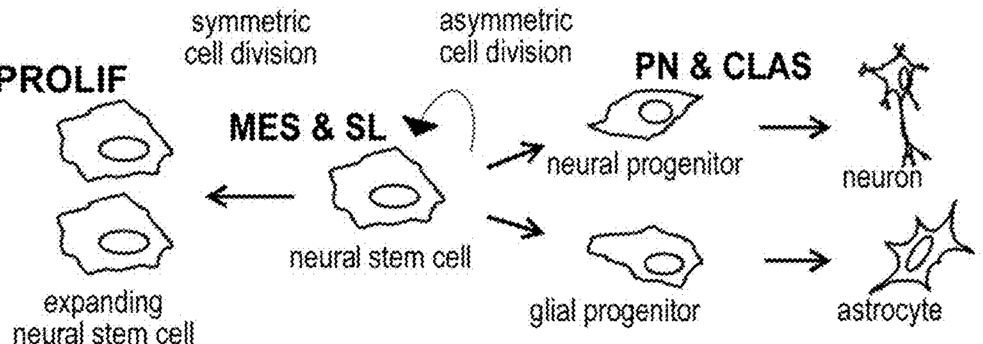

TCGA
GBM195
SYK
CFD
INPP5D
PDGFRB
CDKN1A
KDR
EPAS1
IRS2
PDGFD
PDGFA
GRB10
HSP90B1
PDK1
CHEK1
EZH2
EIF3E
SRSF1
NRAS
SSB
IRS1
WNK1
PKN2
BCL10
TWIST1
PKD2
PALLD
HIF1A
PDGFC
VIM
TRIB3
EIF4EBP1
ACLY
TP53
EIF3B
RAF1
CCND1
EIF3H
FYN
PHLPP1
GAB1
EGFR
EIF3G
AKT1
CDC37
TSC2
PPP2R1A
HSP90AB1
MAPK8IP1
GAB2
PIK3C2B
TSC1
GSK3B
SORBS2
FGFR2
FGFR3
PPP2R2B
PIK3R1
MAP3K5
ATXN1
PPARGC1A
KRAS
CDKN1B
PIK3CA
FOXO3
MES CLAS PROLIF SL PN
MES CLAS PROLIF SL PN

Fig. 12A

GBM195

| | Akt subgroup | C1 | PN | MES |
|---|---|---|---|---|
| Akt | Number of samples | 11 | 33 | 30 |
| | Median silhouette | 0.5632 | 0.6300 | 0.1778 |
| | | | | |
| survival[1] | Median survival (yea | 1.134 | 0.7865 | 1.148 |
| | P-value against rest | 0.7829 | 0.1799 | 0.9771 |
| | Hazard ratio [Confid | 0.9 [0.47-1.74] | 1.4 [0.78 - 2.55] | 1[0.63 - 1.60] |
| | Number of samples | 10 | 19 | 27 |
| | | | | |
| Phillips et. al.[1] | Mesenchymal | 2 | 0 | **21** |
| | Proneural | 0 | **10** | 0 |
| | Prolif | 8 | 0 | 2 |
| | Normal | 0 | **14** | 0 |
| | Unknown | 1 | 9 | 7 |
| | | | | |
| Tissue[1] | MDA | 11 | 8 | 11 |
| | UCLA | | 19 | 15 |
| | UCSF | | 6 | 4 |
| | | | | |
| Clinical[1] | WHO grade IV gliob | 100% | 100% | 100% |
| | Astrocytic histologic | 100% | 100% | 100% |
| | Median age (years) | 48 | 50 | 48.5 |
| | Sex (female) | 10% (1/10) | 50% (5/10) | 43% (10/23) |
| | Sex (male) | 90% (9/10) | 50% (5/10) | 57% (13/23) |
| | Mitosis (yes) | 100% (99/9) | unknown | 100% (7/7) |
| | Microvascular prolif | 100% (9/9) | unknown | 86% (6/7) |
| | Necrosis (yes) | 100% (9/9) | unknown | 86% (6/7) |
| | Pleiomorphism (yes) | 100% (9/9) | unknown | 100% (7/7) |
| | Recurrent tumors | 10% (1/10) | 10% (1/10) | 13% (3/23) |
| | | | | |
| Molecular[1] | chr 7 (gain) | 5 | unknown | 3 |
| | chr 7q (gain) | 0 | unknown | 0 |
| | chr 7 (no gain) | 1 | unknown | 1 |
| | chr 7q (partial loss) | 0 | unknown | 0 |
| | chr 7 (unknown) | 5 | 33 | 26 |
| | | | | |
| | chr 10 (intact) | 1 | unknown | 0 |
| | chr 10 (loss) | 4 | unknown | 4 |
| | chr 10q (loss) | 1 | unknown | 0 |
| | chr 10 (unknown) | 5 | 33 | 26 |
| | | | | |
| | chr 19q (gain) | 0 | unknown | 1 |
| | chr 19q (loss) | 1 | unknown | 0 |
| | chr 19q (nc) | 5 | unknown | 3 |
| | chr 19q (unknown) | 5 | 33 | 26 |

(shaded) $p < 0.05$; subgroup vs rest; Bonferroni corrected

1) Phillips et. al. "Molecular subclasses of high-grade glioma predict prognosis, delineate a pattern of disease progression, and resemble stages in neurogenesis" Cancer Cell, 9:157-173, 2006

Fig. 12B

| CLAS | SL | PROLIF | not assigned | Total |
|---|---|---|---|---|
| 36 | 19 | 38 | 28 | 195 |
| 0.2197 | 0.1842 | 0.1610 | NA | |
| | | | | |
| 1.192 | 3.903 | 0.75 | NA | 1.1 |
| 0.9263 | 0.0005 | 0.0029 | NA | |
| 1.02[0.66 - 1.55] | 0.33 [0.21 - 0.52] | 1.88 [1.12 - 3.17] | NA | |
| 32 | 17 | 32 | NA | 137 |
| | | | | |
| 22 | 0 | 5 | 8 | 58 |
| 0 | 14 | 6 | 8 | 38 |
| 3 | 0 | 14 | 4 | 31 |
| 0 | 0 | 0 | 0 | 14 |
| 11 | 5 | 13 | 8 | 54 |
| | | | | |
| 17 | 8 | 20 | 16 | 91 |
| 8 | 7 | 9 | 7 | 65 |
| 11 | 4 | 9 | 5 | 39 |
| | | | | |
| 100% | 100% | 100% | 100% | 100% |
| 100% | 100% | 100% | 100% | 100% |
| 50 | 38 | 49 | 54 | 49 |
| 24% (6/25) | 43% (6/14) | 56% (14/25) | 45% (9/20) | 40% (51/127) |
| 76% (19/25) | 57% (8/14) | 44% (11/25) | 55% (11/20) | 60% (76/127) |
| 100% (13/13) | 100% (6/6) | 100% (12/12) | 100% (11/11) | 100% (58/58) |
| 100% (13/13) | 83% (5/6) | 100% (12/12) | 91% (10/11) | 95% (55/58) |
| 92% (12/13) | 50% (3/6) | 92% (11/12) | 73% (8/11) | 84% (49/58) |
| 100% (13/13) | 100% (6/6) | 100% (12/12) | 100% (11/11) | 100% (58/58) |
| 16% (4/25) | 14% (2/14) | 28% (7/25) | 25% (5/20) | 18% (23/127) |
| | | | | |
| 10 | 0 | 7 | 1 | 26 |
| 0 | 1 | 0 | 0 | 1 |
| 1 | 3 | 3 | 5 | 14 |
| 0 | 0 | 0 | 1 | 1 |
| 25 | 15 | 28 | 21 | 153 |
| | | | | |
| 0 | 3 | 2 | 1 | 7 |
| 9 | 0 | 6 | 5 | 28 |
| 2 | 1 | 2 | 1 | 7 |
| 25 | 15 | 28 | 21 | 153 |
| | | | | |
| 7 | 0 | 2 | 1 | 11 |
| 1 | 2 | 2 | 0 | 6 |
| 3 | 2 | 6 | 6 | 25 |
| 25 | 15 | 28 | 21 | 153 |

Fig. 13A

| TCGA | | | | |
|---|---|---|---|---|
| Akt | Akt subgroup | C1 | PN |
| | Number of samples | 2 | 97 |
| survival | Median survival (years) | 1.282 | 1.107 |
| | P-value against rest | 0.897 | 0.517 |
| | Hazard ratio [Confidence interval] | 0.87 [0.13 - 5.53] | 0.89 [0.65 - 1.22] |
| | Number of samples with survival | 2 | 55 |
| TCGA subgroup[1] | Classical | 0 | 6 |
| | Mesenchymal | 1 | 4 |
| | Neural | 0 | 10 |
| | Normal | 0 | 10 |
| | Proneural | 0 | 6 |
| | Unknown | 1 | 61 |
| Tissue Source | Case Western | 0 | 10 |
| | Cedars Sinai | 0 | 7 |
| | CHI-Penrose Colorado | 0 | 0 |
| | Christiana Healthcare | 0 | 3 |
| | Duke | 0 | 9 |
| | Emory University | 0 | 3 |
| | Henry Ford Hospital | 1 | 27 |
| | International Genomics Consortium | 0 | 0 |
| | Mayo Clinic - Rochester | 0 | 3 |
| | MD Anderson Cancer Center | 0 | 13 |
| | Memorial Sloan Kettering | 0 | 0 |
| | Milan - Italy, Fondazione IRCCS Instituto Neurolig | 0 | 4 |
| | St. Joseph's Hospital (AZ) | 0 | 1 |
| | Thomas Jefferson University | 0 | 0 |
| | Toronto Western Hospital | 0 | 3 |
| | UCSF | 1 | 14 |
| | University of Florida | 0 | 0 |
| | Washington University | 0 | 0 |
| Clinical | median age (years) | 50 | 60 |
| | sex (male) | 100% (2/2) | 61% (46/75) |
| | sex (female) | 0% (2/2) | 39% (29/75) |
| | pallisading necrosis | 50% (1/2) | 35% (31/88) |
| | endothelial proliferation | 100% (2/2) | 55% (46/84) |
| | G-CIMP tumor[2] | 0% (0/2) | 5% (4/85) |
| | recurrent[3] | 0% (0/2) | 4% (1/27) |
| | post treatment[3] | 0 | 1 |
| | secondary[3] | 0 | 0 |

(shaded) p < 0.05; subgroup vs rest; Bonferroni corrected (boxed) p value < 0.05; subgroup vs. rest; before Bonferroni correction 1: from Veerhak et.al., "Integrated Genomic Analysis Identifies Clinically Relevant Subtypes of Glioblastoma Characterized by Abnormalities in PDGFRA, IDH1, EGFR, and NF1" Cancer Cell, 17:98-110, 2010

2: from Houtan Noushmehr et.al. "Identification of a CpG Island Methylator Phenotype that Defines a Distinct Subgroup of Glioma", Cancer Cell, 17:510-522, 2010

3: fromThe Cancer Genome Research Atlas Network et. al. "Comprehensive genomic characterization defines human glioblastoma genes and core pathways", Nature, 455:1061-1068, 2008

Fig. 13B

| MES | CLAS | SL | PROLIF | Total |
|---|---|---|---|---|
| 115 | 191 | 52 | 126 | 583 |
| | | | | |
| 1.049 | 1.164 | 1.674 | 0.893 | |
| 0.520 | 0.056 | 0.003 | 0.726 | |
| 1.08 [0.83 - 1.42] | 1.25 [0.98 - 1.60] | 0.52 [0.37 - 0.73] | 1.05 [0.77 - 1.43] | |
| 83 | 125 | 28 | 56 | 349 |
| | | | | |
| 7 | 32 | 0 | 4 | 49 |
| 34 | 13 | 0 | 3 | 55 |
| 1 | 13 | 0 | 3 | 27 |
| 0 | 0 | 0 | 0 | 10 |
| 3 | 2 | 17 | 27 | 55 |
| 70 | 131 | 35 | 89 | 387 |
| | | | | |
| 6 | 13 | 4 | 5 | 38 |
| 7 | 8 | 2 | 7 | 31 |
| 0 | 1 | 0 | 0 | 1 |
| 1 | 3 | 1 | 1 | 9 |
| 12 | 27 | 5 | 8 | 61 |
| 4 | 18 | 4 | 10 | 39 |
| 32 | 46 | 9 | 22 | 137 |
| 0 | 1 | 0 | 0 | 1 |
| 0 | 1 | 1 | 0 | 5 |
| 30 | 22 | 10 | 29 | 104 |
| 3 | 0 | 0 | 21 | 24 |
| 3 | 4 | 4 | 2 | 17 |
| 6 | 13 | 3 | 4 | 27 |
| 2 | 5 | 2 | 5 | 14 |
| 0 | 8 | 2 | 1 | 14 |
| 6 | 16 | 4 | 6 | 47 |
| 2 | 5 | 1 | 4 | 12 |
| 1 | 0 | 0 | 1 | 2 |
| | | | | |
| 56 | 60 | 49 | 59 | 59 |
| 65% (68/104) | 61% (113/184) | 64% (30/47) | 55% (46/83) | 62% (305/491) |
| 35% (36/104) | 39% (71/184) | 36% (17/47) | 45% (37/83) | 38% (186/491) |
| 38% (43/113) | 46% (91/199) | 10% (15/155) | 36% (35/96) | 39% (215/551) |
| 71% (77/108) | 67 % (128/190) | 46% (24/52) | 69% (65/94) | 64% (340/528) |
| 2% (2/107) | 0.5% (1/189) | 48% (24/50) | 14% (13/92) | 8% (44/525) |
| 10% (5/51) | 3% (2/67) | 6% (1/18) | 18% (7/38) | 8% (16/201) |
| 6 | 4 | 1 | 8 | 20 |
| 1 | 2 | 0 | 1 | 4 |

Fig. 14

| FOCAL AMPLIFICATIONS | | | | | | | | |
|---|---|---|---|---|---|---|---|---|
| | subgroup | | | | | | known/candidate glioma gene or gene under peak | chr region |
| chromosome | | PN | MES | CLAS | SL | PROLIF | | |
| | 1 | | | 9.37E-05 | | | PRDM2, PDPN | 1p36.21 |
| | | 8.38E-13 | 2.01E-07 | 2.20E-14 | | 0.0003131 | MDM4, PIK3C2B | 1q32.1 |
| | | | | 6.30E-06 | | | olfactory receptor genes | 1q44 |
| | 2 | | | | | 0.0003951 | MYCN | 2p24.3 |
| | 3 | | | | 0.045289 | | PIK3CA | 3q26.32 |
| | | 0.006143 | | | | | SOX2 | 3q26.33 |
| | 5 | 0.041135 | 8.15E-10 | | | | ZDHHC11 | 5p15.33 |
| | 6 | | | | 0.079349 | | ETV7 | 6p21.32 |
| | | | | | 0.075391 | | C6orf89, PPIL1 | 6p21.2 |
| | | | | | 0.079349 | | CCND3 | 6p21.1 |
| | | | | | 0.11908 | | TBCC | 6p21.1 |
| | 7 | | | | 7p14.1 | | TARP | 7p14.1 |
| | 11 | 0.23103 | 0.070876 | | | | olfactory receptor genes | 11q11 |
| | 12 | | | | | 0.0010083 | SLC38A4 | 12q13.13 |
| | | 0.010052 | | | | | CCND2 | 12p13.32 |
| | | | | | 0.0092016 | | CACNA1C | 12p13.33 |
| | | | 3.94E-05 | | | | FAM19A2 | 12q14.1 |
| | | | | 0.002417 | | 0.011049 | SRGAP1 | 12q14.2 |
| | | | | 4.08E-06 | | 0.0002129 | CAND1 | 12q14.3 |
| | | 0.006673 | 6.30E-33 | 4.93E-22 | | 2.47E-14 | MDM2 | 12q15 |
| | | | | | 0.010762 | | no gene | 12q24.21 |
| | | | | | 0.075391 | | GLT1D1 | 12q24.32 |
| | 15 | 0.010052 | 0.001795 | 0.000963 | 0.019323 | | OR4M2 | 15q11.2 |

Fig. 15

| FOCAL DELETIONS | | | | | | | | |
|---|---|---|---|---|---|---|---|---|
| chromosome | | subgroup | | | | | known/candidate glioma gene or gene under peak | chr region |
| | | PN | MES | CLAS | SL | PROLIF | | |
| | 1 | 0.0028672 | | 1.49E-08 | | | TNFRSF9, PER3, UTS2, PARK7, ERRFI1 | 1p36.23 |
| | 1 | | 0.042062 | 0.0015918 | 0.22081 | | ESPNP, MST1P9, MIR3675 | 1p36.13 |
| | 1 | 0.0034136 | | 0.017434 | | 0.11971 | RHD, TMEM50A | 1p36.11 |
| | 1 | | | | | 0.051027 | CDKN2C | 1p33 |
| | 1 | | 0.027676 | 0.015748 | 0.23719 | | no gene | 1q21.1 |
| | 1 | 0.0011517 | 0.0094696 | 0.0012773 | | | CFHR3 | 1q31.3 |
| | 1 | 0.037044 | 2.719E-05 | 1.203E-16 | 0.0008145 | | olfactory receptor genes | 1q44 |
| | 2 | | 0.065408 | 0.10881 | 0.0022343 | | no gene | 2q37.3 |
| | 4 | | | | 0.11804 | | Corf52 | 4p15.32 |
| | 4 | 0.013936 | 0.0003529 | | 0.023007 | | UGT2B28 | 4q13.2 |
| | 4 | | | 0.0060842 | 0.0082467 | 0.0065165 | no gene | 4q35.2 |
| | 6 | 0.0012308 | 1.129E-05 | 0.0009157 | | 0.032441 | HLA gene family | 6p21.32 |
| | 6 | 0.094464 | | 1.104E-06 | | | PARK2, QKI, PACRG | 6q26 |
| | 8 | 0.037044 | 0.025712 | 0.0004596 | | | many | 8p23.1 |
| | 12 | | | | 0.23719 | | TWF1, IRAK4, ADAMTS20, PUS7L, TMEM117 | 12q12 |
| | 15 | 7.281E-06 | 3.78E-05 | 1.23E-07 | | 9.613E-07 | no gene | 15q14 |
| | 16 | 0.071473 | 1.466E-06 | 3.968E-05 | | | CES1P1 | 16q12.2 |
| | 16 | | | 0.0006492 | 0.067283 | 0.041886 | PDPR | 16q22.1 |
| | 19 | | | | | 0.012374 | no gene | 19p12 |
| | 21 | | | 0.012776 | 0.24708 | | TPTE | 21p11.2 |
| | 21 | | | | | 0.10407 | BAGE5 | 21p11.1 |
| | 22 | 5.761E-24 | 6.101E-33 | | 4.596E-06 | | GSTT1 | 22q11.23 |

Fig. 16A

| | C1 | PN | MES | CLAS | SL | PROLIF |
|---|---|---|---|---|---|---|
| SYK | 0.41169 | -0.26207 | 0.66458 | -0.036695 | 0.21251 | -0.086285 |
| CFD | 0.12385 | 0.00572 | 1.09859 | -0.0926 | -0.09165 | -0.1291 |
| INPP5D | -0.46451 | -0.0895 | 0.645645 | 0.014335 | 0.21142 | -0.290955 |
| PDGFRB | -0.17006 | -0.09449 | 0.470735 | 0.236105 | -0.06331 | -0.16959 |
| CDKN1A | 0.00225 | -0.56972 | 0.594845 | 0.56788 | -0.48012 | -0.67927 |
| KDR | 0.00635 | 0.00323 | 0.099365 | 0.23035 | -0.0672 | -0.156625 |
| EPAS1 | 0.16297 | 0.00157 | 0.305115 | 0.382025 | -0.20599 | -0.41363 |
| IRS2 | 0.6133 | -0.0591 | 0.2804 | 0.32805 | -0.1409 | -0.508755 |
| PDGFD | 0.50254 | -0.08581 | 0.214655 | 0.546995 | -0.22597 | -0.141825 |
| PDGFA | 0.21817 | -0.09611 | 0.05722 | 0.797845 | -0.85371 | -0.247365 |
| GRB10 | -0.1482 | -0.1214 | 0.212985 | 0.549075 | -0.68855 | 0.031315 |
| HSP90B1 | 0.73199 | -0.66349 | 0.1136 | 0.27738 | -0.70808 | 0.220075 |
| PDK1 | 0.22172 | -0.19906 | 0.07142 | 0.184025 | -0.3629 | 0.40702 |
| CHEK1 | 0.16432 | -0.25824 | -0.035175 | 0.061105 | -0.11598 | 0.556485 |
| EZH2 | 1.0517 | -1.27971 | -0.499765 | 0.02432 | -0.0587 | 2.188665 |
| EIF3E | 0.4133 | -0.55413 | -0.1205 | 0.10125 | 0.2804 | 0.2704 |
| SRSF1 | 0.49947 | -0.56303 | -0.315605 | 0.10372 | 0.04988 | 0.49366 |
| NRAS | 1.21463 | -0.73761 | -0.352725 | 0.28968 | -0.16946 | 0.499705 |
| SSB | 1.57647 | -0.21963 | -0.314045 | 0.105245 | -0.1391 | 0.180435 |
| IRS1 | 1.66316 | 0.09401 | 0.05314 | -0.411165 | 0.06631 | 0.0112 |
| WNK1 | 1.41069 | -0.01428 | 0.02666 | -0.06165 | -0.10705 | -0.14522 |
| PKN2 | 0.76245 | -0.39095 | 0.01228 | 0.07546 | -0.00947 | 0.014625 |
| BCL10 | 1.02553 | -0.43622 | 0.055865 | -0.0025 | -0.07913 | 0.17875 |
| TWIST1 | 1.03085 | -0.20868 | 0.32096 | 0.17071 | -0.19028 | 0.15917 |
| PKD2 | 0.97691 | -0.5206 | 0.27325 | 0.143775 | -0.42942 | -0.18067 |
| PALLD | 1.21519 | -1.09552 | 0.58895 | 0.33341 | -0.43083 | -0.232625 |
| HIF1A | 0.8365 | -1.08045 | 0.22125 | 0.3257 | -0.1076 | -0.1707 |
| PDGFC | 0.76864 | -0.85422 | 0.15622 | 0.91924 | 0.05146 | -0.14023 |
| VIM | 0.0473 | -1.9498 | 0.20475 | 0.2461 | -0.3264 | 0.03025 |
| TRIB3 | -0.02554 | -0.57139 | 0.173475 | 0.237945 | 0.10512 | 0.08907 |
| EIF4EBP1 | -0.65027 | -1.21042 | 0.023235 | 0.264905 | -0.08922 | 0.6842 |
| ACLY | -0.21066 | -0.45421 | -0.10982 | 0.450275 | 0.06715 | 0.53748 |
| TP53 | -0.58999 | -0.64073 | 0.046995 | 0.56139 | 0.40234 | 0.593755 |
| EIF3B | -0.76848 | -0.71179 | 0.181375 | 0.31969 | 0.0816 | 0.32641 |
| RAF1 | -0.93928 | -0.71165 | -0.11074 | 0.057945 | 0.47403 | 0.458705 |
| CCND1 | 0 | -0.5078 | 0.17577 | -0.09122 | 0.83554 | 0.37897 |
| EIF3H | 0.1582 | -0.2667 | -0.163 | -0.03225 | 0.6242 | 0.373 |
| FYN | -0.651 | -0.2629 | -0.2651 | 0.06385 | 0.5926 | 0.1427 |
| PHLPP1 | -0.39031 | 0.18427 | -0.937345 | -0.086745 | 1.05548 | -0.032945 |
| GAB1 | -0.20955 | 0.0433 | -0.37966 | 0.427775 | 0.21816 | 0.030505 |

Fig. 16B

| | | | | | | |
|---|---|---|---|---|---|---|
| EGFR | -0.73767 | -0.29053 | -0.238575 | 2.62716 | 0.50408 | -0.372555 |
| EIF3G | -1.2816 | -0.44129 | -0.00742 | 0.272995 | 0.17543 | 0.06864 |
| AKT1 | -1.47539 | -0.31473 | 0.05446 | 0.38284 | -0.08595 | 0.0723 |
| CDC37 | -1.17271 | -0.12525 | 0.07167 | 0.2923 | -0.02601 | -0.016315 |
| TSC2 | -2.04178 | 0.22401 | -0.214135 | -0.111525 | 0.54315 | 0.089515 |
| PPP2R1A | -1.98512 | 0.27565 | -0.30678 | 0.14626 | -0.10577 | 0.113105 |
| HSP90AB1 | -0.7772 | 0.38 | -0.3607 | 0.0294 | 0.0062 | 0.12645 |
| MAPK8IP1 | -0.97628 | 0.94612 | -0.459255 | 0.14765 | 0.24049 | -0.18562 |
| GAB2 | -0.42454 | 0.35822 | -0.225285 | -0.093415 | 0.50733 | -0.24581 |
| PIK3C2B | -0.22754 | 0.31961 | -0.15561 | -0.22131 | 0.20599 | -0.173415 |
| TSC1 | -0.0785 | 0.29113 | -0.276995 | -0.47181 | 0.24688 | -0.226365 |
| GSK3B | -0.11768 | 0.30676 | -0.13139 | -0.25868 | 0.01339 | 0.215595 |
| SORBS2 | -0.38951 | 1.55746 | -0.010295 | -0.124755 | -0.48995 | -0.113195 |
| FGFR2 | -0.20067 | 0.99602 | -0.105675 | -0.051065 | -0.17899 | -0.28626 |
| FGFR3 | -0.54315 | 0.91173 | -0.484015 | 0.87716 | -0.48868 | -0.77883 |
| PPP2R2B | 0.32192 | 0.66374 | -0.73616 | 0.05827 | -0.04921 | -0.46383 |
| PIK3R1 | 0.34794 | 0.51153 | -0.508145 | -0.004785 | 0.60956 | -0.375795 |
| MAP3K5 | 0.47626 | 0.37273 | -0.032095 | -0.115655 | 0.2524 | -1.192725 |
| ATXN1 | 0.61354 | 0.4433 | -0.113145 | 0.006195 | 0.01398 | -0.643455 |
| PPARGC1A | 1.04178 | 0.28161 | -0.33465 | 0.15776 | -0.13365 | -0.308905 |
| KRAS | 0.60727 | 0.4583 | -0.36371 | -0.087675 | -0.19746 | 0.026755 |
| CDKN1B | 0.69871 | -0.02234 | -0.811605 | -0.08602 | 0.24653 | 0.3673 |
| PIK3CA | 1.26311 | -0.11844 | -0.162555 | -0.146945 | 0.74825 | 0.13739 |
| FOXO3 | 0.3436 | -0.04921 | -0.057065 | -0.348385 | 0.48372 | -0.10792 |

Fig. 20B
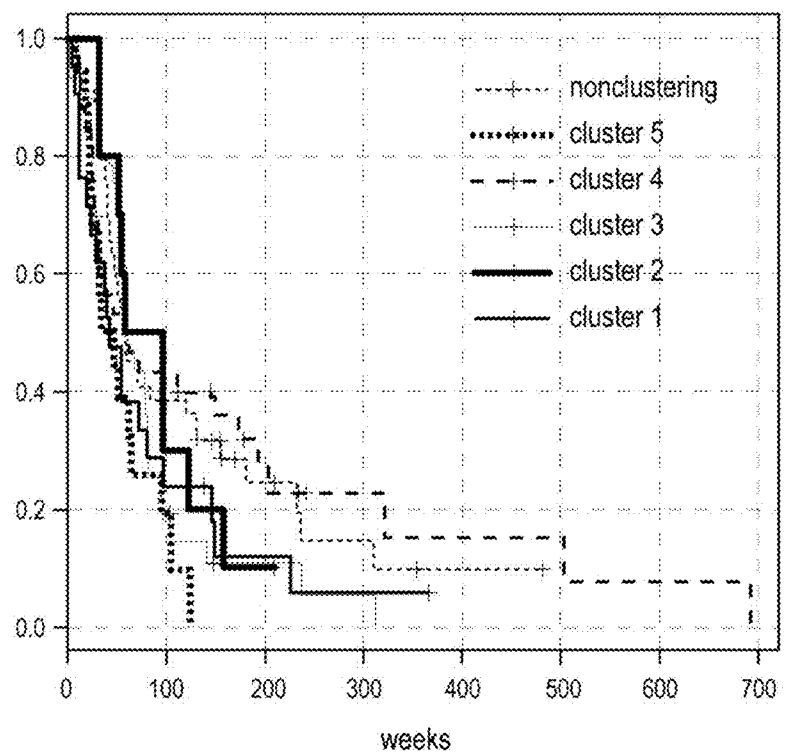
xpr_GBMn_195A_Yurv: clust1vs2
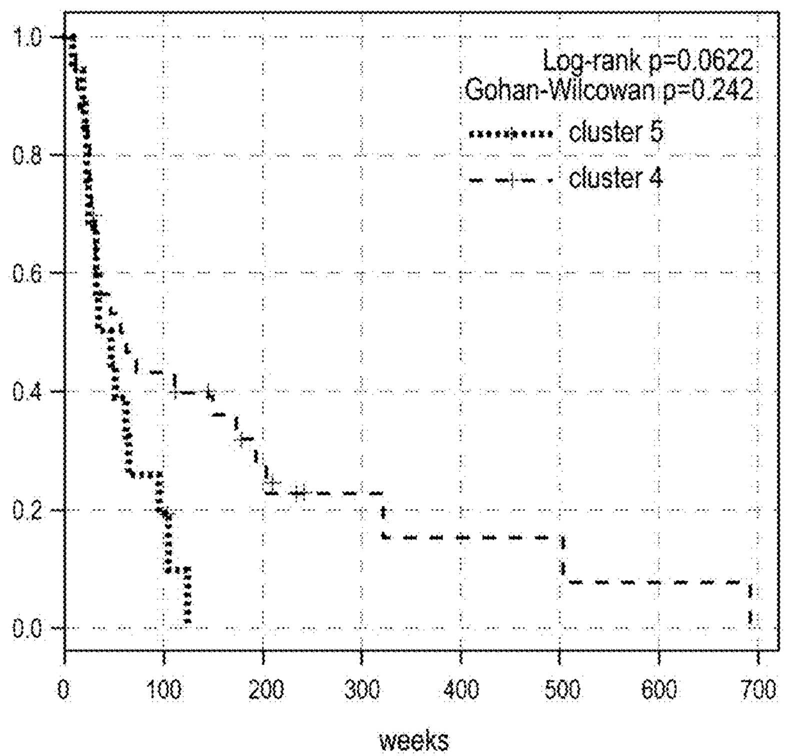

Fig. 20D
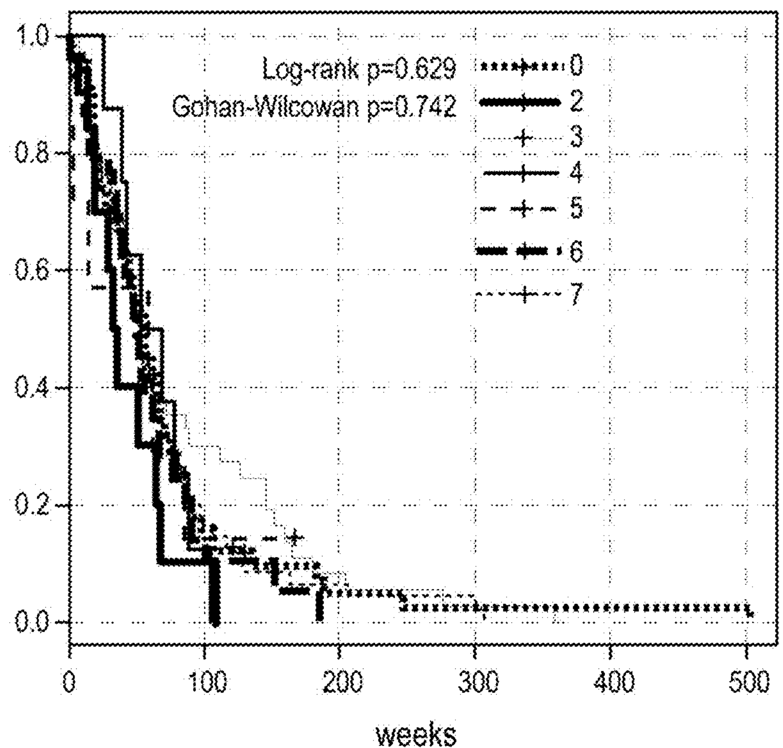
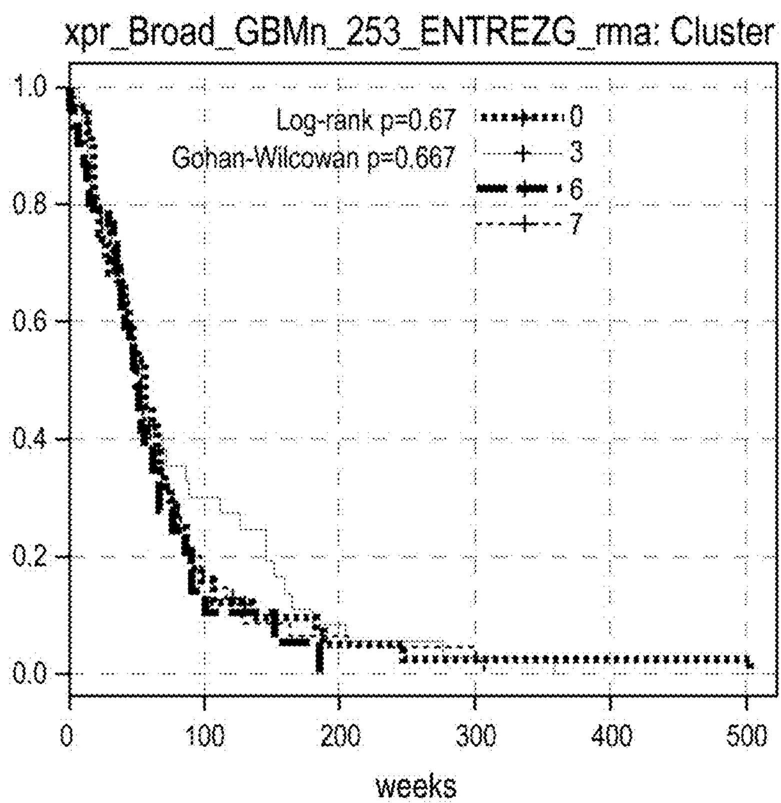

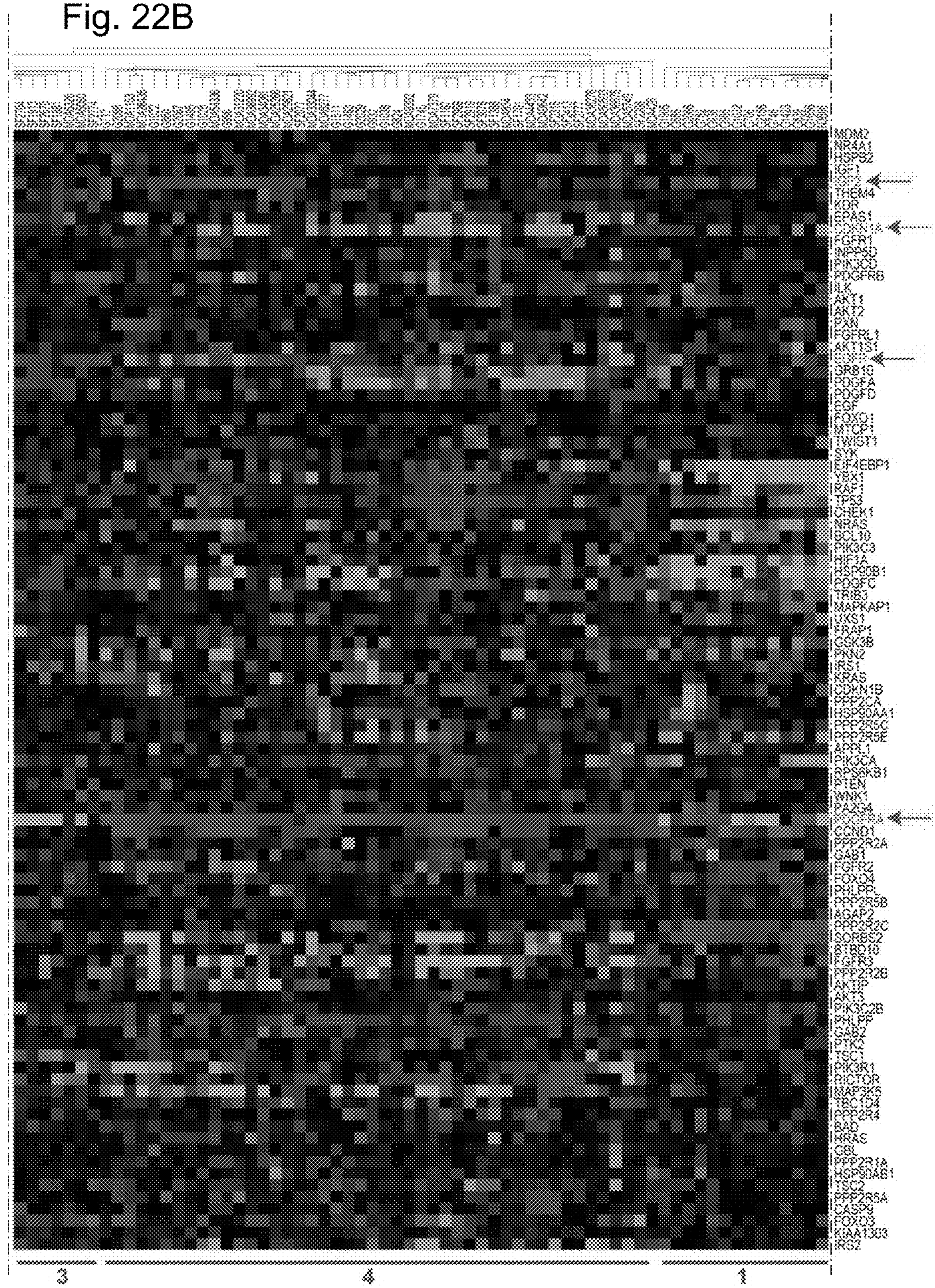
Fig. 22B
MDM2
NR4A1
HSPB2
IGF1
THEM4
KDR
EPAS1
FGFR1
INPP5D
PIK3CD
PDGFRB
ILK
AKT1
AKT2
PXN
FGFRL1
AKT1S1
GRB10
PDGFA
PDGFD
EGF
FOXO1
MTCP1
TWIST1
SYK
EIF4EBP1
YBX1
RAF1
TP53
CHEK1
NRAS
BCL10
PIK3C3
HIF1A
HSP90B1
PDGFC
TRIB3
MAPKAP1
UKS1
FRAP1
GSK3B
PKN2
IRS1
KRAS
CDKN1B
PPP2CA
HSP90AA1
PPP2R5C
PPP2R5E
APPL1
PIK3CA
RPS6KB1
PTEN
WNK1
PA2G4
CCND1
PPP2R2A
GAB1
FGFR2
FOXO4
PHLPPL
PPP2R5B
AGAP2
PPP2R2C
SORBS2
BTBD10
FGFR3
PPP2R2B
AKTIP
AKT3
PIK3C2B
PHLPP
GAB2
PTK2
TSC1
PIK3R1
RICTOR
MAP3K5
TBC1D4
PPP2R4
BAD
HRAS
CBL
PPP2R1A
HSP90AB1
TSC2
PPP2R5A
CASP9
FOXO3
KIAA1303
IRS2
3
4
1

Fig. 24B

| | survival in subgroups | | | |
|---|---|---|---|---|
| subgroup | placebo | TMZ | RT | TMZ + RT |
| 1 | 42 ± 8 | 157 ± 147 | 69 ± 5 | 227 ± 132 |
| 2 | 72 ± 48 | 179 ± 53 ┐ | 119 ± 70 | 228 ± 68 ┐ |
| 3 | 51 ± 7 | 185 ± 123 │ * | 80 ± 52 | 250 ± 151 │ * |
| 4 | 42 ± 23 | 73 ± 29 ┘ | 78 ± 40 | 123 ± 41 ┘ |

* $p < 0.05$

SEQUENCE LISTING

<160> NUMBER OF SEQ ID NOS: 4

<210> SEQ ID NO 1
<211> LENGTH: 18917
<212> TYPE: DNA
<213> ORGANISM: Homo sapiens

<400> SEQUENCE: 1
gggctgagga ggcggggcct gggaggggac aaagccggga agaggaaaag ctcggaccta 60
ccctgtggtc ccgggtttct gcagagtcta cttcagaagc ggaggcactg ggagtccggt 120
ttgggattgc caggctgtgg ttgtgagtct gagcttgtga gcggctgtgg cgccccaact 180
cttcgccagc atatcatccc ggcaggtaac ctcaggctcc aaggggcggc cccggtccct 240
ggctgtggag gggtggctct aattccgcag aaggcaggaa tggggtaaag gaaaaaagcg 300
cagatcttgg gtgtggaggg agtcaaggcc tgcgtgcaaa gaagggaaca aatccaggta 360
ttgagaatgg gaaaagaaaa gggaaggagg ggatgctgga tgcttggata tgcagaaggt 420
ctgcttttgg gcctgggagg gagaaactgg gcggtgagga agttggatgc aacgacaagg 480
ggaaaatcag gtctgcactt gggttggaaa atcgaggggt ggaagttgca agaatgcatg 540
tagaagacta agcctggagt gtaggaggaa gaaaacgtgc agcagctggg ggctggatgc 600
aaagaaggct gtaagccgca gacgggcgtc tgcaggcaac tcaggcggcg aggaatagcc 660
ttgaagccga tccctcgcgt ccgccagggg gcgtggaggg gcggagctcc agcggccttc 720
agaggggtcg ctaggccaca cggggcgaga gggggctggg ggaaacaccc ccgccagttc 780

```
cgggtgcctg gagtttaaaa ggtcccagca ccagcgaggg gaggggaggg gaggggcggg    840
cgtggagacc tggaaggagg taccgatcca gccttgattg cagccctctt gcacaacggc    900
cataaggacg ggtgcaggcc aagagcaagg acatgcaaac cccaagacct gctaacgggc    960
ggcgaagcgg gggcacgccc tcgcacacgc agagataaat tgtgctccca tgacctttat   1020
ttggaaagtg cctgcgggcc taaaattggc ctttgtccca ccgagtacac tcagcactgt   1080
actttaaacc ggataaactg ggctgtctgg caggtactaa aaacagctaa attctcctgt   1140
gagtgttctg tatgttaaca cttttattcc ttgttttgtt ttaggcgata aactacattc   1200
agttgagtct gcaagactgg gaggaactgg ggtgataaga aatctattca ctgtcaaggt   1260
gagaattagc aaattttccc ccttcttctg tactttcttt gatgtggcag tacagtgttt   1320
aactggtctt gggggcaggc cgaggcactg caagggaatg agtgaggaat atttccaaca   1380
acgaattcca acagcttcct tgtttctttt aatacagtgt cttatctgca agagatcctt   1440
tttgcccaga aattattgta gttcatgaac tcggcaaaaa acaatctggc caaaaacttg   1500
aggttgatga aaataatatt aaatggctct tttttttcat taaactactc tgtattgtta   1560
ttccaggttt attttctgga attgcacaat tatgttagga gataggattc agctacttca   1620
tatgagctgg tgcctgctgg tcttggaaca gcccttcctt ctgaagttgg gattgggttg   1680
gagacaaaat ctgaggggca acaaaggtgg agaagtcagt ccagtggggc ctcaagccca   1740
tcccatggaa atcagatcca gaagaaatac aattatgttc cacatggtag taacaataaa   1800
gcttcactgt tttagttaaa agatggtaaa aatttcatgg ctaagtaatg tgaggaaaac   1860
ctgaagcgtc tgaagtatgc attatgagat aaagaaagat tactgcagag agtacagttg   1920
ctttaactga gaaggaaata gtgaactaaa aagatatcag tcttcacatt ttaggtacaa   1980
tatttgacct ctattaactg tatttgccat caagaataaa ttgccatgtc atgactgttg   2040
catcatacta tatagggaca tggccatgga agtgtattat caggaaccag ataagttcac   2100
tgcctccttt tttgctttgt tttaaaacaa ggataggtgt gacagtggaa tcaaacatga   2160
actgaatcat atgctttcag ctgtactaca aattatactt gacattacaa atgggaagta   2220
attgactcat ccacaccatt ctgttcattt cttttagtct agttcagttc cagaaggttc   2280
ccccaaagga atctcctaaa cactagtaag aagaattcta gaattgcgaa tttgggaagt   2340
gaaaatgggc ctggggattg gaaatacatc caggcttgtc aagaaacaga cgcttactgt   2400
ctactaatca ttacattttt atttaaagac caaattactt tagctcaatt tttcaagaaa   2460
gactatttta ggcttcttat ctaataattc tttaaagtca attctcttga ctttttttagt   2520
ccttaagaga ataaaagcaa tttgcagctg tgttgttgga ttaaaaaaga gtttcgatta   2580
gagcatcatt agaaggaata gataactttt agcaggctca gagcttcttc tgcctctagg   2640
gacaagctgg gacagtttca tttcttccaa agcgtccaac cttgcacttt ctgagaatca   2700
gattgatttg tatatgctac ccccacaccc tatccttaaa gtgctgtctt cctaggacaa   2760
tgcacagttt gtcctatccc actcactagc agcttaccct tgcctgtgaa cagccagaag   2820
aagatgacag ggacatgctt gggtcctggg cagtggccct actgtataga gattcttcta   2880
attgagaaat cactttgttg tatttagccc cacatctcca atgtctgtgt tatctctagg   2940
aaaacagttc caccaggaat tcttcgtctc gcttttagac ttaaagtttc cctgaatatg   3000
ggtcacagga accagctgaa tctcctcatg gctagttatt tttattaaat aacaaaaaca   3060
gcctcttaaa ggaggagaaa tgctagcact caccattctg gacatcttga gagcccagta   3120
aaatgatgag ttggactgaa gtgttcaata aacatgagat tgtggaaata atctcatttc   3180
```

```
ttaagacaaa ccagtagttg agaataatga ttgcattatg aagggcacgt tatagggtca   3240
ggctctgcca cgctctagct aggtggcctt gggaaagctc tttttttttt aacaaagtaa   3300
aatggggaaa tgatggccat tttttggat tgttatgagg gctagctcag aaaccgcgtg   3360
tgaaacataa cacaatactt tgttcagaga agatactcaa ttctaatggt aaatagaatt   3420
gctgttacta gctttttatt caactacaca taaattgaat tgcatgaatt gttcttttag   3480
tagtcactac gttgtttata taaacactac gttgtttata tatttcactt tataatgaaa   3540
taaatgacaa ggcatgtatt ttttttttct ttttaggttt attgaagtca aaatgtccaa   3600
aaaaatcagt ggcggttctg tggtagagat gcaaggagat gaaatgacac gaatcatttg   3660
ggaattgatt aaagagaaac tcatttttcc ctacgtggaa ttggatctac ataggtaaat   3720
gagttacccc tccgtgtagc aaactcagaa aggataatct ggctgggcat ggtggtgcac   3780
acgtgaagtc ccagctactt aggaggcaga ggcaggagga tccctcaaga ccaggaattc   3840
aagtccagcc tgggcaacag agtgagaccc catcacttta aaaaaaaaag gaaaaaaaag   3900
ggaaggagaa acaggaaaaa aaaaaagaat ataatctgaa ttattttgag gtgaagttag   3960
cttttttat atagatatag ctgtgttttg tgaataaagt ttgttttaag cctaaatata   4020
ttcagatgaa tcttctaatt ttaacatact gctagaaaaa ctggatttat catctaaaag   4080
tcaagaatta taagggaaag aatgattttc agattcttct aaccttctgt ttcctgtgaa   4140
ggttttattt gtaataaaac agtggctaag aatagtacaa tgtattgaga aaagggaaat   4200
aagagaggat gtaagaaaca gtaaactaaa tgcagttaac acaattttgt catttcaaac   4260
tcaattttct atcactttac ttagtcaatg gacctgtttc cttttcatgc ctcacctttt   4320
gcccttttca tacaattgta gtgcagaaag aattcatgat gtttcttagt tgaacccctc   4380
ctttccagca aaattccctt aaatcctgtg tccctttgcc ctgtgtgtaa agtgcctggg   4440
gacagatgca aaagtctatg taattctctc attttttcg ctgtgttttt cataaacttg   4500
cttctgttct ttgtaccttt aggtagagat agaattttta aaagggtaaa gtggctgaag   4560
actggcatag aaaaatattg agcaacacgt ttcagccaaa ctattggcaa ctctaagtgt   4620
gtttgcctca gcccagaatt agtcatcaaa atttgtccta aggacctgtt tgagtggaga   4680
catttaattc acataatgtc attaaacata ctttttaatt gttctaaacc taagctgctg   4740
atgtctatat tgaaatcatg ataagatata aatacttgca gaagtcaacc aaacataaga   4800
aattaggcat aaaaacatct tccaactagg ttaaaaaaaa aaagcatctt aggaactcct   4860
gtttcaggac tttacatgac agtaggtgaa ctggcagggt tcttttcctt ataatggctg   4920
caactaaaga tgctttgagc ctctttagtg tggaatcatg aggagtttta aaggggagtc   4980
actatgacta ggaggaaaaa atttggtggc tgcagactag ataatttttg gaggctcaaa   5040
caagttttaa atttttccaa aattcctatt attatcactg actggttctt tttcaggaga   5100
atggagcagg tagtttgttt tatgtaggct ggacagtggt ctgggcaatt tgttccttcc   5160
tttcttatct tcttagaaat gttaagaaga caagcaaaaa atctaataat ttgctgatag   5220
attctcctta tgagaaatgg ttcctaggaa cttgaaaact actgatcata cttcctgttg   5280
gagttgggat tggatcaaca tttcctatgc aagaagataa caaaggacat gactttgtta   5340
gatttatatg aattatctaa agtcgaagca gttggaagtt atttttattt ggaaatatgt   5400
caagattact atctctttgt ttgcatcatg agttgggtag gagatctaag aaaggaagat   5460
aagggaacca aaaagaaatc tagaggcagg ttttaagagc tgaaaaacct tttaaatcct   5520
```

-continued

```
tggagaacag aataaacaaa acattatttt gttttcttgc tttttaacaa actattgcat   5580
gcttcaaata aagctttgca gtcattttct atgctccctg gacaactaac attctttcag   5640
ctctgaatga cctgcaatct ttgtgttggt gtatattaag ctattactct ctggtatgta   5700
gaaaaccatt gatggattcc tttacttacc caataaattg taggcttgtt tccagagcaa   5760
acacttgctc aagaattaca gaaggaatta gctgggcatg gtggtgcatg cctgtagtcc   5820
ccgctactgg ggaggctgag gcgggggaat cacttgaacc caggaaggca gaggttgagt   5880
gagccaagat cgtgccactg cactccagcc tgggcaacaa aacgagactc atctaaaaaa   5940
aaaaaaaaaa gggaaaggct cattttatga ctaactggca ttaatgaagt agtcattcgc   6000
atttttggca tcaactgtca catctttacc tcccaccact tcaacgtcaa aatacaaaaa   6060
atcctttaac ccctcccacc cccttttatt tttaaagagc aatatttact aagggaaaaa   6120
ggtggtcctt agacttacac ttattatact aattatatgg agagaaacca ggccattatt   6180
gcctctatct ggtgaaaaac aggaggcaaa gggcagagtt tgatggtttc cattcatttt   6240
cctgatagac agcttcccat tacaagagga ggggcagccc agcagtctag cctctcttag   6300
ttctctttgt agttggcacc catcttctgt gtttagggtg tgccagtgct aaaacttggc   6360
agattttggt gtactcagag ccttcgcttt ctgcataatg agctctatat gccatcactg   6420
cagttgtagg ttataactat ccatttgtct gaaaaacttt gcttctaatt tttctctttc   6480
aagctatgat ttaggcatag agaatcgtga tgccaccaac gaccaagtca ccaaggatgc   6540
tgcagaagct ataaagaagc ataatgttgg cgtcaaatgt gccactatca ctcctgatga   6600
gaagagggtt gaggagttca agttgaaaca aatgtggaaa tcaccaaatg gcaccatacg   6660
aaatattctg ggtggcacgg tcttcagaga agccattatc tgcaaaaata tccccccggct  6720
tgtgagtgga tgggtaaaac ctatcatcat aggtcgtcat gcttatgggg atcaagtaag   6780
tcatgttggc aataatgtga ttttgcatgt tttttttttc atggcccaga aatttccaac   6840
ttgtatgtgt tttattctta tcttttggta tctacaccca ttaagcaagg tatgaaattg   6900
agaaatgcat atatgtataa ctgtatattt acacacattt agctaaaggc aaatacaaat   6960
aaacttacaa ataggcgtcc atctcaacac atttttttttc aaacatgctg tttttttttcc 7020
tttatccttt tattcagtta taccatatga tattgccatt tttatgttgg taatttcata   7080
tggttcaacc agatctgtgg ttttcaacac tggctgcaca ataggatccc cttacaagtt   7140
tttttggtgg ttttgttttg ctttgcttga tttgtttctt tgttttagtt tcaatgcttg   7200
agtaccaccc tacacaaatt aaaatctgaa ttccatgggg ttcaggcatt ttaaagctcc   7260
ccaggtgaat ctaatgtgca aacttgagaa ccaccaaaga ttgtattaaa catgatccca   7320
tcatgcataa aagaaaaaac tggctgggta ctatggttca cacctgtaat cctagcactt   7380
tggaggccaa tttggaagca ctgcttgagg ccaggagttt gagactagcc tggacaacat   7440
agcagaaccc tgtctctaca aaaatgaaaa gtatttcaat aattatgtca attgttcatg   7500
gaagagccag ttttgtttat tcatatacaa agtgagtagg cgaagctgag tggggtggca   7560
tgtgcctata gtcccagcta cttggaaggc tgaggcctga ggatcccttta agcctaggag  7620
ttcaaggtta cagctatgag ctatgatcac accactgcct acgcaacaga gcaagaccct   7680
gtctcgaaaa agaaaaagaa aaaaaaaact gactcggtag ttgaaagcag ccttactaaa   7740
gcattccttc ctgcctggaa aaaaagtatt gcttctttac ttctgtacca gtacacttgt   7800
tgccaaatta agcaaaaaaa ctgccaagta aacaaaatca aagttcagtg ttgaaactga   7860
ggtttcagac tttcacagaa agtagtttat gtcttaaaag gaccttaaaa acaggaatct   7920
```

```
ctcatgctga aatccagagg ttttaatgta gccatcattg aaaacagtgt gttgagggta   7980
aacagtttag tccttgaggg gtcagttaac tttgttccac tctgtggcta aaactatcct   8040
ttcatcctgg ccaaagcctt cagaaatagc tcccaggggc ccaagcaagg gaaggtagat   8100
ggcagtggtg caaactcgct aatcttgtaa aaatcaccct agattctttc cagttcagtc   8160
gtgccttttt tctgcgtata tccttttttgt tttttgtttt tgagacagag tctcgctctg   8220
tcgcccaggc tggagtgcag tggtgtgatc ttggctcact gcaacctctg cctcccgggt   8280
tcaagcaatt ctcctgcctc agcctcttga gtagctggga ttacaggcac atgctaccat   8340
gcccggctaa tttttgtgtt tttagtagag acggggtttc accatgttgg tcaggctggt   8400
ctcaaactcc tgaccttgtg atccgcccgc ctccgcctcc gcctcccaaa gtgctgggat   8460
tacaggcatg ccaccatgcc cggccttcct cttttttttt ttttttttaa ttattttggc   8520
atcagtcatt tgtaaaaatg gccattctat ttattaaagt ccagaaagag aatttcaaac   8580
ctcaggttga ttcatggact gtttaaatat acataaacct atacaaagca tttatggtgc   8640
tttggtacct cagtttctcc cttttcagaa atagtaataa attaccaccc atatttactt   8700
tatggatttt atatgtcaaa aatgttctgt gtaaagtagg tgtttaatct ttattgttac   8760
ttactgctct tttaccagtt gttattagta tttctctaca cttatagatg tggccggcac   8820
ctgctggtac ctaactctgc aagtatctga ttcaattcat tgaagaagat acaatgcagc   8880
aaagacttat ggatgtctag tatatgccag gcatattatt ccactgagta gctgaggccc   8940
atgagggagg tgcctgtcct tgaacagccc tttcctaaaa atcatcatca tcccattgta   9000
gctgctccca gaatgatttg attgctccat atgaacaagt cctataacac tagtaacaat   9060
gataccatga gagaccgagc cccgatggcc taagtaagga cgagacctca agtcctttga   9120
ccctggatgc attatttcta ctatatcata gttccctcct tgtaagactg atgtaagaat   9180
caaatgagat tatgcaagtt aagcatttaa agcatctggc atagagtaag gacaaagcat   9240
tagctacctc agtactacaa ttagtattgt tatcatcacc ctctagggag acttccctga   9300
cttccttcca tggtcacctc ttttcctctg tcatcctata gttttttttt ttttgggggg   9360
ggggtctaat accctctttt ggcatttgaa agctcttata ttgcttttca cttatatatg   9420
tctttatagg gttgtaaact tcctaaagga aagtggctta tgttattctc tgtcctcttc   9480
aaatcagtgc tcagaaaact ttcctatacc tcgtataggc acctaataaa tatttactga   9540
tttaggggaa tgtctggacc tcttcatccc catctcctaa aaaaaaaaaa aaaaaaagaa   9600
gtttgacata ctgccctatt tgtctaggtg tcttctaggt ctatattata tgaatattct   9660
ccttacaatt cctgctaggg tatttttttt ttctttatac ctttttcccc tctacacagt   9720
acagagcaac tgattttgtt gttcctgggc ctggaaaagt agagataacc tacacaccaa   9780
gtgacggaac ccaaaaggtg acatacctgg tacataactt tgaaggtatg tatgactgta   9840
gcataagctt cttttttttt taaacaaatg atttagataa tatttttatt gctttttttg   9900
ttagttatgt gactgcctaa aaatataatc tgaatctaca gtgtttttgc aaaacccgaa   9960
acttgacata aagaagtaat ttgcttccat accttcctgt ggcatgaata aaggcacaaa  10020
agggttaccc acttaattgg aaatgccttt aggcaaagac aaggagatga ttatgcattt  10080
atcttaaagc acagagagaa ggttggcaga aatctgctgt gcatgaatta tatacattaa  10140
atattaatat tctcaaatca cccagcatat aatcctgccc tttgctctgg tagggctctt  10200
gtatctggaa gaggtttcct tatatatttg ctgaagtttt cttcttgccc ttctgggtat  10260
```

```
ttatcctgtg aaaaagtaga acatttgctt tttgcctttt ctttcccagc taccctgcta  10320
cctttgatgg caaatcccac ccaaaagttg ttgaaataat tagtgggccc ttttccttca  10380
ctattgaagt tgttgaaagc actcacacaa acaaaaatac ccaacactca cctacctttt  10440
gtttttcttg cctcttccaa ataatatctg ttggaatctg gttctgcagg cttcagcacc  10500
tttcaccctg aacccaagtt aaccctgagc attggcatgg attcaagttc tatctttaag  10560
taataacaaa gttcaataat agttgtaaaa cacagtgatt acatgtagca taattatttc  10620
tacttatttc taccaactac agtaggagtg ctcagtatcc tccaggagat tataagaatt  10680
ttcattcagt atttgaaatt taagtttttc tcaataactg aggattgagt acacccctaa  10740
agtttaaaat agatgttggg aattgtaaag gtagggtgtt tgtccattct tgcgttgcta  10800
taaagaaata cctgaggctg cgtaagttat aaagaaaaga ggtttaattg gctcatggtt  10860
ctgcaggctg tacaagcctg gctccaacac ctgttcctgg tgagggcctc aggaagcttc  10920
caatcttggc agaaggcaaa cagacaatag gtgtatcaca tggcaagagc gggaacaaga  10980
gaaagagaag ggggaggtcc cagactctta aacaaccaga tttcaagtga attaactgag  11040
cgagaactca cgtaatcacc aaaggggatg gtcctaagcc attcataagg gatccaaccc  11100
catgttccaa tctcctccca ctgggcccca cctccaacac tgggaatcac atttcaacat  11160
gagatttgga agggacaaat atccaaacca tatcagtatg taaaagaagt ttcaaaatta  11220
tttgcctttt cttaaatgta tttctggttc atatcagttt ttggcatttc tgcatcttca  11280
ggattttaaa gactgtatgt tttttcattt ctgctgtcct tccaaaacaa gttagaatgt  11340
ccttatctag aactggcttt tctctcatta tgtgcctcag aaatttgttg gaaacctgtc  11400
tgggacttct gaaatctagt ctcagatgtg agagctgaga agtaggtcat ttggttgtgg  11460
tgggtgattt tagccttatt acaactacat tacatttatt cttctccctt ttttcctctc  11520
actggcttct cctctacaga aggtggtggt gttgccatgg ggatgtataa tcaagataag  11580
tcaattgaag attttgcaca cagttccttc caaatggctc tgtctaaggg ttggcctttg  11640
tatctgagca ccaaaaacac tattctgaag aaatatgatg ggcgttttaa agacatcttt  11700
caggagatat atgacaagta actatagttc tttttttaact ttttctttat tctcaagtaa  11760
gctgacattt gcatatagag tatgtatctc cctatcccta tgattctggg taaattgagt  11820
gaaaatcatc actgtctctt aaagataagg gcaaaactga ggtttagcag gagtgaaaca  11880
aaaccactct gacttgcttt tataagataa acatgttctt aaataaggtc cccacatgaa  11940
ttgttttcag agccaggttc tttaatgttt aaataaacgt acgctgttag tgataagttc  12000
taatttttca tgtgtgagtt tctaagtcag acccatttcc attctttctg aagcccattg  12060
ttagaattta aaattctgtt ggccaggcac ggtggctcat gcctgtaatc ccagcacttt  12120
gggaggccga ggcgggcgga tcacgaggtc aggagatcga gaccatcctg gctaacacgg  12180
tgaaaccctg actctactaa aaataccaaa aattagccgg gcgtggtggc gggcgcctct  12240
agtcccagtt actggggagg ctgaggcagg agaatggcgt gaacccggga ggcggaggtt  12300
gcagtgagcc gaaatcacgc cactgcactg cagcctgggc gacagagcga gactccgtct  12360
caaaaaaaaa aaaagaaaag aaaagaaaaa aaagaattta aaattctgtt ttagtggagt  12420
catttgaact taagtctaag tttataacaa cactggcttc cacagcacag gaggtgagca  12480
tgtgttaata tttaagattg gcataactcc ctttaggtgc aagtgttcag gccaaaatgt  12540
tcctgaggca ttttgattcc tcctcctgct gcccatctat accaagccca gaaactgtct  12600
ggaatatatt ttagtttcct gaatgacacc aagaagtaga acagtctttt caaaaatgta  12660
```

```
ttttaaaaat aagctgaatc tcaagaatct gatctatagt ataatgaaaa ctgaaaagtg  12720
aagtagtcat tgggatactc tactgtctca cttaattctc acggcttccc tgcaaggtgg  12780
gtaaaattgt tcctacagat agtcaaattg agttttacag ttagaaaatg attgggctag  12840
gatttgagcc aatgtctgtc agattcctga gtttctgcta cttctactaa aatatgctgc  12900
ttcttgtgtg tccggtcttc tgtttgggac aagcagatga tatccctaac aaaatcaatt  12960
ttctttatta ttattctctt ttaccttttg tttcccaggc agtacaagtc ccagtttgaa  13020
gctcaaaaga tctggtatga gcataggctc atcgacgaca tggtggccca agctatgaaa  13080
tcagagggag gcttcatctg ggcctgtaaa aactatgatg gtgacgtgca gtcggactct  13140
gtggcccaag gtacagaggt ggagcctggc ctgtaggaac agggtcattc cagggtagtt  13200
ctctaatttg ggaaggggag ttttgtagtc ctttgttgta aaatcttgga atgttaaacc  13260
tccaggtcca ccgtcttacc tgacagctaa ggaaattaag ctcagactag agaaatgatt  13320
tactcaagac cacatgggaa gtaaattagt ggattgacac tcctggctcc agtgtcactc  13380
cttgaagttt taaagcctac ctgatctgaa aatcactccc tttccctgcc ctccttgtcc  13440
tttggtgaaa atgtaaaaaa ccagggcact caggcaagga gggataaagt gaggagcttg  13500
atcatgtcat aaccaagctt tggtgcctgc aaagctcatt tattgggcag caggacctac  13560
tcatgtccct ctgccagctg ctgttctggt agaatataaa acaaatgtgt ttggctgggc  13620
acagtggctc acgcctgtaa tcctagcact ttgagaggcc aaggcagtgg atcacttgag  13680
gccaggagtt caagaccagc ctggccaaca tagcaaaacc ccatctctac ttcaaaaaaa  13740
aaaaaaaaaa aaaattagcc aggtgtggtc gcatgcctat agtccctggc actcaggagg  13800
ctaaagcatg agaatttctt gagcctggga agcggaggtt gcagtgagct gagatcacgc  13860
cactatactc cagcctgggc aacagagcaa gactcttgtc tcaacaacaa caaagaaaaa  13920
gtgtttttgt ttactgctta gcttacacac aaatcaattg agcaaagaac cctaggggct  13980
gtttacagaa attccaggag aagtttcatg catggggtaa gggccaaatc aacagaaaca  14040
cagcgcctgg tttcctcagc accaagttgc ccttcagttt cagttgccct tggtagctgt  14100
atgaacttga atctccccag atgaatgttt gttaacttta attatgtttg tttttcccaa  14160
gaagtactac tttttctgtc tcttatcagt gttaaacatc tcctctcagt ttgaaaatca  14220
gtagatcaac ctggttaaag ataacttttt gccagataaa tgagttacac aactctcctt  14280
accatccttc tgtttctcta catcctcaca atcatttgta ctgaatgcaa cagaggaagg  14340
agtgttattg ctttgtgatg actccgtggt tgattattaa cttcacaggt gatgttggga  14400
ggtagcaaaa atggagaaaa gaagaaaatc aattatatag atataagagt tgtaatgtgg  14460
ttctttcaat aagaaaccac agaagagaac tgttgtactg agggtatgaa agagagcgag  14520
gaagggcaac tgggatgttc ttagatccaa ccgatcctgt gtttacctgc cttctcttcc  14580
cagtcccagc aagtgtatga gcagcttgag ggttcttaag agacagctct cgtccatctt  14640
tatttcccca gaacagcaga gcattgcaca taagaataac aataatagat tgagctctgt  14700
gtccagtact attctaagga atataaatat atattcatat atatttatga atatatgtat  14760
atttatctaa tcccacagca acctagtgaa gtaggtgctg ttattactcc cattttacag  14820
ataagaaaac tgagccgcag tagctatgaa gtcatagaac tagagtggaa tgtaggcagt  14880
tggaccctga accctccatc aaggagtagg tatccctgaa ataagtgagg ggaaaatgca  14940
gcctttccag acccattggc tctgatatct ggagcgggga tcctgccttc tgaaaggcag  15000
```

```
aattattggt gattccatgt gctcttgttt actttgctta ccaagaccta tcaagattga  15060
gtcatttatg ctctcatctc tgagagactc agtgctcttc atgcagttgg acccaacgct  15120
tcatgctcca ctacttacag ggtatggctc tctcggcatg atgaccagcg tgctggtttg  15180
tccagatggc aagacagtag aagcagaggc tgcccacggg actgtaaccc gtcactaccg  15240
catgtaccag aaaggacagg agacgtccac caatcccatt ggtaagatgg tgtttacatt  15300
gatttctcac cagagagtgc tctccaaagc agcccagatg tgttcccttg gctgctcagt  15360
gttttgtgtg caaagtcatc accaagtagc tgatttgttc tactagtaag atctatttga  15420
atatgcttct taaaatatac aatatttgct tttctgtttt gtgggagaac ataggttaca  15480
gagaggaatg ttatcaacaa gcattttcct ttacctctgg tgcagtgaaa tgtcacataa  15540
ggctacaaat ctaaaagtca catggataga tccttttaac aagtttcaaa gatagcactt  15600
caaaaagaga ttacagcctg gaaaaaggag accaatatag acaagagata gaagagattg  15660
tgaccttttt caaattagaa aatgccttaa gtttcaaaca ctagtaccat gccatgaaaa  15720
tgtgtttttt taaagtttct gtttggtaaa atatttctaa ctctcctaaa acttctagcc  15780
catgtggtta gtatctaaag aagtctgtca cctaaacaaa aaactattct gttttgggga  15840
actatgagac atttggaaac ctctataact aggatgattg gagtgttgtg tttttttttcc  15900
cctcttttag cttccatttt tgcctggacc agagggttag cccacagagc aaagcttgat  15960
aacaataaag agcttgcctt ctttgcaaat gctttggaag aagtctctat tgagacaatt  16020
gaggctggct tcatgaccaa ggacttggct gcttgcatta aaggtttacc caagtaagta  16080
taagatgccc tagtttctat ggtcaaatta acacttatcc tcactgggct cagagcatcg  16140
gtgctttctg gaattatata aattgttatt catcatctag ttcaggagtc agcagatatc  16200
tgtaaattgt cagatagtga acattttagg ctttgtggaa catatagtct ttttgcaact  16260
acacaactat tcaactttgc ctctgccatt gtagcaggaa agcagtcata gacaatacag  16320
aatcaaatgg tgtggctggt accaatcaaa cttttatgtt caaaaccagc ctcgatttgg  16380
ttcatgtgct gggctgtaat ttgctgacat cccatctagt tgataatcat tgaacgaaaa  16440
ggttctattt aattttaaga agcagattat agacaaatag aaacaaagat acttcagagg  16500
ctattttatt ctactccttt attttcttta acttactgat gagaaaagtg agcagcacaa  16560
gtttaaggtg tgcaattgat tacagtccct taagtatctg taaccaatat ttgggcaaat  16620
atttgacagc ccatatgttt actgagaatt tttctgagaa catagtagcc agtatcctgg  16680
ggggattgtc tccatatctc aaccagtgca tctgcagagg tcccaggtag ggtcagtata  16740
ccccataatg ggatatact tggtcactgc atgtttctta atttaaattt ccaacaagat  16800
tgcagtgttc gctgggtgct gtggctcatg cctgtaatcc tagcactttg ggaggccgag  16860
gtgggtggat cacgaggtca ggagatcaag accatcctgg ctaacacagt gaaaccccat  16920
ctccactaaa aatacaaaaa attaaccagg cgtggtggcg ggcacctgta gtcccagcta  16980
ctcgggaggc tgaggcagga gaatggcgtg aacctgggag gcggagcttg cagtgagccg  17040
agatggtgcc actgcactcc agcctgcgtg acagagcgag actccatctc aaaaaaaaaa  17100
aaaagattgc agtgttcaaa atggtcttat cagtggaata cctttgtagc ctatttaaca  17160
ggcacctgtc agcaggatta tgttatcctg tcttttgttt ttcttttttt ttcttttttat  17220
tgagacagag tctcgctttg cccaggctgg agtgcagtgg cgtgatcttc gctcactgca  17280
acctccgcct cctgggttca agtgattctt ctgcctcagc ctcccaagta gctgggactt  17340
gtgccacaac acccggctaa tttttttttt tttttttttg tatttttagt agagacgggg  17400
```

```
tttcactttg ttagccagga tggtctccat ctcctgacct catgatccac ccgccttggc  17460

cccccaaagt gctgggatta taggcgtgag ccaccaggcc cggcctgtct tttgtttttc  17520

ttaagacact gatagaaata acaacattat aacttttttt aaggacatgt aacggtttgt  17580

gggaaggtgg gtaaaggttt ggctatgccc tgaataagtt ttgttatgtt taagaatgag  17640

gaagaagtgt gatgattttg gtctcagcag cattagtctg aaccgaaact caatgataat  17700

ttcaccccca aagctacata gcaagaaacc taactgagta tgtatggctg tctctactgc  17760

cggttgccta gagagcctga gtactgagcc tgggtcagcc ccaggaaccc tgaacatagt  17820

cattgtctat agattttgta gcttactaac atgaatgcgt tttcttccag aaacaaatag  17880

aatactattt taagtagcat ttctaggact ttaccactac ctgctaccat atcagagacc  17940

aactaaattt tcttttttttt ttccttcccg ttagtgtgca acgttctgac tacttgaata  18000

catttgagtt catggataaa cttggagaaa acttgaagat caaactagct caggccaaac  18060

tttaagttca tacctgagct aagaaggata attgtctttt ggtaactagg tctacaggtt  18120

tacatttttc tgtgttacac tcaaggataa aggcaaaatc aattttgtaa tttgtttaga  18180

agccagagtt tatcttttct ataagtttac agccttttttc ttatatatac agttattgcc  18240

acctttgtga acatggcaag ggactttttt acaattttta ttttattttc tagtaccagc  18300

ctaggaattc ggttagtact catttgtatt cactgtcact ttttctcatg ttctaattat  18360

aaatgaccaa aatcaagatt gctcaaaagg gtaaatgata gccacagtat tgctccctaa  18420

aatatgcata aagtagaaat tcactgcctt cccctcctgt ccatgacctt gggcacaggg  18480

aagttctggt gtcatagata tcccgttttg tgaggtagag ctgtgcatta aacttgcaca  18540

tgactggaac gaagtatgag tgcaactcaa atgtgttgaa gatactgcag tcatttttgt  18600

aaagaccttg ctgaatgttt ccaatagact aaatactgtt taggccgcag gagagtttgg  18660

aatccggaat aaatactacc tggaggtttg tcctctccat ttttctcttt ctcctcctgg  18720

cctggcctga atattatact actctaaata gcatatttca tccaagtgca ataatgtaag  18780

ctgaatcttt tttggacttc tgctggcctg ttttatttct tttatataaa tgtgatttct  18840

cagaaattga tattaaacac tatcttatct tctcctgaac tgttgatttt aattaaaatt  18900

aagtgctaat taccatt                                                 18917
```

<210> SEQ ID NO 2
<211> LENGTH: 2313
<212> TYPE: DNA
<213> ORGANISM: Homo sapiens

<400> SEQUENCE: 2

```
aggggggcgtg gaggggcgga gctccagcgg ccttcagagg ggtcgctagg ccacacgggg    60

cgagaggggg ctgggggaaa cacccccgcc agttccgggt gcctggagtt taaaaggcga   120

taaactacat tcagttgagt ctgcaagact gggaggaact ggggtgataa gaaatctatt   180

cactgtcaag gtttattgaa gtcaaaatgt ccaaaaaaat cagtggcggt tctgtggtag   240

agatgcaagg agatgaaatg acacgaatca tttgggaatt gattaaagag aaactcattt   300

ttccctacgt ggaattggat ctacatagct atgatttagg catagagaat cgtgatgcca   360

ccaacgacca agtcaccaag gatgctgcag aagctataaa gaagcataat gttggcgtca   420

aatgtgccac tatcactcct gatgagaaga gggttgagga gttcaagttg aaacaaatgt   480

ggaaatcacc aaatggcacc atacgaaata ttctgggtgg cacggtcttc agagaagcca   540
```

```
ttatctgcaa aaatatcccc cggcttgtga gtggatgggt aaaacctatc atcataggtc    600

gtcatgctta tggggatcaa tacagagcaa ctgattttgt tgttcctggg cctggaaaag    660

tagagataac ctacacacca agtgacggaa cccaaaaggt gacatacctg gtacataact    720

ttgaagaagg tggtggtgtt gccatgggga tgtataatca agataagtca attgaagatt    780

ttgcacacag ttccttccaa atggctctgt ctaagggttg gcctttgtat ctgagcacca    840

aaaacactat tctgaagaaa tatgatgggc gttttaaaga catctttcag gagatatatg    900

acaagcagta caagtcccag tttgaagctc aaaagatctg gtatgagcat aggctcatcg    960

acgacatggt ggcccaagct atgaaatcag agggaggctt catctgggcc tgtaaaaact   1020

atgatggtga cgtgcagtcg gactctgtgg cccaagggta tggctctctc ggcatgatga   1080

ccagcgtgct ggtttgtcca gatggcaaga cagtagaagc agaggctgcc cacgggactg   1140

taacccgtca ctaccgcatg taccagaaag gacaggagac gtccaccaat cccattgctt   1200

ccatttttgc ctggaccaga gggttagccc acagagcaaa gcttgataac aataaagagc   1260

ttgccttctt tgcaaatgct ttggaagaag tctctattga gacaattgag gctggcttca   1320

tgaccaagga cttggctgct tgcattaaag gtttacccaa tgtgcaacgt tctgactact   1380

tgaatacatt tgagttcatg gataaacttg gagaaaactt gaagatcaaa ctagctcagg   1440

ccaaacttta agttcatacc tgagctaaga aggataattg tcttttggta actaggtcta   1500

caggtttaca tttttctgtg ttacactcaa ggataaaggc aaaatcaatt ttgtaatttg   1560

tttagaagcc agagtttatc ttttctataa gtttacagcc tttttcttat atatacagtt   1620

attgccacct ttgtgaacat ggcaagggac ttttttacaa tttttatttt attttctagt   1680

accagcctag gaattcggtt agtactcatt tgtattcact gtcacttttt ctcatgttct   1740

aattataaat gaccaaaatc aagattgctc aaaagggtaa atgatagcca cagtattgct   1800

ccctaaaata tgcataaagt agaaattcac tgccttcccc tcctgtccat gaccttgggc   1860

acagggaagt tctggtgtca tagatatccc gttttgtgag gtagagctgt gcattaaact   1920

tgcacatgac tggaacgaag tatgagtgca actcaaatgt gttgaagata ctgcagtcat   1980

ttttgtaaag accttgctga atgtttccaa tagactaaat actgtttagg ccgcaggaga   2040

gtttggaatc cggaataaat actacctgga ggtttgtcct ctccattttt ctctttctcc   2100

tcctggcctg gcctgaatat tatactactc taaatagcat atttcatcca agtgcaataa   2160

tgtaagctga atcttttttg gacttctgct ggcctgtttt atttctttta tataaatgtg   2220

atttctcaga aattgatatt aaacactatc ttatcttctc ctgaactgtt gattttaatt   2280

aaaattaagt gctaattacc attaaaaaaa aaa                                2313
```

<210> SEQ ID NO 3
<211> LENGTH: 2470
<212> TYPE: DNA
<213> ORGANISM: Homo sapiens

<400> SEQUENCE: 3

```
cgtggagacc tggaaggagg taccgatcca gccttgattg cagccctctt gcacaacggc     60

cataaggacg ggtgcaggcc aagagcaagg acatgcaaac cccaagacct gctaacgggc    120

ggcgaagcgg gggcacgccc tcgcacacgc agagataaat tgtgctccca tgacctttat    180

ttggaaagtg cctgcgggcc taaaattggc ctttgtccca ccgagtacac tcagcactgt    240

actttaaacc ggataaactg ggctgtctgg caggcgataa actacattca gttgagtctg    300

caagactggg aggaactggg gtgataagaa atctattcac tgtcaaggtt tattgaagtc    360
```

```
aaaatgtcca aaaaaatcag tggcggttct gtggtagaga tgcaaggaga tgaaatgaca    420
cgaatcattt gggaattgat taaagagaaa ctcatttttc cctacgtgga attggatcta    480
catagctatg atttaggcat agagaatcgt gatgccacca acgaccaagt caccaaggat    540
gctgcagaag ctataaagaa gcataatgtt ggcgtcaaat gtgccactat cactcctgat    600
gagaagaggg ttgaggagtt caagttgaaa caaatgtgga aatcaccaaa tggcaccata    660
cgaaatattc tgggtggcac ggtcttcaga gaagccatta tctgcaaaaa tatccccccgg   720
cttgtgagtg gatgggtaaa acctatcatc ataggtcgtc atgcttatgg ggatcaatac    780
agagcaactg attttgttgt tcctgggcct ggaaaagtag agataaccta cacaccaagt    840
gacggaaccc aaaaggtgac atacctggta cataactttg aagaaggtgg tggtgttgcc    900
atggggatgt ataatcaaga taagtcaatt gaagattttg cacacagttc cttccaaatg    960
gctctgtcta agggttggcc tttgtatctg agcaccaaaa acactattct gaagaaatat   1020
gatgggcgtt ttaaagacat ctttcaggag atatatgaca agcagtacaa gtcccagttt   1080
gaagctcaaa agatctggta tgagcatagg ctcatcgacg acatggtggc ccaagctatg   1140
aaatcagagg gaggcttcat ctgggcctgt aaaaactatg atggtgacgt gcagtcggac   1200
tctgtggccc aagggtatgg ctctctcggc atgatgacca gcgtgctggt ttgtccagat   1260
ggcaagacag tagaagcaga ggctgcccac gggactgtaa cccgtcacta ccgcatgtac   1320
cagaaaggac aggagacgtc caccaatccc attgcttcca tttttgcctg gaccagaggg   1380
ttagcccaca gagcaaagct tgataacaat aaagagcttg ccttctttgc aaatgctttg   1440
gaagaagtct ctattgagac aattgaggct ggcttcatga ccaaggactt ggctgcttgc   1500
attaaaggtt tacccaatgt gcaacgttct gactacttga atacatttga gttcatggat   1560
aaacttggag aaaacttgaa gatcaaacta gctcaggcca aactttaagt tcatacctga   1620
gctaagaagg ataattgtct tttggtaact aggtctacag gtttacattt ttctgtgtta   1680
cactcaagga taaaggcaaa atcaattttg taatttgttt agaagccaga gtttatcttt   1740
tctataagtt tacagccttt ttcttatata tacagttatt gccacctttg tgaacatggc   1800
aagggacttt tttacaattt ttattttatt ttctagtacc agcctaggaa ttcggttagt   1860
actcatttgt attcactgtc actttttctc atgttctaat tataaatgac caaaatcaag   1920
attgctcaaa agggtaaatg atagccacag tattgctccc taaaatatgc ataaagtaga   1980
aattcactgc cttcccctcc tgtccatgac cttgggcaca gggaagttct ggtgtcatag   2040
atatcccgtt ttgtgaggta gagctgtgca ttaaacttgc acatgactgg aacgaagtat   2100
gagtgcaact caaatgtgtt gaagatactg cagtcatttt tgtaaagacc ttgctgaatg   2160
tttccaatag actaaatact gtttaggccg caggagagtt tggaatccgg aataaatact   2220
acctggaggt ttgtcctctc catttttctc tttctcctcc tggcctggcc tgaatattat   2280
actactctaa atagcatatt tcatccaagt gcaataatgt aagctgaatc tttttggac    2340
ttctgctggc ctgttttatt tcttttatat aaatgtgatt tctcagaaat tgatattaaa   2400
cactatctta tcttctcctg aactgttgat tttaattaaa attaagtgct aattaccatt   2460
aaaaaaaaaa                                                          2470
```

<210> SEQ ID NO 4
<211> LENGTH: 1740
<212> TYPE: DNA
<213> ORGANISM: Homo sapiens -continued

```
<400> SEQUENCE: 4

ccagcgttag cccgcggcca ggcagccggg aggagcggcg cgcgctcgga cctctcccgc     60

cctgctcgtt cgctctccag cttgggatgg ccggctacct gcgggtcgtg cgctcgctct    120

gcagagcctc aggctcgcgg ccggcctggg cgccggcggc cctgacagcc cccacctcgc    180

aagagcagcc gcggcgccac tatgccgaca aaaggatcaa ggtggcgaag cccgtggtgg    240

agatggatgg tgatgagatg acccgtatta tctggcagtt catcaaggag aagctcatcc    300

tgccccacgt ggacatccag ctaaagtatt ttgacctcgg gctcccaaac cgtgaccaga    360

ctgatgacca ggtcaccatt gactctgcac tggccaccca gaagtacagt gtggctgtca    420

agtgtgccac catcacccct gatgaggccc gtgtggaaga gttcaagctg aagaagatgt    480

ggaaaagtcc caatggaact atccggaaca tcctgggggg gactgtcttc cgggagccca    540

tcatctgcaa aaacatccca cgcctagtcc ctggctggac caagcccatc accattggca    600

ggcacgccca tggcgaccag tacaaggcca cagactttgt ggcagaccgg gccggcactt    660

tcaaaatggt cttcacccca aaagatggca gtggtgtcaa ggagtgggaa gtgtacaact    720

tccccgcagg cggcgtgggc atgggcatgt acaacaccga cgagtccatc tcaggttttg    780

cgcacagctg cttccagtat gccatccaga agaaatggcc gctgtacatg agcaccaaga    840

acaccatact gaaagcctac gatgggcgtt tcaaggacat cttccaggag atctttgaca    900

agcactataa gaccgacttc gacaagaata agatctggta tgagcaccgg ctcattgatg    960

acatggtggc tcaggtcctc aagtcttcgg gtggctttgt gtgggcctgc aagaactatg   1020

acggagatgt gcagtcagac atcctggccc agggctttgg ctcccttggc ctgatgacgt   1080

ccgtcctggt ctgccctgat gggaagacga ttgaggctga ggccgctcat gggaccgtca   1140

cccgccacta tcgggagcac cagaagggcc ggcccaccag caccaacccc atcgccagca   1200

tctttgcctg gacacgtggc ctggagcacc gggggaagct ggatgggaac caagacctca   1260

tcaggtttgc ccagatgctg gagaaggtgt gcgtggagac ggtggagagt ggagccatga   1320

ccaaggacct ggcgggctgc attcacggcc tcagcaatgt gaagctgaac gagcacttcc   1380

tgaacaccac ggacttcctc gacaccatca agagcaacct ggacagagcc ctgggcaggc   1440

agtaggggga ggcgccaccc atggctgcag tggaggggcc agggctgagc cggcgggtcc   1500

tcctgagcgc ggcagagggt gagcctcaca gcccctctct ggaggccttt ctaggggatg   1560

tttttttata agccagatgt ttttaaaagc atatgtgtgt ttcccctcat ggtgacgtga   1620

ggcaggagca gtgcgtttta cctcagccag tcagtatgtt ttgcatactg taatttatat   1680

tgcccttgga acacatggtg ccatatttag ctactaaaaa gctcttcaca aaaaaaaaaa   1740
```

DIAGNOSING IDH1 RELATED SUBGROUPS AND TREATMENT OF CANCER

CROSS-REFERENCE TO RELATED APPLICATIONS

This application is a continuation-in-part of U.S. patent application Ser. No. 13/515,494, filed Jun. 12, 2012, now abandoned, which is the national phase of International Patent Application No. PCT/US2010/059953, filed Dec. 10, 2010, which designated the U.S. and was published under PCT Article 21(2) in English. This application is a continuation-in-part of International Patent Application No. PCT/US2014/067168, filed Nov. 24, 2014, which designated the U.S. and was published under PCT Article 21(2) in English. This application also includes a claim of priority under 35 U.S.C. § 119(e) to U.S. provisional patent application No. 61/285,936, filed Dec. 11, 2009, and U.S. provisional patent application No. 61/907,987, filed Nov. 22, 2013. The contents of all the related applications cross-referenced herein are herein incorporated by reference in their entirety as though fully set forth.

STATEMENT REGARDING FEDERALLY-SPONSORED RESEARCH OR DEVELOPMENT

This invention was made with government support under Grant No. NS064952 awarded by the National Institutes of Health. The government has certain rights in the invention.

FIELD OF THE INVENTION

The invention relates to medicine, for example, methods, compositions and kits for categorizing/classifying/stratifying and treating tumors.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

WHO grade IV astrocytoma or glioblastoma (GBM) are the most common primary brain tumors and, unfortunately, the most aggressive. Median survival of patients harboring these tumors is approximately 14 months. Despite a committed effort to investigate new chemotherapies, molecularly targeted therapies, immunotherapies, surgical and radiological approaches, there has been little improvement over the last 30 years. Inadequate classification of GBM may have contributed to the difficulty of developing new therapies by decreasing power of clinical trials and underestimating benefit of class-specific drugs. It may also have confounded discovery of class-specific pathways and drug targets.

GBM diagnosed by histopathology is a collection of molecular and clinical subtypes. For example, there are two classes of GBM based on clinical presentation [1], [2]. Primary GBM arise de novo in older patients and are associated with poorer prognosis. Secondary GBM are rare (~5-10% of total GBM), progress from lower grade tumors, occur more frequently in younger patients with better prognosis and have a different molecular profile. Studies using gene expression, DNA copy number, miRNA, and DNA methylation show these molecular characteristics can divide GBM into subclasses, some with different clinical characteristics [3], [4], [5], [6], [7], [8], [9]. Three subtypes emerged in early studies of WHO grade IV GBM (studies that combine histological subtypes or grades of glioma and use molecular classification to distinguish them are excluded from this discussion). These were called proneural (PN), Proliferative (PROLIF) and mesenchymal (MES) and each had characteristic clinical and molecular features [4]. Later approaches find 3-5 GBM subtypes including the PN, MES and Classical (CLAS) subgroups [8], [9], [10], [11]. DNA methylation identifies a subset of PN tumors with glioma CpG island methylator phenotype (GCIMP) that are younger, longer surviving and tightly associated with IDH1 mutations [8].

However, molecular classification of GBM is still in its infancy. There is no consensus on the number of subtypes and which classifiers should be used to classify them. In addition, there is considerable reassignment of tumors to different classes depending on classifier used. There is also little information on which oncogenic pathways are active in subtypes and how subtypes respond to standard and experimental therapeutics.

Alterations in the growth factor receptor/phosphatidylinositol 3-kinase/AKT (GFR/PI3K/AKT) pathway occur in most human cancers including at least 85% of GBM [10]. Pharmacological inhibition of the GFR/PI3K/AKT pathway is a promising strategy for anti-cancer therapy [12], [13]. However, while sporadic responses have been reported, clinical trials of pathway inhibitors in GBM have been largely disappointing [14].

SUMMARY OF THE INVENTION

Various embodiments of the present invention provide a method for categorizing/classifying/stratifying a cancer in a subject. The method may consist of or may consist essentially of or may comprise: obtaining a biological sample from the subject; determining an expression pattern of AKT pathway components in the biological sample; and categorizing/classifying/stratifying the cancer based on the determined expression pattern of AKT pathway components in the biological sample.

Various embodiments of the present invention provide a method for diagnosing whether a subject has a cancer subtype. The method may consist of or may consist essentially of or may comprise: obtaining a biological sample from the subject; determining whether the cancer subtype's expression pattern of AKT pathway components is present in the biological sample; and diagnosing the subject as having the cancer subtype after the cancer subtype's expression pattern of AKT pathway components is determined to be present in the biological sample. In various further embodiments, the method comprises selecting, choosing or prescribing a therapeutic for the subject after diagnosis. In various further embodiments, the method comprises instructing or directing the subject to receive a therapeutic after diagnosis. In various further embodiments, the method comprises administering a therapeutically effective amount of a therapeutic to the subject, thereby treating, preventing, reducing the likelihood of having, reducing the severity of and/or slowing the progression of the diagnosed cancer subtype. In some embodiments, the cancer subtype is an AKT subtype including but not limited to C1, PN, MES, CLAS, SL, and PROLIF subtypes.

Various embodiments of the present invention provide a method for treating, preventing, reducing the likelihood of having, reducing the severity of and/or slowing the progression of a cancer subtype in a subject. The method may consist of or may consist essentially of or may comprise: obtaining a biological sample from the subject; determining whether the cancer subtype's expression pattern of AKT pathway components is present in the biological sample; providing a therapeutic; and administering a therapeutically effective amount of the therapeutic to the subject after the cancer subtype's expression pattern of AKT pathway components is determined to be present in the biological sample, thereby treating, preventing, reducing the likelihood of having, reducing the severity of and/or slowing the progression of the cancer subtype. In some embodiments, the cancer subtype is an AKT subtype including but not limited to C1, PN, MES, CLAS, SL, and PROLIF subtypes.

Various embodiments of the present invention provide a method for treating an AKT cancer subtype in a subject. The method may consist of or may consist essentially of or may comprise: providing a therapeutic; and administering a therapeutically effective amount of the therapeutic to the subject, thereby treating the AKT cancer subtype in the subject.

Various embodiments of the present invention provide a kit for categorizing/classifying/stratifying a cancer in a subject and/or for diagnosing whether a subject has a cancer subtype. The kit may consist of or may consist essentially of or may comprise: one or more detection agents that specifically bind to one or more AKT pathway components; instructions for using the one or more detection agents to classify the cancer in the subject, and/or diagnose whether a subject has the cancer subtype.

Various embodiments of the present invention provide a kit for treating, preventing, reducing the likelihood of having, reducing the severity of and/or slowing the progression of a cancer subtype in a subject. The kit may consist of or may consist essentially of or may comprise: one or more detection agents that specifically bind to one or more AKT pathway components; a quantity of a therapeutic; and instructions for using the one or more detection agents and the therapeutic to treat, prevent, reduce the likelihood of having, reduce the severity of and/or slow the progression of the cancer subtype in the subject Various embodiments of the present invention provide a kit for treating an AKT cancer subtype in a subject. The kit may consist of or may consist essentially of or may comprise: a quantity of a therapeutic; and instructions for using the therapeutic to treat the AKT cancer subtype in the subject.

Various methods, compositions, and kits of the present invention find utility in the classification and treatment of various tumors, including but not limited to various forms of brain tumors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

(FIG. 1A) Consensus heat maps for k=5 to 8 generated with AKT pathway genes in the discovery dataset (GBM195). Red indicates total consensus (consensus index of 1) while white indicates no consensus (consensus index of 0). (FIG. 1B) Silhouette scores for k=5 to 8 were calculated as described [26]. Samples with negative silhouette scores were removed in all further analysis. (FIG. 1C) Consensus CDF for k=2 to 10. (FIG. 1D) Effect of k on survival differences between subgroups. Kaplan Meier curves of patient subgroups were generated for k=2 to 10. For each k, Bonferroni corrected log rank p values were generated by pairwise comparison of subtypes. The smallest pairwise p value for each k is plotted.

FIGS. 2A-2D depict, in accordance with various embodiments of the invention, validation of AKT subgroups in an independent dataset. AKT pathway genes in discovery (FIG. 2A) and validation (FIG. 2B) datasets have similar patterns of expression in subgroups. Tumors in the discovery and validation set were first grouped by AKT subgroup membership then ordered by correlation coefficient. AKT gene order in the discovery set was determined by one-way hierarchical clustering and retained in the validation set. Discovery (FIG. 2C) and validation (FIG. 2D) datasets have similar DNA CNA. The percentage of patients in the discovery (FIG. 2A) and validation (FIG. 2B) datasets with copy number gains or losses in chr7, 10 and 19q is shown.

[55], [56] was used for this analysis (The cBio Cancer Genomics Portal; www.cbioportal.org). Gene expression is represented as z scores calculated relative to diploid tumors for each gene and are the median value of 3 mRNA platforms (Affymetrix U133A and Exon arrays and Agilent custom array). There was a statistically significant enrichment of IDH1 mutations in the SL and EGFR and CDKN2A mutations plus CNA in the CLAS subtype ($p<0.02$).

Figure 7A:
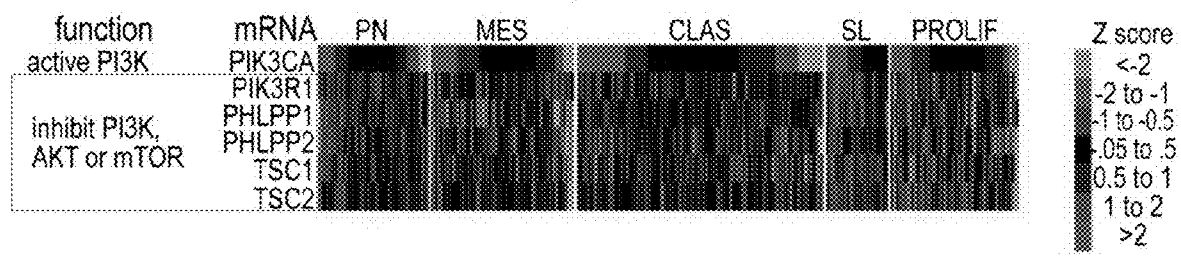
Figure 7B:
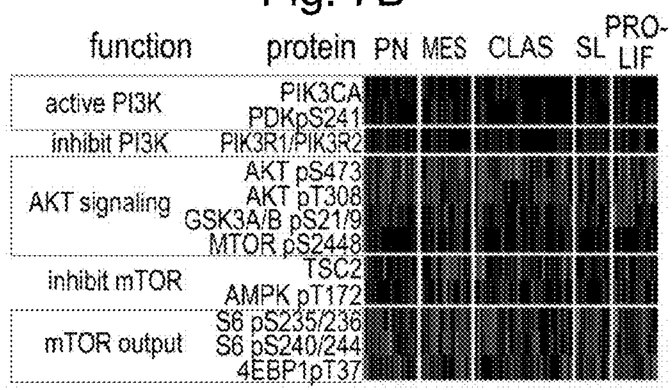
Figure 7C:
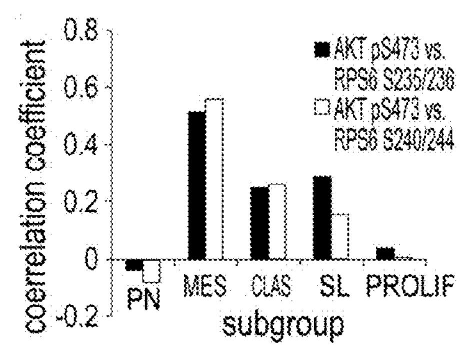
Figure 7D:
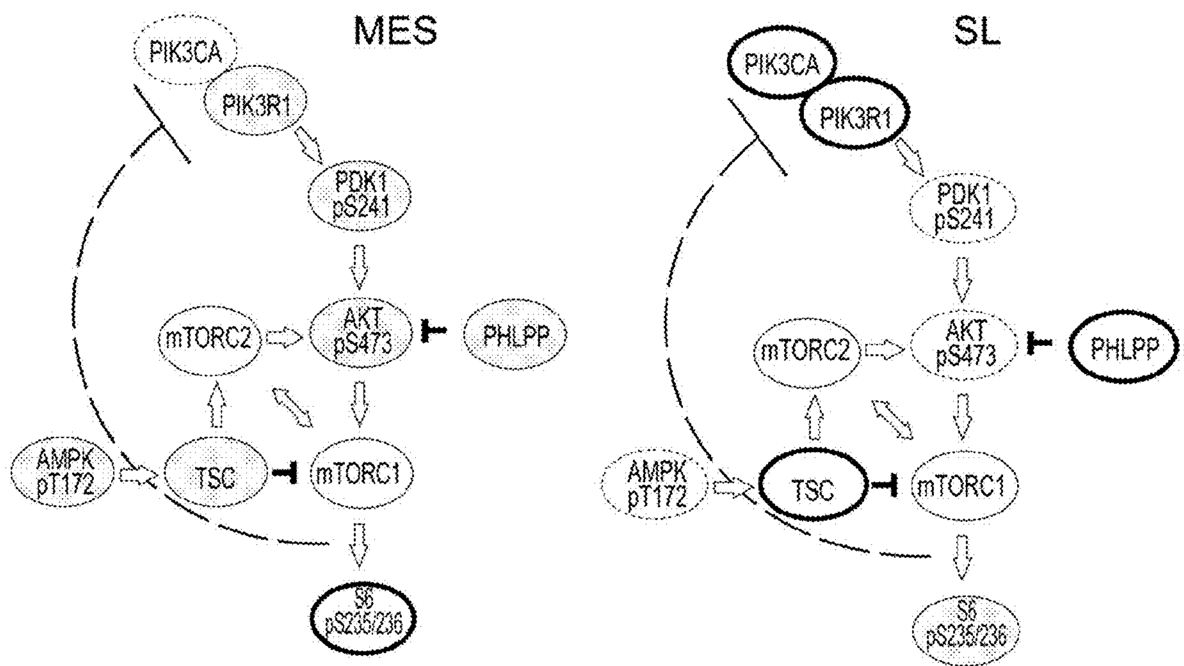

FIGS. 7A-7D depicts, in accordance with various embodiments of the invention, that subgroups have distinct patterns of expression for PI3K/AKT/mTOR pathway components (distinct Akt pathway activation). Tumors (x axis) were grouped by AKT class then Z transformed mRNA (FIG. 7A) or protein and phospho-protein expression (FIG. 7B) color coded to reflect magnitude (y axis). The Pearson correlation coefficient for AKT pS473 vs. RPS6 pS235/236 (light gray) and AKT pS473 vs. RPS6 pS240/244 (dark gray) for each subgroup is shown (FIG. 7C). Proposed AKT/mTOR/S6 pathway map for the MES and SL subtypes based on this data (FIG. 7D). This model shows loss of AKT and mTOR inhibitors (PHLPP, TSC and pAMPK) increases output of the AKT/mTOR/S6 axis (pRPS6) in the MES subgroup. Conversely, increased expression of these inhibitors decreases output in the SL subgroup. Red, grey and green represent high, intermediate and low expression/activity, respectively. Dashed line is indirect interaction.

FIGS. 8A-8B depicts, in accordance with various embodiments of the invention, summary of features in AKT subtypes (AKT C1/subgroup 1; AKT PN/subgroup 2; AKT MES/subgroup 3; AKT CLAS/subgroup 4; AKT SL/subgroup 5; AKT PROLIF/subgroup 6). Clinical and molecular features of AKT subgroups are summarized in (FIG. 8A). Illustration of proposed neurodevelopmental cell of origin for AKT subgroups based on GO terms (FIG. 8B). ND=not determined.

Figure 9:
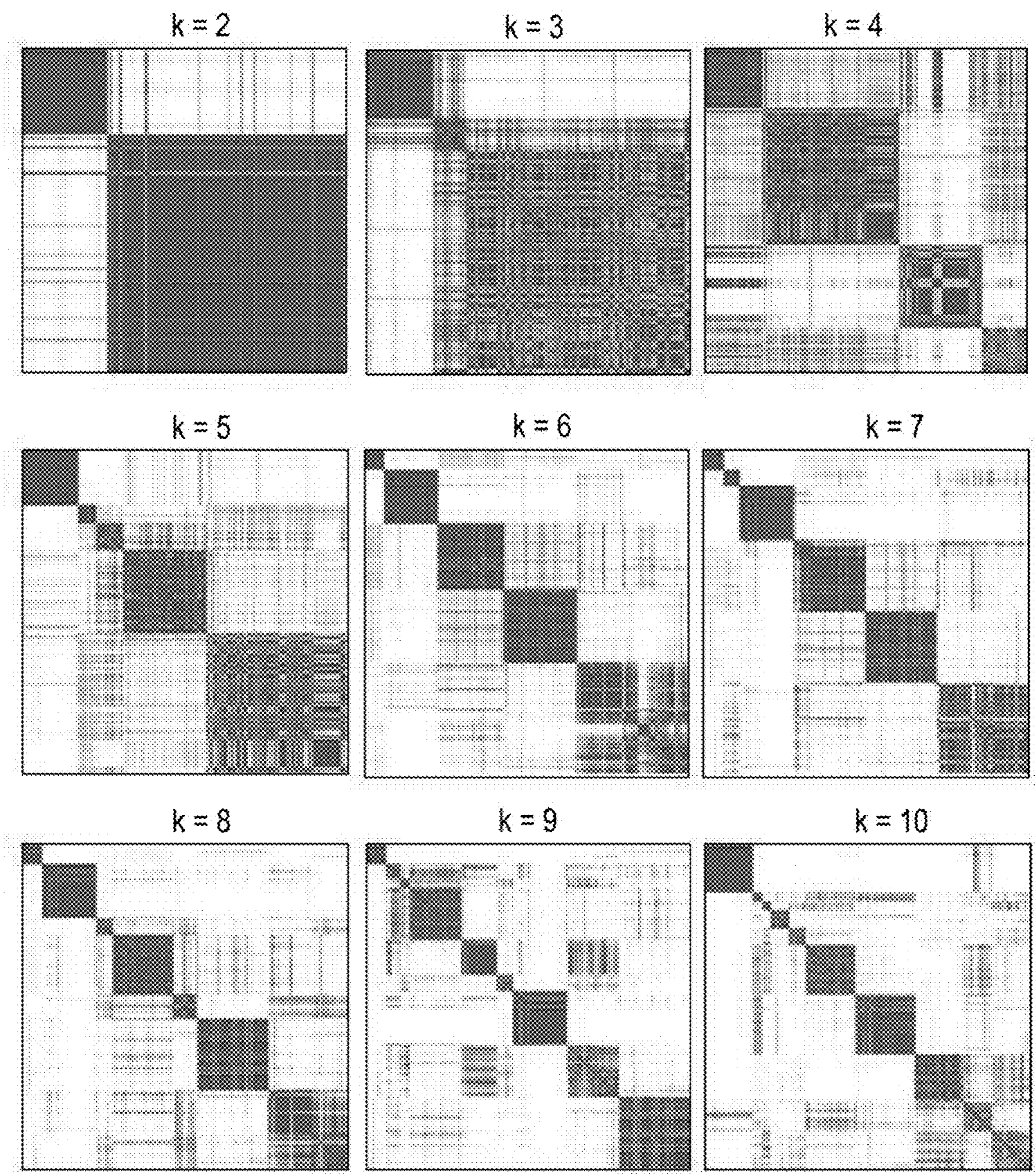

FIG. 9 depicts, in accordance with various embodiments of the invention, consensus k-means heat maps for k=2 to 10 generated with AKT pathway genes in the discovery dataset (GBM195). Red indicates total consensus (consensus index of 1) while white indicates no consensus (consensus index of 0).

Figure 10:
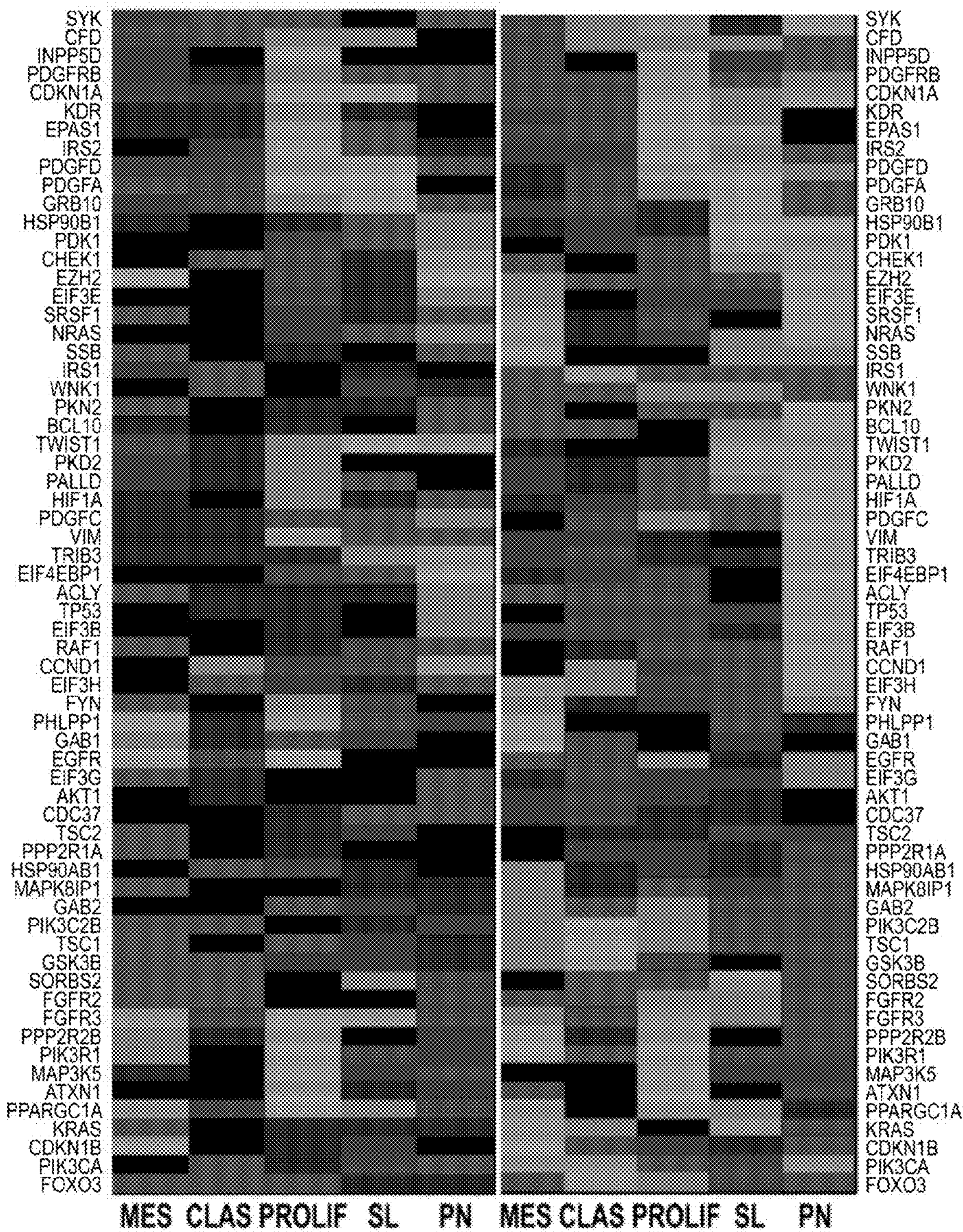

FIG. 10 depicts, in accordance with various embodiments of the invention, average expression of AKT pathway genes in subgroups. Hierarchical clustering using AKT pathway genes was used to group GBM patients and genes in the discovery (GBM 195) dataset. Tumors in the validation dataset were grouped by AKT class keeping the same order of genes. The expression of AKT pathway genes in each class was averaged and is shown as a heatmap; red and green respectively represent high/increased and low/decreased average expression relative to the median of all tumors. Black represents minimal expression difference relative to the median of all tumors. The status of increased expression, decreased expression, or expression not changed significantly (minimal expression difference) of AKT pathway genes are also listed in Table 6.

Figure 11:
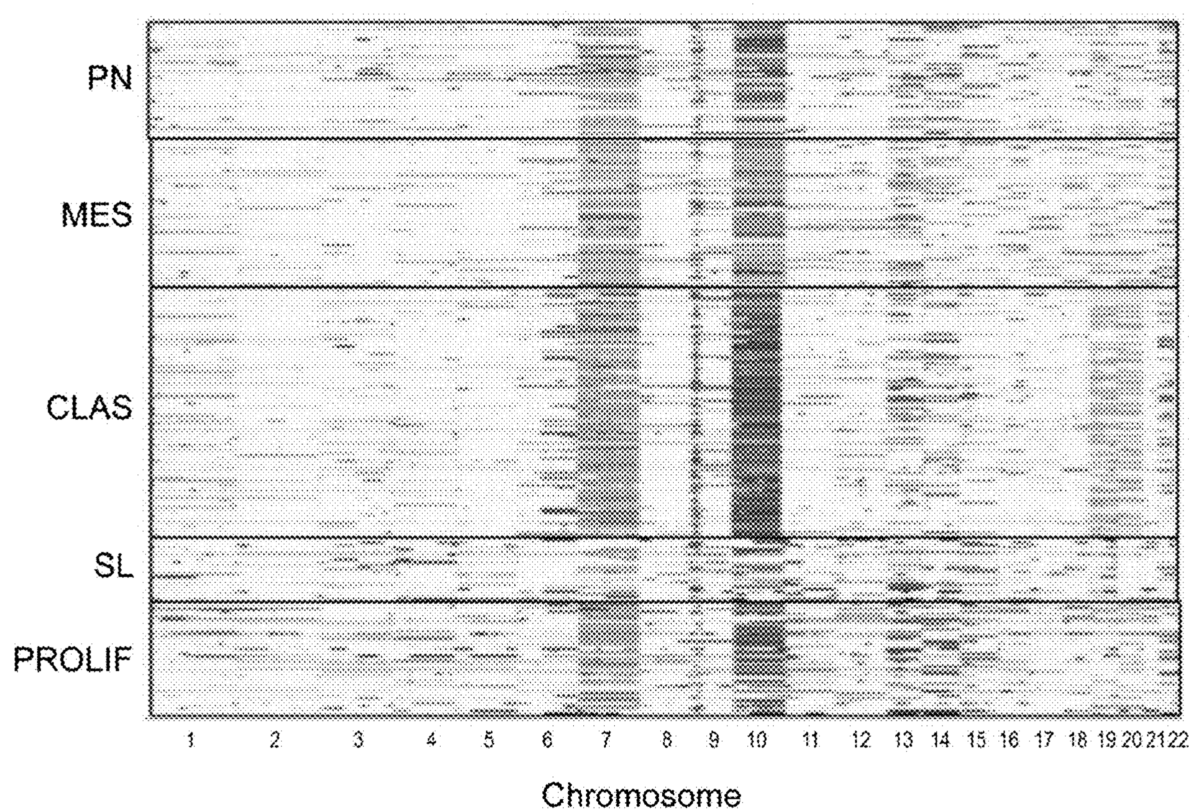

FIG. 11 depicts, in accordance with various embodiments of the invention, Log 2 (tumor/normal) DNA copy number in subgroups. Amplifications (red) and deletions (blue) in subgroups (y axis) were determined by segmentation analysis of normalized signal intensities from TCGA SNP arrays using GISTIC and viewed with IGV by chromosomal location (x axis).

FIGS. 12A-12B depict, in accordance with various embodiments of the invention, distribution of clinical and molecular information by subgroup in the discovery dataset (GBM195). The table lists the number of tumors with the specified feature in each subgroup in the discovery dataset. Features with statistically significant enrichment in a subgroup after Bonferroni correction ($p<0.05$) are highlighted.

FIGS. 13A-13B depict, in accordance with various embodiments of the invention, distribution of clinical and molecular information by subgroup in the validation dataset (TCGA). The table lists the number of tumors with the specified feature in each subgroup in the validation dataset. Features with statistically significant enrichment in a subgroup after Bonferroni correction ($p<0.05$) are highlighted in dark grey. Features with statistically significant enrichment in a subgroup before Bonferroni correction are highlighted in light grey.

FIG. 14 depicts, in accordance with various embodiments of the invention, focal DNA amplifications in subgroups. Copy number alterations in subgroups were evaluated using GISTIC and the q score for statistically significant focal DNA copy number gains (q score<0.25) listed. Focal copy number changes common to all subgroups ($q<0.25$ in all subgroups) are not reported.

FIG. 15 depicts, in accordance with various embodiments of the invention, focal DNA deletions in subgroups. Copy number alterations in subgroups were evaluated using GISTIC and the q score for statistically significant focal DNA copy number losses (q score<0.25) are listed. Focal copy number changes common to all subgroups ($q<0.25$ in all subgroups) are not reported.

FIGS. 16A-16B depict, in accordance with various embodiments of the invention, median expression values of AKT pathway genes in each AKT cancer subgroup in the discovery dataset corresponding to the heatmap in FIG. 10.

Figure 17:
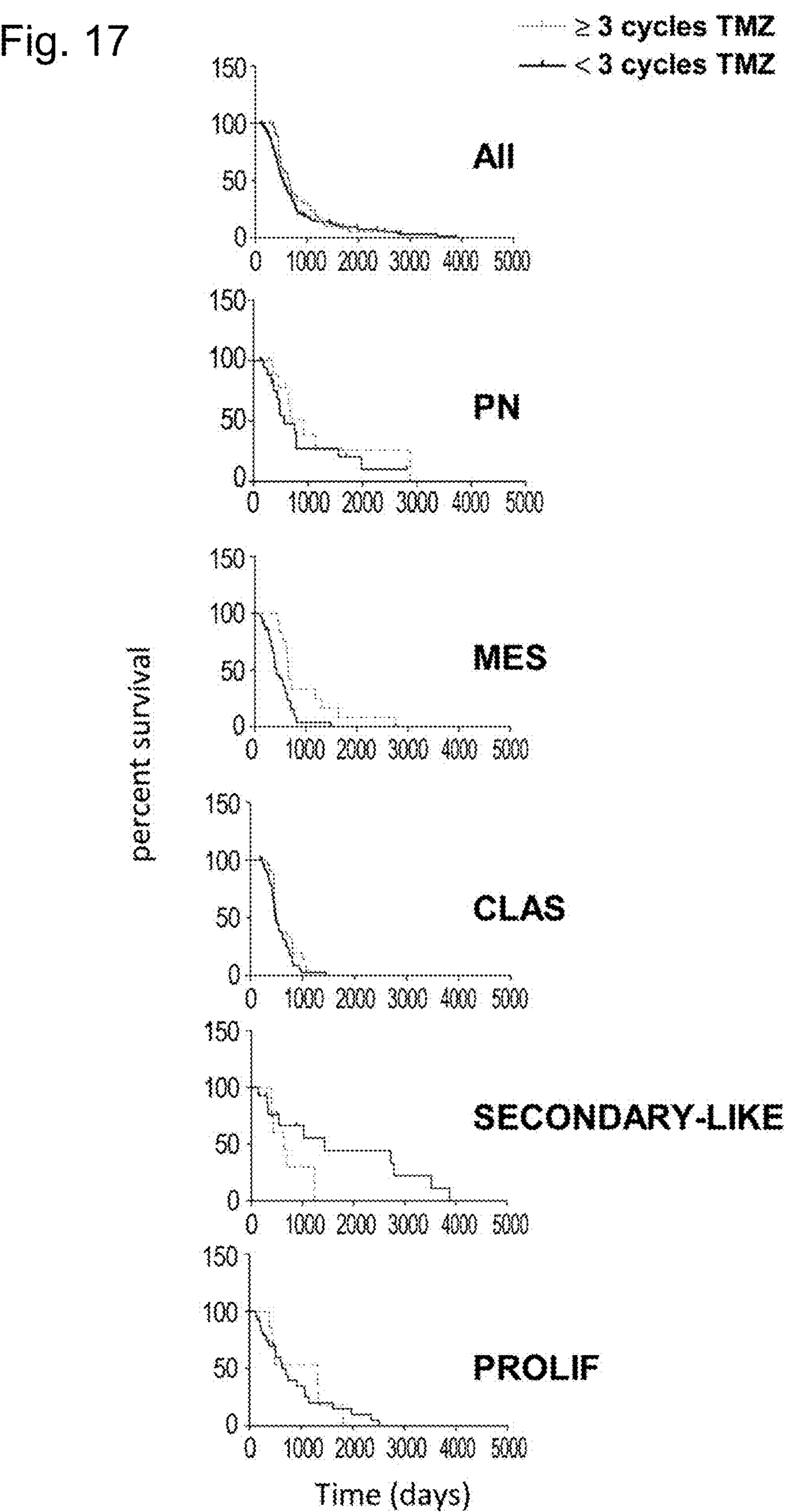

FIG. 17 depicts, in accordance with various embodiments of the invention, evidence that Mesenchymal patients benefit from temozolomide. Kaplan Meier survival curves were plotted within each subgroup for TCGA patients receiving more (≥3 cycles; red) vs. less (<3 cycles; black) temozolomide. Only Mesenchymal patients had a statistically significant difference in survival between treatment arms. Median survival was 0.6 years greater for Mesenchymal patients treated with more temozolomide (1.8 years) vs. less temozolomide (1.2 years); p=0.01 log rank; not age adjusted.

Figure 18A:
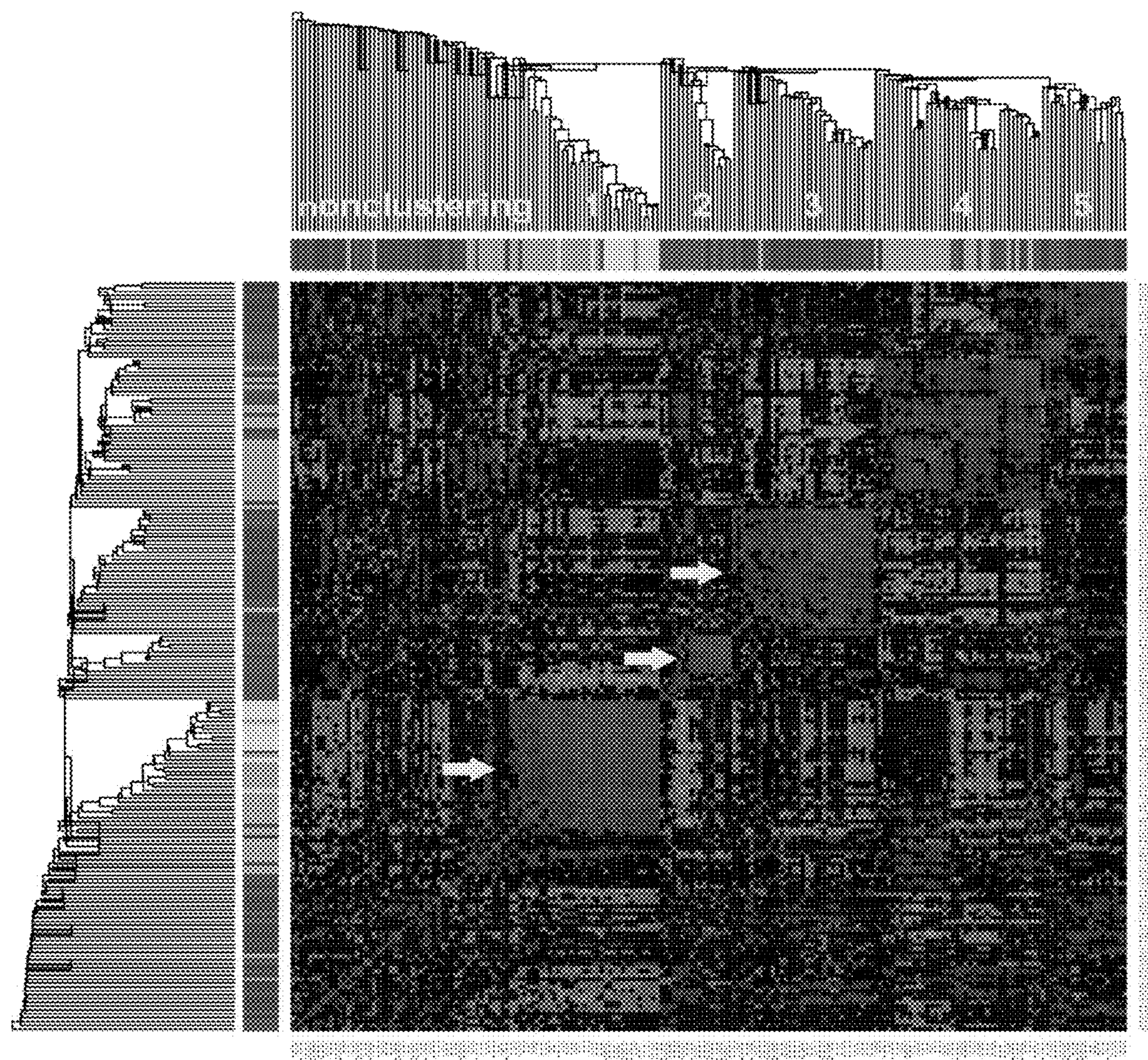
Figure 18B:
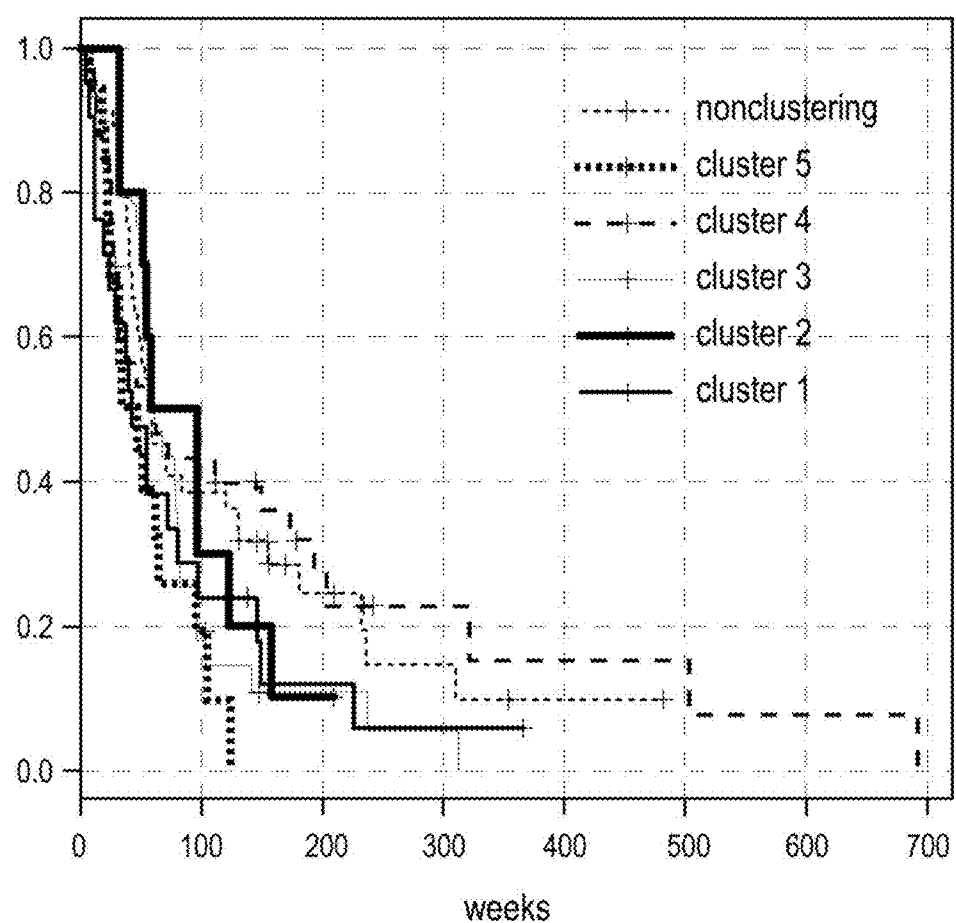
Figure 18C:
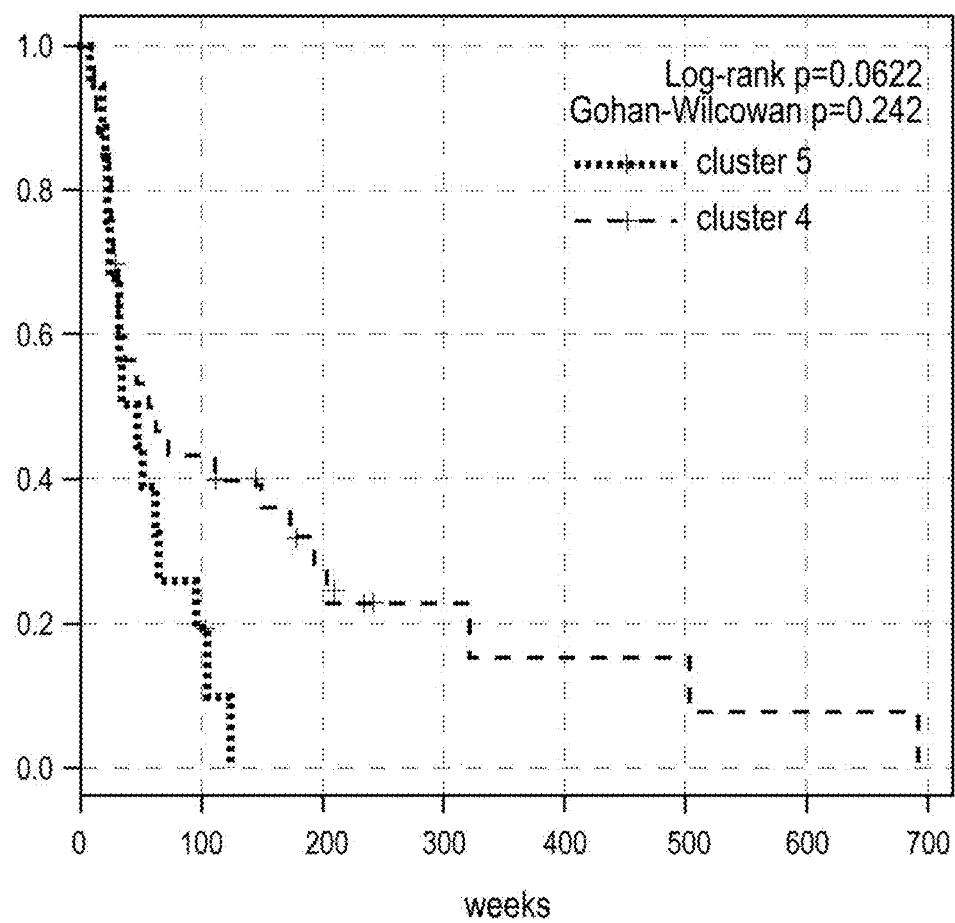
Figure 19A:
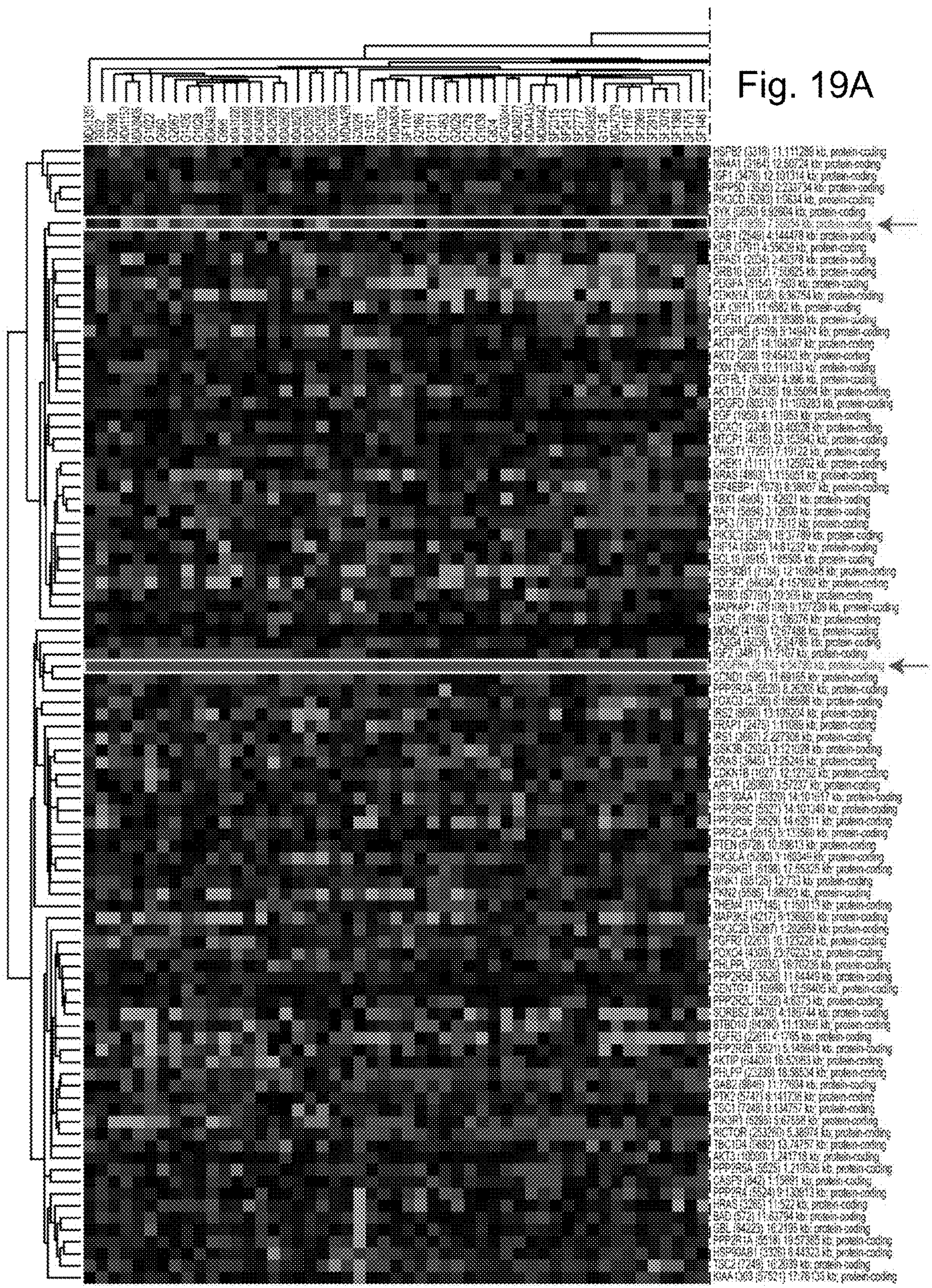
Figure 19B:
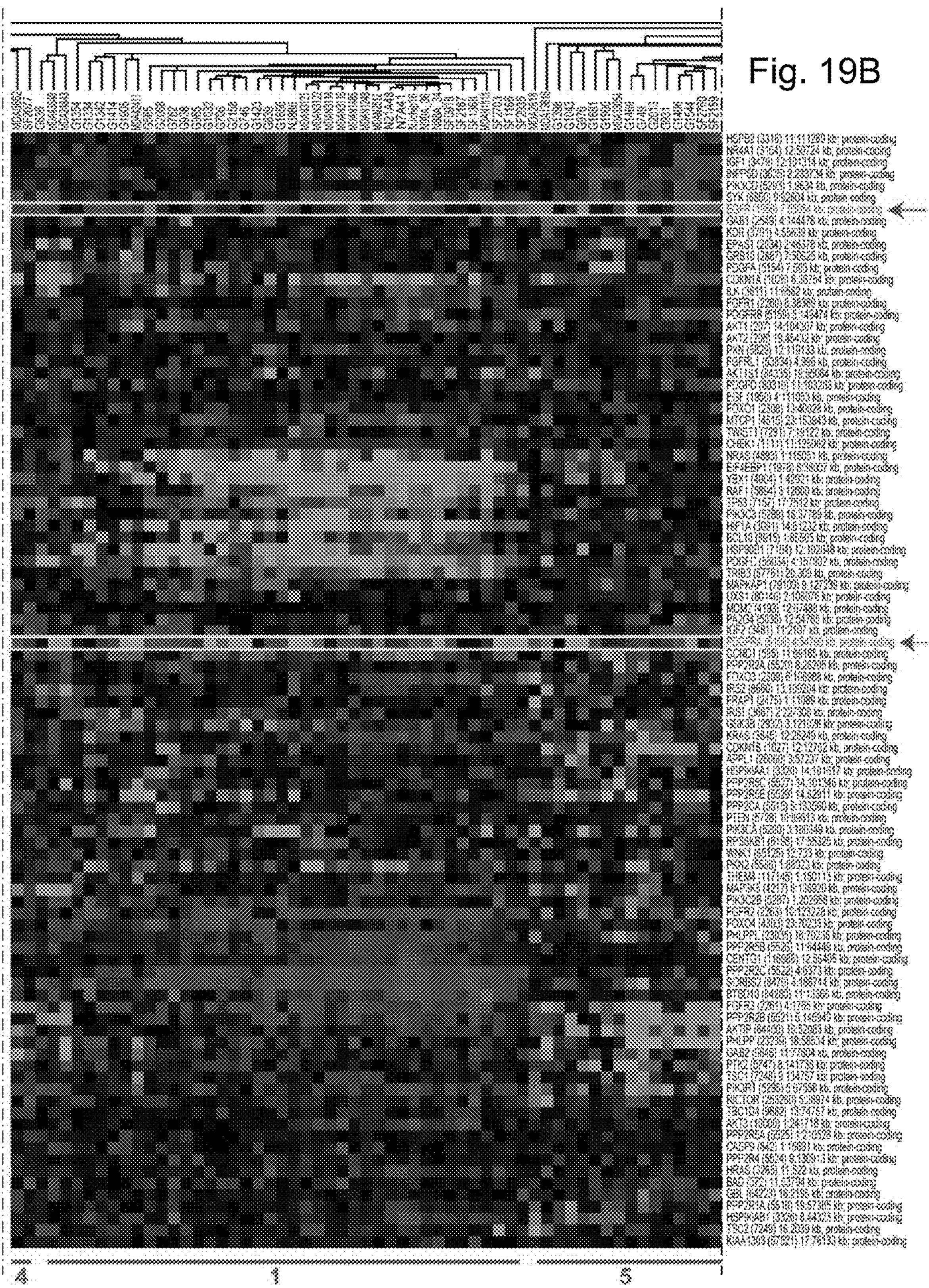
Figure 19C:
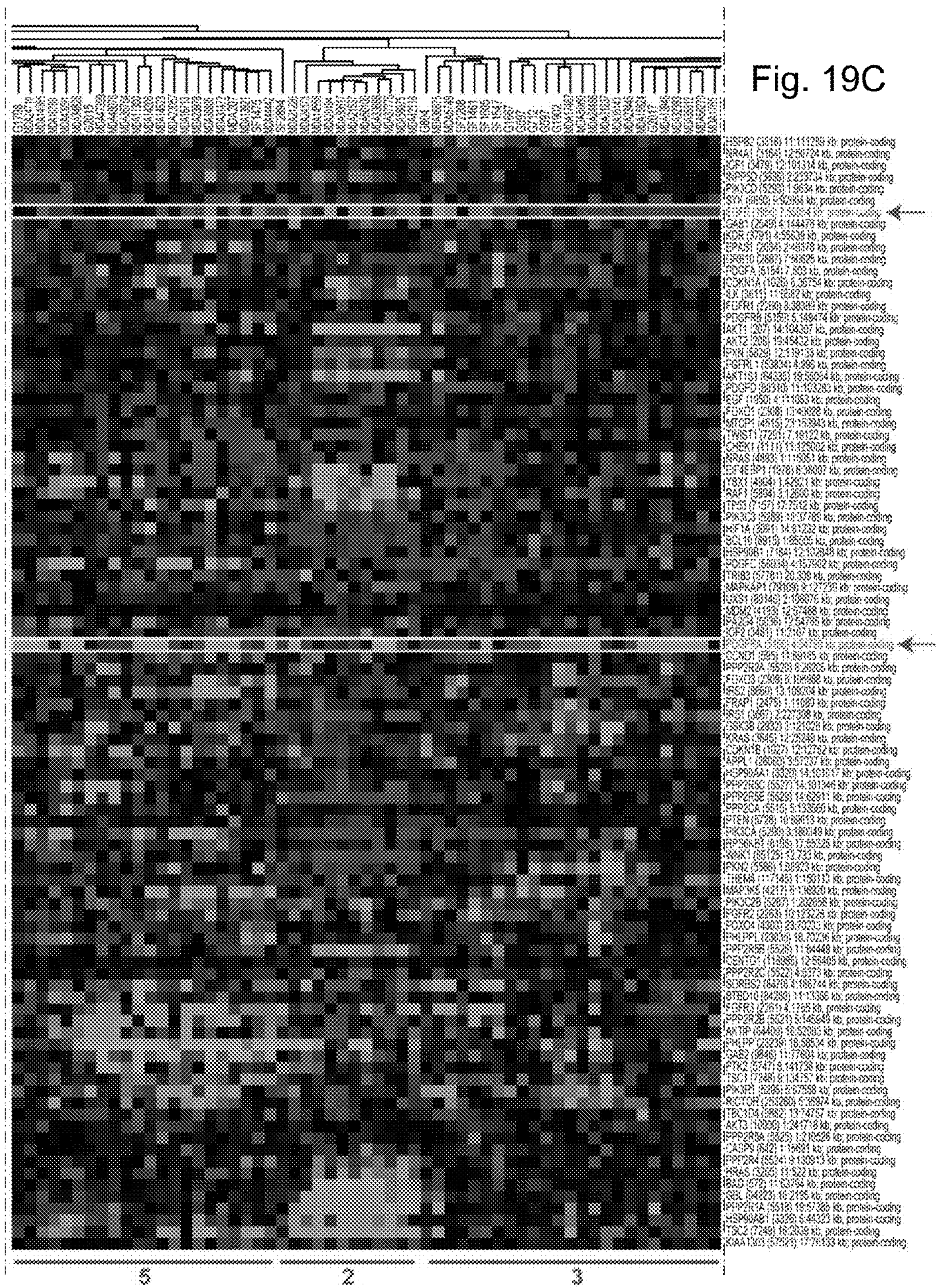

FIGS. 18A-18C depict, in accordance with an embodiment herein, a plot of correlations between clustered samples. (FIG. 18A) Expression profiling of 14 non-neoplastic autopsy specimens from donors with no history of brain tumor or neurological disorder and 181 HGG was performed using Affymetrix U133A and U133B chips on tumors collected at UCSF, MDA, and UCLA (GSE4271 and GSE4412). A sample correlation cluster map was generated using a hand curated list of Aid pathway genes. (FIG. 18B) Kaplan Meier curves for tumors in clusters 1 through 5 and non-clustering tumors. (FIG. 18C) Differences in Kaplan Meier survival curves for patients in subgroups 4 and 5 approach significance; p=0.06 (log rank). Results: There are 5 subgroups of HGG patients that have different expression of Akt pathway genes and different survival curves. There are 3 well defined clusters of tumors (yellow arrows), 2 less defined clusters (pink arrows), and a group of genes (lower left) that are not part of well-defined clusters (cluster 0).

FIGS. 19A-19D depict, in accordance with an embodiment herein, GBM tumors cluster into distinct subtypes based on expression of PI3K/Akt pathway genes. Expression profiling was as described in FIGS. 18A-18C herein. Two way unsupervised hierarchical clustering was performed using Pearson/centroid metric/linkages for PI3K/Akt pathway genes in all tumors and non-neoplastic brain. Cluster numbers 1-5 (labeled at the bottom) contain tumors identified from the plot of correlations between clustered samples shown in FIGS. 18A-18C. Results: PDGFRα is overexpressed in subgroup 4 and EGFR in subgroup 3, among other results.

Figure 20A:
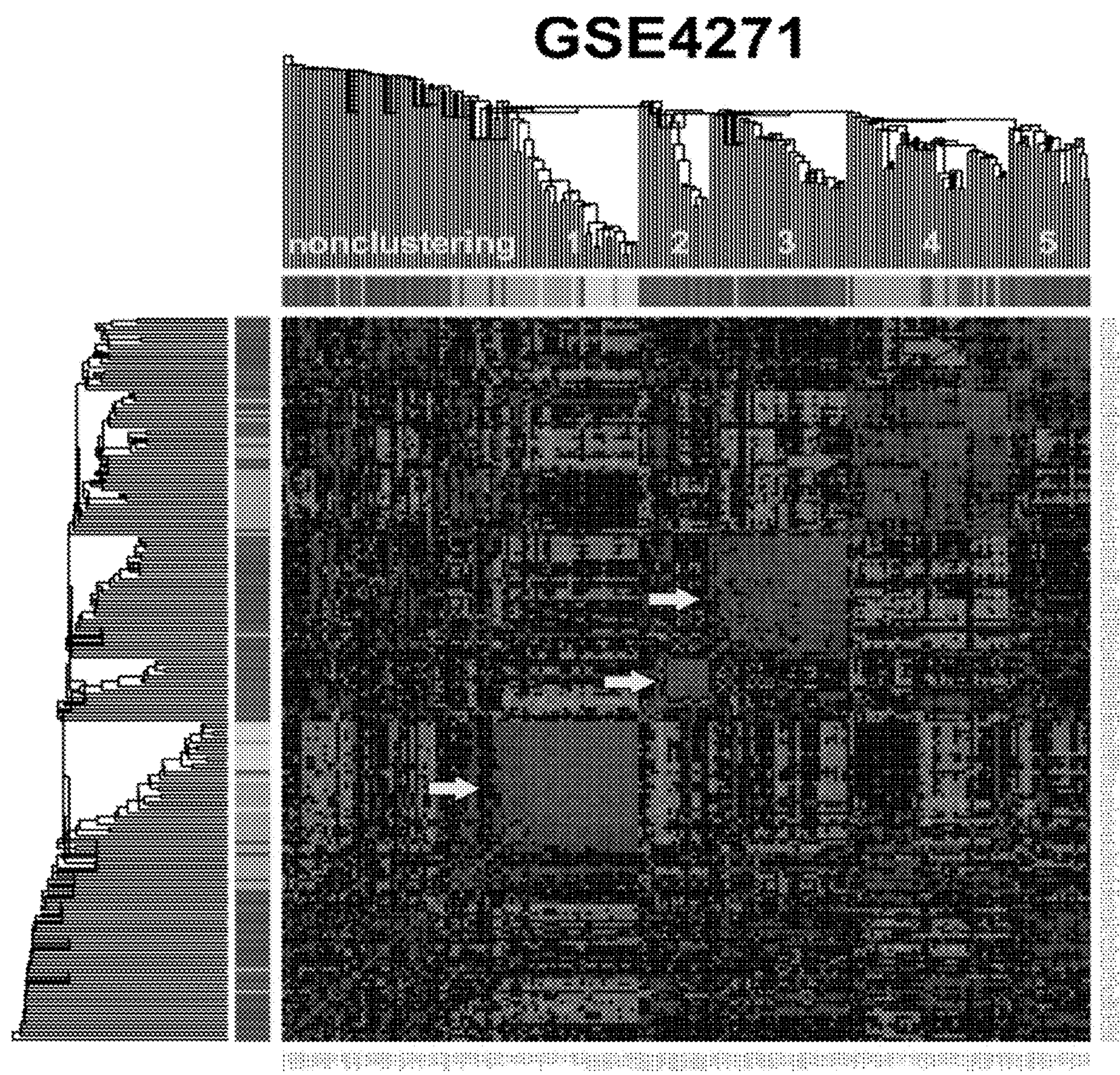
Figure 20C:
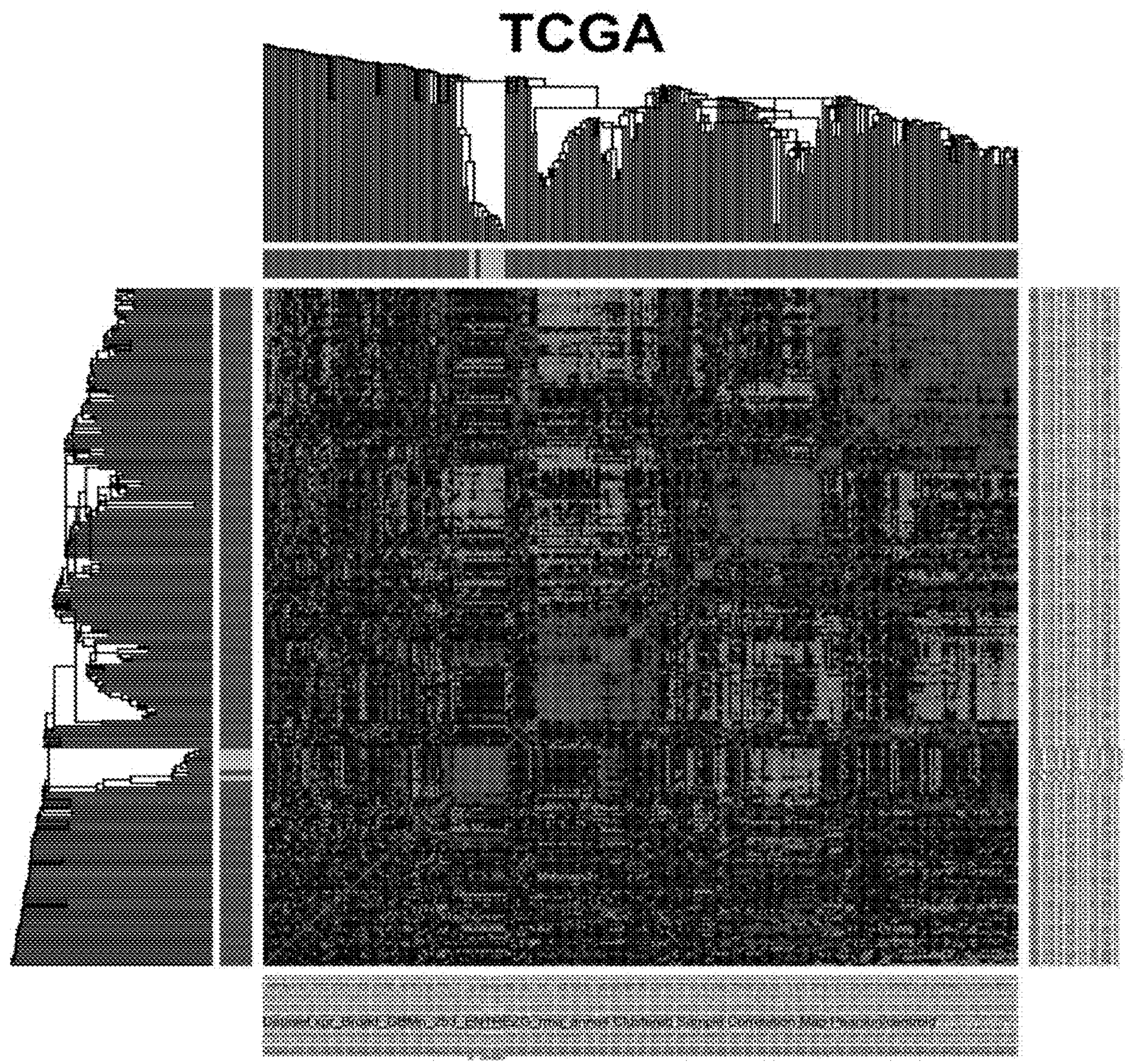

FIGS. 20A-20D depict, in accordance with an embodiment herein, Akt subgroups in GBM. Correlation map generated using Akt pathway genes and GSE4271 (expression profiling results from 171 WHO grade IV astrocytoma and 14 non-neoplastic controls from autopsy). Map generated with a custom program implemented in R (FIGS. 20A-20B). Similar results were obtained using the TCGA dataset (FIGS. 20B-20C). Kaplan Meyer curves are plotted for patient subgroups. Results: There are 5 patient subgroups that have different patterns of Akt pathway gene expression. Differences in survival for patients in clusters 4 and 5 in FIGS. 20A-20B approached significance p=0.06 (log rank).

Figure 21:
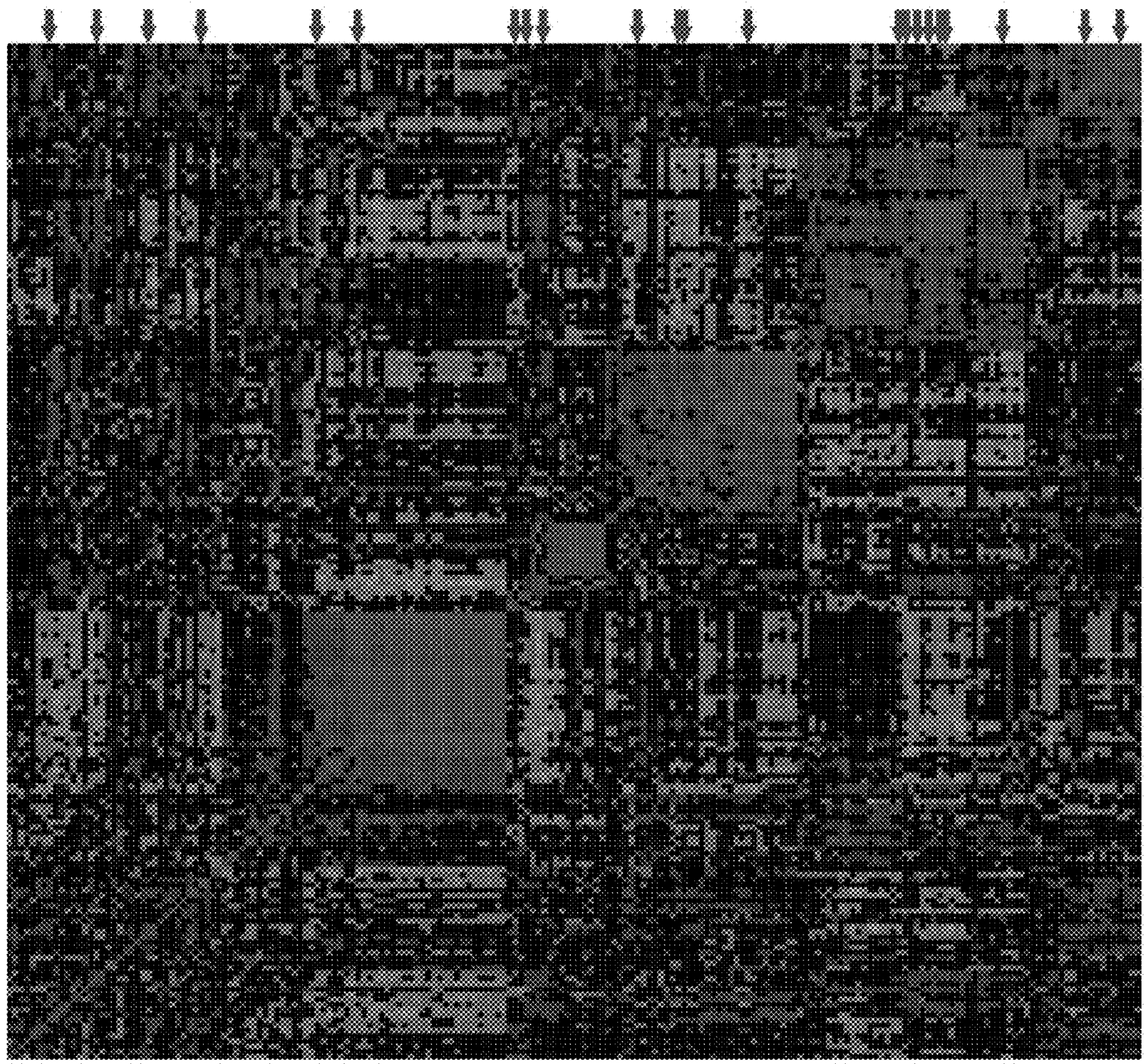

FIG. 21 depicts, in accordance with an embodiment herein, recurrent tumors fall in subgroups 0, 3, 4 and 5. Recurrent tumors in the correlation plot from FIG. 20A are marked with arrows.

Figure 22A:
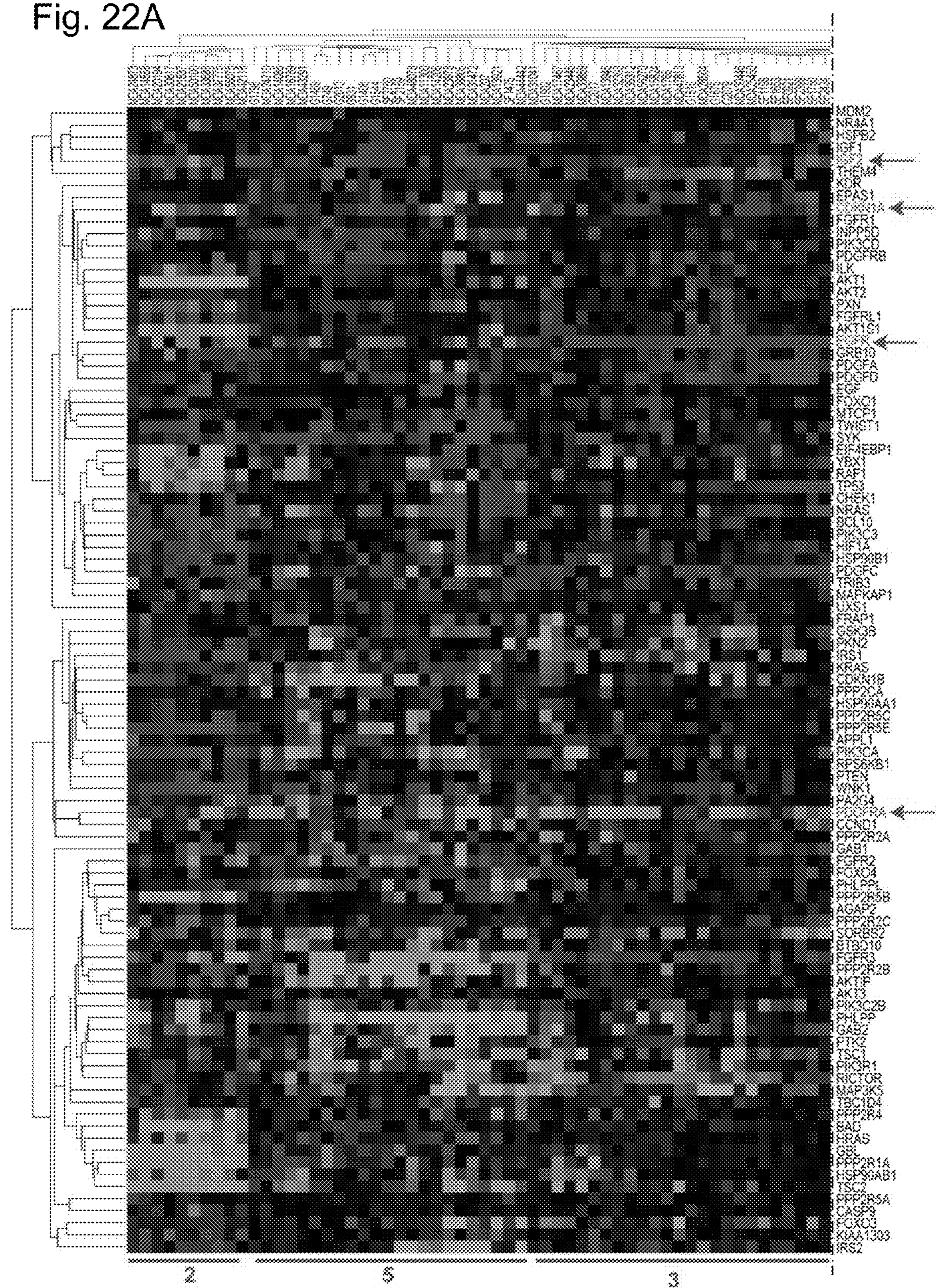
Figure 22C:
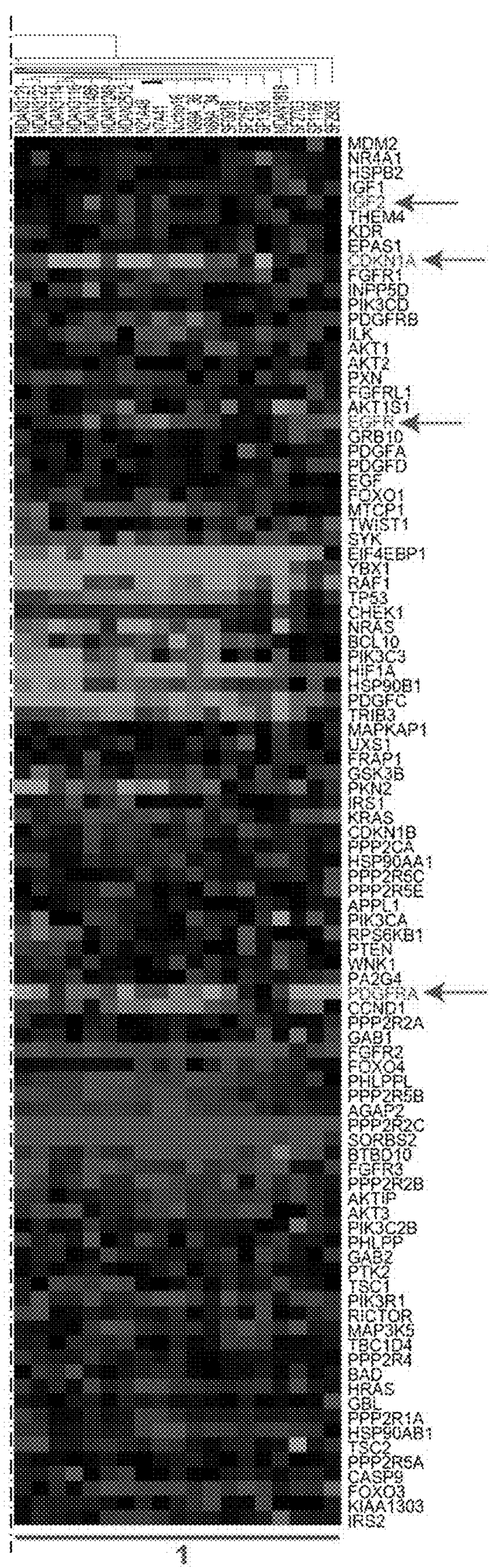

FIGS. 22A-22C depict distribution of Akt pathway genes in subgroups. Two-way unsupervised hierarchical clustering was performed using Pearson/Centroid metric/linkages for Akt pathway genes in GSE4271 with non-clustering tumors removed. Tumors in clusters 1-5 correspond to clusters in FIGS. 20A-20D.

Figure 23:
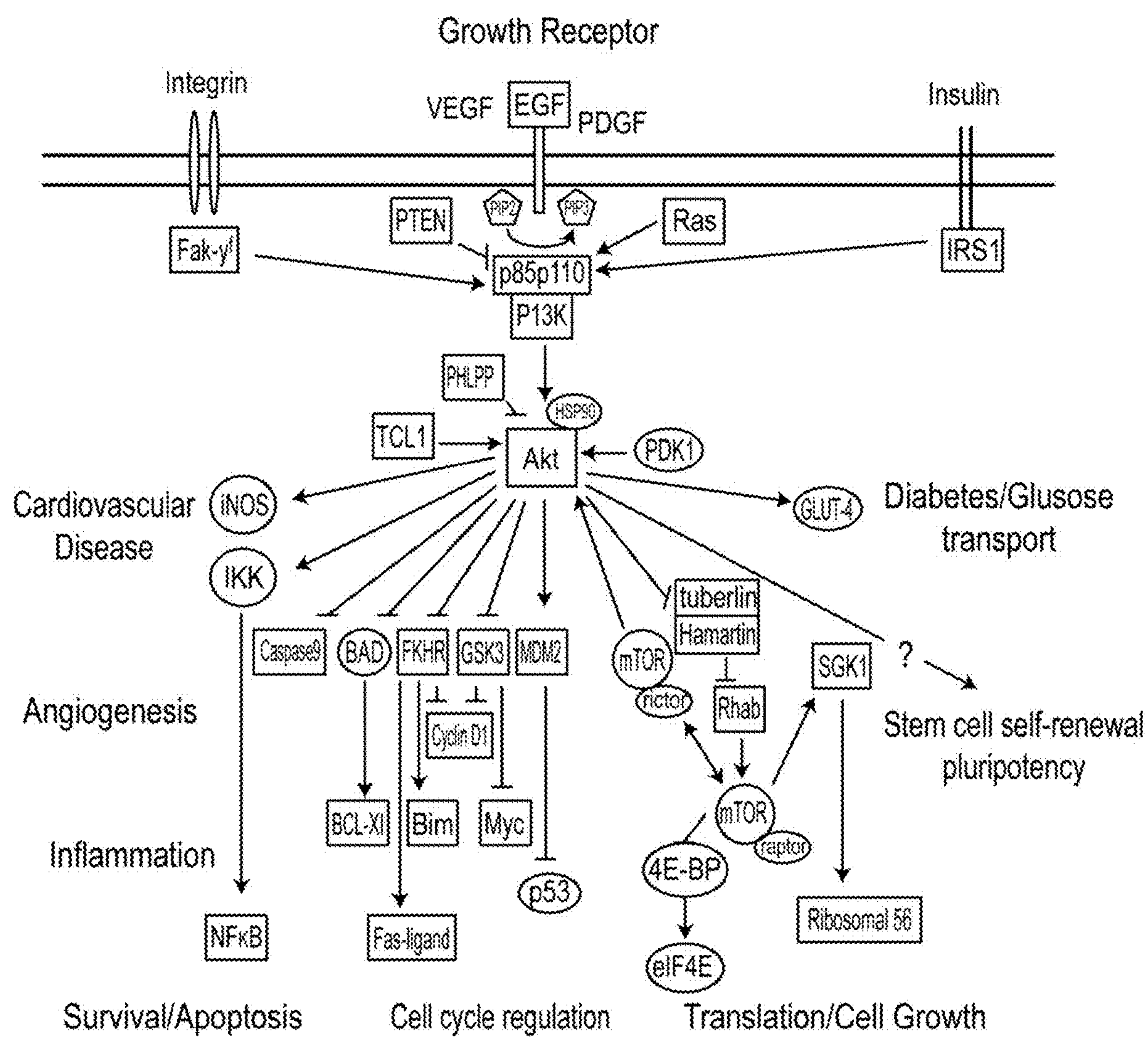

FIG. 23 (prior art) depicts a schematic representation of the Akt pathway.

Figure 24A:
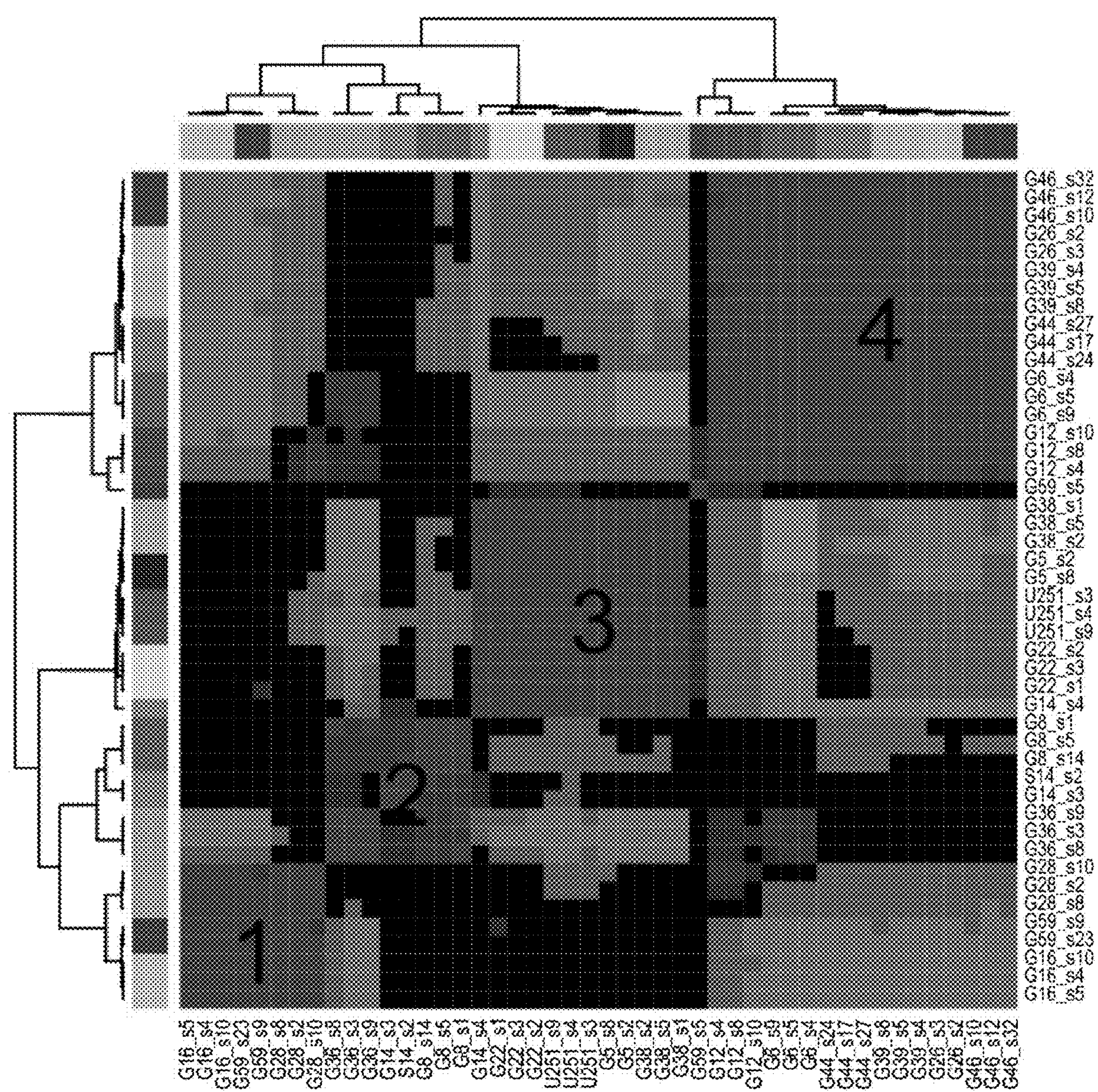

FIGS. 24A-24B depict, in accordance with an embodiment herein, human-rodent xenograft models of Akt subgroups associated with TMZ sensitivity. The inventors analyzed replicates of 15 xenografts and 1 human cell line for Akt classes. Mean survival for placebo, temodar (TMZ), radiation (RT) or concurrent TMZ+RT treated mice in each subgroup (FIG. 24B). Significance determined with a 2-sample, 2-sided t test assuming unequal variance. Intracranial xenografts are prepared from flank passaged GBM tissue.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: *The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a tumor, delay or slowing of a tumor, and amelioration or palliation of symptoms associated with a tumor.

"Disorders", "diseases", "conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. Examples of cancer include, but are not limited to, nervous system tumor, nerve sheath tumor, and brain tumor or cancer. Examples of brain tumor include, but are not limited to, benign brain tumor, malignant brain tumor, primary brain tumor, secondary brain tumor, metastatic brain tumor, glioma, glioblastoma, glioblastoma multiforme (GBM), medulloblastoma, ependymoma, astrocytoma, pilocytic astrocytoma, oligodendroglioma, brainstem glioma, optic nerve glioma, mixed glioma such as oligoastrocytoma, low-grade glioma, high-grade glioma, supratentorial glioma, infratentorial glioma, pontine glioma, meningioma, pituitary adenoma, and nerve sheath tumor. Nervous system tumor or nervous system neoplasm refers to any tumor affecting the nervous system. A nervous system tumor can be a tumor in the central nervous system (CNS), in the peripheral nervous system (PNS), or in both CNS and PNS. Examples of nervous system tumor include but are not limited to brain tumor, nerve sheath tumor, and optic nerve glioma.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a tumor sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or preprocessed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., GBM) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

As used herein, "variants" can include, but are not limited to, those that include conservative amino acid mutations, SNP variants, splicing variants, degenerate variants, and biologically active portions of a gene. A "degenerate variant" as used herein refers to a variant that has a mutated nucleotide sequence, but still encodes the same polypeptide due to the redundancy of the genetic code.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, the term "alkylating agents" refers to compounds and molecules used in cancer treatment that attach an alkyl group ($C_nH_{2n}$+1) to DNA. Examples of alkylating agents include but are not limited to nitrogen mustards such as cyclophosphamide, mechlorethamine or mustine (HN2), uramustine or uracil mustard, melphalan, chlorambucil, ifosfamide, and bendamustine; nitrosoureas such as carmustine (BCNU), lomustine (CCNU), and streptozocinm; alkyl sulfonates such busulfan; thiotepa; and temozolomide; and these alkylating agents' analogs, derivative, and salts.

As used herein, the term "PI3K/AKT/mTOR inhibitor" (also interchangeably called as PI3K/AKT/mTOR blocker, anti-PI3K/AKT/mTOR reagent, agent, drug or therapeutic,) refers to any reagent that inhibits the PI3K/AKT/mTOR signaling, including inhibition of any molecular signaling steps upstream or downstream of PI3K/AKT/mTOR. A PI3K/AKT/mTOR inhibitor can be a small molecule; a nucleic acid such as siRNA, shRNA, and miRNA; a nucleic acid analogue such as PNA, pc-PNA, and LNA; an aptamer; a ribosome; a peptide; a protein; an avimer; an antibody, or variants and fragments thereof. Examples of the PI3K/AKT/mTOR inhibitor include but are not limited to wortmannin, demethoxyviridin, LY294002, perifosine, idelalisib, PX-866, IPI-145, BAY 80-6946, BEZ235, RP6530, TGR 1202, SF1126, INK1117, GDC-0941, BKM120, XL147 (also known as SAR245408), XL765 (also known as SAR245409), Palomid, GSK1059615, ZSTK474, PWT33597, IC87114, TG100-115, CAL263, RP6503, PI-103, GNE-477, CUDC-907, and AEZS-136; VQD-002, miltefosine, and AZD5363; rapamycin, temsirolimus, everolimus, ridaforolimus, epigallocatechin gallate (EGCG), caffeine, curcumin, and resveratrol.

As used herein, the term "IDH" means isocitrate dehydrogenase. SEQ ID NO:1 sets forth one non-limiting example of an IDH1 gene sequence. As further disclosed herein, to characterize subgroups, the inventors found the distribution for alterations in glioma-associated genes in subgroups. It was found that subgroup 5 was enriched in tumors with IDH mutations. For example, IDH mutations in glioma may be found at arginine 132 (R132) residue of isocitrate dehydrogenase I (IDH1) or the R172 residue of IDH2. SEQ ID NO:2 sets forth one non-limiting example of an IDH1 sequence, that is, the cDNA sequence of one variant of IDH1. SEQ ID NO:3 sets forth another non-limiting example of an IDH1 sequence, that is, the cDNA sequence of another variant of IDH1. SEQ ID NO:4 sets forth one non-limiting example of an IDH2 gene sequence.

For cancers such as GBM, many ineffective therapies can result from classifying the disease too generally. However, variations in natural history and therapeutic response, as well as molecular profiling, suggest that there could be molecular subtypes beyond the standard classifications. The ramifications are not insignificant. For example, the failure to classify GBM subtypes can affect patient treatment, drug development and clinical trials. Clinical trials that do not stratify for subgroups are underpowered and could miss subtype-specific drugs. Furthermore, unstratified patients may bear extra expense and toxicity. Targets within a subgroup might be missed if GBM are considered as a whole. The PI3K/Akt pathway is one of the 3 core pathways consistently altered in GBM. It often leads to activation of Akt. Akt is an oncogenic serine/threonine kinase that regulates metabolism, survival, autophagy, proliferation, migration, epithelial to mesenchymal (EMT) transition and angiogenesis. The pathway is a large and complex with many regulators, activators, effectors and feedback loops.

As disclosed herein, the inventors investigated PI3K/Akt/mTOR signaling variations in Akt subgroups, providing therapeutic alternatives for glioblastoma. The GFR/PI3K/Akt pathway is an important therapeutic target in glioblastoma (GB), but in the past, response to pathway inhibitors in clinical trials has been lackluster. The inventors examined whether AKT pathway variations contribute to poor response, and classified GBM based on AKT pathway genes. There were at least 5 GBM AKT subgroups. They were concordant with other found subgroups but subdivided them further to give new groups with distinct features. AKT subgroups had different molecular alterations and median survival. Importantly, the results demonstrated that there is a subset of GB patients sensitive to alkylating agent, and AKT classification can identify them. Akt classification also identified two subgroups enriched in IDH1 mutations with different clinical courses and molecular alterations. To characterize subgroups, the inventor found the distribution for alterations in glioma-associated genes in subgroups, and found subgroup 5 was enriched in tumors with IDH1 mutations. These data suggest AKT classification is a biomarker for sensitivity to alkylating agents and PI3K/AKT pathway inhibitors. The results advance molecular classification of GB and can be used to stratify patients for clinical trials and enhance discovery of class-specific therapeutic targets.

As further disclosed herein, it was found that there was a statistically significant enrichment of IDH1 mutations in the AKT subgroup 5 cluster. Many IDH mutations in glioma are found at arginine 132 (R132) residue of isocitrate dehydrogenase I (IDH1) or the R172 residue of IDH2. There was also evidence found that the AKT subgroup 5 patients as described herein were particularly sensitive to alkylating agents.

In another embodiment, the present invention provides a method of diagnosing a cancer subtype in a subject comprising obtaining a sample from the subject, assaying the sample to determine an AKT expression profile, and diagnosing the cancer subtype based on the AKT expression profile. In another embodiment, the cancer is GBM. In another embodiment, the subject is human. In another embodiment, the subtype is characterized by a cluster defined by the distribution of alterations in glioma associated genes. In one embodiment, the AKT expression profile is defined by a cluster of distribution of alterations in glioma associated genes in the AKT signaling pathway. In one embodiment, wherein the AKT expression profile is made up of one or more genetic loci listed in Table 2, Table 4, Table 5, or Table 6. In one embodiment, the cancer subtype is a cancer subtype of GBM. In one embodiment, the cancer subtype includes the presence of tumors enriched with one or more IDH1 and/or IDH2 mutations.

In one embodiment, the present invention provides a method of diagnosing a cancer subtype in a subject comprising obtaining a sample from the subject, assaying the sample to determine the presence or absence of IDH1 and/or IDH2 mutations, and diagnosing the cancer subtype based on the presence of IDH1 and/or IDH2 mutations. In another embodiment, the cancer is GBM. In one embodiment, the individual is a human. In another embodiment, the presence of one or more IDH1 and/or IDH2 mutations relative to a normal individual is indicative of the cancer subtype AKT subgroup 5.

In another embodiment, the present invention provides a method of prognosing GBM disease by diagnosing a GBM disease subtype based on the AKT expression profile, and determining the severity of the disease based on the GBM disease subtype.

In one embodiment, the present invention provides for a method of treating a subject for cancer comprising obtaining a sample from the subject, assaying the sample to determine a cancer subtype based on what is the AKT expression profile, and treating the subject. In another embodiment, the cancer is GBM. In another embodiment, the subject is human. In another embodiment, the subtype is characterized by a cluster defined by the distribution of alterations in glioma associated genes. In another embodiment, the treatment comprises administering a therapeutically effective dosage of a composition comprising one or more alkylating agents to the individual. In another embodiment, the treatment comprises administering a therapeutically effective dosage of a composition comprising one or more PI3K/Akt/mTOR inhibitors to the individual.

In one embodiment, the present invention provides for a method of treating GBM in a subject comprising obtaining a sample from the subject, assaying the sample to diagnose a GBM subtype based on the presence of an AKT expression profile, and treating the subject. In some embodiments, the AKT subgroup includes the presence of one or more IDH1 and/or IDH2 mutations. In another embodiment, the present invention provides a method of treating an individual for cancer by obtaining a sample from the individual, assaying the sample to determine the presence of one or more IDH1 and/or IDH2 mutations, and treating the individual. In another embodiment, treating the individual comprises administration of a therapeutically effective dosage of a composition comprising one or more alkylating agents to the individual.

In various embodiments, the one or more IDH1 mutations include mutation of arginine 132 (R132) residue of isocitrate dehydrogenase I (IDH1). In various embodiments, the one or more IDH2 mutations include the mutation of arginine 172 (R172) residue of IDH2. In various embodiments, assaying the sample includes determining the presence of a GBM tumor enriched with one or more IDH1 and/or IDH2 mutations.

Activity of GFR/PI3K/AKT pathway inhibitors in glioblastoma clinical trials has not been robust. While not wishing to be bound by any theory, the inventors believe that variations in the pathway between tumors contribute to poor response. The inventors clustered GBM based on AKT pathway genes and discovered new subtypes then characterized their clinical and molecular features. There are at least 5 GBM AKT subtypes having distinct DNA copy number alterations, enrichment in oncogenes and tumor suppressor genes and patterns of expression for PI3K/AKT/mTOR signaling components. Gene Ontology terms indicate a different cell of origin or dominant phenotype for each subgroup. Evidence suggests one subtype is very sensitive to BCNU or CCNU (median survival 5.8 vs. 1.5 years; BCNU/CCNU vs other treatments; respectively). AKT subtyping advances previous approaches by revealing additional subgroups with unique clinical and molecular features. Evidence indicates it is a predictive marker for response to BCNU or CCNU and PI3K/AKT/mTOR pathway inhibitors. The inventors demonstrate that Akt subtyping helps stratify patients for clinical trials and augments discovery of class-specific therapeutic targets.

Classification and Diagnosis Methods

In various embodiments, the present invention provides a method for categorizing/classifying/stratifying a subject with a cancer into a subgroup. The method may consist of, or may consist essentially of, or may comprise: obtaining a sample from the subject; assaying the sample to detect increases and/or decreases in expression levels of AKT pathway components relative to reference samples or values; detecting the subgroup's expression pattern of AKT pathway components in the sample based on the detected increases and/or decreases; and categorizing/classifying/stratifying the subject having the subgroup's expression pattern of AKT pathway components into the subgroup. In various embodiments, the AKT pathway components comprise one, two, three, four, five, six, or more, or all genes listed Table 2, and/or Table 4, and/or Table 5, and/or Table 6.

In various embodiments, the subgroup is C1, PN, MES, CLAS, SL, or PROLIF. In various embodiments, categorizing/classifying/stratifying comprises categorizing/classifying/stratifying the subject having subgroup C1's expression pattern of AKT pathway components into subgroup C1, the subject having subgroup PN's expression pattern of AKT pathway components into subgroup PN, the subject having subgroup MES's expression pattern of AKT pathway components into subgroup MES, the subject having subgroup CLAS's expression pattern of AKT pathway components into subgroup CLAS, the subject having subgroup SL's expression pattern of AKT pathway components into subgroup SL, or the subject having subgroup PROLIF's expression pattern of AKT pathway components into subgroup PROLIF.

FIGS. 6A-6B, 7A-7B, 10 and 16A-B illustrate non-limiting examples of subgroup C1's expression pattern of AKT pathway components, subgroup PN's expression pattern of AKT pathway components, subgroup MES's expression pattern of AKT pathway components, subgroup CLAS's expression pattern of AKT pathway components, subgroup SL's expression pattern of AKT pathway components, and subgroup PROLIF's expression pattern of AKT pathway components.

In some embodiments, in FIGS. 16A-16B, values not less than 0.05 may be considered as increased expression; values not more than −0.05 may be considered as decreased expression; and values between 0.05 and −0.05 may be considered as insignificantly changed expression.

For non-limiting examples, subgroup C1's expression pattern of AKT pathway components may comprise increased expression levels in one or more of ATXN1, BCL10, CDKN1B, CFD, CHEK1, EIF3E, EIF3H, EPAS1, EZH2, FOXO3, HIF1A, HSP90B1, IRS1, IRS2, KRAS, MAP3K5, NRAS, PALLD, PDGFA, PDGFC, PDGFD, PDK1, PIK3CA, PIK3R1, PKD2, PKN2, PPARGC1A, PPP2R2B, SRSF1, SSB, SYK, TWIST1, and WNK1; and/or insignificantly changed expression levels in one or more of CCND1, CDKN1A, KDR, TRIB3, and VIM; and/or decreased expression levels in one or more of ACLY, AKT1, CDC37, EGFR, EIF3B, EIF3G, EIF4EBP1, FGFR2, FGFR3, FYN, GAB1, GAB2, GRB10, GSK3B, HSP90AB1, INPP5D, MAPK8IP1, PDGFRB, PHLPP1, PIK3C2B, PPP2R1A, RAFT, SORBS2, TP53, TSC1, and TSC2.

For non-limiting examples, subgroup PN's expression pattern of AKT pathway components may comprise increased expression levels in one or more of ATXN1, FGFR2, FGFR3, GAB2, GSK3B, HSP90AB1, IRS1, KRAS, MAP3K5, MAPK8IP1, PHLPP1, PIK3C2B, PIK3R1, PPARGC1A, PPP2R1A, PPP2R2B, SORBS2, TSC1, and TSC2; and/or insignificantly changed expression levels in one or more of CDKN1B, CFD, EPAS1, FOXO3, GAB1, KDR, and WNK1; and/or decreased expression levels in one or more of ACLY, AKT1, BCL10, CCND1, CDC37, CDKN1A, CHEK1, EGFR, EIF3B, EIF3E, EIF3G, EIF3H, EIF4EBP1, EZH2, FYN, GRB10, HIF1A, HSP90B1, INPP5D, IRS2, NRAS, PALLD, PDGFA, PDGFC, PDGFD, PDGFRB, PDK1, PIK3CA, PKD2, PKN2, RAF1, SRSF1, SSB, SYK, TP53, TRIB3, TWIST1, and VIM.

For non-limiting examples, subgroup MES's expression pattern of AKT pathway components may comprise increased expression levels in one or more of AKT1, BCL10, CCND1, CDC37, CDKN1A, CFD, EIF3B, EPAS1, GRB10, HIF1A, HSP90B1, INPP5D, IRS1, IRS2, KDR, PALLD, PDGFA, PDGFC, PDGFD, PDGFRB, PDK1, PKD2, SYK, TRIB3, TWIST1, and VIM; and/or insignificantly changed expression levels in one or more of CHEK1, EIF3G, EIF4EBP1, MAP3K5, PKN2, SORBS2, TP53, and WNK1; and/or decreased expression levels in one or more of ACLY, ATXN1, CDKN1B, EGFR, EIF3E, EIF3H, EZH2, FGFR2, FGFR3, FOXO3, FYN, GAB1, GAB2, GSK3B, HSP90AB1, KRAS, MAPK8IP1, NRAS, PHLPP1, PIK3C2B, PIK3CA, PIK3R1, PPARGC1A, PPP2R1A, PPP2R2B, RAF1, SRSF1, SSB, TSC1, and TSC2.

For non-limiting examples, subgroup CLAS's expression pattern of AKT pathway components may comprise increased expression levels in one or more of ACLY, AKT1, CDC37, CDKN1A, CHEK1, EGFR, EIF3B, EIF3E, EIF3G, EIF4EBP1, EPAS1, FGFR3, FYN, GAB1, GRB10, HIF1A, HSP90B1, IRS2, KDR, MAPK8IP1, NRAS, PALLD, PDGFA, PDGFC, PDGFD, PDGFRB, PDK1, PKD2, PKN2, PPARGC1A, PPP2R1A, PPP2R2B, RAF1, SRSF1, SSB, TP53, TRIB3, TWIST1, and VIM; and/or insignificantly changed expression levels in one or more of ATXN1, BCL10, EIF3H, EZH2, HSP90AB1, INPP5D, PIK3R1, and SYK; and/or decreased expression levels in one or more of CCND1, CDKN1B, CFD, FGFR2, FOXO3, GAB2, GSK3B, IRS1, KRAS, MAP3K5, PHLPP1, PIK3C2B, PIK3CA, SORBS2, TSC1, TSC2, and WNK1.

For non-limiting examples, subgroup SL's expression pattern of AKT pathway components may comprise increased expression levels in one or more of ACLY, CCND1, CDKN1B, EGFR, EIF3B, EIF3E, EIF3G, EIF3H, FOXO3, FYN, GAB1, GAB2, INPP5D, IRS1, MAP3K5, MAPK8IP1, PDGFC, PHLPP1, PIK3C2B, PIK3CA, PIK3R1, RAF1, SYK, TP53, TRIB3, TSC1, and TSC2; and/or insignificantly changed expression levels in one or more of ATXN1, CDC37, GSK3B, HSP90AB1, PKN2, PPP2R2B, and SRSF1; and/or decreased expression levels in one or more of AKT1, BCL10, CDKN1A, CFD, CHEK1, EIF4EBP1, EPAS1, EZH2, FGFR2, FGFR3, GRB10, HIF1A, HSP90B1, IRS2, KDR, KRAS, NRAS, PALLD, PDGFA, PDGFD, PDGFRB, PDK1, PKD2, PPARGC1A, PPP2R1A, SORBS2, SSB, TWIST1, VIM, and WNK1.

For non-limiting examples, subgroup PROLIF's expression pattern of AKT pathway components may comprise increased expression levels in one or more of ACLY, AKT1, BCL10, CCND1, CDKN1B, CHEK1, EIF3B, EIF3E, EIF3G, EIF3H, EIF4EBP1, EZH2, FYN, GSK3B, HSP90AB1, HSP90B1, NRAS, PDK1, PIK3CA, PPP2R1A, RAF1, SRSF1, SSB, TP53, TRIB3, TSC2, and TWIST1; and/or insignificantly changed expression levels in one or more of CDC37, GAB1, GRB10, IRS1, KRAS, PHLPP1, PKN2, and VIM; and/or decreased expression levels in one or more of ATXN1, CDKN1A, CFD, EGFR, EPAS1, FGFR2, FGFR3, FOXO3, GAB2, HIF1A, INPP5D, IRS2, KDR, MAP3K5, MAPK8IP1, PALLD, PDGFA, PDGFC, PDGFD, PDGFRB, PIK3C2B, PIK3R1, PKD2, PPARGC1A, PPP2R2B, SORBS2, SYK, TSC1, and WNK1.

In various embodiments, the subgroup is subgroup 0, subgroup 1, subgroup 2, subgroup 3, subgroup 4, or subgroup 5. In various embodiments, categorizing/classifying/stratifying comprises categorizing/classifying/stratifying the subject having subgroup 0's expression pattern of AKT pathway components into subgroup 0, categorizing/classifying/stratifying the subject having subgroup 1's expression pattern of AKT pathway components into subgroup 1, the subject having subgroup 2's expression pattern of AKT pathway components into subgroup 2, the subject having subgroup 3's expression pattern of AKT pathway components into subgroup 3, the subject having subgroup 4's expression pattern of AKT pathway components into subgroup 4, or the subject having subgroup 5's expression pattern of AKT pathway components into subgroup 5. FIGS. 19A-19D and 22A-22C illustrate non-limiting examples of subgroup 0's expression pattern of AKT pathway components, subgroup 1's expression pattern of AKT pathway components, subgroup 2's expression pattern of AKT pathway components, subgroup 3's expression pattern of AKT pathway components, subgroup 4's expression pattern of AKT pathway components, and subgroup 5's expression pattern of AKT pathway components.

In various embodiments, increases and/or decreases in expression levels of AKT pathway components relative to reference samples or values are detected by: contacting the sample with detection agents that specifically bind to AKT pathway components; and detecting the binding levels between the detection agents and the AKT pathway components. In various embodiments, increases and/or decreases in expression levels of AKT pathway components relative to reference samples or values are detected by using a microarray.

In various embodiments, the sample is assayed to detect increases or decreases in mRNA expression levels of one or more genes listed Table 2, Table 4, Table 5, or Table 6 relative to reference samples or values. In various embodiments, the sample is assayed to detect increases or decreases in protein expression levels of one or more genes listed Table 2, Table 4, Table 5, or Table 6 relative to reference samples or values.

In various embodiments, the reference sample is a non-neoplastic sample. In various embodiments, the non-neoplastic sample is obtained from an individual without a brain tumor or a neurological disorder. In various embodiments, the individual and the subject belong to the same species, for example, human. In various embodiments, the reference value is obtained from one or more non-neoplastic samples.

In various embodiments, the present invention provides a method for categorizing/classifying/stratifying a cancer in a subject. The method may consist of or may consist essentially of or may comprise: obtaining a biological sample from the subject; determining an expression pattern of AKT pathway components in the biological sample; and categorizing/classifying/stratifying the cancer based on the determined expression pattern of AKT pathway components in the biological sample. In various embodiments, said classifying comprises categorizing/classifying/stratifying the cancer into C1, PN, MES, CLAS, SL, or PROLIF subtype if the biological sample's expression pattern of AKT pathway components is determined to be C1, PN, MES, CLAS, SL, or PROLIF subtype's expression pattern of AKT pathway components. Non-limiting examples of C1, PN, MES, CLAS, SL, or PROLIF subtype's expression pattern of AKT pathway components may be found in FIG. 10 or Table 6.

In various embodiments, the present invention provides a method for diagnosing whether a subject has a cancer subtype. The method may consist of or may consist essentially of or may comprise: obtaining a biological sample from the subject; determining whether the cancer subtype's expression pattern of AKT pathway components is present in the biological sample; and diagnosing the subject as having the cancer subtype after the cancer subtype's expression pattern of AKT pathway components is determined to be present in the biological sample. In various further embodiments, the method comprises administering a therapeutically effective amount of a therapeutic to the subject, thereby treating, preventing, reducing the likelihood of having, reducing the severity of and/or slowing the progression of the cancer subtype. In some embodiments, the cancer subtype is C1, PN, MES, CLAS, SL, or PROLIF subtype. In various embodiments, the expression pattern is C1, PN, MES, CLAS, SL, or PROLIF subtype's expression pattern of AKT pathway components.

In various embodiments, the cancer is a brain tumor, glioma, high grade glioma (HGG), glioblastoma, or glioblastoma multiforme (GBM). In various embodiments, the subject is a human. In various embodiments, the subject is a mammalian subject including but not limited to human, monkey, ape, dog, cat, cow, horse, goat, pig, rabbit, mouse and rat. In various embodiments, the sample or biological sample is a cancer or tumor sample. In various embodiments, the sample or biological sample comprises a cell, neuron, glia, brain cell, spinal cord cell, brain neuron, brain glia, spinal cord neuron, or spinal cord glia, or a combination thereof. In some embodiments, the sample or biological sample comprises a tumor cell or tissue. In some embodiments, the sample or biological sample comprises a tumor biopsy or sample.

In various embodiments, the AKT pathway components comprise one classifier listed in Table 2, Table 4, Table 5, or Table 6. In various embodiments, the AKT pathway components comprise two classifiers listed in Table 2, Table 4, Table 5, or Table 6. In various embodiments, the AKT pathway components comprise three classifiers listed in Table 2, Table 4, Table 5, or Table 6. In various embodiments, the AKT pathway components comprise four classifiers listed in Table 2, Table 4, Table 5, or Table 6. In various embodiments, the AKT pathway components comprise five or more classifiers listed in Table 2, Table 4, Table 5, or Table 6. In various embodiments, the AKT pathway components comprise all classifiers listed in Table 2, Table 4, Table 5, or Table 6.

In various embodiments, the AKT pathway components comprise ACLY, AKT1, ATXN1, BCL10, CCND1, CDC37, CDKN1A, CDKN1B, CFD, CHEK1, EGFR, EIF3B, EIF3E, EIF3G, EIF3H, EIF4EBP1, EPAS1, EZH2, FGFR2, FGFR3, FOXO3, FYN, GAB1, GAB2, GRB10, GSK3B, HIF1A, HSP90AB1, HSP90B1, INPP5D, IRS1, IRS2, KDR, KRAS, MAP3K5, MAPK8IP1, NRAS, PALLD, PDGFA, PDGFC, PDGFD, PDGFRB, PDK1, PHLPP1, PIK3C2B, PIK3CA, PIK3R1, PKD2, PKN2, PPARGC1A, PPP2R1A, PPP2R2B, RAFT, SORBS2, SRSF1, SSB, SYK, TP53, TRIB3, TSC1, TSC2, TWIST1, VIM, and/or WNK1, or a combination thereof.

In various embodiments, said determining is performed by: contacting the biological sample with one or more detection agents that specifically bind to one or more AKT pathway components; and detecting the level of binding between the one or more detection agents and the one or more AKT pathway components. In various embodiments, said detecting is performed by using a microarray.

In some embodiments, the one or more detection agents are oligonucleotide probes, nucleic acids, DNAs, RNAs, peptides, proteins, antibodies, aptamers, or small molecules, or a combination thereof. In some embodiments, the microarray is an oligonucleotide microarray, DNA microarray, cDNA microarrays, RNA microarray, peptide microarray, protein microarray, or antibody microarray, or a combination thereof.

In various embodiments, the method further comprises selecting, choosing or prescribing a therapeutic for the subject after diagnosis. In various embodiments, the method further comprises instructing or directing the subject to receive a therapeutic after diagnosis. In various embodiments, the method further comprises administering a therapeutically effective amount of a therapeutic to the subject, thereby treating, preventing, reducing the likelihood of having, reducing the severity of and/or slowing the progression of the diagnosed cancer subtype.

Treatment Methods

In various embodiments, the present invention provides a method for treating, preventing, reducing the likelihood of having, reducing the severity of and/or slowing the progression of a cancer in a subject, comprising: obtaining a sample from the subject; assaying the sample to detect increases and/or decreases in expression levels of AKT pathway components relative to reference samples or values; detecting an expression pattern of AKT pathway components in the sample based on the detected increases and/or decreases; and administering a therapeutically effective amount of a therapeutic to the subject, thereby treating, preventing, reducing the likelihood of having, reducing the severity of and/or slowing the progression of the cancer.

In various embodiments, the AKT pathway components comprise one, two, three, four, five, six, or more, or all genes listed Table 2, and/or Table 4, and/or Table 5, and/or Table 6. In various embodiments, the AKT pathway components comprise ACLY, AKT1, ATXN1, BCL10, CCND1, CDC37, CDKN1A, CDKN1B, CFD, CHEK1, EGFR, EIF3B, EIF3E, EIF3G, EIF3H, EIF4EBP1, EPAS1, EZH2, FGFR2, FGFR3, FOXO3, FYN, GAB1, GAB2, GRB10, GSK3B, HIF1A, HSP90AB1, HSP90B1, INPP5D, IRS1, IRS2, KDR, KRAS, MAP3K5, MAPK8IP1, NRAS, PALLD, PDGFA, PDGFC, PDGFD, PDGFRB, PDK1, PHLPP1, PIK3C2B, PIK3CA, PIK3R1, PKD2, PKN2, PPARGC1A, PPP2R1A, PPP2R2B, RAFT, SORBS2, SRSF1, SSB, SYK, TP53, TRIB3, TSC1, TSC2, TWIST1, VIM, and/or WNK1, or a combination thereof.

In various embodiments, the expression pattern of AKT pathway components is C1's expression pattern of AKT pathway components, PN's expression pattern of AKT pathway components, MES's expression pattern of AKT pathway components, CLAS's expression pattern of AKT pathway components, SL's expression pattern of AKT pathway components, or PROLIF's expression pattern of AKT pathway components. In various embodiments, the expression pattern of AKT pathway components is subgroup 0's expression pattern of AKT pathway components, subgroup 1's expression pattern of AKT pathway components, subgroup 2's expression pattern of AKT pathway components, subgroup 3's expression pattern of AKT pathway components, subgroup 4's expression pattern of AKT pathway components, or subgroup 5's expression pattern of AKT pathway components. In some embodiments, the expression pattern of AKT pathway components is SL's expression pattern of AKT pathway components, and the therapeutic is BCNU or CCNU, a functional equivalent, analog, derivative or salt of BCNU or CCNU, or a combination thereof. In some embodiments, the method further comprises instructing/directing the subject not to receive or preventing the subject from receiving TMZ, or a functional equivalent, analog, derivative or salt of TMZ, wherein the expression pattern of AKT pathway components is SL's expression pattern of AKT pathway components. In some embodiments, the method further comprises not administering TMZ, or a functional equivalent, analog, derivative or salt of TMZ to the subject, wherein the expression pattern of AKT pathway components is SL's expression pattern of AKT pathway components. In some embodiments, the expression pattern of AKT pathway components is MES's expression pattern of AKT pathway components, and the therapeutic is TMZ, a functional equivalent, analog, derivative or salt of TMZ, or a combination thereof. In some embodiments, the expression pattern of AKT pathway components is subgroup 3's expression pattern of AKT pathway components, and the therapeutic is an EGFR inhibitor. In some embodiments, the expression pattern of AKT pathway components is subgroup 4's expression pattern of AKT pathway components, and the therapeutic is a PDGFRα inhibitor.

In various embodiments, the present invention provides a method of treating a subject with a cancer, comprising: providing a subject with a cancer categorized/classified/stratified into a subgroup utilizing a categorizing/classifying/stratifying method as disclosed herein; and administering to the subject a therapeutic that specifically benefits the subgroup, thereby treating the subject. In various embodiments, the present invention provides a method of treating a subject with a cancer, comprising: categorizing/classifying/stratifying a subject with a cancer into a subgroup utilizing a categorizing/classifying/stratifying method as disclosed herein; and administering to the subject a therapeutic that specifically benefits the subgroup, thereby treating the subject.

In some embodiments, the subgroup is subgroup SL, and the therapeutic is BCNU or CCNU, a functional equivalent, analog, derivative or salt of BCNU or CCNU, or a combination thereof. In some embodiments, the method further comprises instructing/directing the subject not to receive or preventing the subject from receiving TMZ, or a functional equivalent, analog, derivative or salt of TMZ, wherein the subgroup is subgroup SL. In some embodiments, the method further comprises not administering TMZ, or a functional equivalent, analog, derivative or salt of TMZ to the subject, wherein the subgroup is subgroup SL. In some embodiments, the subgroup is subgroup MES, and the therapeutic is TMZ, a functional equivalent, analog, derivative or salt of TMZ, or a combination thereof. In some embodiments, the subgroup is subgroup 3, and the therapeutic is an EGFR inhibitor. In some embodiments, the subgroup is subgroup 4, and the therapeutic is a PDGFRα inhibitor.

In various embodiments, the present invention provides a method for treating, preventing, reducing the likelihood of having, reducing the severity of and/or slowing the progression of a cancer in a subject, comprising: providing a therapeutic; and administering a therapeutically effective amount of the therapeutic to the subject, thereby treating, preventing, reducing the likelihood of having, reducing the severity of and/or slowing the progression of the cancer. In some embodiment, the method further comprises identifying that the subject has a SL subgroup/subtype cancer or a marker for the SL subgroup/subtype, wherein the therapeutic is BCNU or CCNU, a functional equivalent, analog, derivative or salt of BCNU or CCNU, or a combination thereof. In some embodiments, the method further comprises identifying that the subject has a SL subgroup/subtype cancer or a marker for the SL subgroup/subtype and preventing the subject from receiving TMZ, or a functional equivalent, analog, derivative or salt of TMZ. In some embodiment, the method further comprises identifying that the subject has a MES subgroup/subtype cancer or a marker for the MES subgroup/subtype, wherein the therapeutic is TMZ, a functional equivalent, analog, derivative or salt of TMZ, or a combination thereof.

Figure 6B:
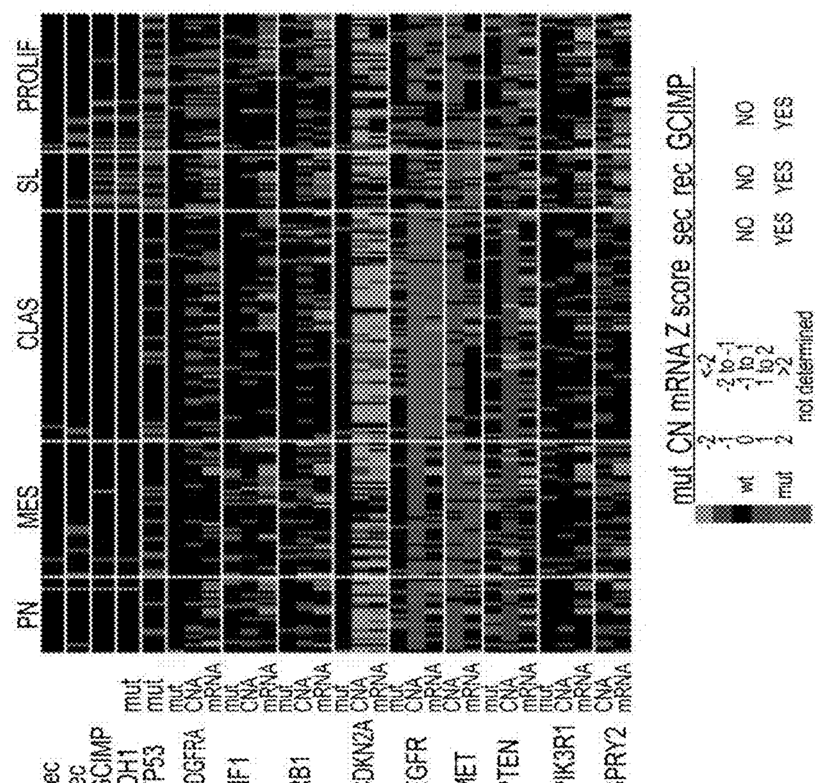
FIG. 6 depicts, in accordance with various embodiments of the invention, that AKT subgroups have distinct genomic alterations. (A) Copy number alterations in TCGA AKT subgroups. The GISTIC method was applied to TCGA samples in each subgroup with copy number information. Data are presented as a G score which is an integrated score of the prevalence of the copy-number change times the average (log 2-transformed) amplitude. The green line shows significance threshold (FDR q values to account for multiple-hypothesis testing). Regions with subgroup-specific CNA are highlighted in yellow. (B) Distribution of clinical information and mutations, CNA and mRNA expression for glioma-associated genes in AKT subgroups. The 218 TCGA GBM cases with gene expression, consensus putative copy number alteration and validated mutation data

In various embodiment, samples are assayed to detect markers for various AKT subgroups/subtypes as disclosed herein. In some embodiments, these markers are themselves AKT pathway components. In other embodiments, these markers are themselves not AKT pathway components. Non-limiting examples of markers for the SL subgroup/subtype include mutations in IDH1 and IDH2. Mutations in IDH1 and IDH2 can be detected by antibodies that specifically recognize IDH1 and IDH2 mutant proteins through various techniques such as IHC, Western blots and protein arrays, or can be detected by genotyping assays, PCR, microarray, DNA sequencing, and RNA sequencing techniques that target IDH and IDH2 genes or mRNAs. FIG. 6B shows more than 50% of SL tumors have mutant IDH1 and very few other subtypes have this mutation. As such, R132H mutant IDH1 may be detected to identify SL patients who are sensitive to nitrosoureas (e.g., BCNU and CCNU). Non-limiting examples of markers for the MES subgroup/subtype include increased expression levels of VIM, CD44, CD45, Fibronectin, Nucleostemin etc. As such, VIM, CD44, CD45, Fibronectin, and Nucleostemin may be detected to identify MES patients who are sensitive to temozolomide. Non-limiting examples of markers for the CLAS subgroup/subtype include mutations in EGFR and CDKN2A, and copy number alterations (CNAs). Proteins of these markers can be detected by various techniques such as IHC, Western blots and protein arrays; and genes and mRNA of these makers can be detected by genotyping assays, PCR, microarray, DNA sequencing, and RNA sequencing techniques. Also, DNA copy number alterations may also assayed to detect the markers for various AKT subgroups/subtypes as disclosed herein.

In various embodiments, the present invention provides a method for treating, preventing, reducing the likelihood of having, reducing the severity of and/or slowing the progression of a cancer in a subject. comprising: obtaining a sample from the subject; assaying the sample to detect a marker for an AKT subgroup/subtype; detecting the marker for the AKT subgroup/subtype in the sample; and administering a therapeutically effective amount of a therapeutic to the subject, thereby treating, preventing, reducing the likelihood of having, reducing the severity of and/or slowing the progression of the cancer. In some embodiments, the AKT subgroup/subtype is C1, PN, MES, CLAS, SL, or PROLIF. In other embodiments, the AKT subgroup/subtype is subgroup 0, subgroup 1, subgroup 2, subgroup 3, subgroup 4, or subgroup 5.

In various embodiments, the marker for the AKT subgroup/subtype comprises one or more mutations in IDH1 and/or IDH2. In one embodiment, the marker for the AKT subgroup/subtype comprises a mutation of R132 in IDH1 including but not limited to R132H, R132C, R132G, R132S, and R132L. In another embodiment, the marker for the AKT subgroup/subtype comprises a mutation of R172 in IDH2 including but not limited to R172K. In certain embodiments, the therapeutic is BCNU or CCNU, a functional equivalent, analog, derivative or salt of BCNU or CCNU, or a combination thereof. In further embodiments, the method comprises preventing the subject from receiving TMZ, or a functional equivalent, analog, derivative or salt of TMZ.

In various embodiments, the maker for the AKT subgroup/subtype comprises an increased expression level in VIM, CD44, CD45, Fibronectin, or Nucleostemin, or a combination thereof. In certain embodiments, the therapeutic is TMZ, a functional equivalent, analog, derivative or salt of TMZ, or a combination thereof.

In various embodiments, the marker for the AKT subgroup/subtype comprises one or more mutations in EGFR and/or CDKN2A, or copy number alterations (CNAs), or combinations thereof.

In various embodiments, the present invention provides a method of treating a SL cancer by administering to the subject BCNU or CCNU, a functional equivalent, analog, derivative or salt of BCNU or CCNU, or a combination thereof. In some embodiments, the method further comprises instructing/directing the subject not to receive or preventing the subject from receiving TMZ, or a functional equivalent, analog, derivative or salt of TMZ. In some embodiments, the method further comprises not administering TMZ, or a functional equivalent, analog, derivative or salt of TMZ to the subject.

In various embodiments, the present invention provides a method of treating a MES cancer by administering to the subject TMZ, a functional equivalent, analog, derivative or salt of TMZ, or a combination thereof.

In various embodiments, the present invention provides a method of treating a subgroup 3 cancer by administering to the subject an EGFR inhibitor.

In various embodiments, the present invention provides a method of treating a subgroup 4 cancer by administering to the subject a PDGFRα inhibitor.

In various embodiments, the present invention provides a method for treating, preventing, reducing the likelihood of having, reducing the severity of and/or slowing the progression of a cancer subtype in a subject. The method may consist of or may consist essentially of or may comprise: obtaining a biological sample from the subject; determining whether the cancer subtype's expression pattern of AKT pathway components is present in the biological sample; providing a therapeutic; and administering a therapeutically effective amount of the therapeutic to the subject after the cancer subtype's expression pattern of AKT pathway components is determined to be present in the biological sample, thereby treating, preventing, reducing the likelihood of having, reducing the severity of and/or slowing the progression of the cancer subtype. In some embodiments, the cancer subtype is C1, PN, MES, CLAS, SL, or PROLIF subtype. In various embodiments, the expression pattern is C1, PN, MES, CLAS, SL, or PROLIF subtype's expression pattern of AKT pathway components. Non-limiting examples of C1, PN, MES, CLAS, SL, or PROLIF subtype's expression pattern of AKT pathway components may be found in FIG. 10 or Table 6.

In various embodiments, the present invention provides a method for treating, preventing, reducing the likelihood of having, reducing the severity of and/or slowing the progression of SL or MES cancer subtype in a subject. The method may consist of or may consist essentially of or may comprise: obtaining a biological sample from the subject; determining whether SL or MES subtype's expression pattern of AKT pathway components is present in the biological sample; providing a therapeutic; and administering a therapeutically effective amount of the therapeutic to the subject after SL or MES subtype's expression pattern of AKT pathway components is determined to be present in the biological sample, thereby treating, preventing, reducing the likelihood of having, reducing the severity of and/or slowing the progression of SL or MES cancer subtype.

In various embodiments, the present invention provides a method for treating an AKT cancer subtype in a subject. The method may consist of or may consist essentially of or may comprise: providing a therapeutic; and administering a therapeutically effective amount of the therapeutic to the subject, thereby treating the AKT cancer subtype in the subject. In some embodiments, the cancer subtype is C1, PN, MES, CLAS, SL, or PROLIF subtype.

In various embodiments, the present invention provides a method for treating SL cancer subtype in a subject. The method may consist of or may consist essentially of or may comprise: providing a therapeutic; and administering a therapeutically effective amount of the therapeutic to the subject, thereby treating SL cancer subtype in the subject. In certain embodiments, the therapeutic is BCNU or CCNU, a functional equivalent, analog, derivative or salt of BCNU or CCNU, or a combination thereof. In some embodiments, the method further comprises instructing/directing the subject not to receive or preventing the subject from receiving TMZ, or a functional equivalent, analog, derivative or salt of TMZ. In some embodiments, the method further comprises not administering TMZ or a functional equivalent, analog, derivative or salt of TMZ to the subject.

In various embodiments, the present invention provides a method for treating MES cancer subtype in a subject. The method may consist of or may consist essentially of or may comprise: providing a therapeutic; and administering a therapeutically effective amount of the therapeutic to the subject, thereby treating MES cancer subtype in the subject.

In certain embodiments, the therapeutic is TMZ, a functional equivalent, analog, derivative or salt of TMZ, or a combination thereof.

In various embodiments, the present invention provides a method for treating an AKT cancer subtype in a subject. The method comprises administering a therapeutically effective amount of the therapeutic to the subject who has been diagnosed with the AKT cancer subtype, thereby treating the AKT cancer subtype in the subject. In some embodiments, the cancer subtype is C1, PN, MES, CLAS, SL, or PROLIF subtype. In some embodiments, the subject has been diagnosed with the AKT cancer subtype via methods as described in the present invention. In various embodiments, the method may further comprise providing the therapeutic.

In various embodiments, the present invention provides a method for treating SL cancer subtype in a subject. The method comprises administering a therapeutically effective amount of the therapeutic to the subject who has been diagnosed with the SL cancer subtype, thereby treating the SL cancer subtype in the subject. In some embodiments, the subject has been diagnosed with the SL cancer subtype via methods as described in the present invention. In various embodiments, the method may further comprise providing the therapeutic. In certain embodiments, the therapeutic is BCNU or CCNU, a functional equivalent, analog, derivative or salt of BCNU or CCNU, or a combination thereof. In some embodiments, the therapeutic is not TMZ or a functional equivalent, analog, derivative or salt of TMZ.

In various embodiments, the present invention provides a method for treating MES cancer subtype in a subject. The method comprises administering a therapeutically effective amount of the therapeutic to the subject who has been diagnosed with the MES cancer subtype, thereby treating the MES cancer subtype in the subject. In some embodiments, the subject has been diagnosed with the MES cancer subtype via methods as described in the present invention. In various embodiments, the method may further comprise providing the therapeutic. In certain embodiments, the therapeutic is TMZ, a functional equivalent, analog, derivative or salt of TMZ, or a combination thereof.

In various embodiments, the present invention provides a method for treating an AKT cancer subtype in a subject. The method comprises ordering a diagnostic test to determine if the subject has an AKT cancer subtype; and administering a therapeutically effective amount of the therapeutic to the subject who has been diagnosed with the AKT cancer subtype, thereby treating the AKT cancer subtype in the subject. In some embodiments, the diagnostic test is performed via methods as described in the present invention. In some embodiments, the cancer subtype is C1, PN, MES, CLAS, SL, or PROLIF subtype. In various embodiments, the method may further comprise providing the therapeutic.

In various embodiments, the present invention provides a method for treating SL cancer subtype in a subject. The method comprises ordering a diagnostic test to determine if the subject has SL cancer subtype; and administering a therapeutically effective amount of the therapeutic to the subject who has been diagnosed with the SL cancer subtype, thereby treating the SL cancer subtype in the subject. In some embodiments, the diagnostic test is performed via methods as described in the present invention. In various embodiments, the method may further comprise providing the therapeutic. In certain embodiments, the therapeutic is BCNU or CCNU, a functional equivalent, analog, derivative or salt of BCNU or CCNU, or a combination thereof. In some embodiments, the therapeutic is not TMZ or a functional equivalent, analog, derivative or salt of TMZ.

In various embodiments, the present invention provides a method for treating MES cancer subtype in a subject. The method comprises ordering a diagnostic test to determine if the subject has MES cancer subtype; and administering a therapeutically effective amount of the therapeutic to the subject who has been diagnosed with the MES cancer subtype, thereby treating the MES cancer subtype in the subject. In some embodiments, the diagnostic test is performed via methods as described in the present invention. In various embodiments, the method may further comprise providing the therapeutic. In certain embodiments, the therapeutic is TMZ, a functional equivalent, analog, derivative or salt of TMZ, or a combination thereof.

In various embodiments, the cancer is a brain tumor, glioma, high grade glioma (HGG), glioblastoma, or glioblastoma multiforme (GBM). In various embodiments, the subject is a human. In various embodiments, the subject is a mammalian subject including but not limited to human, monkey, ape, dog, cat, cow, horse, goat, pig, rabbit, mouse and rat. In various embodiments, the biological sample comprises a cell, neuron, glia, brain cell, spinal cord cell, brain neuron, brain glia, spinal cord neuron, or spinal cord glia, or a combination thereof. In some embodiments, the biological sample comprises a tumor cell or tissue. In some embodiments, the biological sample comprises a tumor biopsy or sample.

In various embodiments, the therapeutic is a nucleic acid, DNA, RNA, peptide, protein, antibody, aptamer, or small molecule, or a combination thereof. In some embodiments, the therapeutic is an alkylating agent, or a PI3K/AKT/mTOR inhibitor, or a combination thereof. In certain embodiments, the therapeutic is BCNU or CCNU, a functional equivalent, analog, derivative or salt of BCNU or CCNU, or a combination thereof. In certain embodiments, the therapeutic is TMZ, a functional equivalent, analog, derivative or salt of TMZ, or a combination thereof.

Typical dosages of an effective amount of the therapeutic can be in the ranges recommended by the manufacturer where known therapeutic molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the therapeutic may be administered once a day (SID/QD), twice a day (BID), three times a day (TID), four times a day (QID), or more, so as to administer an effective amount of the therapeutic to the subject, where the effective amount is any one or more of the doses described herein.

In various embodiments, the therapeutic is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$, or a combination thereof. In various embodiments, the therapeutic is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the therapeutic is administered once, twice, three or more times. In various embodiments, the therapeutic is administered about 1-3 times per day, 1-7 times per week, 1-9 times per month, or 1-12 times per year. In various embodiments, the therapeutic is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the subject, and "mg/m2" refers to mg per m2 body surface area of the subject. In certain embodiments, the therapeutic is administered to a human. In certain embodiments, the therapeutic is BCNU or CCNU, a functional equivalent, analog, derivative or salt of BCNU or CCNU, or a combination thereof. In certain embodiments, the therapeutic is TMZ, a functional equivalent, analog, derivative or salt of TMZ, or a combination thereof.

In various embodiments, the effective amount of the therapeutic is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 μg/kg/day, or a combination thereof. In various embodiments, the effective amount of the therapeutic is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 μg/$m^2$/day, or a combination thereof. In various embodiments, the effective amount of the therapeutic is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of the therapeutic is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/$m^2$/day, or a combination thereof. Here, "μg/kg/day" or "mg/kg/day" refers to μg or mg per kg body weight of the subject per day, and "μg/m2/day" or "mg/m2/day" refers to μg or mg per m2 body surface area of the subject per day.

In some embodiments, the therapeutic may be administered at the prevention stage of a condition (i.e., when the subject has not developed the condition but is likely to or in the process to develop the condition). In other embodiments, the therapeutic may be administered at the treatment stage of a condition (i.e., when the subject has already developed the condition). As a non-limiting example, the target condition is GBM. In this exemplar situation, the patient may be treated with the methods described herein when the patient has not yet developed GBM, or is likely to develop GBM, or is in the process of developing GBM, or has already developed GBM.

In accordance with the invention, the therapeutic may be administered using the appropriate modes of administration, for instance, the modes of administration recommended by the manufacturer for each of the therapeutic. In accordance with the invention, various routes may be utilized to administer the therapeutic of the claimed methods, including but not limited to aerosol, nasal, oral, transmucosal, transdermal, parenteral, enteral, topical, local, implantable pump, continuous infusion, capsules and/or injections. In various embodiments, the therapeutic is administered intracranially, intraventricularly, intrathecally, epidurally, intradurally, topically, intravascularly, intravenously, intraarterially, intratumorally, intramuscularly, subcutaneously, intraperitoneally, intranasally, or orally.

In various embodiments, the therapeutic is provided as a pharmaceutical composition. In various embodiments, the composition is formulated for via any route of administration, including but not limited to intracranial, intraventricular, intrathecal, epidural, intradural, topical, intravascular, intravenous, intraarterial, intratumoral, intramuscular, subcutaneous, intraperitoneal, intranasal or oral administration. Methods for these administrations are known to one skilled in the art. Preferred pharmaceutical compositions will also exhibit minimal toxicity when administered to a mammal.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The pharmaceutical composition according to the invention can also be a bead system for delivering the therapeutic agent to the target cells. For example, pectin/zein hydrogel bead system may be used to deliver Neuregulin-4 or a pharmaceutical equivalent, analog, derivative or a salt thereof, to the target cells in the subject (Yan F. et al., J Clin Invest. 2011 June; 121(6):2242-53).

Kits of the Invention

The present invention is also directed to a kit that is used to classify, diagnose and/or treat cancers. The kit is an assemblage of materials or components, including at least one of the inventive elements or modules. Thus, in some embodiments the kit contains one or more detection agents that specifically bind to one or more AKT pathway components, as described above; and in other embodiments the kit contains a cancer therapeutic, as described above. In certain embodiments the kit contains a composition including a drug delivery molecule complexed with a cancer therapeutic, as described above.

In various embodiments, the present invention provides a kit for categorizing/classifying/stratifying a cancer in a subject. The kit may consist of or may consist essentially of or may comprise: one or more detection agents that specifically bind to one or more AKT pathway components; instructions for using the one or more detection agents to classify the cancer in the subject.

In various embodiments, the present invention provides a kit for diagnosing whether a subject has a cancer subtype. The kit may consist of or may consist essentially of or may comprise: one or more detection agents that specifically bind to one or more AKT pathway components; instructions for using the one or more detection agents to diagnose whether a subject has the cancer subtype.

In various embodiments, the present invention provides a kit for treating, preventing, reducing the likelihood of having, reducing the severity of and/or slowing the progression of a cancer subtype in a subject. The kit may consist of or may consist essentially of or may comprise: one or more detection agents that specifically bind to one or more AKT pathway components; a quantity of a therapeutic; and instructions for using the one or more detection agents and the therapeutic to treat, prevent, reduce the likelihood of having, reduce the severity of and/or slow the progression of the cancer subtype in the subject In various embodiments, the present invention provides a kit for treating an AKT cancer subtype in a subject. The kit may consist of or may consist essentially of or may comprise: a quantity of a therapeutic; and instructions for using the therapeutic to treat the AKT cancer subtype in the subject.

In various embodiments, the subject is a human. In various embodiments, the cancer is a brain tumor, glioma, high grade glioma (HGG), glioblastoma, or glioblastoma multiforme (GBM). In various embodiments, the cancer subtype is C1, PN, MES, CLAS, SL, or PROLIF subtype.

In various embodiments, the one or more detection agents are applied to contact a biological sample obtained from the subject; and the level of binding between the one or more detection agents and the one or more AKT pathway components is detected to determine expression patterns of AKT pathway components. In some embodiments, the one or more detection agents are oligonucleotide probes, nucleic acids, DNAs, RNAs, peptides, proteins, antibodies, aptamers, or small molecules, or a combination thereof. In various embodiments, the level of binding is detected using a microarray. In some embodiments, the microarray is an oligonucleotide microarray, DNA microarray, cDNA microarrays, RNA microarray, peptide microarray, protein microarray, or antibody microarray, or a combination thereof.

In various embodiments, the therapeutic is a nucleic acid, DNA, RNA, peptide, protein, antibody, aptamer, or small molecule, or a combination thereof. In some embodiments, the therapeutic is an alkylating agent, or a PI3K/AKT/mTOR inhibitor, or a combination thereof. In certain embodiments, the therapeutic is BCNU or CCNU, a functional equivalent, analog, derivative or salt of BCNU or CCNU, or a combination thereof. In certain embodiments, the therapeutic is TMZ, a functional equivalent, analog, derivative or salt of TMZ, or a combination thereof.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the detection agents and/or cancer therapeutics can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in assays and therapies. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

Compositions

The present invention is also directed to a composition that is used to classify and/or diagnose cancers and cancer subtypes.

In some embodiments, the composition comprises one or more detection agents that specifically bind to one or more AKT pathway components, as described herein; and a biological sample from a subject desiring a classification or diagnosis regarding a cancer.

In various embodiments, the composition comprises one or more detection agents that specifically bind to one or more AKT pathway components; as described herein; and a biological sample from a subject desiring a classification regarding a cancer.

In various embodiments, the composition one or more detection agents that specifically bind to one or more AKT pathway components; and a biological sample from a subject desiring a subject diagnosis on whether he/she has the cancer subtype.

In various embodiments, the cancer subtype is C1, PN, MES, CLAS, SL, or PROLIF subtype.

Systems and Computers

In certain embodiments, the methods of the invention implement a computer program to calculate a copy number, copy number loss, copy number gain, LOH, mutation, deletion and expression levels. For example, a computer program can be used to perform the algorithms described herein. A computer system can also store and manipulate data generated by the methods of the present invention which comprises a plurality of hybridization signal changes/profiles during approach to equilibrium in different hybridization measurements and which can be used by a computer system in implementing the methods of this invention. In certain embodiments, a computer system receives probe hybridization data; (ii) stores probe hybridization data; and (iii) compares probe hybridization data to determine the state of AKT pathway components and genomic loci in a biological sample from cancerous or pre-cancerous tissue. The copy number, copy number loss, copy number gain, LOH, mutation, deletion and expression levels is then calculated. In some embodiments, a computer system (i) compares the determined copy number, copy number loss, copy number gain, LOH, mutation, deletion and expression levels to a threshold value or reference value; and (ii) outputs an indication of whether said copy number, copy number loss, copy number gain, LOH, mutation, deletion and expression levels is above or below a threshold value, or a genetic signature based on said indication. In certain embodiments, such computer systems are also considered part of the present invention.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; CRLMM software described in Silver et al. (2007) *Cell* 128, 991-1002; Aroma Affymetrix software described in Richardson et al. (2006) *Cancer Cell* 9, 121-132. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.). In certain embodiments, the computer comprises a database for storage of hybridization signal profiles. Such stored profiles can be accessed and used to calculate a copy number, copy number loss, copy number gain, LOH, mutation, deletion and expression level. For example, of the hybridization signal profile of a sample derived from the non-cancerous tissue of a subject and/or profiles generated from population-based distributions of AKT pathway components and genomic loci in relevant populations of the same species were stored, it could then be compared to the hybridization signal profile of a sample derived from the cancerous tissue of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Once a laboratory technician or laboratory professional or group of laboratory technicians or laboratory professionals determines whether a sample has a copy number, copy number gain, copy number loss, or expression level as described above (e.g., step (1) in many of the methods above), the same or a different laboratory technician or laboratory professional (or group) can analyze a plurality of tests of AKT pathway components and genomic loci to determine whether there is a copy number, copy number loss, copy number gain, LOH, mutation, or deletion to determine the expression levels (e.g., step (2) in many of the methods above). Next, the same or a different laboratory technician or laboratory professional (or group) can combine copy number, copy number loss, copy number gain, LOH, mutation, or deletion, or expression level data from the test of AKT pathway components and genomic loci to derive a copy number, copy number loss, copy number gain, LOH, mutation, or deletion, or expression level (e.g., step (3) in many of the methods above). Optionally, the same or a different laboratory technician or laboratory professional (or group) can correlate the copy number, copy number loss, LOH, mutation, or deletion, or expression level to an increased or decreased likelihood of response to a particular therapy (e.g., those mentioned above).

In various embodiments, provided herein is a computer readable storage medium comprising: a storing data module containing data from a sample comprising a cancer cell obtained from a subject that represents an expression level from an assay for AKT pathway components and genomic loci; a comparison module that compares the data stored on the storing data module with a reference data and/or control data, and to provide a comparison content, and an output module displaying the comparison content for the user, wherein the expression pattern of AKT pathway components and genomic loci indicates that the subject is has a certain AKT cancer subtype and an appropriate therapy that is likely effective to this AKT cancer subtype should be selected or prescribed and administered to the subject as the subject may not adequately respond to other therapies. Also, the subject may be instructed to take the appropriate therapy that is likely effective to his or her AKT cancer subtype.

In various embodiments, the control data comprises data from a population of cancer patients. In various embodiments, the control data comprises data from a population of non-cancerous healthy individuals. In various embodiments, the control data comprises data from a housekeeping gene expression.

Embodiments of the invention can be described through functional modules, which are defined by computer executable instructions recorded on computer readable media and which cause a computer to perform method steps when executed. The modules are segregated by function, for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks), BLU-RAY disc or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include for example, at a measuring module, a storage module, a comparison module, and an output module. The functional modules can be executed on one, or multiple, computers, or by using one, or multiple, computer networks. The measuring module has computer executable instructions to provide e.g., expression information in non-transitory computer readable form.

The measuring module can comprise any system for detecting the expression patterns of AKT pathway components and status of genetic loci (e.g., copy number alterations, copy number gain or loss, LOH, mutations, amplifications and deletions). Such systems can include DNA microarrays, RNA expression arrays, any ELISA detection system and/or any Western blotting detection system.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon expression level or protein level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment the reference data stored in the storage module to be read by the comparison module is, for example, expression data obtained from a population of non-cancer subjects, a population of cancer subjects, or expression data obtained from the same subject at a prior time point using the measuring module.

The "comparison module" can use a variety of available software programs and formats for the comparison operative to compare expression data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the expression patterns of AKT pathway components and status of genetic loci (e.g., copy number alterations, copy number gain or loss, LOH, mutations, amplifications and deletions) in an individual, efficacy of treatment in an individual, and/or method for treating an individual.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets. An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content-based in part on the comparison result that may be stored and output as requested by a user using an output module.

The content based on the comparison result, may be an expression value compared to a reference showing the susceptibility/adequate response or nonsusceptibility/non-adequate response from standard, conventional or certain therapy.

In various embodiments of the invention, the content based on the comparison result is displayed on a computer monitor. In various embodiments of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The present invention therefore provides for systems (and computer readable media for causing computer systems) to perform methods for selecting treatment of cancer in an individual. As used herein, "selecting treatment" refers to selecting, choosing or prescribing a cancer treatment for the individual, or instructing or directing the individual to receive a cancer treatment.

Systems and computer readable media described herein are merely illustrative embodiments of the invention for detecting the expression patterns of AKT pathway components and status of genetic loci (e.g., copy number alterations, copy number gain or loss, LOH, mutations, amplifications and deletions) in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

In some cases, a computing system provided herein can include computer-executable instructions or a computer program (e.g., software) containing computer-executable instructions for formatting an output providing an indication the expression patterns of AKT pathway components and status of genetic loci (e.g., copy number alterations, copy number gain or loss, LOH, mutations, amplifications and deletions) or a likelihood that a cancer patient will respond to a particular cancer treatment regimen (e.g., a regimen as described above), or a combination of these items. In some cases, a computing system provided herein can include computer-executable instructions or a computer program (e.g., software) containing computer-executable instructions for determining a desired cancer treatment regimen for a particular patient based at least in part on the expression patterns of AKT pathway components and status of genetic loci (e.g., copy number alterations, copy number gain or loss, LOH, mutations, amplifications and deletions).

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

Expression Pattern Assay—RNA

In various embodiments, determining an expression pattern of AKT pathway components in the biological sample comprises assaying mRNA levels. In various embodiments, assaying mRNA levels comprises using RNA sequencing, northern blot, in situ hybridization, hybridization array, serial analysis of gene expression (SAGE), reverse transcription PCR, real-time PCR, real-time reverse transcription PCR, quantitative PCR, or microarray, or a combination thereof.

In various embodiments, assaying mRNA levels comprises contacting the biological sample with polynucleotide probes capable of specifically hybridizing to mRNA of one or more AKT pathway components and thereby forming probe-target hybridization complexes.

Hybridization-based RNA assays include, but are not limited to, traditional "direct probe" methods such as, northern blot or in situ hybridization (e.g., Angerer (1987) Meth. Enzymol 152: 649). The methods can be used in a wide variety of formats including, but not limited to, substrate (e.g. membrane or glass) bound methods or array-based approaches. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases. Hybridization protocols suitable for use with the methods of the invention are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In situ Hybridization Protocols, Choo, ed., Humana Press, Totowa, N.J. (1994), Pinkel, et al. (1998) Nature Genetics 20: 207-211, and/or Kallioniemi (1992) Proc. Natl Acad Sci USA 89:5321-5325 (1992). In some applications, it is necessary to block the hybridization capacity of repetitive sequences. Thus, in some embodiments, tRNA, human genomic DNA, or Cot-I DNA is used to block non-specific hybridization.

In various embodiments, assaying mRNA levels comprises contacting the biological sample with polynucleotide primers capable of specifically hybridizing to mRNAs of genes listed in Table 2, Table 4, Table 5, or Table 6, forming primer-template hybridization complexes, and performing a PCR reaction. In some embodiments, the polynucleotide primers comprises about 15-45, 20-40, or 25-35 bp sequences that are identical (for forward primers) or complementary (for reverse primers) to sequences of genes listed in Table 2, Table 4, Table 5, or Table 6. As a non-liming example, the polynucleotide primers for ACLY (e.g., transcript variant 1 NM_001096.2 with 4450 bp) can comprise sequences that are identical (for forward primers) or complementary (for reverse primers) to ACLY's by 1-20, 5-25, 10-30, 15-35, 20-40, 25-45, 30-50, so on and so forth, until the end of ACLY, 4410-4430, 4415-4435, 4420-4440, 4425-4445, 4430-4450. While not listed here exhaustively because of the space, all these polynucleotide primers for ACLY and other genes listed in Table 2, Table 4, Table 5, or Table 6 can be used in the present invention. In various embodiments, the polynucleotide primers are labeled with radioisotopes or fluorescent molecules. As the labeled primers emit radio or fluorescent signals, the PCR products containing the labeled primers can be detected and analyzed with a variety of imaging equipment.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, A Guide to Methods and Applications, Academic Press, Inc. N.Y.). Measurement of DNA copy number at microsatellite loci using quantitative PCR analysis is described in Ginzonger, et al. (2000) Cancer Research 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green. Other suitable amplification methods include, but are not limited to, ligase chain reaction (LCR) (see Wu and Wallace (1989) Genomics 4: 560, Landegren, et al. (1988) Science 241: 1077, and Barringer et al. (1990) Gene 89: 117), transcription amplification (Kwoh, et al. (1989) Proc. Natl. Acad. Sci. USA 86: 1173), self-sustained sequence replication (Guatelli, et al. (1990) Proc. Nat. Acad. Sci. USA 87: 1874), dot PCR, and linker adapter PCR, etc.

Expression Level Assay—Protein

In various embodiments, determining an expression pattern of AKT pathway components in the biological sample comprises assaying protein levels. In various embodiments, assaying a protein level comprises using western blot, enzyme-linked immunosorbent assay (ELISA), radioimmunoassay, or mass spectrometry, or a combination thereof.

In various embodiments, assaying protein levels comprises contacting the biological sample with antibodies capable of specifically binding to proteins encoded by genes listed in Table 2, Table 4, Table 5, or Table 6 and thereby forming antigen-antibody complexes. In the methods and assays of the invention, the expression levels of proteins encoded by genes listed in Table 2, Table 4, Table 5, or Table 6, or fragments or variants thereof can be determined using antibodies specific for those individual proteins or fragments or variants thereof and detecting immunospecific binding of each antibody to its respective cognate biomarker protein.

Antibodies, both polyclonal and monoclonal, can be produced by a skilled artisan either by themselves using well known methods or they can be manufactured by service providers who specialize making antibodies based on known protein sequences. In the present invention, the protein sequences of AKT pathway genes are known and thus production of antibodies against them is a matter of routine.

For example, production of monoclonal antibodies can be performed using the traditional hybridoma method by first immunizing mice with an antigen which may be an isolated protein of choice or fragment thereof (for example, a protein encode by a gene listed in Table 2, Table 4, Table 5, or Table 6, or a fragment thereof or a variant thereof) and making hybridoma cell lines that each produce a specific monoclonal antibody. The antibodies secreted by the different clones are then assayed for their ability to bind to the antigen using, e.g., ELISA or Antigen Microarray Assay, or immuno-dot blot techniques. The antibodies that are most specific for the detection of the protein of interest can be selected using routine methods and using the antigen used for immunization and other antigens as controls. The antibody that most specifically detects the desired antigen and protein and no other antigens or proteins are selected for the processes, assays and methods described herein. The best clones can then be grown indefinitely in a suitable cell culture medium. They can also be injected into mice (in the peritoneal cavity, surrounding the gut) where they produce an antibody-rich ascites fluid from which the antibodies can be isolated and purified. The antibodies can be purified using techniques that are well known to one of ordinary skill in the art.

Any suitable immunoassay method may be utilized, including those which are commercially available, to determine the expression level of an AKT pathway protein or a variant thereof assayed according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc.

For example, in the assays of the invention, "sandwich-type" assay formats can be used. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule.

The antibodies can be labeled. In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease.

The antibody can be attached to a surface. Examples of useful surfaces on which the antibody can be attached for the purposes of detecting the desired antigen include nitrocellulose, PVDF, polystyrene, and nylon.

In some embodiments of the processes, assays and methods described herein, detecting the level of antibodies reactive to an AKT pathway protein or a variant thereof includes contacting the sample from the cancer patient with an antibody or a fragment thereof that specifically binds an AKT pathway protein or a variant thereof, forming an antibody-protein complex between the antibody and the AKT pathway protein or the variant thereof present in the sample, washing the sample to remove the unbound antibody, adding a detection antibody that is labeled and is reactive to the antibody bound to the AKT pathway protein or a variant thereof in the sample, washing to remove the unbound labeled detection antibody and converting the label to a detectable signal, wherein the detectable signal is indicative of the level of AKT pathway protein or a variant thereof in the sample from the patient. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The level of AKT pathway protein may be obtained by assaying a light scattering intensity resulting from the formation of an antibody-protein complex formed by a reaction of AKT pathway protein in the sample with the antibody, wherein the light scattering intensity of at least 10% above a control light scattering intensity indicates the likelihood of chemotherapy resistance.

Reference Value of Expression Level

Various methods described herein may compare an AKT pathway gene's expression level in a subject's biological sample to a pre-determined reference value of the AKT pathway gene. In various embodiments, an AKT pathway gene's reference value of expression level is the AKT pathway gene's median or mean expression level from all tumor samples in the discovery dataset. In various embodiments, an AKT pathway gene's reference value of expression level is the AKT pathway gene's median or mean expression level from all GBM samples in the discovery dataset. In various embodiments, an AKT pathway gene's reference value of expression level is the AKT pathway gene's median or mean expression level from all tumor samples in the validation dataset. In various embodiments, an AKT pathway gene's reference value of expression level is the AKT pathway gene's median or mean expression level from all GBM samples in the validation dataset. In various embodiments, an AKT pathway gene's reference value of expression level is the AKT pathway gene's median or mean expression level from non-cancerous, non-tumorous, or non-neoplastic cells or tissues. In accordance with the present invention, AKT pathway genes include but are not limited to those listed in Table 2, Table 4, Table 5, or Table 6.

Reference values may be obtained by various methods known in the field. For example, one or more biopsies from one cancer patient' tumor (hereinafter "Tumor-1") may be collected, processed and analyzed to obtain the expression level of one AKT pathway gene (hereinafter "Gene-1") in this tumor (hereinafter "Expression-Tumor-1-Gene-1"). The same step is used to obtain Gene-1's expression levels in another 10, 100, 200, 300, 400, 500, 600, 700, 800, 900, 1000 or more cancer patients' tumors (hereinafter "Tumor-N), that is, "Expression-Tumor-N-Gene-1" (N is 1, 2, 3, 4, 5, 6, 7, . . . ). Then, Gene-1's median or mean expression level from all tumors may be used as the reference value of Gene-1 (hereinafter "REF-Gene-1"), to which Gene-1's expression in a subject's biological sample is compared to so as to determine if Gene-1's expression is high or low in the subject's biological sample. In other words, REF-Gene-1 is the median or mean of Expression-Tumor-N-Gene-1. Similar steps may be used to obtain another 5, 10, 15, 20, 25, 30, 35, 40, 45, 50, 55, 60, 65, 70, 75, 80, 85, 90, 95, 100, or more AKT pathway genes' reference values, that is, "REF-Gene-M" (M=1, 2, 3, 4, 5, 6, 7, . . . ). In various embodiments, non-limiting AKT pathway genes (i.e., Gene-M) are listed in Table 2, Table 4, Table 5, or Table 6. To determine the expression pattern of AKT pathway genes in a subject's biological sample, one may compare one, two, three, four, five, or more AKT pathway genes' expression levels to their respective reference values.

As used herein, "expression pattern", "expression profile" and "expression signature" are exchangeable terms referring to the specific combination or setting of one or more genes' high (increased) expressions and/or low (decreased) expressions relative to reference values. In various embodiments, AKT cancer subtypes' expression patterns are the specific combinations of AKT pathway genes' high and low expressions. For non-limiting example, FIG. 10 or Table 6 shows the expression patterns of AKT MES, CLAS, PROLIF, SL and SN subtypes in the validation and discovery datasets. Among the 64 exemplar AKT pathway genes shown in FIG. 10 or Table 6, those having high expressions relative to reference values are shown as red, and those having low expressions relative to reference values are shown as green.

Various statistical methods, for example, a two-tailed student t-test with unequal variation, may be used to measure the differences in expression levels of an AKT pathway gene between the subject's sample and a reference value of expression level generate by computer algorithm pooling many tumor samples, as described herein, for example, all the GBM samples in the discovery dataset and/or validation dataset. Various statistical methods, for example, a two-tailed student t-test with unequal variation, may be used to measure the differences in expression levels of an AKT pathway gene between the subject's sample and a control sample from a normal/healthy individual. Various statistical methods, for example, a two-tailed student t-test with unequal variation, may be used to measure the differences in expression levels of an AKT pathway gene between the subject's sample and a reference value of expression level generate by computer algorithm pooling many control samples, as described herein. A significant difference may be achieved where the p value is equal to or less than 0.05.

In various embodiments, the expression level of an AKT pathway gene or a variant thereof in the subject as compared to the reference value is higher by at least or about 5, 10, 15, 20, 25, 30, 35, 40, 45, 50, 55, 60, 65, 70, 75, 80, 85, 90, 95, or 100%. In various embodiments, the expression level of an AKT pathway gene or a variant thereof in the subject as compared to the reference value is lower by at least or about 5, 10, 15, 20, 25, 30, 35, 40, 45, 50, 55, 60, 65, 70, 75, 80, 85, 90, 95, or 100%. In various embodiments, the expression level ratio between an AKT pathway gene or a variant thereof in the subject and the reference value is at least or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 4:1, 5:1, 6:1, 7:1, 8:1, 9:1 or 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. In various embodiments, the expression level ratio between the reference value and an AKT pathway gene or a variant thereof in the subject is at least or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 4:1, 5:1, 6:1, 7:1, 8:1, 9:1 or 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1: Materials and Methods

Patient Information

The discovery dataset (GBM195) consisted of 181 GBM (WHO grade IV astrocytoma; (159 primary and 22 recurrent) from 3 datasets [3], [4], [21] and 14 non-neoplastic samples from 2 sources: (1) six samples from patients undergoing temporal lobe epilepsy surgery [3] and (2) eight samples from autopsy specimens of cerebral cortex from donors with no history of neurological disorders obtained from the National Neurological Research Brain Bank (Los Angeles, Calif.) [4]. Two datasets are in GEO (GSE4271, GSE4412) and the third has been submitted. Table 1 lists GEO ID's and clinical information for GBM195 tumors. Tissue collection and processing, pathological review, and microarray analysis for the discovery dataset (GBM195) has been described elsewhere ([3] Nigro et al. 2005, [4] Phillips et a. 2006, and [21] Freije et al. 2004, which are incorporated herein by reference in their entirety as though fully set forth.) The validation dataset consisted of 583 samples; 573 GBM (16 recurrent and 3 secondary) and 10 non-neoplastic samples from The Cancer Genome Atlas (TCGA). Samples were collected and processed as described ([5] Atlas TCG 2008, which is incorporated herein by reference in its entirety as though fully set forth.). IRB or Committee on Human Research approval was obtained for samples used in the discovery and validation datasets as described [3], [4], [10], [21].

TABLE 1

Clinical information for tumors in GBM195

| id | GEO_Accessions (U133A/U133B) | Histology | Anat. Site | Recurrence | Phillips Subclass | Gender | Age | Survival Weeks | Censoring Status |
|---|---|---|---|---|---|---|---|---|---|
| G1022 | GSM99544, GSM99545 | GBM | | | Mes | male | 31 | 18 | D |
| G1028 | GSM99465, GSM99464 | GBM | | | Unk | female | 20 | 7.7 | D |
| G1032 | GSM99483, GSM99482 | GBM | | | PN | female | 34 | 12.9 | D |
| G1038 | GSM99581, GSM99580 | GBM | | | PN | female | 33 | 178.1 | A |
| G1043 | GSM99560, GSM99561 | GBM | | | Mes | female | 23 | 155.6 | D |
| G1334 | GSM99529, GSM99528 | GBM | | | PN | female | 36 | 43.1 | D |
| G1342 | GSM99471, GSM99470 | GBM | | | PN | male | 54 | 32 | D |
| G1354 | GSM99551, GSM99550 | GBM | | | Mes | male | 42 | 60 | D |
| G1398 | GSM99491, GSM99490 | GBM | | | Mes | female | 49 | 41.9 | D |
| G1406 | GSM99543, GSM99542 | GBM | | | Mes | male | 29 | 33.7 | D |
| G1414 | GSM99466, GSM99467 | GBM | | | Mes | female | 69 | 9.1 | D |
| G1423 | GSM99493, GSM99492 | GBM | | | PN | female | 54 | 13.7 | D |
| G1463 | GSM99475, GSM99474 | GBM | | | PN | male | 30 | 37.9 | D |
| G1469 | GSM99494, GSM99495 | GBM | | | Mes | male | 56 | 21.9 | D |
| G1478 | GSM99553, GSM99552 | GBM | | | PN | male | 40 | 155.4 | A |
| G1495 | GSM99457, GSM99456 | GBM | | | PN | female | 82 | 10.1 | D |
| G1511 | GSM99451, GSM99450 | GBM | | | PN | male | 27 | 12.1 | D |
| G1516 | GSM99555, GSM99554 | GBM | | | Mes | female | 41 | 147.3 | A |
| G1521 | GSM99563, GSM99562 | GBM | | | PN | female | 23 | 146 | A |
| G1544 | GSM99488, GSM99489 | GBM | | | Mes | female | 49 | 21.1 | D |
| G1656 | GSM99440, GSM99441 | GBM | | | PN | male | 48 | 137.3 | A |
| G1667 | GSM99447, GSM99446 | GBM | | | Mes | male | 44 | 84 | D |
| G1675 | GSM99565, GSM99564 | GBM | | | Mes | male | 61 | 97.6 | D |
| G1681 | GSM99589, GSM99588 | GBM | | | Mes | male | 40 | 132.4 | A |
| G1745 | GSM99448, GSM99449 | GBM | | | PN | female | 42 | 111.4 | A |
| G1798 | GSM99556, GSM99557 | GBM | | | Mes | female | 47 | 103.3 | A |
| G1900 | GSM99485, GSM99484 | GBM | | | Prolif | female | 45 | 39.9 | D |
| G1902 | GSM99442, GSM99443 | GBM | | | Mes | female | 56 | 46.4 | D |
| G1905 | GSM99583, GSM99582 | GBM | | | PN | male | 75 | 55.6 | D |

TABLE 1-continued

Clinical information for tumors in GBM195

| id | GEO_Accessions (U133A/U133B) | Histology | Anat. Site | Recurrence | Phillips Subclass | Gender | Age | Survival Weeks | Censoring Status |
|---|---|---|---|---|---|---|---|---|---|
| G2013 | GSM99591, GSM99590 | GBM | | | Mes | female | 70 | 56.6 | A |
| G2015 | GSM99445, GSM99444 | GBM | | | Mes | male | 78 | 56.6 | A |
| G2017 | GSM99578, GSM99579 | GBM | | | Mes | male | 60 | 33.9 | D |
| G2028 | GSM99531, GSM99530 | GBM | | | PN | female | 42 | 31.9 | D |
| G2029 | GSM99533, GSM99532 | GBM | | | PN | female | 42 | 31.9 | D |
| G2067 | GSM99538, GSM99539 | GBM | | | PN | female | 42 | 24 | D |
| G2068 | GSM99540, GSM99541 | GBM | | | PN | female | 42 | 24 | D |
| G2079 | GSM99486, GSM99487 | GBM | | | Mes | male | 64 | 42.6 | A |
| G2098 | GSM99585, GSM99584 | GBM | | | Mes | male | 65 | 29 | A |
| G2158 | GSM99472, GSM99473 | GBM | | | PN | female | 62 | 13.6 | D |
| G2166 | GSM99559, GSM99558 | GBM | | | PN | female | 39 | 156.9 | A |
| G585 | GSM99587, GSM99586 | GBM | | | PN | female | 63 | 43.1 | D |
| G597 | GSM99534, GSM99535 | GBM | | | Mes | male | 35 | 1 | D |
| G604 | GSM99572, GSM99573 | GBM | | | Mes | male | 66 | 26.4 | D |
| G636 | GSM99476, GSM99477 | GBM | | | Prolif | female | 54 | 58.9 | D |
| G660 | GSM99546, GSM99547 | GBM | | | PN | female | 75 | 16 | D |
| G697 | GSM99436, GSM99437 | GBM | | | Mes | female | 64 | 50.9 | D |
| G706 | GSM99453, GSM99452 | GBM | | | PN | male | 54 | 72.3 | D |
| G712 | GSM99432, GSM99433 | GBM | | | Mes | male | 49 | 26.9 | D |
| G746 | GSM99525, GSM99524 | GBM | | | PN | male | 52 | 6.1 | D |
| G749 | GSM99462, GSM99463 | GBM | | | Mes | male | 39 | 7.6 | D |
| G782 | GSM99577, GSM99576 | GBM | | | PN | female | 24 | 20 | D |
| G824 | GSM99478, GSM99479 | GBM | | | PN | female | 50 | 26.6 | D |
| G839 | GSM99481, GSM99480 | GBM | | | PN | male | 82 | 40.9 | D |
| G931 | GSM99438, GSM99439 | GBM | | | Mes | female | 58 | 26 | D |
| G932 | GSM99435, GSM99434 | GBM | | | PN | female | 18 | 14 | D |
| G938 | GSM99536, GSM99537 | GBM | | | PN | male | 29 | 81.3 | D |
| G976 | GSM99548, GSM99549 | GBM | | | Mes | female | 43 | 59.7 | D |
| G985 | GSM99454, GSM99455 | GBM | | | PN | female | 76 | 8 | D |
| G996 | GSM99527, GSM99526 | GBM | | | Prolif | male | 45 | 32 | D |
| MDA10334 | GSM97053, GSM96953 | GBM | | 0 | PN | male | 38 | 210 | A |
| MDA11300 | GSM97002, GSM97102 | GBM | | 0 | Prolif | female | 68 | 91 | D |
| MDA1153 | S | GBM | | 1 | Unk | male | 12 | | |
| MDA1351 | GSM96999, GSM97099 | GBM | | 1 | Mes | male | 57 | | |
| MDA13818 | S | GBM | | 0 | Unk | female | 8 | 481 | A |
| MDA13921 | GSM96979, GSM97079 | GBM | | 0 | Prolif | female | 60 | 32 | D |
| MDA13945 | GSM96955, GSM97055 | GBM | | 0 | PN | male | 49 | 34 | D |
| MDA14085 | GSM97089, GSM96989 | GBM | | 0 | Mes | male | 49 | 106 | D |
| MDA14206 | GSM97103, GSM97003 | GBM | | 1 | Prolif | female | 68 | | |
| MDA14523 | GSM97007, GSM97107 | GBM | | 0 | Prolif | female | 30 | 41 | D |
| MDA14558 | GSM97073, GSM96973 | GBM | | 0 | Prolif | male | 76 | 52 | D |
| MDA15824 | GSM97075, GSM96975 | GBM | | 1 | Mes | male | 43 | | |
| MDA16713 | GSM96960, GSM97060 | GBM | | 1 | Mes | female | 43 | | |
| MDA16789 | GSM96987, GSM97087 | GBM | | 0 | Mes | male | 34 | 33 | D |
| MDA17467 | GSM97005, GSM97105 | GBM | | 1 | Mes | male | 72 | | |
| MDA1765 | GSM96952, GSM97052 | GBM | | 0 | Mes | male | 43 | 313 | D |
| MDA18395 | S | GBM | | 0 | Unk | male | 12 | 170 | A |
| MDA20194 | S | GBM | | 0 | Unk | female | 55.7 | 158 | D |
| MDA207 | GSM97097, GSM96997 | GBM | | 0 | Prolif | female | 32 | 51 | D |
| MDA21226 | GSM97080, GSM96980 | GBM | | 0 | Mes | female | 68 | 131 | D |
| MDA21537 | GSM97067, GSM96967 | GBM | | 0 | Mes | male | 59 | 32 | D |
| MDA23057 | GSM97010, GSM97110 | GBM | | 0 | Prolif | male | 57 | 70 | D |
| MDA23445 | GSM97064, GSM96964 | GBM | | 0 | Mes | male | 49 | 59 | D |
| MDA23978 | GSM97086, GSM96986 | GBM | | 1 | Prolif | female | 32 | | |
| MDA24488 | GSM97123, GSM97023 | GBM | | 0 | Mes | male | 43 | 47 | D |
| MDA24710 | GSM97093, GSM96993 | GBM | | 0 | Mes | male | 54 | 125 | D |
| MDA24843 | S | GBM | | 0 | Prolif | male | 17 | 120 | D |
| MDA24873 | GSM96969, GSM97069 | GBM | | 0 | Prolif | male | 82 | 55 | D |
| MDA25266 | GSM96985, GSM97085 | GBM | | 0 | Prolif | male | 48 | 111 | D |
| MDA25450 | GSM97008, GSM97108 | GBM | | 0 | Mes | male | 39 | 53 | D |
| MDA2618 | GSM96950, GSM97050 | GBM | | 0 | Mes | male | 60 | 131 | D |
| MDA28435 | S | GBM | | 2 | Unk | male | 12 | | |
| MDA28504 | GSM97059, GSM96959 | GBM | | 0 | Prolif | male | 55 | 238 | D |
| MDA29621 | GSM96978, GSM97078 | GBM | | 0 | Prolif | male | 57 | 242 | A |
| MDA30446 | GSM97101, GSM97001 | GBM | | 1 | Mes | male | 57 | | |
| MDA30617 | GSM96976, GSM97076 | GBM | | 0 | Prolif | male | 54 | 97 | D |
| MDA31041 | GSM97140, GSM97040 | GBM | | 0 | Mes | male | 54 | 53 | D |
| MDA31220 | GSM97128, GSM97028 | GBM | | 1 | Mes | male | 54 | | |
| MDA31237 | GSM96951, GSM97051 | GBM | | 0 | Mes | female | 48 | 236 | D |
| MDA31472 | GSM96998, GSM97098 | GBM | | 1 | Mes | female | 32 | | |
| MDA32393 | GSM97011, GSM97111 | GBM | | 0 | Mes | male | 50 | 3 | D |
| MDA33044 | GSM97091, GSM96991 | GBM | | 0 | PN | female | 36 | 150 | D |
| MDA33054 | GSM96996, GSM97096 | GBM | | 0 | Prolif | female | 43 | 12 | D |
| MDA33688 | GSM97070, GSM96970 | GBM | | 0 | Prolif | male | 41 | 59 | D |
| MDA33825 | GSM97141, GSM97041 | GBM | | 0 | Mes | male | 54.1 | 53.1 | D |

TABLE 1-continued

Clinical information for tumors in GBM195

| id | GEO_Accessions (U133A/U133B) | Histology | Anat. Site | Recurrence | Phillips Subclass | Gender | Age | Survival Weeks | Censoring Status |
|---|---|---|---|---|---|---|---|---|---|
| MDA33859 | GSM96977, GSM97077 | GBM | | 0 | Prolif | male | 40 | 95 | D |
| MDA34061 | GSM96988, GSM97088 | GBM | | 0 | Mes | male | 55 | 57 | D |
| MDA34826 | S | GBM | | 1 | Mes | male | 14 | | |
| MDA35143 | GSM96958, GSM97058 | GBM | | 0 | Mes | male | 57 | 181 | D |
| MDA35312 | GSM96981, GSM97081 | GBM | | 0 | Mes | male | 47 | 77 | D |
| MDA36675 | GSM96971, GSM97071 | GBM | | 1 | Prolif | male | 45 | | |
| MDA36764 | GSM96961, GSM97061 | GBM | | 0 | Mes | male | 50 | 311 | D |
| MDA37775 | GSM96965, GSM97065 | GBM | | 0 | Mes | male | 48 | 97 | D |
| MDA38276 | GSM96990, GSM97090 | GBM | | 0 | PN | female | 53 | 62 | D |
| MDA38490 | GSM96992, GSM97092 | GBM | | 0 | Mes | male | 48 | 154 | A |
| MDA38805 | GSM96984, GSM97084 | GBM | | 0 | Prolif | female | 34 | 16 | D |
| MDA38992 | GSM97018, GSM97118 | GBM | | 0 | PN | male | 24 | 145 | A |
| MDA42116 | GSM96966, GSM97066 | GBM | | 0 | Prolif | male | 44 | 33 | D |
| MDA42411 | GSM97009, GSM97109 | GBM | | 0 | Prolif | male | 72 | 57 | D |
| MDA426 | GSM97126, GSM97026 | GBM | | 0 | PN | male | 44 | 174 | D |
| MDA43291 | S | GBM | | 2 | Mes | male | 14 | | |
| MDA43849 | GSM97094, GSM96994 | GBM | | 0 | Prolif | female | 32 | 39 | D |
| MDA4433 | GSM97019, GSM97119 | GBM | | 0 | PN | male | 55 | 234 | A |
| MDA44442 | GSM97062, GSM96962 | GBM | | 0 | Prolif | male | 54 | 62 | D |
| MDA47399 | GSM97006, GSM97106 | GBM | | 1 | Mes | female | 72 | | |
| MDA47813 | GSM97100, GSM97000 | GBM | | 0 | Mes | male | 57 | 62 | D |
| MDA48078 | GSM97104, GSM97004 | GBM | | 0 | Mes | female | 72 | 65 | D |
| MDA50100 | GSM96972, GSM97072 | GBM | | 0 | Prolif | female | 43 | 210 | A |
| MDA50593 | GSM97037, GSM97137 | GBM | | 0 | PN | female | 49 | 73 | D |
| MDA5060 | GSM97057, GSM96957 | GBM | | 1 | Mes | male | 48 | | |
| MDA53520 | GSM96968, GSM97068 | GBM | | 1 | Prolif | male | 60 | | |
| MDA54336 | GSM97083, GSM96983 | GBM | | 0 | Prolif | male | 54 | 32 | D |
| MDA56075 | GSM96974, GSM97074 | GBM | | 0 | Prolif | male | 29 | 123 | D |
| MDA56270 | GSM96982, GSM97082 | GBM | | 0 | Mes | female | 48 | 56 | D |
| MDA5749 | GSM97054, GSM96954 | GBM | | 0 | Prolif | male | 45 | 70 | D |
| MDA6326 | GSM96995, GSM97095 | GBM | | 0 | Prolif | female | 58 | 79 | D |
| MDA7074 | GSM97114, GSM97014 | GBM | | 0 | PN | female | 22.1 | 353.6 | A |
| MDA7379 | GSM97144, GSM97044 | GBM | | 1 | PN | female | 49 | | |
| MDA8277 | GSM97063, GSM96963 | GBM | | 0 | PN | male | 34 | 203 | D |
| MDA834 | GSM96956, GSM97056 | GBM | | 1 | PN | male | 34 | | |
| MDA8662 | S | GBM | | 0 | Mes | male | 14 | 42 | D |
| MDA9392 | GSM97132, GSM97032 | GBM | | 1 | PN | male | 23 | | |
| MDA9642 | GSM97042, GSM97142 | GBM | | 0 | PN | male | 45 | 322 | D |
| MDAN1248 | S | Normal | | | norm | | | | |
| MDAN1486 | S | Normal | | | norm | | | | |
| MDAN1818 | S | Normal | | | norm | | | | |
| MDAN2512 | S | Normal | | | norm | | | | |
| MDAN3114 | S | Normal | | | norm | | | | |
| MDAN3116 | S | Normal | | | norm | | | | |
| MDAN3121 | S | Normal | | | norm | | | | |
| MDAN3122 | S | Normal | | | norm | | | | |
| N21A48 | S | Normal | non-neoplastic epileptic plug | | norm | | | | |
| N3886 | S | Normal | non-neoplastic epileptic plug | | norm | | | | |
| N7A41 | S | Normal | non-neoplastic epileptic plug | | norm | | | | |
| N88A_34 | S | Normal | non-neoplastic epileptic plug | | norm | | | | |
| N99A_36 | S | Normal | non-neoplastic epileptic plug | | norm | | | | |
| NJchip16 | S | Normal | Normal tissue from GBM case | | norm | | | | |
| SF0918 | S | GBM | | | PN | male | 42.4 | 54.9 | D |
| SF0921 | S | GBM | | | Mes | female | 54.5 | 80.3 | D |
| SF1166 | S | GBM | Cerebrum: Frontal lobe | | PN | female | 42.6 | 28.9 | D |

TABLE 1-continued

| Clinical information for tumors in GBM195 | | | | | | | | | |
|---|---|---|---|---|---|---|---|---|---|
| id | GEO_Accessions (U133A/U133B) | Histology | Anat. Site | Recurrence | Phillips Subclass | Gender | Age | Survival Weeks | Censoring Status |
| SF1167 | S | GBM | Cerebrum: Parietal lobe | | PN | female | 46.5 | 692.3 | D |
| SF1198 | S | GBM | | | Unk | male | 54.9 | 18.3 | D |
| SF1368 | S | GBM | Cerebrum: Parietal lobe | | Unk | male | 61.6 | 364.9 | A |
| SF1388 | S | GBM | Cerebrum: Frontal lobe | 1 | PN | female | 29 | 24.7 | D |
| SF1461 | S | GBM | Cerebrum: Frontal lobe | | Unk | male | 54.6 | 33.1 | D |
| SF1475 | S | GBM | | | Unk | female | 42 | 22.3 | D |
| SF1481 | S | GBM | Cerebrum: Parietal lobe | | PN | female | 44.2 | 49 | D |
| SF1547 | S | GBM | Cerebrum: Frontal lobe | | Prolif | female | 35 | 33.6 | D |
| SF1605 | S | GBM | Cerebrum: Frontal Temporal lobe | | Unk | female | 41 | 232 | D |
| SF1653 | S | GBM | Cerebrum: Parietal lobe | | Unk | male | 51.3 | 58.3 | D |
| SF1701 | S | GBM | Cerebrum: Frontal lobe | | PN | male | 66.4 | 503.4 | D |
| SF1750 | S | GBM | Cerebrum: Temporal lobe | | Prolif | female | 45.1 | 67.7 | D |
| SF1751 | S | GBM | Cerebrum: Frontal lobe | | PN | female | 38.3 | 70.4 | D |
| SF1881 | S | GBM | Cerebrum: Frontal lobe | | Mes | male | 54 | 5.3 | D |
| SF1913 | S | GBM | Cerebrum: Temporal lobe | | Mes | male | 47.6 | 82 | D |
| SF2077 | S | GBM | Cerebrum: Frontal lobe | | Unk | male | 66.3 | 141.1 | D |
| SF2159 | S | GBM | Cerebrum: Frontal lobe | | Unk | male | 43.2 | 47 | D |
| SF2167 | S | GBM | Cerebrum: Temporal lobe | | PN | male | 25.5 | 145.7 | D |
| SF2208 | S | GBM | Cerebrum: Parietal lobe | | Unk | female | 50 | 9.1 | D |
| SF2315 | S | GBM | Cerebrum: Frontal lobe | | PN | male | 32.6 | 193 | D |
| SF2399 | S | GBM | Cerebrum: Frontal lobe | | Unk | male | 38.9 | 50.4 | D |
| SF2413 | S | GBM | Cerebrum: Frontal lobe | | PN | female | 50.1 | 226.6 | D |
| SF2434 | S | GBM | Cerebrum: Temporal lobe | | Mes | female | 53.4 | 60.9 | D |
| SF2560 | S | GBM | Cerebrum: Frontal lobe | | Unk | male | 51.7 | 40.3 | D |
| SF2670 | S | GBM | Cerebrum: Temporal lobe | | Mes | male | 51.1 | 31.3 | D |
| SF2703 | S | GBM | Cerebrum: Temporal lobe | 1 | PN | male | 27.6 | 37.7 | D |
| SF2704 | S | GBM | Cerebrum: Frontal lobe | | Mes | male | 54.2 | 103.6 | D |
| SF2737 | S | GBM | Cerebrum: Temporal lobe | | Mes | male | 50 | 38.7 | D |
| SF2760 | S | GBM | Cerebrum: Frontal Temporal lobe | 0 | Mes | male | 47.5 | 97.1 | D |
| SF2774 | S | GBM | Cerebrum: Temporal lobe | | Mes | male | 37.6 | 83 | D |

TABLE 1-continued

| Clinical information for tumors in GBM195 | | | | | | | | | |
|---|---|---|---|---|---|---|---|---|---|
| id | GEO_Accessions (U133A/U133B) | Histology | Anat. Site | Recurrence | Phillips Subclass | Gender | Age | Survival Weeks | Censoring Status |
| SF2777 | S | GBM | Cerebrum: Temporal lobe | | PN | female | 29.3 | 97.9 | D |
| SF2894 | S | GBM | Multifocal | 0 | Mes | male | 44.6 | 14 | D |
| SF2919 | S | GBM | Cerebrum: Frontal lobe | | Unk | male | 44.7 | 46.1 | D |
| SF2935 | S | GBM | Cerebrum: Parietal lobe | 1 | Unk | female | 44.9 | 148 | D |
| SF2969 | S | GBM | Cerebrum: Frontal lobe | | Unk | female | 34.9 | 24.9 | D |
| SF3076 | S | GBM | Cerebrum: Temporal lobe | | Unk | male | 23.7 | 29 | A |

S = submitted to GEO

The following publications have additional clinical or molecular information for some of these tumors: Phillips H S. et al. (2006) *Molecular subclasses of high-grade glioma predict prognosis, delineate a pattern of disease progression, and resemble stages in neurogenesis*. Cancer cell 9: 157-173. AND Freije W A. et al. (2004) *Gene expression profiling of gliomas strongly predicts survival*. Cancer research 64: 6503-6510.

Processing and Analysis of Microarray Data

The PI3K/AKT pathway integrates information on cellular environment, energy status, stress and developmental stage to regulate apoptosis, autophagy, translation, metabolism, stem cell function and cell cycle [20], [22]. This involves multiple sites of crosstalk with other pathways. To capture the full function the inventors generated a gene list that includes upstream and downstream gene products that directly or indirectly regulate or are regulated by AKT. This includes: (1) proteins or members of protein complexes that bind to, modify or regulate activity or subcellular localization of AKT (2) proteins or members of protein complexes phosphorylated or regulated by AKT, (3) proteins known to regulate or be regulated directly or indirectly by AKT (e.g. AKT through MDM2 regulates levels of TP53 protein). These genes were taken from: (1) a database of AKT interacting proteins (BOND [23]), (2) a database of AKT substrates (kinasource.co.uk/Database/substrateList.php) (3) evidence from Pubmed of phosphorylation by AKT (search term AKT, January 2008), (4) evidence from Pubmed that a gene regulates or is regulated by AKT either directly or indirectly (search term AKT, January 2008). Eliminating the genes with low variability across tumors within the discovery dataset left the 69 most variable genes used to classify AKT subgroups in the discovery dataset (Table 2). Five probes were not present in the validation dataset resulting in 64 of 69 AKT pathway genes applied during validation (Table 2). In accordance with the present invention, Table 2 lists non-limiting examples of the various genes that may be used to cluster AKT subgroups to diagnose and define GBM.

TABLE 2

| AKT pathway gene classifiers used for the discovery and validation datasets | | |
|---|---|---|
| discovery Akt pathway gene list | validation Akt pathway gene list | |
| ACLY | ACLY | ATP citrate lyase |
| AKT1 | AKT1 | V-akt murine thymoma viral oncogene homolog 1 |
| ATXN1 | ATXN1 | Ataxin 1 |
| BCL10 | BCL10 | B-cell CLL/lymphoma 10 |
| CCND1 | CCND1 | Cyclin D1 |
| CDC37 | CDC37 | Cell division cycle 37 |
| CDKN1A | CDKN1A | Cyclin-dependent kinase inhibitor 1A (p21, Cip1) |
| CDKN1B | CDKN1B | Cyclin-dependent kinase inhibitor 1B (p27, Kip1) |
| CFD | CFD | Complement factor D (adipsin) |
| CHEK1 | CHEK1 | Checkpoint kinase 1 |
| EGFR | EGFR | Epidermal growth factor receptor |
| EIF3B | EIF3B | Eukaryotic translation initiation factor 3, subunit B |
| EIF3E | EIF3E | Eukaryotic translation initiation factor 3, subunit E |
| EIF3G | EIF3G | Eukaryotic translation initiation factor 3, subunit G |
| EIF3H | EIF3H | Eukaryotic translation initiation factor 3, subunit H |
| EIF4EBP1 | EIF4EBP1 | Eukaryotic translation initiation factor 4E binding protein 1 |
| EPAS1 | EPAS1 | Endothelial PAS domain protein 1 |
| EZH2 | EZH2 | Enhancer of zeste homolog 2 (*Drosophila*) |
| FGFR2 | FGFR2 | Fibroblast growth factor receptor 2 |
| FGFR3 | FGFR3 | Fibroblast growth factor receptor 3 |
| FOXO3 | FOXO3 | Forkhead box 03 |
| FYN | FYN | FYN oncogene related to SRC, FGR, YES |

TABLE 2-continued

AKT pathway gene classifiers used for the discovery and validation datasets

| discovery Akt pathway gene list | validation Akt pathway gene list | |
|---|---|---|
| GAB1 | GAB1 | GRB2-associated binding protein 1 |
| GAB2 | GAB2 | GRB2-associated binding protein 2 |
| GRB10 | GRB10 | Growth factor receptor-bound protein 10 |
| GSK3B | GSK3B | Glycogen synthase kinase 3 beta |
| HIF1A | HIF1A | Hypoxia inducible factor 1, alpha subunit |
| HSP90AB1 | HSP90AB1 | Heat shock protein 90 alpha (cytosolic), class B member 1 |
| HSP90B1 | HSP90B1 | Heat shock protein 90 kDa beta (Grp94), member 1 |
| INPP5D | INPP5D | Inositol polyphosphate-5-phosphatase, 145 kDa |
| IRS1 | IRS1 | Insulin receptor substrate 1 |
| IRS2 | IRS2 | Insulin receptor substrate 2 |
| KDR | KDR | Kinase insert domain receptor (a type III receptor tyrosine kinase) |
| KRAS | KRAS | V-Ki-ras2 Kirsten rat sarcoma viral oncogene homolog |
| MAP3K5 | MAP3K5 | Mitogen-activated protein kinase kinase kinase 5 |
| MAPK8IP1 | MAPK8IP1 | Mitogen-activated protein kinase 8 interacting protein 1 |
| NRAS | NRAS | Neuroblastoma RAS viral (v-ras) oncogene homolog |
| PALLD | PALLD | Palladin, cytoskeletal associated protein |
| PDGFA | PDGFA | Platelet-derived growth factor alpha polypeptide |
| PDGFC | PDGFC | Platelet derived growth factor C |
| PDGFD | PDGFD | Platelet derived growth factor D |
| PDGFRB | PDGFRB | Platelet-derived growth factor receptor, beta polypeptide |
| PDK1 | PDK1 | 3-phosphoinositide dependent protein kinase-1 |
| PHLPP | PHLPP1 | PH domain and leucine rich repeat protein phosphatase 1 |
| PIK3C2B | PIK3C2B | Phosphatidylinositol-4-phosphate 3-kinase, catalytic subunit type 2 beta |
| PIK3CA | PIK3CA | Phosphatidylinositol-4,5-bisphosphate 3-kinase, catalytic subunit alpha |
| PIK3R1 | PIK3R1 | Phosphoinositide-3-kinase, regulatory subunit 1 (alpha) |
| PKD2 | PKD2 | Polycystic kidney disease 2 (autosomal dominant) |
| PKN2 | PKN2 | Protein kinase N2 |
| PPARGC1A | PPARGC1A | Peroxisome proliferator-activated receptor gamma, coactivator 1 alpha |
| PPP2R1A | PPP2R1A | Protein phosphatase 2, regulatory subunit A, alpha |
| PPP2R2B | PPP2R2B | Protein phosphatase 2, regulatory subunit B, beta |
| RAF1 | RAF1 | V-raf-1 murine leukemia viral oncogene homolog 1 |
| SFRS1 | SRSF1 | Serine/arginine-rich splicing factor 1 |
| SORBS2 | SORBS2 | Sorbin and SH3 domain containing 2 |
| SSB | SSB | Sjogren syndrome antigen B (autoantigen La) |
| SYK | SYK | Spleen tyrosine kinase |
| TP53 | TP53 | Tumor protein p53 |
| TRIB3 | TRIB3 | Tribbles homolog 3 (*Drosophila*) |
| TSC1 | TSC1 | Tuberous sclerosis 1 |
| TSC2 | TSC2 | Tuberous sclerosis 2 |
| TWIST1 | TWIST1 | Twist basic helix-loop-helix transcription factor 1 |
| VIM | VIM | Vimentin |
| WNK1 | WNK1 | WNK lysine deficient protein kinase 1 |
| AKT1S1 | | AKT1 substrate 1 (proline-rich) |
| IGF2 | | Insulin-like growth factor 2 (somatomedin A) |
| PPP2R2C | | Protein phosphatase 2, regulatory subunit B, gamma |
| RICTOR | | RPTOR independent companion of MTOR, complex 2 |
| YBX1 | | Y box binding protein 1 |

The inventors isolated patient subgroups in the discovery dataset using RMA normalized and median centered data [24]. The inventors applied consensus k-means clustering with the Pearson's correlation coefficient as the similarity (1-distance) and complete linkage with 10,000 iterations using a sub-sampling ratio of 0.8. The inventors then plotted the consensus distribution function (CDF) to find the optimal number of AKT subgroups [25]. Silhouette width values were computed for each sample [26] and only samples with a positive silhouette width were used in further analyses.

The inventors isolated AKT subgroups in the TCGA validation dataset using raw data preprocessed as described for the discovery dataset. TCGA samples were mapped onto AKT subgroups in the discovery dataset by adapting the k means clustering algorithm. First, the inventors found boundaries for each AKT subgroup in the discovery set by calculating the pairwise correlation coefficients between all samples within a subgroup. The minimum pairwise correlation coefficient was used as the lower boundary for each subgroup. TCGA samples were classified by computing the correlation coefficient between each TCGA and GBM195 sample. TCGA samples were assigned to an AKT subgroup if the average pairwise correlation coefficient with members of the group was greater than the lower boundary of that group. Ties were resolved by selecting the closest cluster.

Analysis of GO Terms

Conventional Gene Ontology (GO) enrichment analysis was dominated by generic GBM biological processes; therefore the inventors used a single-sample approach analogous to the method used by Verhaak and Barbie [10]. To identify GO biological processes enriched within each individual sample the inventors applied the hypergeometric test with Benjamini and Hochberg's correction on all expressed genes (using a two-fold change threshold from the median to determine up- and down-regulated genes). Neurodevelopmental terms enriched in >20% of tumors were considered for analysis.

Analysis of aCGH Data

The GISTIC algorithm [27] was applied to the 456 TCGA samples with copy number information and results visualized using the Integrated Genomic Viewer (IGV) [28] to find copy number alterations (CNA) in the validation set. Broad copy number alterations in the discovery dataset were found as described previously [29] using a customized version of the Sanger CNV database www.sanger.ac.uk/research/areas/humangenetics/cnv. For experiments that compare broad CNA in the discovery and validation dataset the inventors identified broad copy number alterations in the validation dataset as follows. Briefly, the inventors found the average q value (generated from the GISTIC algorithm) for 15 genes spaced evenly across the region of interest. If >50% of genes had a q value less than expected by chance after correcting for multiple testing (q<0.25), that region was called as a copy number alteration.

Reverse Phase Protein Arrays

Level 3 (median centered, normalized, Z transformed) reverse phase protein array (RPPA) data was downloaded from the cBio Cancer Genomics Portal (www.cbioportal.org/public-portal). One hundred and eighty six of the 215 tumors with RPPA data could be assigned to an AKT class and were used for analysis. Correlation coefficients between two antibodies against the same protein were high indicating adequate antibody specificity and pre-processing of data (Pearson correlation coefficient=0.83-0.98 for antibody pairs (GSK3A/B pS9/21, MAPK1, FOXO3, GATA3, S338 p-RAF1).

Statistics

Differences between one subgroup and the rest were assessed using the F test for clinical variables and the likelihood ratio test for categorical variables. The Bonferroni method [30] was applied to correct for multiple hypotheses. The inventors applied the Tukey HSD test to find pairwise differences between groups and correct for multiple comparisons [31]. Survival differences between subgroups were assessed using the Chi-squared test. Age was added to build a multivariate Cox model. For survival comparisons of BCNU/CCNU treatment between subgroups there were not enough observations to correct for age. After deleting all observations younger than 45, survival was no longer related to age. Significance was then determined using log rank. The Pearson goodness-of-fit test was used to assess the null hypothesis that proportions of G-CIMP tumors by subgroup and recurrent tumors by subgroup are equal to the proportions for all tumors by subgroup. P-values for these tests were calculated by Monte Carlo simulation since the counts of tumors by subgroup were too small to apply the large sample chi-square approximation. If the null hypothesis was rejected, then standardized residuals were used to determine which subgroups showed significant differences.

Example 2: AKT Pathway Genes Define 5 Prognostic Subgroups in Glioblastoma

AKT Pathway Gene Expression Divides GBM into at Least Six Subgroups

Figure 1A:
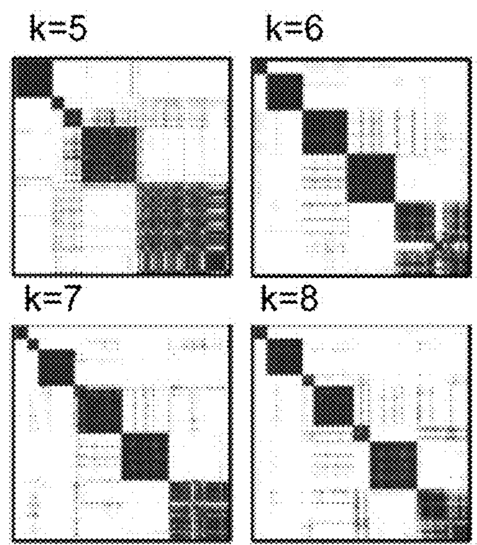
FIGS. 1A-1D depict, in accordance with various embodiments of the invention, that AKT pathway gene expression classifies GBM.
Figure 1B:
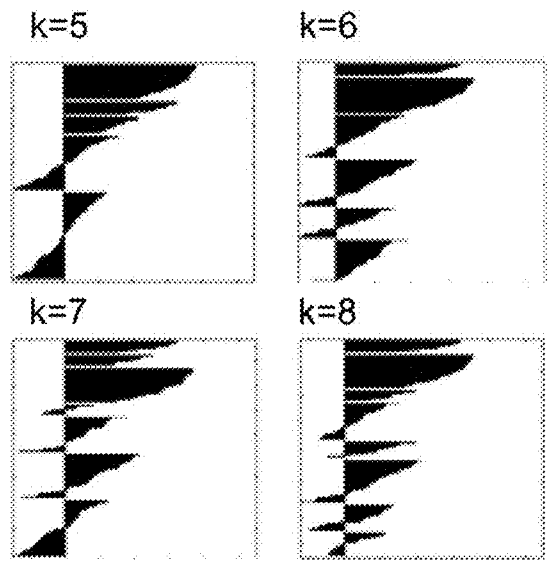
Figure 1C:
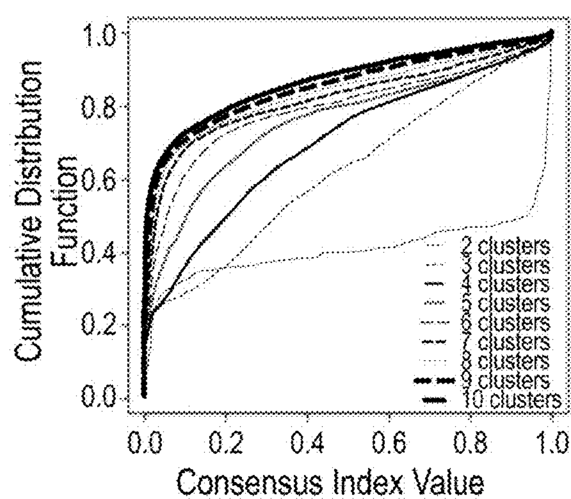

The inventors investigated AKT pathway variations in GBM by developing a list of AKT pathway genes (Table 2) then applying consensus clustering for the number of clusters k=2 to 10 (FIG. 9; FIG. 1A shows results for k=5 to 8). The inventors evaluated cluster stability using the consensus cumulative distribution function (CDF) plot of the consensus index (FIG. 1C) [25]. Cluster stability increased for k=2 to 6 but not appreciably for k>6 (FIG. 1C); suggesting six is the optimum number of GBM AKT subgroups. Silhouette width values were computed for each sample [26] (FIG. 1B) and samples with a positive silhouette width were selected for further analyses.

Figure 1D:
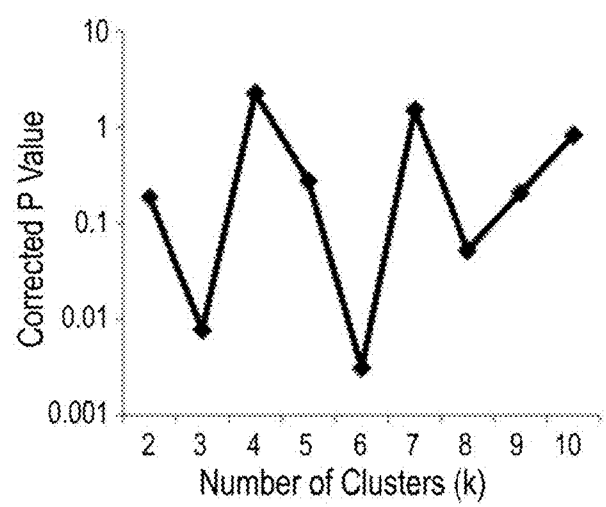

The inventors aim to have a classification system where clinical differences are maximized. Here, the inventors investigated how survival of patient subgroups varies with k. FIG. 1D plots the corrected p value between the longest and shortest surviving subgroups for each k. p values were low for k=3 and 6; k=6 was the lowest (FIG. 1D). This supports the CDF results selecting 6 clusters. The 6 consensus k-means subgroups were named AKT cluster 1 (AKT C1; AKT subgroup 1), AKT proneural (AKT PN; AKT subgroup 2), AKT mesenchymal (AKT MES; AKT subgroup 3), AKT classical (AKT CLAS; AKT subgroup 4), AKT secondary-like (AKT SL; AKT subgroup 5) and AKT proliferative (AKT PROLIF; AKT subgroup 6) based on their molecular and clinical features and prior naming [4], [32].

Validation of AKT Subgroups in an Independent Dataset

The inventors next validated AKT subgroups in an independent dataset of non-overlapping samples. TCGA samples were mapped onto discovery AKT subgroups by assigning a sample to the closest Akt subtype, as described in the methods section. Only two samples were assigned to AKT subgroup C1, therefore this subgroup was dropped from all further analysis. FIGS. 2A-2B compare AKT pathway gene expression in the discovery (FIG. 2A) and validation (FIG. 2B) sets. It shows the pattern of expression of AKT pathway genes within subgroups is similar in both datasets. Interestingly, the PN subgroup in both datasets contained all non-neoplastic samples (not shown). The inventors examined expression of AKT pathway genes in subgroups (FIG. 10 or Table 6). These data show AKT classes arise from complex patterns of gene expression in subgroups. It did not point to a role for a specific part of the AKT pathway within any subgroup.

The inventors next investigated correspondence between copy number alterations (CNA) in AKT subgroups from discovery (FIG. 2C) and validation (FIG. 2D) datasets. The PN subgroup was omitted since it had no CNA information in the discovery dataset. CNA within subgroups were similar in the discovery and validation datasets: a high percentage of tumors with 7 gain/10 loss occurred in every subgroup except SL, the SL subgroup had greater frequency of 19q loss and the CLAS subgroup had increased gain of chr19q relative to the rest. Therefore all subgroup-associated trends in CNA within the discovery dataset were recapitulated in the validation dataset.

TCGA, Phillips and G-CIMP Subgroups Distribute Non-Randomly in AKT Subgroups

Figure 3:
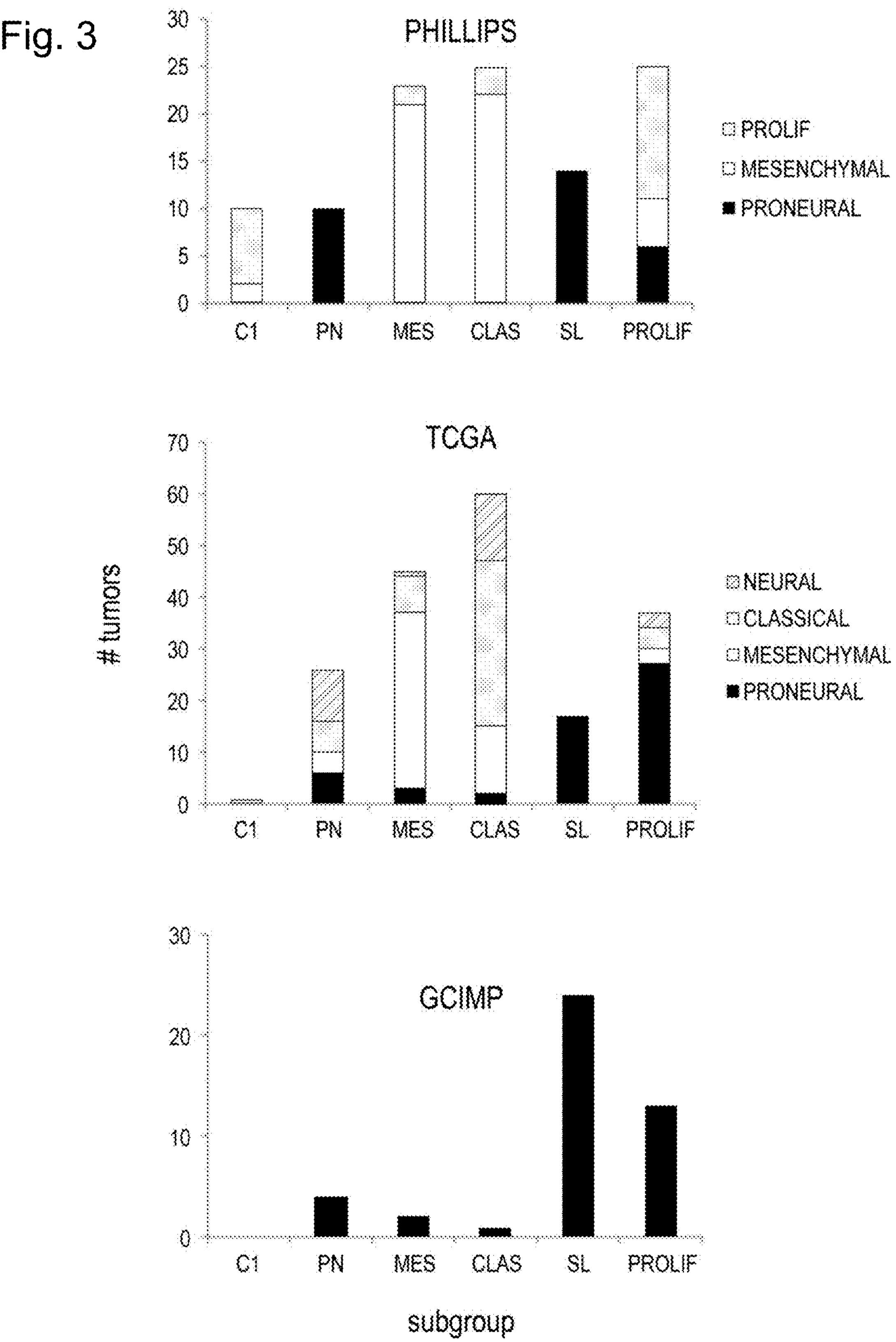
FIG. 3 depicts, in accordance with various embodiments of the invention, Akt classification for 5 glioblastoma subgroups. Previous classification systems distribute non-randomly in AKT subgroups. Distribution of Phillips (top), TCGA (midddle) and G-CIMP (bottom) subgroups in AKT subgroups.

Phillips, TCGA and G-CIMP subgroups distributed non-randomly in AKT subgroups (FIG. 3; FIGS. 12 and 13). There was a tendency for AKT subtyping to split each Phillips subgroup in two. The AKT PN and SL subtypes were significantly enriched in the Phillips PN subtype (FIG. 3, FIGS. 12A and 12B; p<0.5 Bonferroni corrected). The AKT MES and CLAS subtypes were significantly enriched in Phillips MES subtype (FIG. 3, FIGS. 12A and 12B, p<0.5; Bonferroni corrected). The AKT PROLIF subtype was significantly enriched in the Phillips PROLIF subtype (FIG. 3, FIGS. 12A and 12B; p<0.5; Bonferroni corrected). The enrichment of Phillips PROLIF tumors in AKT C1 subtype did not reach significance. AKT subgroups had less concordance with TCGA subgroups [10]. AKT SL and PROLIF subtypes were significantly enriched in TCGA PN subtype; while AKT MES and CL subgroups were enriched in the TCGA MES and CL subtype, respectively (FIG. 3, FIGS. 13A and 13B; p<0.5; Bonferroni corrected). The AKT PN subtype was a mixture of all the TCGA subgroups. The AKT SL and PROLIF subgroups contained the majority of G-CIMP tumors (FIG. 3). Taken together these data show AKT classification divides existing subgroups further.

Patients in the SL Subgroup are Younger and have Longer Survival

Figure 4A:
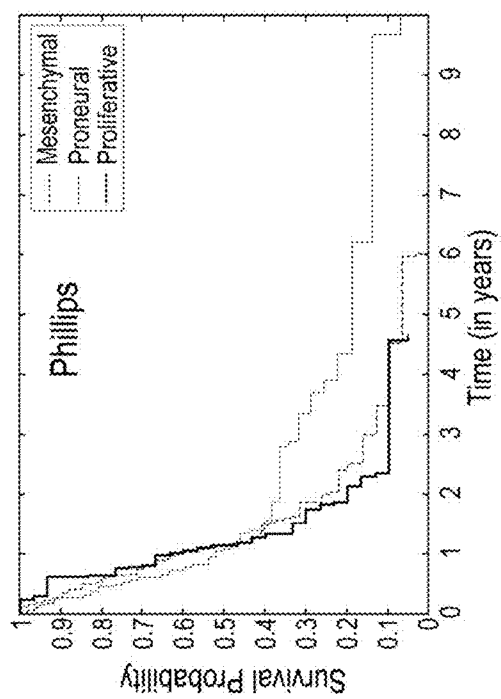
FIGS. 4A-4D depict, in accordance with various embodiments of the invention, that AKT subgroups are prognostic. Kaplan Meier survival curves plotted for Phillips (FIG. 4A) and AKT (FIG. 4B) subgroups in the discovery dataset and for TCGA (FIG. 4C) and AKT (FIG. 4D) subgroups in the validation dataset. Log rank p value=0.0005 (FIG. 4B; SL vs. rest); 0.0029 (B; PROLIF vs. rest) and 0.003 (FIG. 4D; SL vs rest). Survival differences did not reach significance in (FIG. 4A) and (FIG. 4C).
Figure 4B:
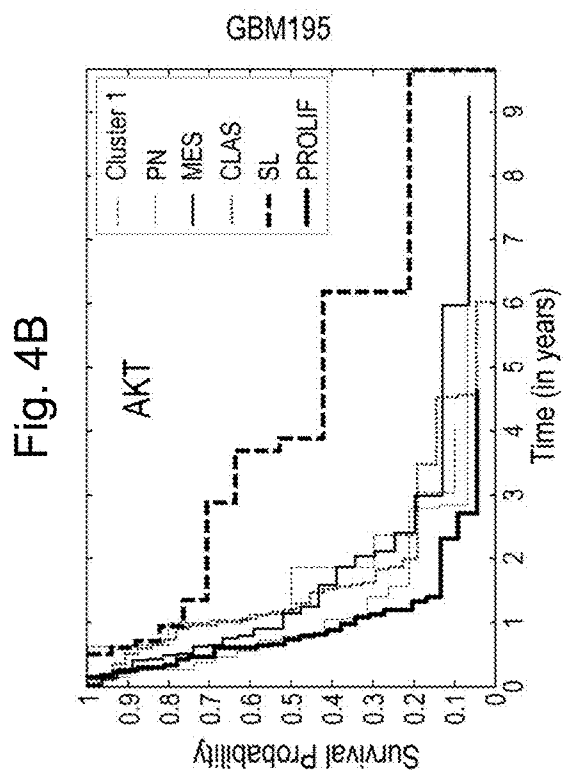
Figure 4C:
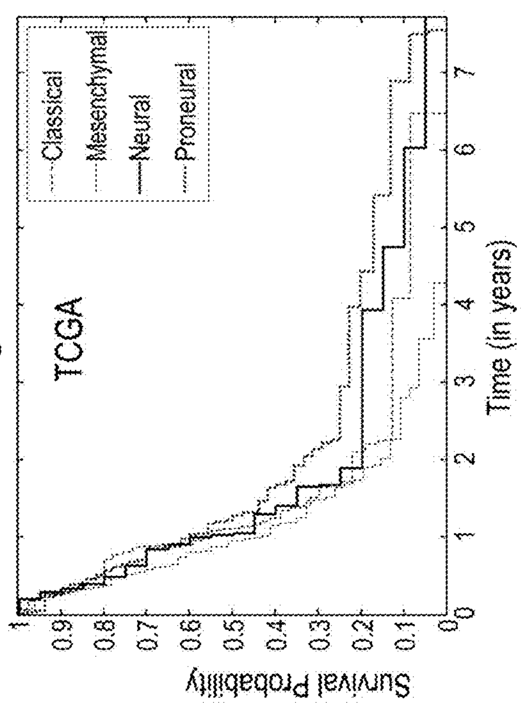
Figure 4D:
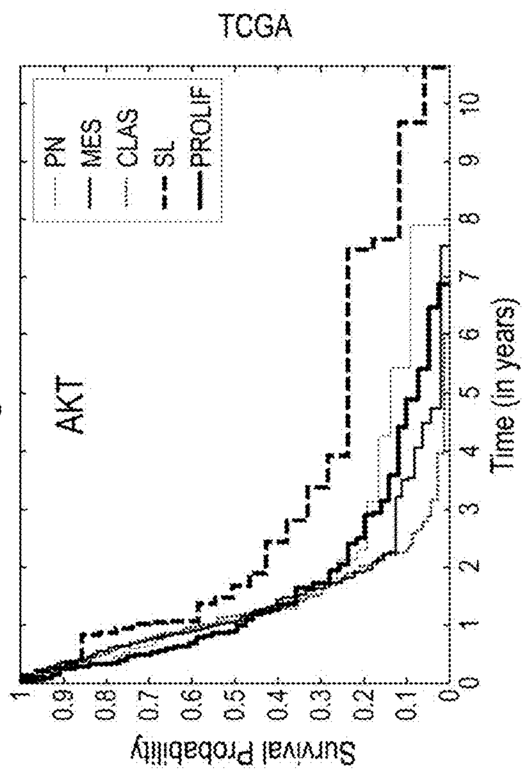

AKT subgroups have different clinical characteristics (FIGS. 4B and D; FIGS. 12 and 13). SL patients in the discovery dataset had longer median survival (3.9 vs. 1.05 yrs.; p=0.0005; FIG. 4B; SL vs. the rest) and were younger (median age=38 vs. 49; SL vs. total; p=0.05 using Tukey HSD test to correct for multiple comparisons; FIGS. 12A and 12B). After adjusting for age in Cox multivariate analysis, SL status remained a significant predictor of survival (p=0.027; SL vs. the rest). The PROLIF subgroup had statistically significant shorter survival than the rest (0.75 vs. 1.25 yrs.; p=0.0029; FIG. 4B) although age of these patients was not different than all patients (median age=49 vs. 49 years; PROLIF vs. total; FIGS. 12A and 12B). Although the magnitude was diminished, a similar trend was observed for SL patients in the validation dataset for survival (1.67 vs. 1.1 yrs.; p=0.003 SL vs. rest; FIG. 4D) and age (median age=49 vs. 59 yrs.; p=0.07; SL vs. total, FIGS. 13A and 13B) although the age difference was not statistically significant. In comparison, patient subgroups defined using Phillips (FIG. 4A) and TCGA (FIG. 4C) methods using the same database have no statistically significant differences in survival.

Consistent with the less aggressive character of SL tumors, there was a trend toward decreased endothelial proliferation (46% vs. 66%; p=0.017 vs. rest; uncorrected), and palisading necrosis (10% vs. 51%; p=0.07 vs. rest; uncorrected) in the validation dataset (FIGS. 13A and 13B). There were similar trends in the discovery set although they also did not reach significance (FIGS. 12A and 12B). Taken together these data show subgroups in the discovery and validation datasets have similar clinical features. It also shows AKT subtypes have distinct clinical characteristics.

Evidence AKT Subtyping is a Predictive Marker for Sensitivity to BCNU/CCNU

Figure 5:
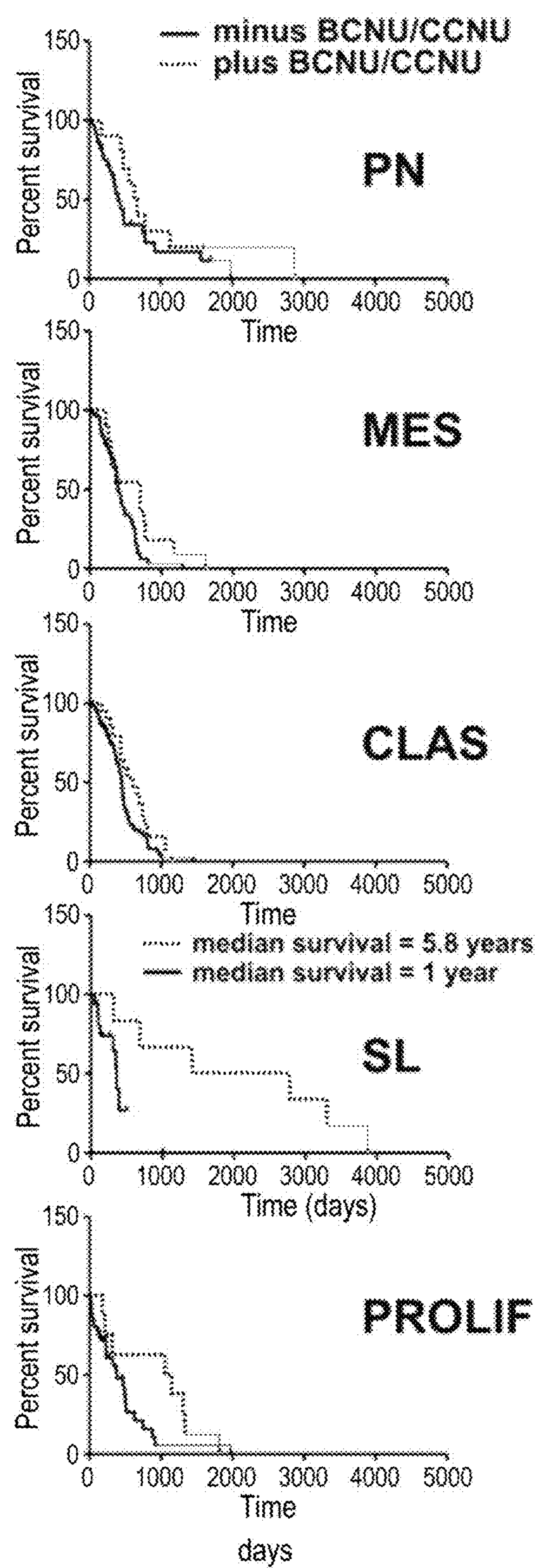
FIG. 5 depicts, in accordance with various embodiments of the invention, evidence that SL subtype (AKT subgroup 5) patients are sensitive to alkylating agents BCNU and CCNU. Kaplan Meier survival curves for TCGA patients receiving (solid line) or not receiving (dashed line) alkylating agent (BCNU and/or CCNU) by subgroup. p=0.03 after correcting for age (SL subtype; log rank). n=6 and 16 for SL patients receiving or not receiving BCNU/CCNU, respectively.

Survival differences between subgroups suggest AKT subtypes are either prognostic or predictive (forecasts tumor aggressiveness or response to therapy, respectively). Since AKT influences response to chemotherapy [33], while not wishing to be bound by any theory, the inventors believe AKT subgroups are predictive markers. Indeed, TCGA SL patients treated with BCNU or CCNU had longer median survival than those receiving other treatments (FIG. 5; median survival=5.8 vs. 1.05 years; p=0.03 after correcting for age; log rank). Those receiving BCNU or CCNU were older and had less IDH1 mutations than those that didn't (median age=54 vs. 49 years; % with IDH1 mutations=17% vs. 32%; with vs. without BCNU/CCNU respectively); indicating age and IDH1 mutation status do not account their increased survival. This finding indicates patients in the SL subgroup are sensitive to BCNU and CCNU.

Subgroups have Distinct Genomic Alterations

Figure 6A:
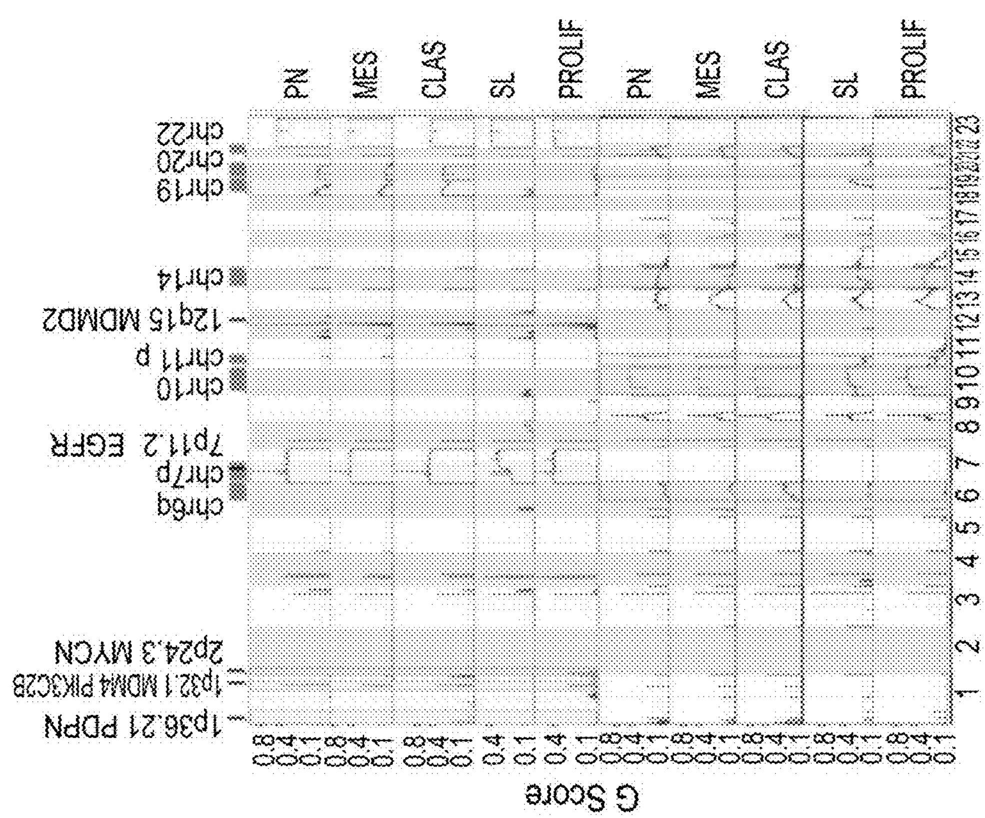

The inventors used TCGA data to investigate how molecular alterations partition in subgroups. All subgroups had unique broad (FIG. 6A; FIG. 11) and/or focal (FIGS. 14 and 15) DNA CNA. The CLAS subtype was enriched in broad CNA previously associated with more aggressive tumors such as loss of chromosome regions 6q and gain of 19q and 20q [34] (FIG. 6A). The SL subtype was enriched in broad CNA associated with better prognosis (loss of 19q; FIG. 6A) [34]. Each subgroup had unique focal CNA (FIGS. 14 and 15). This data shows AKT subtyping groups tumors with similar molecular characteristics.

An integrated analysis of mutations, CNA and mRNA expression in glioma-associated genes shows some AKT subgroups had similar features as TCGA subgroups (FIG. 6B). The AKT CLAS subgroup was significantly enriched in alterations in EGFR and CDKN2A similar to TCGA CLAS subgroup [10]. The AKT MES subtype was characterized by mutations in NF1 and RB1 and increased mRNA for the mesenchymal marker, MET, similar to the TCGA MES subgroup [10], although these did not reach statistical significance. The SL subtype was enriched in IDH1 mutations (42% vs 3% SL vs. rest) and GCIMP (47% vs. 4%; SL vs. rest) although only the enrichment in IDH1 mutant tumors was significant. The PROLIF subtype was also slightly enriched in IDH1 mutations (11%) in this dataset containing 218 validated samples. However that dropped to 7% when considering all TCGA tumors with IDH1 mutation information (not shown). Both the SL and PROLIF subgroups were also enriched in alterations found more frequently in secondary tumors including TP53 mutations and increased mRNA and CN gains for PDGFRA. The PROLIF was distinguished from SL subtype by an increase in mutations and copy number alterations in EGFR and CDKN2A (FIG. 6B) and enrichment in recurrent tumors (18% vs 8%; PROLIF vs rest; FIGS. 13A and 13B). Genomic alterations in other RTK/RAS/PI3K/AKT pathway members were either not significantly enriched in any subgroup (PTEN, PIK3R1, MET, SPRY2; FIG. 6B) or the frequency was too low to evaluate (ERBB2, KRAS, NRAS, HRAS, PIK3CA, FOXO1, FOXO3, AKT1, AKT2, AKT3; not shown); although MET mRNA was enriched and SPRY2 mRNA was low in the MES and CLAS subtypes, respectively (FIG. 6B). Taken together these data suggest involvement of oncogenic and tumor suppressor pathways can differ between subgroups.

Subgroups have Distinct Patterns of Expression for PI3K/AKT/mTOR Components

The inventors find subgroups have distinct patterns of expression of mRNA (FIG. 7A), protein and phosphoproteins (FIG. 7B) for PI3K/AKT/mTOR pathway components. The most notable patterns were in the MES and SL subgroups. The MES subtype had decreased expression for inhibitors of mTOR, AKT and PI3K (TSC2 and p-AMPK protein; TSC1, TSC2, PHLPP1, PHLPP2 and PI3KR1 message). Consistent with increased activity of the AKT/mTOR/S6 axis, this subgroup also had elevated p-S6 (FIG. 7B) and a high positive correlation between p-AKT and p-S6 (FIG. 7C). The long surviving SL subgroup had the opposite pattern of expression; high expression of AKT and mTOR inhibitors (FIGS. 7A and B), decreased expression of pS6 (FIG. 7B) and lower correlation between pAKT and pS6 (FIG. 7C). The inventors' proposed pathway map for the MES and SL subgroups (7D) based on this data posits how expression of pathway inhibitors affects output of the AKT/mTOR/S6 axis. This data indicates subgroups will have different sensitivities to pathway inhibitors.

GO Terms Suggest Subgroups have a Different Dominant Biological Process and Cell of Origin The inventors used Gene Ontology (GO) to investigate the biological role of genes expressed in tumors and how terms partition in subgroups. Each subgroup, except CLAS, had a high percentage of tumors with functionally related terms that suggested a different dominate biological process (Table 3). The CLAS subgroup had a mixture of terms. Each subgroup also had GO terms associated with neurodevelopment (Table 3; highlighted with bolded text; summarized in FIG. 8B). The PN and CLAS subgroups had only terms associated with neurogenesis suggesting a committed neural precursor cell of origin. The MES, SL and PROLIF subgroups had terms associated with both neuro- and gliogenesis suggesting a stem cell or early uncommitted progenitor cell of origin. These data suggest the cell of origin and dominant biological process can differ in subgroups.

TABLE 3

GO term analysis of genes differentially expressed in subgroups

| Proportion of Samples | Biological Process | Biological Process Name |
|---|---|---|
| | | C1 (2 Samples) |
| 100% | GO: 0000087 | M phase of mitotic cell cycle |
| 100% | GO: 0000236 | mitotic prometaphase |
| 100% | GO: 0000278 | mitotic cell cycle |
| 100% | GO: 0000279 | M phase |
| 100% | GO: 0000280 | nuclear division |
| 100% | GO: 0007067 | mitosis |
| 100% | GO: 0022402 | cell cycle process |
| 100% | GO: 0022403 | cell cycle phase |
| 100% | GO: 0048285 | organelle fission |
| 50% | GO: 0006336 | DNA replication-independent nucleosome assembly |
| 50% | GO: 0007051 | spindle organization |
| 50% | GO: 0007059 | chromosome segregation |
| 50% | GO: 0007091 | mitotic metaphase/anaphase transition |
| 50% | GO: 0007094 | mitotic cell cycle spindle assembly checkpoint |
| 50% | GO: 0030071 | regulation of mitotic metaphase/anaphase transition |
| 50% | GO: 0031055 | chromatin remodeling at centromere |
| 50% | GO: 0031577 | spindle checkpoint |
| 50% | GO: 0034080 | CenH3-containing nucleosome assembly at centromere |
| 50% | GO: 0034724 | DNA replication-independent nucleosome organization |
| 50% | GO: 0043486 | histone exchange |
| 50% | GO: 0045841 | negative regulation of mitotic metaphase/anaphase transition |
| 50% | GO: 0046826 | negative regulation of protein export from nucleus |
| 50% | GO: 0051301 | cell division |
| 50% | GO: 0051983 | regulation of chromosome segregation |
| 50% | GO: 0071173 | spindle assembly checkpoint |
| 50% | GO: 0071174 | mitotic cell cycle spindle checkpoint |
| | | PN (30 Samples) |
| 100% | GO: 0001505 | regulation of neurotransmitter levels |
| 100% | GO: 0003001 | generation of a signal involved in cell-cell signaling |
| 100% | GO: 0006836 | neurotransmitter transport |
| 100% | GO: 0007268 | synaptic transmission |
| 100% | GO: 0007269 | neurotransmitter secretion |
| 100% | GO: 0014047 | glutamate secretion |
| 100% | GO: 0019226 | transmission of nerve impulse |
| 100% | GO: 0023061 | signal release |
| 100% | GO: 0035637 | multicellular organismal signaling |
| 100% | GO: 0048489 | synaptic vesicle transport |
| 97% | GO: 0007267 | cell-cell signaling |
| 97% | GO: 0031644 | regulation of neurological system process |
| 97% | GO: 0050877 | neurological system process |
| 97% | GO: 0051969 | regulation of transmission of nerve impulse |
| 93% | GO: 0050804 | regulation of synaptic transmission |
| **90%** | **GO: 0007399** | **nervous system development** |
| 90% | GO: 0016079 | synaptic vesicle exocytosis |
| 87% | GO: 0032940 | secretion by cell |
| 83% | GO: 0048167 | regulation of synaptic plasticity |
| **80%** | **GO: 0022008** | **neurogenesis** |
| **80%** | **GO: 0030182** | **neuron differentiation** |
| **77%** | **GO: 0048667** | **cell morphogenesis involved in neuron differentiation** |
| **77%** | **GO: 0048699** | **generation of neurons** |
| 77% | GO: 0048812 | neuron projection morphogenesis |
| 73% | GO: 0007409 | axonogenesis |
| 73% | GO: 0031175 | neuron projection development |
| **73%** | **GO: 0048666** | **neuron development** |
| 67% | GO: 0000904 | cell morphogenesis involved in differentiation |
| 63% | GO: 0007611 | learning or memory |
| 63% | GO: 0030030 | cell projection organization |
| 63% | GO: 0048858 | cell projection morphogenesis |
| 60% | GO: 0003008 | system process |
| 60% | GO: 0032990 | cell part morphogenesis |
| 60% | GO: 0048488 | synaptic vesicle endocytosis |
| 57% | GO: 0042391 | regulation of membrane potential |
| 57% | GO: 0046903 | secretion |
| 57% | GO: 0050890 | cognition |
| 53% | GO: 0007612 | learning |
| 50% | GO: 0006887 | exocytosis |
| 50% | GO: 0007214 | gamma-aminobutyric acid signaling pathway |

TABLE 3-continued

GO term analysis of genes differentially expressed in subgroups

| Proportion of Samples | Biological Process | Biological Process Name |
|---|---|---|
| 47% | GO: 0044057 | regulation of system process |
| 47% | GO: 0048168 | regulation of neuronal synaptic plasticity |
| 47% | GO: 0050773 | regulation of dendrite development |
| 43% | GO: 0002504 | antigen processing and presentation of peptide or polysaccharide antigen via MHC class II |
| 43% | GO: 0007610 | behavior |
| 40% | GO: 0000902 | cell morphogenesis |
| 40% | GO: 0051899 | membrane depolarization |
| 40% | GO: 0060333 | interferon-gamma-mediated signaling pathway |
| 37% | GO: 0090072 | positive regulation of sodium ion transport via voltage-gated sodium channel activity |
| 33% | GO: 0010243 | response to organic nitrogen |
| 33% | GO: 0060627 | regulation of vesicle-mediated transport |
| 30% | GO: 0007272 | ensheathment of neurons |
| 30% | GO: 0008366 | axon ensheathment |
| 30% | GO: 0071346 | cellular response to interferon-gamma |
| 27% | GO: 0017157 | regulation of exocytosis |
| 27% | GO: 0032989 | cellular component morphogenesis |
| 27% | GO: 0034341 | response to interferon-gamma |
| 27% | GO: 0042552 | myelination |
| 23% | GO: 0001508 | regulation of action potential |
| 23% | GO: 0019228 | regulation of action potential in neuron |
| 23% | GO: 0051592 | response to calcium ion |
| 23% | GO: 0055082 | cellular chemical homeostasis |
| 20% | GO: 0006873 | cellular ion homeostasis |
| 20% | GO: 0010975 | regulation of neuron projection development |
| 17% | GO: 0006821 | chloride transport |
| 17% | GO: 0010970 | microtubule-based transport |
| 17% | GO: 0048468 | cell development |
| 13% | GO: 0006413 | translational initiation |
| 13% | GO: 0006415 | translational termination |
| 13% | GO: 0006614 | SRP-dependent cotranslational protein targeting to membrane |
| 13% | GO: 0008088 | axon cargo transport |
| 13% | GO: 0015698 | inorganic anion transport |
| 13% | GO: 0019080 | viral genome expression |
| 13% | GO: 0019083 | viral transcription |
| 13% | GO: 0019725 | cellular homeostasis |
| 13% | GO: 0043241 | protein complex disassembly |
| 13% | GO: 0043624 | cellular protein complex disassembly |
| 13% | GO: 0045047 | protein targeting to ER |
| 13% | GO: 0060079 | regulation of excitatory postsynaptic membrane potential |
| 13% | GO: 0060314 | regulation of ryanodine-sensitive calcium-release channel activity |
| 13% | GO: 0070972 | protein localization in endoplasmic reticulum |
| 13% | GO: 0072599 | establishment of protein localization in endoplasmic reticulum |
| 10% | GO: 0002480 | antigen processing and presentation of exogenous peptide antigen via MHC class I, TAP-independent |
| 10% | GO: 0006414 | translational elongation |
| 10% | GO: 0006612 | protein targeting to membrane |
| 10% | GO: 0006613 | cotranslational protein targeting to membrane |
| 10% | GO: 0009263 | deoxyribonucleotide biosynthetic process |
| 10% | GO: 0010001 | glial cell differentiation |
| 10% | GO: 0014075 | response to amine stimulus |
| 10% | GO: 0019058 | viral infectious cycle |
| 10% | GO: 0022411 | cellular component disassembly |
| 10% | GO: 0023052 | signaling |
| 10% | GO: 0030001 | metal ion transport |
| 10% | GO: 0030168 | platelet activation |
| 10% | GO: 0030705 | cytoskeleton-dependent intracellular transport |
| 10% | GO: 0031344 | regulation of cell projection organization |
| 10% | GO: 0031646 | positive regulation of neurological system process |
| 10% | GO: 0032984 | macromolecular complex disassembly |
| 10% | GO: 0034623 | cellular macromolecular complex disassembly |
| 10% | GO: 0042063 | gliogenesis |
| 10% | GO: 0048709 | oligodendrocyte differentiation |
| 10% | GO: 0050805 | negative regulation of synaptic transmission |
| 10% | GO: 0050806 | positive regulation of synaptic transmission |
| 10% | GO: 0051049 | regulation of transport |
| 10% | GO: 0051823 | regulation of synapse structural plasticity |
| 10% | GO: 0051971 | positive regulation of transmission of nerve impulse |
| 10% | GO: 0071417 | cellular response to organic nitrogen |
| 10% | GO: 0071418 | cellular response to amine stimulus |
| 10% | GO: 0071845 | cellular component disassembly at cellular level |
| 10% | GO: 0072594 | establishment of protein localization to organelle |
| 7% | GO: 0000184 | nuclear-transcribed mRNA catabolic process, nonsense-mediated decay |
| 7% | GO: 0002495 | antigen processing and presentation of peptide antigen via MHC class II |

TABLE 3-continued

GO term analysis of genes differentially expressed in subgroups

| Proportion of Samples | Biological Process | Biological Process Name |
|---|---|---|
| 7% | GO: 0006820 | anion transport |
| 7% | GO: 0007154 | cell communication |
| 7% | GO: 0014003 | oligodendrocyte development |
| 7% | GO: 0015800 | acidic amino acid transport |
| 7% | GO: 0016081 | synaptic vesicle docking involved in exocytosis |
| 7% | GO: 0017156 | calcium ion-dependent exocytosis |
| 7% | GO: 0019886 | antigen processing and presentation of exogenous peptide antigen via MHC class II |
| 7% | GO: 0022010 | central nervous system myelination |
| 7% | GO: 0022415 | viral reproductive process |
| 7% | GO: 0030224 | monocyte differentiation |
| 7% | GO: 0031111 | negative regulation of microtubule polymerization or depolymerization |
| 7% | GO: 0032291 | axon ensheathment in central nervous system |
| 7% | GO: 0034340 | response to type I interferon |
| 7% | GO: 0042274 | ribosomal small subunit biogenesis |
| 7% | GO: 0043090 | amino acid import |
| 7% | GO: 0043092 | L-amino acid import |
| 7% | GO: 0048169 | regulation of long-term neuronal synaptic plasticity |
| 7% | GO: 0060337 | type I interferon-mediated signaling pathway |
| 7% | GO: 0065008 | regulation of biological quality |
| 7% | GO: 0071229 | cellular response to acid |
| 7% | GO: 0071357 | cellular response to type I interferon |
| 3% | GO: 0000956 | nuclear-transcribed mRNA catabolic process |
| 3% | GO: 0001101 | response to acid |
| 3% | GO: 0001504 | neurotransmitter uptake |
| 3% | GO: 0001766 | membrane raft polarization |
| 3% | GO: 0001915 | negative regulation of T cell mediated cytotoxicity |
| 3% | GO: 0002237 | response to molecule of bacterial origin |
| 3% | GO: 0002246 | wound healing involved in inflammatory response |
| 3% | GO: 0002250 | adaptive immune response |
| 3% | GO: 0002252 | immune effector process |
| 3% | GO: 0002253 | activation of immune response |
| 3% | GO: 0002376 | immune system process |
| 3% | GO: 0002429 | immune response-activating cell surface receptor signaling pathway |
| 3% | GO: 0002443 | leukocyte mediated immunity |
| 3% | GO: 0002449 | lymphocyte mediated immunity |
| 3% | GO: 0002455 | humoral immune response mediated by circulating immunoglobulin |
| 3% | GO: 0002460 | adaptive immune response based on somatic recombination of immune receptors built from immunoglobulin superfamily domains |
| 3% | GO: 0002474 | antigen processing and presentation of peptide antigen via MHC class I |
| 3% | GO: 0002478 | antigen processing and presentation of exogenous peptide antigen |
| 3% | GO: 0002479 | antigen processing and presentation of exogenous peptide antigen via MHC class I, TAP-dependent |
| 3% | GO: 0002682 | regulation of immune system process |
| 3% | GO: 0002683 | negative regulation of immune system process |
| 3% | GO: 0002684 | positive regulation of immune system process |
| 3% | GO: 0002685 | regulation of leukocyte migration |
| 3% | GO: 0002686 | negative regulation of leukocyte migration |
| 3% | GO: 0002688 | regulation of leukocyte chemotaxis |
| 3% | GO: 0002689 | negative regulation of leukocyte chemotaxis |
| 3% | GO: 0002694 | regulation of leukocyte activation |
| 3% | GO: 0002696 | positive regulation of leukocyte activation |
| 3% | GO: 0002757 | immune response-activating signal transduction |
| 3% | GO: 0002764 | immune response-regulating signaling pathway |
| 3% | GO: 0002768 | immune response-regulating cell surface receptor signaling pathway |
| 3% | GO: 0006401 | RNA catabolic process |
| 3% | GO: 0006402 | mRNA catabolic process |
| 3% | GO: 0006412 | translation |
| 3% | GO: 0006605 | protein targeting |
| 3% | GO: 0006826 | iron ion transport |
| 3% | GO: 0006886 | intracellular protein transport |
| 3% | GO: 0006935 | chemotaxis |
| 3% | GO: 0006952 | defense response |
| 3% | GO: 0006954 | inflammatory response |
| 3% | GO: 0006955 | immune response |
| 3% | GO: 0006956 | complement activation |
| 3% | GO: 0006958 | complement activation, classical pathway |
| 3% | GO: 0006959 | humoral immune response |
| 3% | GO: 0007026 | negative regulation of microtubule depolymerization |
| 3% | GO: 0007417 | central nervous system development |
| 3% | GO: 0009265 | 2'-deoxyribonucleotide biosynthetic process |
| 3% | GO: 0009607 | response to biotic stimulus |
| 3% | GO: 0009611 | response to wounding |
| 3% | GO: 0009615 | response to virus |
| 3% | GO: 0009617 | response to bacterium |

TABLE 3-continued

| GO term analysis of genes differentially expressed in subgroups | | |
|---|---|---|
| Proportion of Samples | Biological Process | Biological Process Name |
| 3% | GO: 0009914 | hormone transport |
| 3% | GO: 0015682 | ferric iron transport |
| 3% | GO: 0015813 | L-glutamate transport |
| 3% | GO: 0015988 | energy coupled proton transport, against electrochemical gradient |
| 3% | GO: 0015991 | ATP hydrolysis coupled proton transport |
| 3% | GO: 0016064 | immunoglobulin mediated immune response |
| 3% | GO: 0016188 | synaptic vesicle maturation |
| 3% | GO: 0019724 | B cell mediated immunity |
| 3% | GO: 0019882 | antigen processing and presentation |
| 3% | GO: 0019884 | antigen processing and presentation of exogenous antigen |
| 3% | GO: 0021675 | nerve development |
| 3% | GO: 0021782 | glial cell development |
| 3% | GO: 0030198 | extracellular matrix organization |
| 3% | GO: 0030199 | collagen fibril organization |
| 3% | GO: 0030334 | regulation of cell migration |
| 3% | GO: 0030534 | adult behavior |
| 3% | GO: 0030595 | leukocyte chemotaxis |
| 3% | GO: 0031102 | neuron projection regeneration |
| 3% | GO: 0031114 | regulation of microtubule depolymerization |
| 3% | GO: 0031294 | lymphocyte costimulation |
| 3% | GO: 0031295 | T cell costimulation |
| 3% | GO: 0031345 | negative regulation of cell projection organization |
| 3% | GO: 0031580 | membrane raft distribution |
| 3% | GO: 0031645 | negative regulation of neurological system process |
| 3% | GO: 0032101 | regulation of response to external stimulus |
| 3% | GO: 0032103 | positive regulation of response to external stimulus |
| 3% | GO: 0032496 | response to lipopolysaccharide |
| 3% | GO: 0033124 | regulation of GTP catabolic process |
| 3% | GO: 0033365 | protein localization to organelle |
| 3% | GO: 0033572 | transferrin transport |
| 3% | GO: 0034097 | response to cytokine stimulus |
| 3% | GO: 0040012 | regulation of locomotion |
| 3% | GO: 0042330 | taxis |
| 3% | GO: 0042493 | response to drug |
| 3% | GO: 0042590 | antigen processing and presentation of exogenous peptide antigen via MHC class I |
| 3% | GO: 0042592 | homeostatic process |
| 3% | GO: 0043062 | extracellular structure organization |
| 3% | GO: 0043087 | regulation of GTPase activity |
| 3% | GO: 0043200 | response to amino acid stimulus |
| 3% | GO: 0043242 | negative regulation of protein complex disassembly |
| 3% | GO: 0043368 | positive T cell selection |
| 3% | GO: 0045059 | positive thymic T cell selection |
| 3% | GO: 0045061 | thymic T cell selection |
| 3% | GO: 0045087 | innate immune response |
| 3% | GO: 0045163 | clustering of voltage-gated potassium channels |
| 3% | GO: 0045663 | positive regulation of myoblast differentiation |
| 3% | GO: 0045730 | respiratory burst |
| 3% | GO: 0045766 | positive regulation of angiogenesis |
| 3% | GO: 0046928 | regulation of neurotransmitter secretion |
| 3% | GO: 0048002 | antigen processing and presentation of peptide antigen |
| 3% | GO: 0048015 | phosphatidylinositol-mediated signaling |
| 3% | GO: 0048017 | inositol lipid-mediated signaling |
| 3% | GO: 0048583 | regulation of response to stimulus |
| 3% | GO: 0048584 | positive regulation of response to stimulus |
| 3% | GO: 0048678 | response to axon injury |
| 3% | GO: 0048731 | system development |
| 3% | GO: 0048878 | chemical homeostasis |
| 3% | GO: 0050776 | regulation of immune response |
| 3% | GO: 0050778 | positive regulation of immune response |
| 3% | GO: 0050795 | regulation of behavior |
| 3% | GO: 0050801 | ion homeostasis |
| 3% | GO: 0050851 | antigen receptor-mediated signaling pathway |
| 3% | GO: 0050863 | regulation of T cell activation |
| 3% | GO: 0050865 | regulation of cell activation |
| 3% | GO: 0050867 | positive regulation of cell activation |
| 3% | GO: 0050870 | positive regulation of T cell activation |
| 3% | GO: 0050920 | regulation of chemotaxis |
| 3% | GO: 0050921 | positive regulation of chemotaxis |
| 3% | GO: 0051050 | positive regulation of transport |
| 3% | GO: 0051056 | regulation of small GTPase mediated signal transduction |
| 3% | GO: 0051129 | negative regulation of cellular component organization |
| 3% | GO: 0051239 | regulation of multicellular organismal process |
| 3% | GO: 0051249 | regulation of lymphocyte activation |
| 3% | GO: 0051665 | membrane raft localization |

TABLE 3-continued

| GO term analysis of genes differentially expressed in subgroups | | |
|---|---|---|
| Proportion of Samples | Biological Process | Biological Process Name |
| 3% | GO: 0051707 | response to other organism |
| 3% | GO: 0051938 | L-glutamate import |
| 3% | GO: 0051970 | negative regulation of transmission of nerve impulse |
| 3% | GO: 0060078 | regulation of postsynaptic membrane potential |
| 3% | GO: 0060326 | cell chemotaxis |
| 3% | GO: 0060384 | innervation |
| 3% | GO: 0070098 | chemokine-mediated signaling pathway |
| 3% | GO: 0071205 | protein localization to juxtaparanode region of axon |
| 3% | GO: 0071219 | cellular response to molecule of bacterial origin |
| 3% | GO: 0071222 | cellular response to lipopolysaccharide |
| 3% | GO: 0071230 | cellular response to amino acid stimulus |
| 3% | GO: 0071402 | cellular response to lipoprotein particle stimulus |
| 3% | GO: 0072012 | glomerulus vasculature development |
| 3% | GO: 0072239 | metanephric glomerulus vasculature development |
| 3% | GO: 0090025 | regulation of monocyte chemotaxis |
| 3% | GO: 2000145 | regulation of cell motility |
| 3% | GO: 2000300 | regulation of synaptic vesicle exocytosis |
| MES (34 Samples) | | |
| 68% | GO: 0006952 | defense response |
| 68% | GO: 0009611 | response to wounding |
| 65% | GO: 0006955 | immune response |
| 65% | GO: 0045087 | innate immune response |
| 62% | GO: 0002376 | immune system process |
| 62% | GO: 0051707 | response to other organism |
| 59% | GO: 0006954 | inflammatory response |
| 59% | GO: 0007155 | cell adhesion |
| 59% | GO: 0009607 | response to biotic stimulus |
| 59% | GO: 0022610 | biological adhesion |
| 56% | GO: 0002504 | antigen processing and presentation of peptide or polysaccharide antigen via MHC class II |
| 56% | GO: 0009617 | response to bacterium |
| 56% | GO: 0034341 | response to interferon-gamma |
| 53% | GO: 0002250 | adaptive immune response |
| 53% | GO: 0002460 | adaptive immune response based on somatic recombination of immune receptors built from immunoglobulin superfamily domains |
| 53% | GO: 0006956 | complement activation |
| 53% | GO: 0006959 | humoral immune response |
| 53% | GO: 0016064 | immunoglobulin mediated immune response |
| 53% | GO: 0019724 | B cell mediated immunity |
| 53% | GO: 0030198 | extracellular matrix organization |
| 53% | GO: 0043062 | extracellular structure organization |
| 53% | GO: 0045765 | regulation of angiogenesis |
| 53% | GO: 0050900 | leukocyte migration |
| 50% | GO: 0002237 | response to molecule of bacterial origin |
| 50% | GO: 0002252 | immune effector process |
| 50% | GO: 0002253 | activation of immune response |
| 50% | GO: 0006950 | response to stress |
| 50% | GO: 0032496 | response to lipopolysaccharide |
| 50% | GO: 0034097 | response to cytokine stimulus |
| 50% | GO: 0040011 | locomotion |
| 50% | GO: 0071346 | cellular response to interferon-gamma |
| 47% | GO: 0001568 | blood vessel development |
| 47% | GO: 0001944 | vasculature development |
| 47% | GO: 0002443 | leukocyte mediated immunity |
| 47% | GO: 0016477 | cell migration |
| 47% | GO: 0030199 | collagen fibril organization |
| 47% | GO: 0032101 | regulation of response to external stimulus |
| 47% | GO: 0043200 | response to amino acid stimulus |
| 47% | GO: 0050776 | regulation of immune response |
| 44% | GO: 0001101 | response to acid |
| 44% | GO: 0002449 | lymphocyte mediated immunity |
| 44% | GO: 0002684 | positive regulation of immune system process |
| 44% | GO: 0006928 | cellular component movement |
| 44% | GO: 0006935 | chemotaxis |
| 44% | GO: 0009605 | response to external stimulus |
| 44% | GO: 0010033 | response to organic substance |
| 44% | GO: 0030334 | regulation of cell migration |
| 44% | GO: 0042060 | wound healing |
| 44% | GO: 0042330 | taxis |
| 44% | GO: 0050778 | positive regulation of immune response |
| 41% | GO: 0002576 | platelet degranulation |
| 41% | GO: 0002682 | regulation of immune system process |
| 41% | GO: 0006958 | complement activation, classical pathway |
| 41% | GO: 0010243 | response to organic nitrogen |

TABLE 3-continued

| GO term analysis of genes differentially expressed in subgroups | | |
|---|---|---|
| Proportion of Samples | Biological Process | Biological Process Name |
| 41% | GO: 0022603 | regulation of anatomical structure morphogenesis |
| 41% | GO: 0040017 | positive regulation of locomotion |
| 41% | GO: 0042221 | response to chemical stimulus |
| 41% | GO: 0048731 | system development |
| 41% | GO: 0048870 | cell motility |
| 41% | GO: 0051674 | localization of cell |
| 41% | GO: 0060326 | cell chemotaxis |
| 41% | GO: 0060333 | interferon-gamma-mediated signaling pathway |
| 38% | GO: 0002455 | humoral immune response mediated by circulating immunoglobulin |
| 38% | GO: 0002495 | antigen processing and presentation of peptide antigen via MHC class II |
| 38% | GO: 0002685 | regulation of leukocyte migration |
| 38% | GO: 0009612 | response to mechanical stimulus |
| 38% | GO: 0019886 | antigen processing and presentation of exogenous peptide antigen via MHC class II |
| 38% | GO: 0030595 | leukocyte chemotaxis |
| 38% | GO: 0040012 | regulation of locomotion |
| 38% | GO: 0050920 | regulation of chemotaxis |
| 38% | GO: 0051272 | positive regulation of cellular component movement |
| 38% | GO: 0072358 | cardiovascular system development |
| 38% | GO: 0072359 | circulatory system development |
| 38% | GO: 0072376 | protein activation cascade |
| 38% | GO: 2000145 | regulation of cell motility |
| 35% | GO: 0001775 | cell activation |
| **35%** | **GO: 0007399** | **nervous system development** |
| 35% | GO: 0030155 | regulation of cell adhesion |
| 35% | GO: 0030335 | positive regulation of cell migration |
| 35% | GO: 0031960 | response to corticosteroid stimulus |
| 35% | GO: 0048468 | cell development |
| 35% | GO: 0048583 | regulation of response to stimulus |
| 35% | GO: 0051239 | regulation of multicellular organismal process |
| 35% | GO: 0051270 | regulation of cellular component movement |
| 35% | GO: 2000147 | positive regulation of cell motility |
| 32% | GO: 0001525 | angiogenesis |
| 32% | GO: 0002764 | immune response-regulating signaling pathway |
| 32% | GO: 0007275 | multicellular organismal development |
| 32% | GO: 0009653 | anatomical structure morphogenesis |
| 32% | GO: 0014075 | response to amine stimulus |
| 32% | GO: 0042742 | defense response to bacterium |
| 32% | GO: 0048514 | blood vessel morphogenesis |
| 32% | GO: 0048584 | positive regulation of response to stimulus |
| 32% | GO: 0048856 | anatomical structure development |
| 32% | GO: 0050793 | regulation of developmental process |
| 32% | GO: 0050921 | positive regulation of chemotaxis |
| 32% | GO: 0051384 | response to glucocorticoid stimulus |
| 32% | GO: 0055093 | response to hyperoxia |
| 32% | GO: 0070482 | response to oxygen levels |
| 29% | GO: 0000904 | cell morphogenesis involved in differentiation |
| 29% | GO: 0002544 | chronic inflammatory response |
| 29% | GO: 0002688 | regulation of leukocyte chemotaxis |
| 29% | GO: 0002757 | immune response-activating signal transduction |
| 29% | GO: 0007162 | negative regulation of cell adhesion |
| 29% | GO: 0019221 | cytokine-mediated signaling pathway |
| 29% | GO: 0031099 | regeneration |
| 29% | GO: 0031294 | lymphocyte costimulation |
| 29% | GO: 0031295 | T cell costimulation |
| **29%** | **GO: 0042063** | **gliogenesis** |
| 29% | GO: 0050870 | positive regulation of T cell activation |
| 29% | GO: 0071222 | cellular response to lipopolysaccharide |
| 29% | GO: 0071229 | cellular response to acid |
| 29% | GO: 2000026 | regulation of multicellular organismal development |
| 26% | GO: 0002768 | immune response-regulating cell surface receptor signaling pathway |
| 26% | GO: 0006909 | phagocytosis |
| 26% | GO: 0010035 | response to inorganic substance |
| 26% | GO: 0016525 | negative regulation of angiogenesis |
| **26%** | **GO: 0022008** | **neurogenesis** |
| 26% | GO: 0030168 | platelet activation |
| **26%** | **GO: 0030182** | **neuron differentiation** |
| 26% | GO: 0031175 | neuron projection development |
| 26% | GO: 0032103 | positive regulation of response to external stimulus |
| 26% | GO: 0032940 | secretion by cell |
| 26% | GO: 0032964 | collagen biosynthetic process |
| 26% | GO: 0042127 | regulation of cell proliferation |
| 26% | GO: 0048812 | neuron projection morphogenesis |
| 26% | GO: 0051704 | multi-organism process |
| 26% | GO: 0065008 | regulation of biological quality |

TABLE 3-continued

GO term analysis of genes differentially expressed in subgroups

| Proportion of Samples | Biological Process | Biological Process Name |
|---|---|---|
| 26% | GO: 0070887 | cellular response to chemical stimulus |
| 26% | GO: 0071216 | cellular response to biotic stimulus |
| 26% | GO: 0071219 | cellular response to molecule of bacterial origin |
| 26% | GO: 0071345 | cellular response to cytokine stimulus |
| 24% | GO: 0002429 | immune response-activating cell surface receptor signaling pathway |
| 24% | GO: 0002687 | positive regulation of leukocyte migration |
| 24% | GO: 0007568 | aging |
| 24% | GO: 0007596 | blood coagulation |
| 24% | GO: 0007599 | hemostasis |
| 24% | GO: 0008360 | regulation of cell shape |
| 24% | GO: 0014070 | response to organic cyclic compound |
| 24% | GO: 0030593 | neutrophil chemotaxis |
| 24% | GO: 0032502 | developmental process |
| 24% | GO: 0033628 | regulation of cell adhesion mediated by integrin |
| 24% | GO: 0045766 | positive regulation of angiogenesis |
| 24% | GO: 0048545 | response to steroid hormone stimulus |
| 24% | GO: 0048585 | negative regulation of response to stimulus |
| **24%** | **GO: 0048666** | **neuron development** |
| **24%** | **GO: 0048667** | **cell morphogenesis involved in neuron differentiation** |
| 24% | GO: 0050730 | regulation of peptidyl-tyrosine phosphorylation |
| 24% | GO: 0050817 | coagulation |
| 24% | GO: 0050865 | regulation of cell activation |
| 24% | GO: 0050867 | positive regulation of cell activation |
| 24% | GO: 0071230 | cellular response to amino acid stimulus |
| 21% | GO: 0000302 | response to reactive oxygen species |
| 21% | GO: 0001666 | response to hypoxia |
| 21% | GO: 0001817 | regulation of cytokine production |
| 21% | GO: 0002274 | myeloid leukocyte activation |
| 21% | GO: 0002690 | positive regulation of leukocyte chemotaxis |
| 21% | GO: 0002694 | regulation of leukocyte activation |
| 21% | GO: 0007409 | axonogenesis |
| 21% | GO: 0009719 | response to endogenous stimulus |
| 21% | GO: 0009888 | tissue development |
| 21% | GO: 0018149 | peptide cross-linking |
| 21% | GO: 0030030 | cell projection organization |
| 21% | GO: 0032570 | response to progesterone stimulus |
| 21% | GO: 0032989 | cellular component morphogenesis |
| 21% | GO: 0048660 | regulation of smooth muscle cell proliferation |
| **21%** | **GO: 0048699** | **generation of neurons** |
| 21% | GO: 0048771 | tissue remodeling |
| 21% | GO: 0048858 | cell projection morphogenesis |
| 21% | GO: 0050727 | regulation of inflammatory response |
| 21% | GO: 0050732 | negative regulation of peptidyl-tyrosine phosphorylation |
| 21% | GO: 0050795 | regulation of behavior |
| 21% | GO: 0050851 | antigen receptor-mediated signaling pathway |
| 21% | GO: 0050863 | regulation of T cell activation |
| 21% | GO: 0051094 | positive regulation of developmental process |
| 21% | GO: 0051249 | regulation of lymphocyte activation |
| 21% | GO: 0051251 | positive regulation of lymphocyte activation |
| 21% | GO: 0060337 | type I interferon-mediated signaling pathway |
| 21% | GO: 0071357 | cellular response to type I interferon |
| 18% | GO: 0000902 | cell morphogenesis |
| 18% | GO: 0001501 | skeletal system development |
| 18% | GO: 0002696 | positive regulation of leukocyte activation |
| 18% | GO: 0006887 | exocytosis |
| 18% | GO: 0010038 | response to metal ion |
| 18% | GO: 0010574 | regulation of vascular endothelial growth factor production |
| 18% | GO: 0019228 | regulation of action potential in neuron |
| 18% | GO: 0030154 | cell differentiation |
| 18% | GO: 0032501 | multicellular organismal process |
| 18% | GO: 0032963 | collagen metabolic process |
| 18% | GO: 0032990 | cell part morphogenesis |
| 18% | GO: 0034340 | response to type I interferon |
| 18% | GO: 0045059 | positive thymic T cell selection |
| 18% | GO: 0045730 | respiratory burst |
| 18% | GO: 0048513 | organ development |
| 18% | GO: 0048520 | positive regulation of behavior |
| 18% | GO: 0050878 | regulation of body fluid levels |
| 18% | GO: 0051128 | regulation of cellular component organization |
| 18% | GO: 0061041 | regulation of wound healing |
| 18% | GO: 0070372 | regulation of ERK1 and ERK2 cascade |
| 18% | GO: 0071418 | cellular response to amine stimulus |
| 15% | GO: 0001503 | ossification |
| 15% | GO: 0002683 | negative regulation of immune system process |
| 15% | GO: 0006879 | cellular iron ion homeostasis |

TABLE 3-continued

GO term analysis of genes differentially expressed in subgroups

| Proportion of Samples | Biological Process | Biological Process Name |
|---|---|---|
| 15% | GO: 0006957 | complement activation, alternative pathway |
| 15% | GO: 0008284 | positive regulation of cell proliferation |
| 15% | GO: 0010466 | negative regulation of peptidase activity |
| 15% | GO: 0016337 | cell-cell adhesion |
| 15% | GO: 0042493 | response to drug |
| 15% | GO: 0045321 | leukocyte activation |
| 15% | GO: 0046903 | secretion |
| 15% | GO: 0048646 | anatomical structure formation involved in morphogenesis |
| 15% | GO: 0048869 | cellular developmental process |
| 15% | GO: 0050852 | T cell receptor signaling pathway |
| 15% | GO: 0050896 | response to stimulus |
| 15% | GO: 0055072 | iron ion homeostasis |
| 15% | GO: 0060548 | negative regulation of cell death |
| 15% | GO: 0071310 | cellular response to organic substance |
| 15% | GO: 0071675 | regulation of mononuclear cell migration |
| 15% | GO: 2000097 | regulation of smooth muscle cell-matrix adhesion |
| 12% | GO: 0001819 | positive regulation of cytokine production |
| 12% | GO: 0001936 | regulation of endothelial cell proliferation |
| 12% | GO: 0002697 | regulation of immune effector process |
| 12% | GO: 0007159 | leukocyte cell-cell adhesion |
| 12% | GO: 0007229 | integrin-mediated signaling pathway |
| 12% | GO: 0007417 | central nervous system development |
| 12% | GO: 0008285 | negative regulation of cell proliferation |
| 12% | GO: 0009628 | response to abiotic stimulus |
| 12% | GO: 0010951 | negative regulation of endopeptidase activity |
| 12% | GO: 0019882 | antigen processing and presentation |
| 12% | GO: 0030097 | hemopoiesis |
| 12% | GO: 0030193 | regulation of blood coagulation |
| 12% | GO: 0031100 | organ regeneration |
| 12% | GO: 0031102 | neuron projection regeneration |
| 12% | GO: 0035767 | endothelial cell chemotaxis |
| 12% | GO: 0042542 | response to hydrogen peroxide |
| 12% | GO: 0043542 | endothelial cell migration |
| 12% | GO: 0044259 | multicellular organismal macromolecule metabolic process |
| 12% | GO: 0045582 | positive regulation of T cell differentiation |
| 12% | GO: 0050678 | regulation of epithelial cell proliferation |
| 12% | GO: 0050764 | regulation of phagocytosis |
| 12% | GO: 0050804 | regulation of synaptic transmission |
| 12% | GO: 0050853 | B cell receptor signaling pathway |
| 12% | GO: 0051093 | negative regulation of developmental process |
| 12% | GO: 0052547 | regulation of peptidase activity |
| 12% | GO: 0055082 | cellular chemical homeostasis |
| 12% | GO: 0071417 | cellular response to organic nitrogen |
| 12% | GO: 0090022 | regulation of neutrophil chemotaxis |
| 12% | GO: 1900046 | regulation of hemostasis |
| 9% | GO: 0001505 | regulation of neurotransmitter levels |
| 9% | GO: 0001933 | negative regulation of protein phosphorylation |
| 9% | GO: 0002275 | myeloid cell activation involved in immune response |
| 9% | GO: 0002520 | immune system development |
| 9% | GO: 0002699 | positive regulation of immune effector process |
| 9% | GO: 0002886 | regulation of myeloid leukocyte mediated immunity |
| 9% | GO: 0002920 | regulation of humoral immune response |
| 9% | GO: 0003013 | circulatory system process |
| 9% | GO: 0006836 | neurotransmitter transport |
| 9% | GO: 0006873 | cellular ion homeostasis |
| 9% | GO: 0006875 | cellular metal ion homeostasis |
| 9% | GO: 0006897 | endocytosis |
| 9% | GO: 0007267 | cell-cell signaling |
| 9% | GO: 0007268 | synaptic transmission |
| 9% | GO: 0007272 | ensheathment of neurons |
| 9% | GO: 0008015 | blood circulation |
| 9% | GO: 0008366 | axon ensheathment |
| 9% | GO: 0009887 | organ morphogenesis |
| 9% | GO: 0009968 | negative regulation of signal transduction |
| 9% | GO: 0009991 | response to extracellular stimulus |
| 9% | GO: 0010001 | glial cell differentiation |
| 9% | GO: 0010324 | membrane invagination |
| 9% | GO: 0010332 | response to gamma radiation |
| 9% | GO: 0010543 | regulation of platelet activation |
| 9% | GO: 0010646 | regulation of cell communication |
| 9% | GO: 0010648 | negative regulation of cell communication |
| 9% | GO: 0010758 | regulation of macrophage chemotaxis |
| 9% | GO: 0010759 | positive regulation of macrophage chemotaxis |
| 9% | GO: 0010810 | regulation of cell-substrate adhesion |
| 9% | GO: 0010812 | negative regulation of cell-substrate adhesion |

TABLE 3-continued

GO term analysis of genes differentially expressed in subgroups

| Proportion of Samples | Biological Process | Biological Process Name |
|---|---|---|
| 9% | GO: 0014910 | regulation of smooth muscle cell migration |
| 9% | GO: 0019226 | transmission of nerve impulse |
| 9% | GO: 0019800 | peptide cross-linking via chondroitin 4-sulfate glycosaminoglycan |
| 9% | GO: 0021529 | spinal cord oligodendrocyte cell differentiation |
| 9% | GO: 0021530 | spinal cord oligodendrocyte cell fate specification |
| 9% | GO: 0023051 | regulation of signaling |
| 9% | GO: 0023057 | negative regulation of signaling |
| 9% | GO: 0030003 | cellular cation homeostasis |
| 9% | GO: 0030098 | lymphocyte differentiation |
| 9% | GO: 0030323 | respiratory tube development |
| 9% | GO: 0030324 | lung development |
| 9% | GO: 0031644 | regulation of neurological system process |
| 9% | GO: 0031663 | lipopolysaccharide-mediated signaling pathway |
| 9% | GO: 0032835 | glomerulus development |
| 9% | GO: 0032944 | regulation of mononuclear cell proliferation |
| 9% | GO: 0035637 | multicellular organismal signaling |
| 9% | GO: 0042102 | positive regulation of T cell proliferation |
| 9% | GO: 0043066 | negative regulation of apoptotic process |
| 9% | GO: 0043069 | negative regulation of programmed cell death |
| 9% | GO: 0043368 | positive T cell selection |
| 9% | GO: 0044057 | regulation of system process |
| 9% | GO: 0044087 | regulation of cellular component biogenesis |
| 9% | GO: 0044236 | multicellular organismal metabolic process |
| 9% | GO: 0045058 | T cell selection |
| 9% | GO: 0045597 | positive regulation of cell differentiation |
| 9% | GO: 0045621 | positive regulation of lymphocyte differentiation |
| 9% | GO: 0046635 | positive regulation of alpha-beta T cell activation |
| 9% | GO: 0048534 | hemopoietic or lymphoid organ development |
| 9% | GO: 0050670 | regulation of lymphocyte proliferation |
| 9% | GO: 0050729 | positive regulation of inflammatory response |
| 9% | GO: 0051240 | positive regulation of multicellular organismal process |
| 9% | GO: 0051969 | regulation of transmission of nerve impulse |
| 9% | GO: 0055001 | muscle cell development |
| 9% | GO: 0055002 | striated muscle cell development |
| 9% | GO: 0055065 | metal ion homeostasis |
| 9% | GO: 0070098 | chemokine-mediated signaling pathway |
| 9% | GO: 0070208 | protein heterotrimerization |
| 9% | GO: 0070663 | regulation of leukocyte proliferation |
| 9% | GO: 0071622 | regulation of granulocyte chemotaxis |
| 9% | GO: 0071901 | negative regulation of protein serine/threonine kinase activity |
| 9% | GO: 0090090 | negative regulation of canonical Wnt receptor signaling pathway |
| 6% | GO: 0000041 | transition metal ion transport |
| 6% | GO: 0000188 | inactivation of MAPK activity |
| 6% | GO: 0001504 | neurotransmitter uptake |
| 6% | GO: 0001508 | regulation of action potential |
| 6% | GO: 0001763 | morphogenesis of a branching structure |
| 6% | GO: 0001776 | leukocyte homeostasis |
| 6% | GO: 0001782 | B cell homeostasis |
| 6% | GO: 0001953 | negative regulation of cell-matrix adhesion |
| 6% | GO: 0002260 | lymphocyte homeostasis |
| 6% | GO: 0002521 | leukocyte differentiation |
| 6% | GO: 0002686 | negative regulation of leukocyte migration |
| 6% | GO: 0002698 | negative regulation of immune effector process |
| 6% | GO: 0002819 | regulation of adaptive immune response |
| 6% | GO: 0002821 | positive regulation of adaptive immune response |
| 6% | GO: 0002822 | regulation of adaptive immune response based on somatic recombination of immune receptors built from immunoglobulin superfamily domains |
| 6% | GO: 0002824 | positive regulation of adaptive immune response based on somatic recombination of immune receptors built from immunoglobulin superfamily domains |
| 6% | GO: 0003008 | system process |
| 6% | GO: 0003094 | glomerular filtration |
| 6% | GO: 0006469 | negative regulation of protein kinase activity |
| 6% | GO: 0006911 | phagocytosis, engulfment |
| 6% | GO: 0006916 | anti-apoptosis |
| 6% | GO: 0007269 | neurotransmitter secretion |
| 6% | GO: 0007411 | axon guidance |
| 6% | GO: 0007566 | embryo implantation |
| 6% | GO: 0009266 | response to temperature stimulus |
| 6% | GO: 0009306 | protein secretion |
| 6% | GO: 0009615 | response to virus |
| 6% | GO: 0009725 | response to hormone stimulus |
| 6% | GO: 0009743 | response to carbohydrate stimulus |
| 6% | GO: 0009966 | regulation of signal transduction |
| 6% | GO: 0010575 | positive regulation vascular endothelial growth factor production |

TABLE 3-continued

| GO term analysis of genes differentially expressed in subgroups | | |
|---|---|---|
| Proportion of Samples | Biological Process | Biological Process Name |
| 6% | GO: 0010594 | regulation of endothelial cell migration |
| 6% | GO: 0010769 | regulation of cell morphogenesis involved in differentiation |
| 6% | GO: 0010955 | negative regulation of protein processing |
| 6% | GO: 0014052 | regulation of gamma-aminobutyric acid secretion |
| 6% | GO: 0014706 | striated muscle tissue development |
| 6% | GO: 0014805 | smooth muscle adaptation |
| 6% | GO: 0014829 | vascular smooth muscle contraction |
| 6% | GO: 0019725 | cellular homeostasis |
| 6% | GO: 0021545 | cranial nerve development |
| 6% | GO: 0021781 | glial cell fate commitment |
| 6% | GO: 0022604 | regulation of cell morphogenesis |
| 6% | GO: 0022904 | respiratory electron transport chain |
| 6% | GO: 0030029 | actin filament-based process |
| 6% | GO: 0030111 | regulation of Wnt receptor signaling pathway |
| 6% | GO: 0030178 | negative regulation of Wnt receptor signaling pathway |
| 6% | GO: 0030217 | T cell differentiation |
| 6% | GO: 0030224 | monocyte differentiation |
| 6% | GO: 0031347 | regulation of defense response |
| 6% | GO: 0031348 | negative regulation of defense response |
| 6% | GO: 0031349 | positive regulation of defense response |
| 6% | GO: 0031579 | membrane raft organization |
| 6% | GO: 0031589 | cell-substrate adhesion |
| 6% | GO: 0031646 | positive regulation of neurological system process |
| 6% | GO: 0031915 | positive regulation of synaptic plasticity |
| 6% | GO: 0032102 | negative regulation of response to external stimulus |
| 6% | GO: 0032355 | response to estradiol stimulus |
| 6% | GO: 0032642 | regulation of chemokine production |
| 6% | GO: 0032760 | positive regulation of tumor necrosis factor production |
| 6% | GO: 0033003 | regulation of mast cell activation |
| 6% | GO: 0033006 | regulation of mast cell activation involved in immune response |
| 6% | GO: 0033673 | negative regulation of kinase activity |
| 6% | GO: 0034059 | response to anoxia |
| 6% | GO: 0034614 | cellular response to reactive oxygen species |
| 6% | GO: 0035457 | cellular response to interferon-alpha |
| 6% | GO: 0040007 | growth |
| 6% | GO: 0042129 | regulation of T cell proliferation |
| 6% | GO: 0042246 | tissue regeneration |
| 6% | GO: 0042326 | negative regulation of phosphorylation |
| 6% | GO: 0042327 | positive regulation of phosphorylation |
| 6% | GO: 0042552 | myelination |
| 6% | GO: 0042592 | homeostatic process |
| 6% | GO: 0042692 | muscle cell differentiation |
| 6% | GO: 0043304 | regulation of mast cell degranulation |
| 6% | GO: 0043407 | negative regulation of MAP kinase activity |
| 6% | GO: 0043408 | regulation of MAPK cascade |
| 6% | GO: 0043409 | negative regulation of MAPK cascade |
| 6% | GO: 0043627 | response to estrogen stimulus |
| 6% | GO: 0045123 | cellular extravasation |
| 6% | GO: 0045333 | cellular respiration |
| 6% | GO: 0045576 | mast cell activation |
| 6% | GO: 0045586 | regulation of gamma-delta T cell differentiation |
| 6% | GO: 0045588 | positive regulation of gamma-delta T cell differentiation |
| 6% | GO: 0045664 | regulation of neuron differentiation |
| 6% | GO: 0045906 | negative regulation of vasoconstriction |
| 6% | GO: 0046649 | lymphocyte activation |
| 6% | GO: 0048010 | vascular endothelial growth factor receptor signaling pathway |
| 6% | GO: 0048167 | regulation of synaptic plasticity |
| 6% | GO: 0048247 | lymphocyte chemotaxis |
| 6% | GO: 0048286 | lung alveolus development |
| 6% | GO: 0048661 | positive regulation of smooth muscle cell proliferation |
| 6% | GO: 0048709 | oligodendrocyte differentiation |
| 6% | GO: 0048747 | muscle fiber development |
| 6% | GO: 0048872 | homeostasis of number of cells |
| 6% | GO: 0048878 | chemical homeostasis |
| 6% | GO: 0050654 | chondroitin sulfate proteoglycan metabolic process |
| 6% | GO: 0050679 | positive regulation of epithelial cell proliferation |
| 6% | GO: 0050777 | negative regulation of immune response |
| 6% | GO: 0050801 | ion homeostasis |
| 6% | GO: 0050818 | regulation of coagulation |
| 6% | GO: 0050864 | regulation of B cell activation |
| 6% | GO: 0050877 | neurological system process |
| 6% | GO: 0051146 | striated muscle cell differentiation |
| 6% | GO: 0051216 | cartilage development |
| 6% | GO: 0051346 | negative regulation of hydrolase activity |
| 6% | GO: 0051348 | negative regulation of transferase activity |

TABLE 3-continued

GO term analysis of genes differentially expressed in subgroups

| Proportion of Samples | Biological Process | Biological Process Name |
|---|---|---|
| 6% | GO: 0051591 | response to cAMP |
| 6% | GO: 0051592 | response to calcium ion |
| 6% | GO: 0051971 | positive regulation of transmission of nerve impulse |
| 6% | GO: 0055006 | cardiac cell development |
| 6% | GO: 0055013 | cardiac muscle cell development |
| 6% | GO: 0055080 | cation homeostasis |
| 6% | GO: 0060056 | mammary gland involution |
| 6% | GO: 0060071 | Wnt receptor signaling pathway, planar cell polarity pathway |
| 6% | GO: 0060284 | regulation of cell development |
| 6% | GO: 0060348 | bone development |
| 6% | GO: 0060537 | muscle tissue development |
| 6% | GO: 0060541 | respiratory system development |
| 6% | GO: 0070374 | positive regulation of ERK1 and ERK2 cascade |
| 6% | GO: 0070665 | positive regulation of leukocyte proliferation |
| 6% | GO: 0072012 | glomerulus vasculature development |
| 6% | GO: 0080134 | regulation of response to stress |
| 6% | GO: 0090175 | regulation of establishment of planar polarity |
| 6% | GO: 0097066 | response to thyroid hormone stimulus |
| 6% | GO: 0097067 | cellular response to thyroid hormone stimulus |
| 6% | GO: 0097205 | renal filtration |
| 6% | GO: 2000377 | regulation of reactive oxygen species metabolic process |
| 3% | GO: 0000272 | polysaccharide catabolic process |
| 3% | GO: 0001300 | chronological cell aging |
| 3% | GO: 0001523 | retinoid metabolic process |
| 3% | GO: 0001562 | response to protozoan |
| 3% | GO: 0001569 | patterning of blood vessels |
| 3% | GO: 0001570 | vasculogenesis |
| 3% | GO: 0001649 | osteoblast differentiation |
| 3% | GO: 0001656 | metanephros development |
| 3% | GO: 0001706 | endoderm formation |
| 3% | GO: 0001754 | eye photoreceptor cell differentiation |
| 3% | GO: 0001766 | membrane raft polarization |
| 3% | GO: 0001774 | microglial cell activation |
| 3% | GO: 0001816 | cytokine production |
| 3% | GO: 0001822 | kidney development |
| 3% | GO: 0001838 | embryonic epithelial tube formation |
| 3% | GO: 0001843 | neural tube closure |
| 3% | GO: 0001878 | response to yeast |
| 3% | GO: 0001894 | tissue homeostasis |
| 3% | GO: 0001938 | positive regulation of endothelial cell proliferation |
| 3% | GO: 0001957 | intramembranous ossification |
| 3% | GO: 0001974 | blood vessel remodeling |
| 3% | GO: 0002009 | morphogenesis of an epithelium |
| 3% | GO: 0002062 | chondrocyte differentiation |
| 3% | GO: 0002064 | epithelial cell development |
| 3% | GO: 0002138 | retinoic acid biosynthetic process |
| 3% | GO: 0002218 | activation of innate immune response |
| 3% | GO: 0002238 | response to molecule of fungal origin |
| 3% | GO: 0002263 | cell activation involved in immune response |
| 3% | GO: 0002279 | mast cell activation involved in immune response |
| 3% | GO: 0002281 | macrophage activation involved in immune response |
| 3% | GO: 0002282 | microglial cell activation involved in immune response |
| 3% | GO: 0002283 | neutrophil activation involved in immune response |
| 3% | GO: 0002366 | leukocyte activation involved in immune response |
| 3% | GO: 0002431 | Fc receptor mediated stimulatory signaling pathway |
| 3% | GO: 0002444 | myeloid leukocyte mediated immunity |
| 3% | GO: 0002448 | mast cell mediated immunity |
| 3% | GO: 0002478 | antigen processing and presentation of exogenous peptide antigen |
| 3% | GO: 0002507 | tolerance induction |
| 3% | GO: 0002526 | acute inflammatory response |
| 3% | GO: 0002532 | production of molecular mediator involved in inflammatory response |
| 3% | GO: 0002543 | activation of blood coagulation via clotting cascade |
| 3% | GO: 0002577 | regulation of antigen processing and presentation |
| 3% | GO: 0002634 | regulation of germinal center formation |
| 3% | GO: 0002673 | regulation of acute inflammatory response |
| 3% | GO: 0002675 | positive regulation of acute inflammatory response |
| 3% | GO: 0002679 | respiratory burst involved in defense response |
| 3% | GO: 0002689 | negative regulation of leukocyte chemotaxis |
| 3% | GO: 0002700 | regulation of production of molecular mediator of immune response |
| 3% | GO: 0002703 | regulation of leukocyte mediated immunity |
| 3% | GO: 0002705 | positive regulation of leukocyte mediated immunity |
| 3% | GO: 0002708 | positive regulation of lymphocyte mediated immunity |
| 3% | GO: 0002820 | negative regulation of adaptive immune response |
| 3% | GO: 0003007 | heart morphogenesis |
| 3% | GO: 0003009 | skeletal muscle contraction |

TABLE 3-continued

GO term analysis of genes differentially expressed in subgroups

| Proportion of Samples | Biological Process | Biological Process Name |
|---|---|---|
| 3% | GO: 0003012 | muscle system process |
| 3% | GO: 0003073 | regulation of systemic arterial blood pressure |
| 3% | GO: 0003081 | regulation of systemic arterial blood pressure by renin-angiotensin |
| 3% | GO: 0003158 | endothelium development |
| 3% | GO: 0003205 | cardiac chamber development |
| 3% | GO: 0003206 | cardiac chamber morphogenesis |
| 3% | GO: 0003208 | cardiac ventricle morphogenesis |
| 3% | GO: 0003231 | cardiac ventricle development |
| 3% | GO: 0003382 | epithelial cell morphogenesis |
| 3% | GO: 0005976 | polysaccharide metabolic process |
| 3% | GO: 0006006 | glucose metabolic process |
| 3% | GO: 0006022 | aminoglycan metabolic process |
| 3% | GO: 0006029 | proteoglycan metabolic process |
| 3% | GO: 0006090 | pyruvate metabolic process |
| 3% | GO: 0006096 | glycolysis |
| 3% | GO: 0006120 | mitochondrial electron transport, NADH to ubiquinone |
| 3% | GO: 0006599 | phosphagen metabolic process |
| 3% | GO: 0006600 | creatine metabolic process |
| 3% | GO: 0006633 | fatty acid biosynthetic process |
| 3% | GO: 0006690 | icosanoid metabolic process |
| 3% | GO: 0006720 | isoprenoid metabolic process |
| 3% | GO: 0006790 | sulfur compound metabolic process |
| 3% | GO: 0006826 | iron ion transport |
| 3% | GO: 0006910 | phagocytosis, recognition |
| 3% | GO: 0006929 | substrate-dependent cell migration |
| 3% | GO: 0006936 | muscle contraction |
| 3% | GO: 0006937 | regulation of muscle contraction |
| 3% | GO: 0006941 | striated muscle contraction |
| 3% | GO: 0006968 | cellular defense response |
| 3% | GO: 0006979 | response to oxidative stress |
| 3% | GO: 0007026 | negative regulation of microtubule depolymerization |
| 3% | GO: 0007132 | meiotic metaphase I |
| 3% | GO: 0007154 | cell communication |
| 3% | GO: 0007157 | heterophilic cell-cell adhesion |
| 3% | GO: 0007160 | cell-matrix adhesion |
| 3% | GO: 0007165 | signal transduction |
| 3% | GO: 0007166 | cell surface receptor signaling pathway |
| 3% | GO: 0007199 | G-protein signaling, coupled to cGMP nucleotide second messenger |
| 3% | GO: 0007263 | nitric oxide mediated signal transduction |
| 3% | GO: 0007422 | peripheral nervous system development |
| 3% | GO: 0007507 | heart development |
| 3% | GO: 0007517 | muscle organ development |
| 3% | GO: 0007519 | skeletal muscle tissue development |
| 3% | GO: 0007584 | response to nutrient |
| 3% | GO: 0007589 | body fluid secretion |
| 3% | GO: 0007610 | behavior |
| 3% | GO: 0007611 | learning or memory |
| 3% | GO: 0007612 | learning |
| 3% | GO: 0008217 | regulation of blood pressure |
| 3% | GO: 0008277 | regulation of G-protein coupled receptor protein signaling pathway |
| 3% | GO: 0008283 | cell proliferation |
| 3% | GO: 0008347 | glial cell migration |
| 3% | GO: 0009620 | response to fungus |
| 3% | GO: 0009746 | response to hexose stimulus |
| 3% | GO: 0009756 | carbohydrate mediated signaling |
| 3% | GO: 0010172 | embryonic body morphogenesis |
| 3% | GO: 0010212 | response to ionizing radiation |
| 3% | GO: 0010447 | response to acidity |
| 3% | GO: 0010561 | negative regulation of glycoprotein biosynthetic process |
| 3% | GO: 0010563 | negative regulation of phosphorus metabolic process |
| 3% | GO: 0010595 | positive regulation of endothelial cell migration |
| 3% | GO: 0010740 | positive regulation of intracellular protein kinase cascade |
| 3% | GO: 0010811 | positive regulation of cell-substrate adhesion |
| 3% | GO: 0010927 | cellular component assembly involved in morphogenesis |
| 3% | GO: 0010939 | regulation of necrotic cell death |
| 3% | GO: 0010975 | regulation of neuron projection development |
| 3% | GO: 0014003 | oligodendrocyte development |
| 3% | GO: 0014013 | regulation of gliogenesis |
| 3% | GO: 0014020 | primary neural tube formation |
| 3% | GO: 0014047 | glutamate secretion |
| 3% | GO: 0014068 | positive regulation of phosphatidylinositol 3-kinase cascade |
| 3% | GO: 0014820 | tonic smooth muscle contraction |
| 3% | GO: 0015682 | ferric iron transport |
| 3% | GO: 0016049 | cell growth |
| 3% | GO: 0016101 | diterpenoid metabolic process |

TABLE 3-continued

GO term analysis of genes differentially expressed in subgroups

| Proportion of Samples | Biological Process | Biological Process Name |
|---|---|---|
| 3% | GO: 0016331 | morphogenesis of embryonic epithelium |
| 3% | GO: 0016339 | calcium-dependent cell-cell adhesion |
| 3% | GO: 0018108 | peptidyl-tyrosine phosphorylation |
| 3% | GO: 0018212 | peptidyl-tyrosine modification |
| 3% | GO: 0019220 | regulation of phosphate metabolic process |
| 3% | GO: 0019229 | regulation of vasoconstriction |
| 3% | GO: 0019302 | D-ribose biosynthetic process |
| 3% | GO: 0019693 | ribose phosphate metabolic process |
| 3% | GO: 0019827 | stem cell maintenance |
| 3% | GO: 0019884 | antigen processing and presentation of exogenous antigen |
| 3% | GO: 0021542 | dentate gyrus development |
| 3% | GO: 0021602 | cranial nerve morphogenesis |
| 3% | GO: 0021675 | nerve development |
| 3% | GO: 0021782 | glial cell development |
| 3% | GO: 0022614 | membrane to membrane docking |
| 3% | GO: 0022900 | electron transport chain |
| 3% | GO: 0023052 | signaling |
| 3% | GO: 0030036 | actin cytoskeleton organization |
| 3% | GO: 0030048 | actin filament-based movement |
| 3% | GO: 0030049 | muscle filament sliding |
| 3% | GO: 0030194 | positive regulation of blood coagulation |
| 3% | GO: 0030204 | chondroitin sulfate metabolic process |
| 3% | GO: 0030225 | macrophage differentiation |
| 3% | GO: 0030239 | myofibril assembly |
| 3% | GO: 0030240 | skeletal muscle thin filament assembly |
| 3% | GO: 0030278 | regulation of ossification |
| 3% | GO: 0030336 | negative regulation of cell migration |
| 3% | GO: 0030855 | epithelial cell differentiation |
| 3% | GO: 0031032 | actomyosin structure organization |
| 3% | GO: 0031112 | positive regulation of microtubule polymerization or depolymerization |
| 3% | GO: 0031113 | regulation of microtubule polymerization |
| 3% | GO: 0031116 | positive regulation of microtubule polymerization |
| 3% | GO: 0031344 | regulation of cell projection organization |
| 3% | GO: 0031345 | negative regulation of cell projection organization |
| 3% | GO: 0031394 | positive regulation of prostaglandin biosynthetic process |
| 3% | GO: 0031580 | membrane raft distribution |
| 3% | GO: 0031664 | regulation of lipopolysaccharide-mediated signaling pathway |
| 3% | GO: 0031667 | response to nutrient levels |
| 3% | GO: 0032649 | regulation of interferon-gamma production |
| 3% | GO: 0032675 | regulation of interleukin-6 production |
| 3% | GO: 0032677 | regulation of interleukin-8 production |
| 3% | GO: 0032879 | regulation of localization |
| 3% | GO: 0032928 | regulation of superoxide anion generation |
| 3% | GO: 0032930 | positive regulation of superoxide anion generation |
| 3% | GO: 0032946 | positive regulation of mononuclear cell proliferation |
| 3% | GO: 0032956 | regulation of actin cytoskeleton organization |
| 3% | GO: 0032970 | regulation of actin filament-based process |
| 3% | GO: 0033275 | actin-myosin filament sliding |
| 3% | GO: 0033572 | transferrin transport |
| 3% | GO: 0033630 | positive regulation of cell adhesion mediated by integrin |
| 3% | GO: 0033993 | response to lipid |
| 3% | GO: 0034121 | regulation of toll-like receptor signaling pathway |
| 3% | GO: 0034136 | negative regulation of toll-like receptor 2 signaling pathway |
| 3% | GO: 0034284 | response to monosaccharide stimulus |
| 3% | GO: 0034329 | cell junction assembly |
| 3% | GO: 0034330 | cell junction organization |
| 3% | GO: 0034612 | response to tumor necrosis factor |
| 3% | GO: 0034637 | cellular carbohydrate biosynthetic process |
| 3% | GO: 0034755 | iron ion transmembrane transport |
| 3% | GO: 0035148 | tube formation |
| 3% | GO: 0035239 | tube morphogenesis |
| 3% | GO: 0035295 | tube development |
| 3% | GO: 0035385 | Roundabout signaling pathway |
| 3% | GO: 0035583 | sequestering of TGFbeta in extracellular matrix |
| 3% | GO: 0035860 | glial cell-derived neurotrophic factor receptor signaling pathway |
| 3% | GO: 0035924 | cellular response to vascular endothelial growth factor stimulus |
| 3% | GO: 0036072 | direct ossification |
| 3% | GO: 0040013 | negative regulation of locomotion |
| 3% | GO: 0042035 | regulation of cytokine biosynthetic process |
| 3% | GO: 0042108 | positive regulation of cytokine biosynthetic process |
| 3% | GO: 0042110 | T cell activation |
| 3% | GO: 0042116 | macrophage activation |
| 3% | GO: 0042384 | cilium assembly |
| 3% | GO: 0042391 | regulation of membrane potential |
| 3% | GO: 0042730 | fibrinolysis |

TABLE 3-continued

GO term analysis of genes differentially expressed in subgroups

| Proportion of Samples | Biological Process | Biological Process Name |
|---|---|---|
| 3% | GO: 0042743 | hydrogen peroxide metabolic process |
| 3% | GO: 0042832 | defense response to protozoan |
| 3% | GO: 0043092 | L-amino acid import |
| 3% | GO: 0043270 | positive regulation of ion transport |
| 3% | GO: 0043277 | apoptotic cell clearance |
| 3% | GO: 0043279 | response to alkaloid |
| 3% | GO: 0043299 | leukocyte degranulation |
| 3% | GO: 0043303 | mast cell degranulation |
| 3% | GO: 0043383 | negative T cell selection |
| 3% | GO: 0043405 | regulation of MAP kinase activity |
| 3% | GO: 0043410 | positive regulation of MAPK cascade |
| 3% | GO: 0043535 | regulation of blood vessel endothelial cell migration |
| 3% | GO: 0043536 | positive regulation of blood vessel endothelial cell migration |
| 3% | GO: 0043549 | regulation of kinase activity |
| 3% | GO: 0044319 | wound healing, spreading of cells |
| 3% | GO: 0045055 | regulated secretory pathway |
| 3% | GO: 0045060 | negative thymic T cell selection |
| 3% | GO: 0045061 | thymic T cell selection |
| 3% | GO: 0045088 | regulation of innate immune response |
| 3% | GO: 0045089 | positive regulation of innate immune response |
| 3% | GO: 0045446 | endothelial cell differentiation |
| 3% | GO: 0045595 | regulation of cell differentiation |
| 3% | GO: 0045596 | negative regulation of cell differentiation |
| 3% | GO: 0045619 | regulation of lymphocyte differentiation |
| 3% | GO: 0045638 | negative regulation of myeloid cell differentiation |
| 3% | GO: 0045667 | regulation of osteoblast differentiation |
| 3% | GO: 0045785 | positive regulation of cell adhesion |
| 3% | GO: 0045859 | regulation of protein kinase activity |
| 3% | GO: 0045923 | positive regulation of fatty acid metabolic process |
| 3% | GO: 0045936 | negative regulation of phosphate metabolic process |
| 3% | GO: 0046364 | monosaccharide biosynthetic process |
| 3% | GO: 0046390 | ribose phosphate biosynthetic process |
| 3% | GO: 0046456 | icosanoid biosynthetic process |
| 3% | GO: 0046530 | photoreceptor cell differentiation |
| 3% | GO: 0046634 | regulation of alpha-beta T cell activation |
| 3% | GO: 0046643 | regulation of gamma-delta T cell activation |
| 3% | GO: 0046645 | positive regulation of gamma-delta T cell activation |
| 3% | GO: 0048002 | antigen processing and presentation of peptide antigen |
| 3% | GO: 0048168 | regulation of neuronal synaptic plasticity |
| 3% | GO: 0048488 | synaptic vesicle endocytosis |
| 3% | GO: 0048489 | synaptic vesicle transport |
| 3% | GO: 0048518 | positive regulation of biological process |
| 3% | GO: 0048519 | negative regulation of biological process |
| 3% | GO: 0048522 | positive regulation of cellular process |
| 3% | GO: 0048589 | developmental growth |
| 3% | GO: 0048638 | regulation of developmental growth |
| 3% | GO: 0048644 | muscle organ morphogenesis |
| 3% | GO: 0048662 | negative regulation of smooth muscle cell proliferation |
| 3% | GO: 0048678 | response to axon injury |
| 3% | GO: 0048704 | embryonic skeletal system morphogenesis |
| 3% | GO: 0048705 | skeletal system morphogenesis |
| 3% | GO: 0048729 | tissue morphogenesis |
| 3% | GO: 0048738 | cardiac muscle tissue development |
| 3% | GO: 0048754 | branching morphogenesis of a tube |
| 3% | GO: 0050663 | cytokine secretion |
| 3% | GO: 0050671 | positive regulation of lymphocyte proliferation |
| 3% | GO: 0050680 | negative regulation of epithelial cell proliferation |
| 3% | GO: 0050728 | negative regulation of inflammatory response |
| 3% | GO: 0050766 | positive regulation of phagocytosis |
| 3% | GO: 0050767 | regulation of neurogenesis |
| 3% | GO: 0050770 | regulation of axonogenesis |
| 3% | GO: 0050806 | positive regulation of synaptic transmission |
| 3% | GO: 0050808 | synapse organization |
| 3% | GO: 0050830 | defense response to Gram-positive bacterium |
| 3% | GO: 0050854 | regulation of antigen receptor-mediated signaling pathway |
| 3% | GO: 0050866 | negative regulation of cell activation |
| 3% | GO: 0050890 | cognition |
| 3% | GO: 0050922 | negative regulation of chemotaxis |
| 3% | GO: 0050926 | regulation of positive chemotaxis |
| 3% | GO: 0051055 | negative regulation of lipid biosynthetic process |
| 3% | GO: 0051129 | negative regulation of cellular component organization |
| 3% | GO: 0051130 | positive regulation of cellular component organization |
| 3% | GO: 0051174 | regulation of phosphorus metabolic process |
| 3% | GO: 0051241 | negative regulation of multicellular organismal process |
| 3% | GO: 0051271 | negative regulation of cellular component movement |

TABLE 3-continued

GO term analysis of genes differentially expressed in subgroups

| Proportion of Samples | Biological Process | Biological Process Name |
|---|---|---|
| 3% | GO: 0051305 | chromosome movement towards spindle pole |
| 3% | GO: 0051338 | regulation of transferase activity |
| 3% | GO: 0051387 | negative regulation of nerve growth factor receptor signaling pathway |
| 3% | GO: 0051547 | regulation of keratinocyte migration |
| 3% | GO: 0051549 | positive regulation of keratinocyte migration |
| 3% | GO: 0051593 | response to folic acid |
| 3% | GO: 0051607 | defense response to virus |
| 3% | GO: 0051665 | membrane raft localization |
| 3% | GO: 0051716 | cellular response to stimulus |
| 3% | GO: 0051895 | negative regulation of focal adhesion assembly |
| 3% | GO: 0051896 | regulation of protein kinase B signaling cascade |
| 3% | GO: 0051897 | positive regulation of protein kinase B signaling cascade |
| 3% | GO: 0051917 | regulation of fibrinolysis |
| 3% | GO: 0051928 | positive regulation of calcium ion transport |
| 3% | GO: 0051960 | regulation of nervous system development |
| 3% | GO: 0055003 | cardiac myofibril assembly |
| 3% | GO: 0055007 | cardiac muscle cell differentiation |
| 3% | GO: 0055008 | cardiac muscle tissue morphogenesis |
| 3% | GO: 0060137 | maternal process involved in parturition |
| 3% | GO: 0060231 | mesenchymal to epithelial transition |
| 3% | GO: 0060236 | regulation of mitotic spindle organization |
| 3% | GO: 0060271 | cilium morphogenesis |
| 3% | GO: 0060349 | bone morphogenesis |
| 3% | GO: 0060415 | muscle tissue morphogenesis |
| 3% | GO: 0060420 | regulation of heart growth |
| 3% | GO: 0060426 | lung vasculature development |
| 3% | GO: 0060429 | epithelium development |
| 3% | GO: 0060441 | epithelial tube branching involved in lung morphogenesis |
| 3% | GO: 0060485 | mesenchyme development |
| 3% | GO: 0060538 | skeletal muscle organ development |
| 3% | GO: 0060547 | negative regulation of necrotic cell death |
| 3% | GO: 0060560 | developmental growth involved in morphogenesis |
| 3% | GO: 0060562 | epithelial tube morphogenesis |
| 3% | GO: 0060606 | tube closure |
| 3% | GO: 0060666 | dichotomous subdivision of terminal units involved in salivary gland branching |
| 3% | GO: 0060741 | prostate gland stromal morphogenesis |
| 3% | GO: 0061061 | muscle structure development |
| 3% | GO: 0061138 | morphogenesis of a branching epithelium |
| 3% | GO: 0061318 | renal filtration cell differentiation |
| 3% | GO: 0070168 | negative regulation of biomineral tissue development |
| 3% | GO: 0070201 | regulation of establishment of protein localization |
| 3% | GO: 0070206 | protein trimerization |
| 3% | GO: 0070252 | actin-mediated cell contraction |
| 3% | GO: 0070301 | cellular response to hydrogen peroxide |
| 3% | GO: 0070391 | response to lipoteichoic acid |
| 3% | GO: 0070486 | leukocyte aggregation |
| 3% | GO: 0070507 | regulation of microtubule cytoskeleton organization |
| 3% | GO: 0071214 | cellular response to abiotic stimulus |
| 3% | GO: 0071223 | cellular response to lipoteichoic acid |
| 3% | GO: 0071241 | cellular response to inorganic substance |
| 3% | GO: 0071260 | cellular response to mechanical stimulus |
| 3% | GO: 0071277 | cellular response to calcium ion |
| 3% | GO: 0071322 | cellular response to carbohydrate stimulus |
| 3% | GO: 0071347 | cellular response to interleukin-1 |
| 3% | GO: 0071356 | cellular response to tumor necrosis factor |
| 3% | GO: 0071402 | cellular response to lipoprotein particle stimulus |
| 3% | GO: 0071453 | cellular response to oxygen levels |
| 3% | GO: 0071456 | cellular response to hypoxia |
| 3% | GO: 0071671 | regulation of smooth muscle cell chemotaxis |
| 3% | GO: 0071780 | mitotic cell cycle G2/M transition checkpoint |
| 3% | GO: 0071900 | regulation of protein serine/threonine kinase activity |
| 3% | GO: 0072001 | renal system development |
| 3% | GO: 0072006 | nephron development |
| 3% | GO: 0072010 | glomerular epithelium development |
| 3% | GO: 0072015 | glomerular visceral epithelial cell development |
| 3% | GO: 0072102 | glomerulus morphogenesis |
| 3% | GO: 0072109 | glomerular mesangium development |
| 3% | GO: 0072112 | glomerular visceral epithelial cell differentiation |
| 3% | GO: 0072175 | epithelial tube formation |
| 3% | GO: 0072310 | glomerular epithelial cell development |
| 3% | GO: 0072311 | glomerular epithelial cell differentiation |
| 3% | GO: 0090023 | positive regulation of neutrophil chemotaxis |
| 3% | GO: 0090025 | regulation of monocyte chemotaxis |
| 3% | GO: 0090026 | positive regulation of monocyte chemotaxis |

TABLE 3-continued

GO term analysis of genes differentially expressed in subgroups

| Proportion of Samples | Biological Process | Biological Process Name |
|---|---|---|
| 3% | GO: 0090050 | positive regulation of cell migration involved in sprouting angiogenesis |
| 3% | GO: 0090092 | regulation of transmembrane receptor protein serine/threonine kinase signaling pathway |
| 3% | GO: 0090257 | regulation of muscle system process |
| 3% | GO: 0097006 | regulation of plasma lipoprotein particle levels |
| 3% | GO: 1900048 | positive regulation of hemostasis |
| 3% | GO: 2000052 | positive regulation of non-canonical Wnt receptor signaling pathway |
| 3% | GO: 2000098 | negative regulation of smooth muscle cell-matrix adhesion |
| 3% | GO: 2000146 | negative regulation of cell motility |
| 3% | GO: 2000177 | regulation of neural precursor cell proliferation |
| 3% | GO: 2000402 | negative regulation of lymphocyte migration |
| 3% | GO: 2001280 | positive regulation of unsaturated fatty acid biosynthetic process |
| | | CLAS (32 Samples) |
| **53%** | **GO: 0007399** | **nervous system development** |
| 38% | GO: 0007155 | cell adhesion |
| 38% | GO: 0022610 | biological adhesion |
| 38% | GO: 0048731 | system development |
| 38% | GO: 0071230 | cellular response to amino acid stimulus |
| 34% | GO: 0001944 | vasculature development |
| **34%** | **GO: 0022008** | **neurogenesis** |
| 34% | GO: 0030198 | extracellular matrix organization |
| 34% | GO: 0043062 | extracellular structure organization |
| 31% | GO: 0001568 | blood vessel development |
| 31% | GO: 0009611 | response to wounding |
| **31%** | **GO: 0030182** | **neuron differentiation** |
| 31% | GO: 0048514 | blood vessel morphogenesis |
| **31%** | **GO: 0048666** | **neuron development** |
| **31%** | **GO: 0048699** | **generation of neurons** |
| 31% | GO: 0048856 | anatomical structure development |
| 31% | GO: 0071346 | cellular response to interferon-gamma |
| 28% | GO: 0000904 | cell morphogenesis involved in differentiation |
| 28% | GO: 0006952 | defense response |
| 28% | GO: 0007275 | multicellular organismal development |
| 28% | GO: 0009607 | response to biotic stimulus |
| 28% | GO: 0009653 | anatomical structure morphogenesis |
| 28% | GO: 0010033 | response to organic substance |
| 28% | GO: 0030334 | regulation of cell migration |
| 28% | GO: 0031175 | neuron projection development |
| 28% | GO: 0032502 | developmental process |
| 28% | GO: 0034340 | response to type I interferon |
| 28% | GO: 0034341 | response to interferon-gamma |
| 28% | GO: 0040012 | regulation of locomotion |
| **28%** | **GO: 0048667** | **cell morphogenesis involved in neuron differentiation** |
| 28% | GO: 0048812 | neuron projection morphogenesis |
| 28% | GO: 0060333 | interferon-gamma-mediated signaling pathway |
| 28% | GO: 0060337 | type I interferon-mediated signaling pathway |
| 28% | GO: 0071229 | cellular response to acid |
| 28% | GO: 0071357 | cellular response to type I interferon |
| 28% | GO: 0072358 | cardiovascular system development |
| 28% | GO: 0072359 | circulatory system development |
| 28% | GO: 2000145 | regulation of cell motility |
| 25% | GO: 0000902 | cell morphogenesis |
| 25% | GO: 0007409 | axonogenesis |
| 25% | GO: 0019221 | cytokine-mediated signaling pathway |
| 25% | GO: 0030154 | cell differentiation |
| 25% | GO: 0032989 | cellular component morphogenesis |
| 25% | GO: 0032990 | cell part morphogenesis |
| 25% | GO: 0034097 | response to cytokine stimulus |
| 25% | GO: 0040011 | locomotion |
| 25% | GO: 0045765 | regulation of angiogenesis |
| 25% | GO: 0048468 | cell development |
| 25% | GO: 0048858 | cell projection morphogenesis |
| 25% | GO: 0048869 | cellular developmental process |
| 25% | GO: 0051270 | regulation of cellular component movement |
| 25% | GO: 0051707 | response to other organism |
| 25% | GO: 0055093 | response to hyperoxia |
| 22% | GO: 0001101 | response to acid |
| 22% | GO: 0002376 | immune system process |
| 22% | GO: 0002504 | antigen processing and presentation of peptide or polysaccharide antigen via MHC class II |
| 22% | GO: 0009605 | response to external stimulus |
| 22% | GO: 0009615 | response to virus |
| 22% | GO: 0010243 | response to organic nitrogen |
| 22% | GO: 0016477 | cell migration |

TABLE 3-continued

| GO term analysis of genes differentially expressed in subgroups | | |
|---|---|---|
| Proportion of Samples | Biological Process | Biological Process Name |
| 22% | GO: 0030030 | cell projection organization |
| 22% | GO: 0042221 | response to chemical stimulus |
| 22% | GO: 0043200 | response to amino acid stimulus |
| 22% | GO: 0048545 | response to steroid hormone stimulus |
| 22% | GO: 0050900 | leukocyte migration |
| 22% | GO: 0070482 | response to oxygen levels |
| 22% | GO: 0071345 | cellular response to cytokine stimulus |
| 22% | GO: 0071417 | cellular response to organic nitrogen |
| 22% | GO: 0071418 | cellular response to amine stimulus |
| 22% | GO: 2000147 | positive regulation of cell motility |
| 19% | GO: 0006935 | chemotaxis |
| 19% | GO: 0006955 | immune response |
| 19% | GO: 0007596 | blood coagulation |
| 19% | GO: 0007599 | hemostasis |
| 19% | GO: 0009612 | response to mechanical stimulus |
| 19% | GO: 0009888 | tissue development |
| 19% | GO: 0030199 | collagen fibril organization |
| 19% | GO: 0030335 | positive regulation of cell migration |
| 19% | GO: 0040017 | positive regulation of locomotion |
| 19% | GO: 0042060 | wound healing |
| 19% | GO: 0042330 | taxis |
| 19% | GO: 0050817 | coagulation |
| 19% | GO: 0050878 | regulation of body fluid levels |
| 19% | GO: 0051272 | positive regulation of cellular component movement |
| 16% | GO: 0001525 | angiogenesis |
| 16% | GO: 0001822 | kidney development |
| 16% | GO: 0002237 | response to molecule of bacterial origin |
| 16% | GO: 0006950 | response to stress |
| 16% | GO: 0006954 | inflammatory response |
| 16% | GO: 0007272 | ensheathment of neurons |
| **16%** | **GO: 0007417** | **central nervous system development** |
| 16% | GO: 0007568 | aging |
| 16% | GO: 0008366 | axon ensheathment |
| 16% | GO: 0030155 | regulation of cell adhesion |
| 16% | GO: 0030168 | platelet activation |
| 16% | GO: 0032355 | response to estradiol stimulus |
| 16% | GO: 0032496 | response to lipopolysaccharide |
| **16%** | **GO: 0042063** | **gliogenesis** |
| 16% | GO: 0042552 | myelination |
| 16% | GO: 0045087 | innate immune response |
| 16% | GO: 0050793 | regulation of developmental process |
| 16% | GO: 0070887 | cellular response to chemical stimulus |
| 16% | GO: 0071310 | cellular response to organic substance |
| 13% | GO: 0001666 | response to hypoxia |
| 13% | GO: 0001775 | cell activation |
| 13% | GO: 0002495 | antigen processing and presentation of peptide antigen via MHC class II |
| 13% | GO: 0003008 | system process |
| 13% | GO: 0006928 | cellular component movement |
| 13% | GO: 0007162 | negative regulation of cell adhesion |
| 13% | GO: 0010035 | response to inorganic substance |
| 13% | GO: 0014075 | response to amine stimulus |
| 13% | GO: 0016064 | immunoglobulin mediated immune response |
| 13% | GO: 0019228 | regulation of action potential in neuron |
| 13% | GO: 0019886 | antigen processing and presentation of exogenous peptide antigen via MHC class II |
| 13% | GO: 0022603 | regulation of anatomical structure morphogenesis |
| 13% | GO: 0032101 | regulation of response to external stimulus |
| 13% | GO: 0032570 | response to progesterone stimulus |
| 13% | GO: 0043627 | response to estrogen stimulus |
| 13% | GO: 0048583 | regulation of response to stimulus |
| 13% | GO: 0048584 | positive regulation of response to stimulus |
| 13% | GO: 0048870 | cell motility |
| 13% | GO: 0051239 | regulation of multicellular organismal process |
| 13% | GO: 0051674 | localization of cell |
| 13% | GO: 0051704 | multi-organism process |
| 13% | GO: 0060326 | cell chemotaxis |
| 13% | GO: 0060541 | respiratory system development |
| 13% | GO: 2000026 | regulation of multicellular organismal development |
| 9% | GO: 0001505 | regulation of neurotransmitter levels |
| 9% | GO: 0001508 | regulation of action potential |
| 9% | GO: 0002250 | adaptive immune response |
| 9% | GO: 0002252 | immune effector process |
| 9% | GO: 0002253 | activation of immune response |
| 9% | GO: 0002443 | leukocyte mediated immunity |
| 9% | GO: 0002449 | lymphocyte mediated immunity |

TABLE 3-continued

GO term analysis of genes differentially expressed in subgroups

| Proportion of Samples | Biological Process | Biological Process Name |
|---|---|---|
| 9% | GO: 0002460 | adaptive immune response based on somatic recombination of immune receptors built from immunoglobulin superfamily domains |
| 9% | GO: 0002576 | platelet degranulation |
| 9% | GO: 0002682 | regulation of immune system process |
| 9% | GO: 0002684 | positive regulation of immune system process |
| 9% | GO: 0002768 | immune response-regulating cell surface receptor signaling pathway |
| 9% | GO: 0006836 | neurotransmitter transport |
| 9% | GO: 0006959 | humoral immune response |
| 9% | GO: 0007267 | cell-cell signaling |
| 9% | GO: 0007268 | synaptic transmission |
| 9% | GO: 0007269 | neurotransmitter secretion |
| 9% | GO: 0007411 | axon guidance |
| 9% | GO: 0008347 | glial cell migration |
| 9% | GO: 0009266 | response to temperature stimulus |
| 9% | GO: 0009617 | response to bacterium |
| 9% | GO: 0009719 | response to endogenous stimulus |
| 9% | GO: 0014003 | oligodendrocyte development |
| 9% | GO: 0014013 | regulation of gliogenesis |
| 9% | GO: 0014047 | glutamate secretion |
| 9% | GO: 0014910 | regulation of smooth muscle cell migration |
| 9% | GO: 0016525 | negative regulation of angiogenesis |
| 9% | GO: 0019226 | transmission of nerve impulse |
| 9% | GO: 0019724 | B cell mediated immunity |
| 9% | GO: 0030593 | neutrophil chemotaxis |
| 9% | GO: 0031099 | regeneration |
| 9% | GO: 0032501 | multicellular organismal process |
| 9% | GO: 0032835 | glomerulus development |
| 9% | GO: 0032879 | regulation of localization |
| 9% | GO: 0032964 | collagen biosynthetic process |
| 9% | GO: 0035637 | multicellular organismal signaling |
| 9% | GO: 0042391 | regulation of membrane potential |
| 9% | GO: 0042493 | response to drug |
| 9% | GO: 0044259 | multicellular organismal macromolecule metabolic process |
| 9% | GO: 0045428 | regulation of nitric oxide biosynthetic process |
| 9% | GO: 0045766 | positive regulation of angiogenesis |
| 9% | GO: 0048488 | synaptic vesicle endocytosis |
| 9% | GO: 0048489 | synaptic vesicle transport |
| 9% | GO: 0048513 | organ development |
| 9% | GO: 0048585 | negative regulation of response to stimulus |
| 9% | GO: 0048709 | oligodendrocyte differentiation |
| 9% | GO: 0050730 | regulation of peptidyl-tyrosine phosphorylation |
| 9% | GO: 0050776 | regulation of immune response |
| 9% | GO: 0050778 | positive regulation of immune response |
| 9% | GO: 0050804 | regulation of synaptic transmission |
| 9% | GO: 0050865 | regulation of cell activation |
| 9% | GO: 0050877 | neurological system process |
| 9% | GO: 0050920 | regulation of chemotaxis |
| 9% | GO: 0051969 | regulation of transmission of nerve impulse |
| 9% | GO: 0055082 | cellular chemical homeostasis |
| 9% | GO: 0060236 | regulation of mitotic spindle organization |
| 9% | GO: 0070208 | protein heterotrimerization |
| 9% | GO: 0071219 | cellular response to molecule of bacterial origin |
| 9% | GO: 0071222 | cellular response to lipopolysaccharide |
| 9% | GO: 0072001 | renal system development |
| 9% | GO: 0072012 | glomerulus vasculature development |
| 9% | GO: 0072239 | metanephric glomerulus vasculature development |
| 6% | GO: 0000075 | cell cycle checkpoint |
| 6% | GO: 0000087 | M phase of mitotic cell cycle |
| 6% | GO: 0000236 | mitotic prometaphase |
| 6% | GO: 0000278 | mitotic cell cycle |
| 6% | GO: 0000279 | M phase |
| 6% | GO: 0000280 | nuclear division |
| 6% | GO: 0000302 | response to reactive oxygen species |
| 6% | GO: 0001501 | skeletal system development |
| 6% | GO: 0001504 | neurotransmitter uptake |
| 6% | GO: 0001817 | regulation of cytokine production |
| 6% | GO: 0002429 | immune response-activating cell surface receptor signaling pathway |
| 6% | GO: 0002455 | humoral immune response mediated by circulating immunoglobulin |
| 6% | GO: 0002520 | immune system development |
| 6% | GO: 0002521 | leukocyte differentiation |
| 6% | GO: 0002544 | chronic inflammatory response |
| 6% | GO: 0002675 | positive regulation of acute inflammatory response |
| 6% | GO: 0002683 | negative regulation of immune system process |
| 6% | GO: 0002685 | regulation of leukocyte migration |
| 6% | GO: 0002690 | positive regulation of leukocyte chemotaxis |

TABLE 3-continued

GO term analysis of genes differentially expressed in subgroups

| Proportion of Samples | Biological Process | Biological Process Name |
|---|---|---|
| 6% | GO: 0002694 | regulation of leukocyte activation |
| 6% | GO: 0003001 | generation of a signal involved in cell-cell signaling |
| 6% | GO: 0006260 | DNA replication |
| 6% | GO: 0006693 | prostaglandin metabolic process |
| 6% | GO: 0006873 | cellular ion homeostasis |
| 6% | GO: 0006909 | phagocytosis |
| 6% | GO: 0006916 | anti-apoptosis |
| 6% | GO: 0006956 | complement activation |
| 6% | GO: 0006958 | complement activation, classical pathway |
| 6% | GO: 0007067 | mitosis |
| 6% | GO: 0007160 | cell-matrix adhesion |
| 6% | GO: 0007166 | cell surface receptor signaling pathway |
| 6% | GO: 0007416 | synapse assembly |
| 6% | GO: 0008284 | positive regulation of cell proliferation |
| 6% | GO: 0008285 | negative regulation of cell proliferation |
| 6% | GO: 0009628 | response to abiotic stimulus |
| 6% | GO: 0009887 | organ morphogenesis |
| 6% | GO: 0010001 | glial cell differentiation |
| 6% | GO: 0010564 | regulation of cell cycle process |
| 6% | GO: 0010646 | regulation of cell communication |
| 6% | GO: 0010647 | positive regulation of cell communication |
| 6% | GO: 0010812 | negative regulation of cell-substrate adhesion |
| 6% | GO: 0014014 | negative regulation of gliogenesis |
| 6% | GO: 0014070 | response to organic cyclic compound |
| 6% | GO: 0016337 | cell-cell adhesion |
| 6% | GO: 0019229 | regulation of vasoconstriction |
| 6% | GO: 0019882 | antigen processing and presentation |
| 6% | GO: 0022402 | cell cycle process |
| 6% | GO: 0022403 | cell cycle phase |
| 6% | GO: 0023051 | regulation of signaling |
| 6% | GO: 0023052 | signaling |
| 6% | GO: 0023056 | positive regulation of signaling |
| 6% | GO: 0023061 | signal release |
| 6% | GO: 0030097 | hemopoiesis |
| 6% | GO: 0030098 | lymphocyte differentiation |
| 6% | GO: 0030595 | leukocyte chemotaxis |
| 6% | GO: 0031102 | neuron projection regeneration |
| 6% | GO: 0031294 | lymphocyte costimulation |
| 6% | GO: 0031295 | T cell costimulation |
| 6% | GO: 0031589 | cell-substrate adhesion |
| 6% | GO: 0031644 | regulation of neurological system process |
| 6% | GO: 0031663 | lipopolysaccharide-mediated signaling pathway |
| 6% | GO: 0031960 | response to corticosteroid stimulus |
| 6% | GO: 0032103 | positive regulation of response to external stimulus |
| 6% | GO: 0032940 | secretion by cell |
| 6% | GO: 0035295 | tube development |
| 6% | GO: 0035457 | cellular response to interferon-alpha |
| 6% | GO: 0035924 | cellular response to vascular endothelial growth factor stimulus |
| 6% | GO: 0042127 | regulation of cell proliferation |
| 6% | GO: 0042476 | odontogenesis |
| 6% | GO: 0043086 | negative regulation of catalytic activity |
| 6% | GO: 0044057 | regulation of system process |
| 6% | GO: 0044236 | multicellular organismal metabolic process |
| 6% | GO: 0045321 | leukocyte activation |
| 6% | GO: 0045429 | positive regulation of nitric oxide biosynthetic process |
| 6% | GO: 0046903 | secretion |
| 6% | GO: 0048010 | vascular endothelial growth factor receptor signaling pathway |
| 6% | GO: 0048167 | regulation of synaptic plasticity |
| 6% | GO: 0048285 | organelle fission |
| 6% | GO: 0048519 | negative regulation of biological process |
| 6% | GO: 0048520 | positive regulation of behavior |
| 6% | GO: 0048706 | embryonic skeletal system development |
| 6% | GO: 0050727 | regulation of inflammatory response |
| 6% | GO: 0050729 | positive regulation of inflammatory response |
| 6% | GO: 0050732 | negative regulation of peptidyl-tyrosine phosphorylation |
| 6% | GO: 0050795 | regulation of behavior |
| 6% | GO: 0050808 | synapse organization |
| 6% | GO: 0050851 | antigen receptor-mediated signaling pathway |
| 6% | GO: 0050867 | positive regulation of cell activation |
| 6% | GO: 0050870 | positive regulation of T cell activation |
| 6% | GO: 0050896 | response to stimulus |
| 6% | GO: 0050921 | positive regulation of chemotaxis |
| 6% | GO: 0051050 | positive regulation of transport |
| 6% | GO: 0051384 | response to glucocorticoid stimulus |
| 6% | GO: 0052547 | regulation of peptidase activity |

TABLE 3-continued

GO term analysis of genes differentially expressed in subgroups

| Proportion of Samples | Biological Process | Biological Process Name |
|---|---|---|
| 6% | GO: 0060627 | regulation of vesicle-mediated transport |
| 6% | GO: 0061041 | regulation of wound healing |
| 6% | GO: 0061298 | retina vasculature development in camera-type eye |
| 6% | GO: 0070372 | regulation of ERK1 and ERK2 cascade |
| 6% | GO: 0071156 | regulation of cell cycle arrest |
| 6% | GO: 0071216 | cellular response to biotic stimulus |
| 6% | GO: 0072006 | nephron development |
| 6% | GO: 0072224 | metanephric glomerulus development |
| 6% | GO: 0072376 | protein activation cascade |
| 6% | GO: 0080134 | regulation of response to stress |
| 6% | GO: 2000097 | regulation of smooth muscle cell-matrix adhesion |
| 3% | GO: 0000070 | mitotic sister chromatid segregation |
| 3% | GO: 0000082 | G1/S transition of mitotic cell cycle |
| 3% | GO: 0000226 | microtubule cytoskeleton organization |
| 3% | GO: 0000819 | sister chromatid segregation |
| 3% | GO: 0001655 | urogenital system development |
| 3% | GO: 0001656 | metanephros development |
| 3% | GO: 0001736 | establishment of planar polarity |
| 3% | GO: 0001796 | regulation of type IIa hypersensitivity |
| 3% | GO: 0001798 | positive regulation of type IIa hypersensitivity |
| 3% | GO: 0001889 | liver development |
| 3% | GO: 0001893 | maternal placenta development |
| 3% | GO: 0001915 | negative regulation of T cell mediated cytotoxicity |
| 3% | GO: 0001933 | negative regulation of protein phosphorylation |
| 3% | GO: 0002011 | morphogenesis of an epithelial sheet |
| 3% | GO: 0002138 | retinoic acid biosynthetic process |
| 3% | GO: 0002175 | protein localization to paranode region of axon |
| 3% | GO: 0002246 | wound healing involved in inflammatory response |
| 3% | GO: 0002274 | myeloid leukocyte activation |
| 3% | GO: 0002474 | antigen processing and presentation of peptide antigen via MHC class I |
| 3% | GO: 0002478 | antigen processing and presentation of exogenous peptide antigen |
| 3% | GO: 0002479 | antigen processing and presentation of exogenous peptide antigen via MHC class I, TAP-dependent |
| 3% | GO: 0002480 | antigen processing and presentation of exogenous peptide antigen via MHC class I, TAP-independent |
| 3% | GO: 0002507 | tolerance induction |
| 3% | GO: 0002526 | acute inflammatory response |
| 3% | GO: 0002673 | regulation of acute inflammatory response |
| 3% | GO: 0002687 | positive regulation of leukocyte migration |
| 3% | GO: 0002688 | regulation of leukocyte chemotaxis |
| 3% | GO: 0002697 | regulation of immune effector process |
| 3% | GO: 0002698 | negative regulation of immune effector process |
| 3% | GO: 0002699 | positive regulation of immune effector process |
| 3% | GO: 0002703 | regulation of leukocyte mediated immunity |
| 3% | GO: 0002706 | regulation of lymphocyte mediated immunity |
| 3% | GO: 0002709 | regulation of T cell mediated immunity |
| 3% | GO: 0002718 | regulation of cytokine production involved in immune response |
| 3% | GO: 0002757 | immune response-activating signal transduction |
| 3% | GO: 0002764 | immune response-regulating signaling pathway |
| 3% | GO: 0002765 | immune response-inhibiting signal transduction |
| 3% | GO: 0002767 | immune response-inhibiting cell surface receptor signaling pathway |
| 3% | GO: 0002774 | Fc receptor mediated inhibitory signaling pathway |
| 3% | GO: 0002819 | regulation of adaptive immune response |
| 3% | GO: 0002820 | negative regulation of adaptive immune response |
| 3% | GO: 0002822 | regulation of adaptive immune response based on somatic recombination of immune receptors built from immunoglobulin superfamily domains |
| 3% | GO: 0002888 | positive regulation of myeloid leukocyte mediated immunity |
| 3% | GO: 0002889 | regulation of immunoglobulin mediated immune response |
| 3% | GO: 0002892 | regulation of type II hypersensitivity |
| 3% | GO: 0002894 | positive regulation of type II hypersensitivity |
| 3% | GO: 0003002 | regionalization |
| 3% | GO: 0003013 | circulatory system process |
| 3% | GO: 0003094 | glomerular filtration |
| 3% | GO: 0003149 | membranous septum morphogenesis |
| 3% | GO: 0003150 | muscular septum morphogenesis |
| 3% | GO: 0003281 | ventricular septum development |
| 3% | GO: 0006259 | DNA metabolic process |
| 3% | GO: 0006261 | DNA-dependent DNA replication |
| 3% | GO: 0006270 | DNA-dependent DNA replication initiation |
| 3% | GO: 0006271 | DNA strand elongation involved in DNA replication |
| 3% | GO: 0006281 | DNA repair |
| 3% | GO: 0006323 | DNA packaging |
| 3% | GO: 0006333 | chromatin assembly or disassembly |
| 3% | GO: 0006334 | nucleosome assembly |
| 3% | GO: 0006336 | DNA replication-independent nucleosome assembly |

TABLE 3-continued

GO term analysis of genes differentially expressed in subgroups

| Proportion of Samples | Biological Process | Biological Process Name |
|---|---|---|
| 3% | GO: 0006692 | prostanoid metabolic process |
| 3% | GO: 0006811 | ion transport |
| 3% | GO: 0006812 | cation transport |
| 3% | GO: 0006814 | sodium ion transport |
| 3% | GO: 0006821 | chloride transport |
| 3% | GO: 0006826 | iron ion transport |
| 3% | GO: 0006879 | cellular iron ion homeostasis |
| 3% | GO: 0006887 | exocytosis |
| 3% | GO: 0006996 | organelle organization |
| 3% | GO: 0007010 | cytoskeleton organization |
| 3% | GO: 0007017 | microtubule-based process |
| 3% | GO: 0007018 | microtubule-based movement |
| 3% | GO: 0007049 | cell cycle |
| 3% | GO: 0007051 | spindle organization |
| 3% | GO: 0007059 | chromosome segregation |
| 3% | GO: 0007076 | mitotic chromosome condensation |
| 3% | GO: 0007093 | mitotic cell cycle checkpoint |
| 3% | GO: 0007094 | mitotic cell cycle spindle assembly checkpoint |
| 3% | GO: 0007156 | homophilic cell adhesion |
| 3% | GO: 0007159 | leukocyte cell-cell adhesion |
| 3% | GO: 0007164 | establishment of tissue polarity |
| 3% | GO: 0007165 | signal transduction |
| 3% | GO: 0007179 | transforming growth factor beta receptor signaling pathway |
| 3% | GO: 0007194 | negative regulation of adenylate cyclase activity |
| 3% | GO: 0007199 | G-protein signaling, coupled to cGMP nucleotide second messenger |
| 3% | GO: 0007214 | gamma-aminobutyric acid signaling pathway |
| 3% | GO: 0007229 | integrin-mediated signaling pathway |
| 3% | GO: 0007346 | regulation of mitotic cell cycle |
| 3% | GO: 0007420 | brain development |
| 3% | GO: 0007431 | salivary gland development |
| 3% | GO: 0007517 | muscle organ development |
| 3% | GO: 0007610 | behavior |
| 3% | GO: 0007611 | learning or memory |
| 3% | GO: 0007612 | learning |
| 3% | GO: 0007613 | memory |
| 3% | GO: 0008015 | blood circulation |
| 3% | GO: 0008217 | regulation of blood pressure |
| 3% | GO: 0008360 | regulation of cell shape |
| 3% | GO: 0008406 | gonad development |
| 3% | GO: 0009221 | pyrimidine deoxyribonucleotide biosynthetic process |
| 3% | GO: 0009263 | deoxyribonucleotide biosynthetic process |
| 3% | GO: 0009306 | protein secretion |
| 3% | GO: 0009725 | response to hormone stimulus |
| 3% | GO: 0009743 | response to carbohydrate stimulus |
| 3% | GO: 0009746 | response to hexose stimulus |
| 3% | GO: 0009749 | response to glucose stimulus |
| 3% | GO: 0009792 | embryo development ending in birth or egg hatching |
| 3% | GO: 0009952 | anterior/posterior pattern specification |
| 3% | GO: 0009954 | proximal/distal pattern formation |
| 3% | GO: 0009967 | positive regulation of signal transduction |
| 3% | GO: 0010038 | response to metal ion |
| 3% | GO: 0010332 | response to gamma radiation |
| 3% | GO: 0010466 | negative regulation of peptidase activity |
| 3% | GO: 0010563 | negative regulation of phosphorus metabolic process |
| 3% | GO: 0010574 | regulation of vascular endothelial growth factor production |
| 3% | GO: 0010648 | negative regulation of cell communication |
| 3% | GO: 0010716 | negative regulation of extracellular matrix disassembly |
| 3% | GO: 0010718 | positive regulation of epithelial to mesenchymal transition |
| 3% | GO: 0010720 | positive regulation of cell development |
| 3% | GO: 0010721 | negative regulation of cell development |
| 3% | GO: 0010758 | regulation of macrophage chemotaxis |
| 3% | GO: 0010759 | positive regulation of macrophage chemotaxis |
| 3% | GO: 0010810 | regulation of cell-substrate adhesion |
| 3% | GO: 0010811 | positive regulation of cell-substrate adhesion |
| 3% | GO: 0010935 | regulation of macrophage cytokine production |
| 3% | GO: 0010936 | negative regulation of macrophage cytokine production |
| 3% | GO: 0010941 | regulation of cell death |
| 3% | GO: 0010951 | negative regulation of endopeptidase activity |
| 3% | GO: 0010955 | negative regulation of protein processing |
| 3% | GO: 0014015 | positive regulation of gliogenesis |
| 3% | GO: 0014706 | striated muscle tissue development |
| 3% | GO: 0014805 | smooth muscle adaptation |
| 3% | GO: 0015672 | monovalent inorganic cation transport |
| 3% | GO: 0015698 | inorganic anion transport |
| 3% | GO: 0015807 | L-amino acid transport |

TABLE 3-continued

GO term analysis of genes differentially expressed in subgroups

| Proportion of Samples | Biological Process | Biological Process Name |
|---|---|---|
| 3% | GO: 0016043 | cellular component organization |
| 3% | GO: 0016048 | detection of temperature stimulus |
| 3% | GO: 0016079 | synaptic vesicle exocytosis |
| 3% | GO: 0016188 | synaptic vesicle maturation |
| 3% | GO: 0016339 | calcium-dependent cell-cell adhesion |
| 3% | GO: 0018149 | peptide cross-linking |
| 3% | GO: 0019725 | cellular homeostasis |
| 3% | GO: 0019884 | antigen processing and presentation of exogenous antigen |
| 3% | GO: 0021529 | spinal cord oligodendrocyte cell differentiation |
| 3% | GO: 0021530 | spinal cord oligodendrocyte cell fate specification |
| 3% | GO: 0021537 | telencephalon development |
| 3% | GO: 0021543 | pallium development |
| 3% | GO: 0021778 | oligodendrocyte cell fate specification |
| 3% | GO: 0021780 | glial cell fate specification |
| 3% | GO: 0021782 | glial cell development |
| 3% | GO: 0021882 | regulation of transcription from RNA polymerase II promoter involved in forebrain neuron fate commitment |
| 3% | GO: 0021893 | cerebral cortex GABAergic interneuron fate commitment |
| 3% | GO: 0021953 | central nervous system neuron differentiation |
| 3% | GO: 0021954 | central nervous system neuron development |
| 3% | GO: 0022010 | central nervous system myelination |
| 3% | GO: 0022406 | membrane docking |
| 3% | GO: 0022409 | positive regulation of cell-cell adhesion |
| 3% | GO: 0022602 | ovulation cycle process |
| 3% | GO: 0022604 | regulation of cell morphogenesis |
| 3% | GO: 0022614 | membrane to membrane docking |
| 3% | GO: 0022616 | DNA strand elongation |
| 3% | GO: 0023057 | negative regulation of signaling |
| 3% | GO: 0030001 | metal ion transport |
| 3% | GO: 0030036 | actin cytoskeleton organization |
| 3% | GO: 0030071 | regulation of mitotic metaphase/anaphase transition |
| 3% | GO: 0030100 | regulation of endocytosis |
| 3% | GO: 0030111 | regulation of Wnt receptor signaling pathway |
| 3% | GO: 0030217 | T cell differentiation |
| 3% | GO: 0030261 | chromosome condensation |
| 3% | GO: 0030323 | respiratory tube development |
| 3% | GO: 0030324 | lung development |
| 3% | GO: 0030800 | negative regulation of cyclic nucleotide metabolic process |
| 3% | GO: 0030803 | negative regulation of cyclic nucleotide biosynthetic process |
| 3% | GO: 0030809 | negative regulation of nucleotide biosynthetic process |
| 3% | GO: 0030815 | negative regulation of cAMP metabolic process |
| 3% | GO: 0030818 | negative regulation of cAMP biosynthetic process |
| 3% | GO: 0031055 | chromatin remodeling at centromere |
| 3% | GO: 0031100 | organ regeneration |
| 3% | GO: 0031280 | negative regulation of cyclase activity |
| 3% | GO: 0031344 | regulation of cell projection organization |
| 3% | GO: 0031347 | regulation of defense response |
| 3% | GO: 0031497 | chromatin assembly |
| 3% | GO: 0031577 | spindle checkpoint |
| 3% | GO: 0031646 | positive regulation of neurological system process |
| 3% | GO: 0032091 | negative regulation of protein binding |
| 3% | GO: 0032228 | regulation of synaptic transmission, GABAergic |
| 3% | GO: 0032291 | axon ensheathment in central nervous system |
| 3% | GO: 0032680 | regulation of tumor necrosis factor production |
| 3% | GO: 0032763 | regulation of mast cell cytokine production |
| 3% | GO: 0032944 | regulation of mononuclear cell proliferation |
| 3% | GO: 0032963 | collagen metabolic process |
| 3% | GO: 0033003 | regulation of mast cell activation |
| 3% | GO: 0034080 | CenH3-containing nucleosome assembly at centromere |
| 3% | GO: 0034220 | ion transmembrane transport |
| 3% | GO: 0034284 | response to monosaccharide stimulus |
| 3% | GO: 0034447 | very-low-density lipoprotein particle clearance |
| 3% | GO: 0034508 | centromere complex assembly |
| 3% | GO: 0034612 | response to tumor necrosis factor |
| 3% | GO: 0034724 | DNA replication-independent nucleosome organization |
| 3% | GO: 0034728 | nucleosome organization |
| 3% | GO: 0035239 | tube morphogenesis |
| 3% | GO: 0035567 | non-canonical Wnt receptor signaling pathway |
| 3% | GO: 0035850 | epithelial cell differentiation involved in kidney development |
| 3% | GO: 0042129 | regulation of T cell proliferation |
| 3% | GO: 0042312 | regulation of vasodilation |
| 3% | GO: 0042326 | negative regulation of phosphorylation |
| 3% | GO: 0042554 | superoxide anion generation |
| 3% | GO: 0042590 | antigen processing and presentation of exogenous peptide antigen via MHC class I |

TABLE 3-continued

GO term analysis of genes differentially expressed in subgroups

| Proportion of Samples | Biological Process | Biological Process Name |
|---|---|---|
| 3% | GO: 0042592 | homeostatic process |
| 3% | GO: 0042742 | defense response to bacterium |
| 3% | GO: 0042981 | regulation of apoptotic process |
| 3% | GO: 0043009 | chordate embryonic development |
| 3% | GO: 0043044 | ATP-dependent chromatin remodeling |
| 3% | GO: 0043066 | negative regulation of apoptotic process |
| 3% | GO: 0043069 | negative regulation of programmed cell death |
| 3% | GO: 0043092 | L-amino acid import |
| 3% | GO: 0043299 | leukocyte degranulation |
| 3% | GO: 0043368 | positive T cell selection |
| 3% | GO: 0043393 | regulation of protein binding |
| 3% | GO: 0043405 | regulation of MAP kinase activity |
| 3% | GO: 0043408 | regulation of MAPK cascade |
| 3% | GO: 0043486 | histone exchange |
| 3% | GO: 0043550 | regulation of lipid kinase activity |
| 3% | GO: 0043552 | positive regulation of phosphatidylinositol 3-kinase activity |
| 3% | GO: 0043584 | nose development |
| 3% | GO: 0043588 | skin development |
| 3% | GO: 0044092 | negative regulation of molecular function |
| 3% | GO: 0044246 | regulation of multicellular organismal metabolic process |
| 3% | GO: 0045058 | T cell selection |
| 3% | GO: 0045059 | positive thymic T cell selection |
| 3% | GO: 0045061 | thymic T cell selection |
| 3% | GO: 0045137 | development of primary sexual characteristics |
| 3% | GO: 0045596 | negative regulation of cell differentiation |
| 3% | GO: 0045664 | regulation of neuron differentiation |
| 3% | GO: 0045665 | negative regulation of neuron differentiation |
| 3% | GO: 0045685 | regulation of glial cell differentiation |
| 3% | GO: 0045686 | negative regulation of glial cell differentiation |
| 3% | GO: 0045787 | positive regulation of cell cycle |
| 3% | GO: 0045839 | negative regulation of mitosis |
| 3% | GO: 0045841 | negative regulation of mitotic metaphase/anaphase transition |
| 3% | GO: 0045907 | positive regulation of vasoconstriction |
| 3% | GO: 0045909 | positive regulation of vasodilation |
| 3% | GO: 0045936 | negative regulation of phosphate metabolic process |
| 3% | GO: 0045980 | negative regulation of nucleotide metabolic process |
| 3% | GO: 0046697 | decidualization |
| 3% | GO: 0048002 | antigen processing and presentation of peptide antigen |
| 3% | GO: 0048008 | platelet-derived growth factor receptor signaling pathway |
| 3% | GO: 0048168 | regulation of neuronal synaptic plasticity |
| 3% | GO: 0048523 | negative regulation of cellular process |
| 3% | GO: 0048534 | hemopoietic or lymphoid organ development |
| 3% | GO: 0048568 | embryonic organ development |
| 3% | GO: 0048608 | reproductive structure development |
| 3% | GO: 0048646 | anatomical structure formation involved in morphogenesis |
| 3% | GO: 0048660 | regulation of smooth muscle cell proliferation |
| 3% | GO: 0048661 | positive regulation of smooth muscle cell proliferation |
| 3% | GO: 0048663 | neuron fate commitment |
| 3% | GO: 0048676 | axon extension involved in development |
| 3% | GO: 0048678 | response to axon injury |
| 3% | GO: 0048704 | embryonic skeletal system morphogenesis |
| 3% | GO: 0048705 | skeletal system morphogenesis |
| 3% | GO: 0048713 | regulation of oligodendrocyte differentiation |
| 3% | GO: 0048715 | negative regulation of oligodendrocyte differentiation |
| 3% | GO: 0048736 | appendage development |
| 3% | GO: 0048741 | skeletal muscle fiber development |
| 3% | GO: 0048771 | tissue remodeling |
| 3% | GO: 0048872 | homeostasis of number of cells |
| 3% | GO: 0048878 | chemical homeostasis |
| 3% | GO: 0050000 | chromosome localization |
| 3% | GO: 0050663 | cytokine secretion |
| 3% | GO: 0050665 | hydrogen peroxide biosynthetic process |
| 3% | GO: 0050670 | regulation of lymphocyte proliferation |
| 3% | GO: 0050767 | regulation of neurogenesis |
| 3% | GO: 0050777 | negative regulation of immune response |
| 3% | GO: 0050801 | ion homeostasis |
| 3% | GO: 0050806 | positive regulation of synaptic transmission |
| 3% | GO: 0050852 | T cell receptor signaling pathway |
| 3% | GO: 0050864 | regulation of B cell activation |
| 3% | GO: 0050890 | cognition |
| 3% | GO: 0050922 | negative regulation of chemotaxis |
| 3% | GO: 0050926 | regulation of positive chemotaxis |
| 3% | GO: 0050927 | positive regulation of positive chemotaxis |
| 3% | GO: 0051049 | regulation of transport |
| 3% | GO: 0051093 | negative regulation of developmental process |

TABLE 3-continued

GO term analysis of genes differentially expressed in subgroups

| Proportion of Samples | Biological Process | Biological Process Name |
|---|---|---|
| 3% | GO: 0051094 | positive regulation of developmental process |
| 3% | GO: 0051098 | regulation of binding |
| 3% | GO: 0051100 | negative regulation of binding |
| 3% | GO: 0051128 | regulation of cellular component organization |
| 3% | GO: 0051216 | cartilage development |
| 3% | GO: 0051240 | positive regulation of multicellular organismal process |
| 3% | GO: 0051241 | negative regulation of multicellular organismal process |
| 3% | GO: 0051249 | regulation of lymphocyte activation |
| 3% | GO: 0051276 | chromosome organization |
| 3% | GO: 0051301 | cell division |
| 3% | GO: 0051303 | establishment of chromosome localization |
| 3% | GO: 0051325 | interphase |
| 3% | GO: 0051329 | interphase of mitotic cell cycle |
| 3% | GO: 0051346 | negative regulation of hydrolase activity |
| 3% | GO: 0051350 | negative regulation of lyase activity |
| 3% | GO: 0051383 | kinetochore organization |
| 3% | GO: 0051482 | elevation of cytosolic calcium ion concentration involved in G-protein signaling coupled to IP3 second messenger |
| 3% | GO: 0051668 | localization within membrane |
| 3% | GO: 0051716 | cellular response to stimulus |
| 3% | GO: 0051726 | regulation of cell cycle |
| 3% | GO: 0051782 | negative regulation of cell division |
| 3% | GO: 0051784 | negative regulation of nuclear division |
| 3% | GO: 0051960 | regulation of nervous system development |
| 3% | GO: 0051971 | positive regulation of transmission of nerve impulse |
| 3% | GO: 0051983 | regulation of chromosome segregation |
| 3% | GO: 0055002 | striated muscle cell development |
| 3% | GO: 0055072 | iron ion homeostasis |
| 3% | GO: 0055085 | transmembrane transport |
| 3% | GO: 0060071 | Wnt receptor signaling pathway, planar cell polarity pathway |
| 3% | GO: 0060173 | limb development |
| 3% | GO: 0060348 | bone development |
| 3% | GO: 0060412 | ventricular septum morphogenesis |
| 3% | GO: 0060441 | epithelial tube branching involved in lung morphogenesis |
| 3% | GO: 0060537 | muscle tissue development |
| 3% | GO: 0060548 | negative regulation of cell death |
| 3% | GO: 0060712 | spongiotrophoblast layer development |
| 3% | GO: 0061008 | hepaticobiliary system development |
| 3% | GO: 0061061 | muscle structure development |
| 3% | GO: 0061138 | morphogenesis of a branching epithelium |
| 3% | GO: 0061318 | renal filtration cell differentiation |
| 3% | GO: 0061351 | neural precursor cell proliferation |
| 3% | GO: 0065004 | protein-DNA complex assembly |
| 3% | GO: 0065008 | regulation of biological quality |
| 3% | GO: 0070374 | positive regulation of ERK1 and ERK2 cascade |
| 3% | GO: 0070555 | response to interleukin-1 |
| 3% | GO: 0070613 | regulation of protein processing |
| 3% | GO: 0070663 | regulation of leukocyte proliferation |
| 3% | GO: 0070664 | negative regulation of leukocyte proliferation |
| 3% | GO: 0071103 | DNA conformation change |
| 3% | GO: 0071173 | spindle assembly checkpoint |
| 3% | GO: 0071174 | mitotic cell cycle spindle checkpoint |
| 3% | GO: 0071248 | cellular response to metal ion |
| 3% | GO: 0071260 | cellular response to mechanical stimulus |
| 3% | GO: 0071276 | cellular response to cadmium ion |
| 3% | GO: 0071277 | cellular response to calcium ion |
| 3% | GO: 0071347 | cellular response to interleukin-1 |
| 3% | GO: 0071356 | cellular response to tumor necrosis factor |
| 3% | GO: 0071455 | cellular response to hyperoxia |
| 3% | GO: 0071637 | regulation of monocyte chemotactic protein-1 production |
| 3% | GO: 0071675 | regulation of mononuclear cell migration |
| 3% | GO: 0071824 | protein-DNA complex subunit organization |
| 3% | GO: 0071840 | cellular component organization or biogenesis |
| 3% | GO: 0071841 | cellular component organization or biogenesis at cellular level |
| 3% | GO: 0071842 | cellular component organization at cellular level |
| 3% | GO: 0072010 | glomerular epithelium development |
| 3% | GO: 0072109 | glomerular mesangium development |
| 3% | GO: 0072110 | glomerular mesangial cell proliferation |
| 3% | GO: 0072112 | glomerular visceral epithelial cell differentiation |
| 3% | GO: 0072311 | glomerular epithelial cell differentiation |
| 3% | GO: 0090025 | regulation of monocyte chemotaxis |
| 3% | GO: 0090049 | regulation of cell migration involved in sprouting angiogenesis |
| 3% | GO: 0090175 | regulation of establishment of planar polarity |
| 3% | GO: 0090224 | regulation of spindle organization |
| 3% | GO: 0097205 | renal filtration |

TABLE 3-continued

GO term analysis of genes differentially expressed in subgroups

| Proportion of Samples | Biological Process | Biological Process Name |
|---|---|---|
| 3% | GO: 2000300 | regulation of synaptic vesicle exocytosis |
| 3% | GO: 2000401 | regulation of lymphocyte migration |
| 3% | GO: 2000402 | negative regulation of lymphocyte migration |
| 3% | GO: 2000501 | regulation of natural killer cell chemotaxis |
| | | SL (20 Samples) |
| **80%** | **GO: 0007399** | **nervous system development** |
| **55%** | **GO: 0022008** | **neurogenesis** |
| **50%** | **GO: 0048699** | **generation of neurons** |
| 40% | GO: 0002504 | antigen processing and presentation of peptide or polysaccharide antigen via MHC class II |
| **40%** | **GO: 0042063** | **gliogenesis** |
| **35%** | **GO: 0030182** | **neuron differentiation** |
| 35% | GO: 0048468 | cell development |
| **30%** | **GO: 0007417** | **central nervous system development** |
| 30% | GO: 0048167 | regulation of synaptic plasticity |
| 30% | GO: 0048731 | system development |
| 30% | GO: 0048856 | anatomical structure development |
| 30% | GO: 0050793 | regulation of developmental process |
| 25% | GO: 0001568 | blood vessel development |
| **25%** | **GO: 0010001** | **glial cell differentiation** |
| 25% | GO: 0010033 | response to organic substance |
| 25% | GO: 0031960 | response to corticosteroid stimulus |
| 25% | GO: 0034341 | response to interferon-gamma |
| 25% | GO: 0051384 | response to glucocorticoid stimulus |
| 25% | GO: 0060333 | interferon-gamma-mediated signaling pathway |
| 25% | GO: 0071229 | cellular response to acid |
| 25% | GO: 0071346 | cellular response to interferon-gamma |
| 20% | GO: 0001101 | response to acid |
| 20% | GO: 0001944 | vasculature development |
| 20% | GO: 0002495 | antigen processing and presentation of peptide antigen via MHC class II |
| 20% | GO: 0006952 | defense response |
| 20% | GO: 0007267 | cell-cell signaling |
| 20% | GO: 0007268 | synaptic transmission |
| 20% | GO: 0007269 | neurotransmitter secretion |
| 20% | GO: 0007275 | multicellular organismal development |
| 20% | GO: 0010243 | response to organic nitrogen |
| **20%** | **GO: 0014013** | **regulation of gliogenesis** |
| 20% | GO: 0014047 | glutamate secretion |
| 20% | GO: 0019226 | transmission of nerve impulse |
| 20% | GO: 0019886 | antigen processing and presentation of exogenous peptide antigen via MHC class II |
| 20% | GO: 0031644 | regulation of neurological system process |
| 20% | GO: 0032940 | secretion by cell |
| 20% | GO: 0035295 | tube development |
| 20% | GO: 0035637 | multicellular organismal signaling |
| 20% | GO: 0048168 | regulation of neuronal synaptic plasticity |
| 20% | GO: 0048489 | synaptic vesicle transport |
| **20%** | **GO: 0048709** | **oligodendrocyte differentiation** |
| **20%** | **GO: 0050767** | **regulation of neurogenesis** |
| 20% | GO: 0050804 | regulation of synaptic transmission |
| 20% | GO: 0050877 | neurological system process |
| 20% | GO: 0051093 | negative regulation of developmental process |
| **20%** | **GO: 0051960** | **regulation of nervous system development** |
| 20% | GO: 0051969 | regulation of transmission of nerve impulse |
| 20% | GO: 2000026 | regulation of multicellular organismal development |
| 15% | GO: 0000904 | cell morphogenesis involved in differentiation |
| 15% | GO: 0001505 | regulation of neurotransmitter levels |
| 15% | GO: 0001822 | kidney development |
| 15% | GO: 0003001 | generation of a signal involved in cell-cell signaling |
| 15% | GO: 0003008 | system process |
| 15% | GO: 0006836 | neurotransmitter transport |
| 15% | GO: 0007155 | cell adhesion |
| 15% | GO: 0007409 | axonogenesis |
| 15% | GO: 0008284 | positive regulation of cell proliferation |
| 15% | GO: 0009611 | response to wounding |
| 15% | GO: 0009653 | anatomical structure morphogenesis |
| 15% | GO: 0016064 | immunoglobulin mediated immune response |
| 15% | GO: 0019228 | regulation of action potential in neuron |
| 15% | GO: 0019724 | B cell mediated immunity |
| 15% | GO: 0022603 | regulation of anatomical structure morphogenesis |
| 15% | GO: 0022610 | biological adhesion |
| 15% | GO: 0023061 | signal release |
| 15% | GO: 0030030 | cell projection organization |
| 15% | GO: 0030154 | cell differentiation |

TABLE 3-continued

GO term analysis of genes differentially expressed in subgroups

| Proportion of Samples | Biological Process | Biological Process Name |
|---|---|---|
| 15% | GO: 0030323 | respiratory tube development |
| 15% | GO: 0030324 | lung development |
| 15% | GO: 0031175 | neuron projection development |
| 15% | GO: 0034097 | response to cytokine stimulus |
| 15% | GO: 0035239 | tube morphogenesis |
| 15% | GO: 0042127 | regulation of cell proliferation |
| 15% | GO: 0042221 | response to chemical stimulus |
| 15% | GO: 0043066 | negative regulation of apoptotic process |
| 15% | GO: 0043069 | negative regulation of programmed cell death |
| 15% | GO: 0043200 | response to amino acid stimulus |
| 15% | GO: 0044057 | regulation of system process |
| 15% | GO: 0045595 | regulation of cell differentiation |
| 15% | GO: 0045596 | negative regulation of cell differentiation |
| 15% | GO: 0045915 | positive regulation of catecholamine metabolic process |
| 15% | GO: 0045964 | positive regulation of dopamine metabolic process |
| **15%** | **GO: 0048666** | **neuron development** |
| 15% | GO: 0048667 | cell morphogenesis involved in neuron differentiation |
| 15% | GO: 0048712 | negative regulation of astrocyte differentiation |
| 15% | GO: 0048812 | neuron projection morphogenesis |
| 15% | GO: 0048869 | cellular developmental process |
| 15% | GO: 0050890 | cognition |
| 15% | GO: 0051239 | regulation of multicellular organismal process |
| 15% | GO: 0060541 | respiratory system development |
| 15% | GO: 0072001 | renal system development |
| 10% | GO: 0000902 | cell morphogenesis |
| 10% | GO: 0001838 | embryonic epithelial tube formation |
| 10% | GO: 0002250 | adaptive immune response |
| 10% | GO: 0002252 | immune effector process |
| 10% | GO: 0002376 | immune system process |
| 10% | GO: 0002443 | leukocyte mediated immunity |
| 10% | GO: 0002449 | lymphocyte mediated immunity |
| 10% | GO: 0002460 | adaptive immune response based on somatic recombination of immune receptors built from immunoglobulin superfamily domains |
| 10% | GO: 0002682 | regulation of immune system process |
| 10% | GO: 0002684 | positive regulation of immune system process |
| 10% | GO: 0006887 | exocytosis |
| 10% | GO: 0006955 | immune response |
| 10% | GO: 0006956 | complement activation |
| 10% | GO: 0006959 | humoral immune response |
| 10% | GO: 0007214 | gamma-aminobutyric acid signaling pathway |
| 10% | GO: 0007219 | Notch signaling pathway |
| 10% | GO: 0007272 | ensheathment of neurons |
| 10% | GO: 0007610 | behavior |
| 10% | GO: 0007611 | learning or memory |
| 10% | GO: 0008366 | axon ensheathment |
| 10% | GO: 0009719 | response to endogenous stimulus |
| 10% | GO: 0014075 | response to amine stimulus |
| 10% | GO: 0016477 | cell migration |
| 10% | GO: 0019221 | cytokine-mediated signaling pathway |
| 10% | GO: 0019827 | stem cell maintenance |
| 10% | GO: 0021778 | oligodendrocyte cell fate specification |
| 10% | GO: 0021780 | glial cell fate specification |
| 10% | GO: 0021781 | glial cell fate commitment |
| 10% | GO: 0030168 | platelet activation |
| 10% | GO: 0030199 | collagen fibril organization |
| 10% | GO: 0030334 | regulation of cell migration |
| 10% | GO: 0030595 | leukocyte chemotaxis |
| 10% | GO: 0032101 | regulation of response to external stimulus |
| 10% | GO: 0032501 | multicellular organismal process |
| 10% | GO: 0032989 | cellular component morphogenesis |
| 10% | GO: 0032990 | cell part morphogenesis |
| 10% | GO: 0034340 | response to type I interferon |
| 10% | GO: 0035019 | somatic stem cell maintenance |
| 10% | GO: 0035148 | tube formation |
| 10% | GO: 0040011 | locomotion |
| 10% | GO: 0042391 | regulation of membrane potential |
| 10% | GO: 0042552 | myelination |
| 10% | GO: 0045087 | innate immune response |
| 10% | GO: 0045664 | regulation of neuron differentiation |
| 10% | GO: 0045665 | negative regulation of neuron differentiation |
| 10% | GO: 0046903 | secretion |
| 10% | GO: 0048488 | synaptic vesicle endocytosis |
| 10% | GO: 0048514 | blood vessel morphogenesis |
| 10% | GO: 0048545 | response to steroid hormone stimulus |
| 10% | GO: 0048583 | regulation of response to stimulus |

TABLE 3-continued

| GO term analysis of genes differentially expressed in subgroups | | |
|---|---|---|
| Proportion of Samples | Biological Process | Biological Process Name |
| 10% | GO: 0048584 | positive regulation of response to stimulus |
| 10% | GO: 0048729 | tissue morphogenesis |
| 10% | GO: 0048858 | cell projection morphogenesis |
| 10% | GO: 0048864 | stem cell development |
| 10% | GO: 0048870 | cell motility |
| 10% | GO: 0050806 | positive regulation of synaptic transmission |
| 10% | GO: 0050900 | leukocyte migration |
| 10% | GO: 0050920 | regulation of chemotaxis |
| 10% | GO: 0051050 | positive regulation of transport |
| 10% | GO: 0051674 | localization of cell |
| 10% | GO: 0060284 | regulation of cell development |
| 10% | GO: 0060326 | cell chemotaxis |
| 10% | GO: 0060337 | type I interferon-mediated signaling pathway |
| 10% | GO: 0060548 | negative regulation of cell death |
| 10% | GO: 0060562 | epithelial tube morphogenesis |
| 10% | GO: 0060627 | regulation of vesicle-mediated transport |
| 10% | GO: 0071357 | cellular response to type I interferon |
| 10% | GO: 0072070 | loop of Henle development |
| 10% | GO: 0072175 | epithelial tube formation |
| 5% | GO: 0000302 | response to reactive oxygen species |
| 5% | GO: 0001504 | neurotransmitter uptake |
| 5% | GO: 0001655 | urogenital system development |
| 5% | GO: 0001656 | metanephros development |
| 5% | GO: 0001738 | morphogenesis of a polarized epithelium |
| 5% | GO: 0001796 | regulation of type IIa hypersensitivity |
| 5% | GO: 0001798 | positive regulation of type IIa hypersensitivity |
| 5% | GO: 0001843 | neural tube closure |
| 5% | GO: 0002009 | morphogenesis of an epithelium |
| 5% | GO: 0002053 | positive regulation of mesenchymal cell proliferation |
| 5% | GO: 0002237 | response to molecule of bacterial origin |
| 5% | GO: 0002253 | activation of immune response |
| 5% | GO: 0002274 | myeloid leukocyte activation |
| 5% | GO: 0002282 | microglial cell activation involved in immune response |
| 5% | GO: 0002429 | immune response-activating cell surface receptor signaling pathway |
| 5% | GO: 0002431 | Fc receptor mediated stimulatory signaling pathway |
| 5% | GO: 0002455 | humoral immune response mediated by circulating immunoglobulin |
| 5% | GO: 0002507 | tolerance induction |
| 5% | GO: 0002576 | platelet degranulation |
| 5% | GO: 0002685 | regulation of leukocyte migration |
| 5% | GO: 0002687 | positive regulation of leukocyte migration |
| 5% | GO: 0002688 | regulation of leukocyte chemotaxis |
| 5% | GO: 0002690 | positive regulation of leukocyte chemotaxis |
| 5% | GO: 0002694 | regulation of leukocyte activation |
| 5% | GO: 0002696 | positive regulation of leukocyte activation |
| 5% | GO: 0002757 | immune response-activating signal transduction |
| 5% | GO: 0002764 | immune response-regulating signaling pathway |
| 5% | GO: 0002768 | immune response-regulating cell surface receptor signaling pathway |
| 5% | GO: 0002886 | regulation of myeloid leukocyte mediated immunity |
| 5% | GO: 0002888 | positive regulation of myeloid leukocyte mediated immunity |
| 5% | GO: 0002892 | regulation of type II hypersensitivity |
| 5% | GO: 0002894 | positive regulation of type II hypersensitivity |
| 5% | GO: 0003094 | glomerular filtration |
| 5% | GO: 0006119 | oxidative phosphorylation |
| 5% | GO: 0006120 | mitochondrial electron transport, NADH to ubiquinone |
| 5% | GO: 0006821 | chloride transport |
| 5% | GO: 0006928 | cellular component movement |
| 5% | GO: 0006935 | chemotaxis |
| 5% | GO: 0006954 | inflammatory response |
| 5% | GO: 0006958 | complement activation, classical pathway |
| 5% | GO: 0007160 | cell-matrix adhesion |
| 5% | GO: 0007263 | nitric oxide mediated signal transduction |
| 5% | GO: 0007568 | aging |
| 5% | GO: 0007584 | response to nutrient |
| 5% | GO: 0007596 | blood coagulation |
| 5% | GO: 0007599 | hemostasis |
| 5% | GO: 0007612 | learning |
| 5% | GO: 0007626 | locomotory behavior |
| 5% | GO: 0008347 | glial cell migration |
| 5% | GO: 0009124 | nucleoside monophosphate biosynthetic process |
| 5% | GO: 0009605 | response to external stimulus |
| 5% | GO: 0009612 | response to mechanical stimulus |
| 5% | GO: 0009888 | tissue development |
| 5% | GO: 0009967 | positive regulation of signal transduction |
| 5% | GO: 0009991 | response to extracellular stimulus |
| 5% | GO: 0010035 | response to inorganic substance |

TABLE 3-continued

GO term analysis of genes differentially expressed in subgroups

| Proportion of Samples | Biological Process | Biological Process Name |
|---|---|---|
| 5% | GO: 0010212 | response to ionizing radiation |
| 5% | GO: 0010332 | response to gamma radiation |
| 5% | GO: 0010563 | negative regulation of phosphorus metabolic process |
| 5% | GO: 0010574 | regulation of vascular endothelial growth factor production |
| 5% | GO: 0010575 | positive regulation vascular endothelial growth factor production |
| 5% | GO: 0010621 | negative regulation of transcription by transcription factor localization |
| 5% | GO: 0010646 | regulation of cell communication |
| 5% | GO: 0010647 | positive regulation of cell communication |
| 5% | GO: 0010765 | positive regulation of sodium ion transport |
| 5% | GO: 0010812 | negative regulation of cell-substrate adhesion |
| 5% | GO: 0010873 | positive regulation of cholesterol esterification |
| 5% | GO: 0010935 | regulation of macrophage cytokine production |
| 5% | GO: 0014014 | negative regulation of gliogenesis |
| 5% | GO: 0014015 | positive regulation of gliogenesis |
| 5% | GO: 0014020 | primary neural tube formation |
| 5% | GO: 0014032 | neural crest cell development |
| 5% | GO: 0014033 | neural crest cell differentiation |
| 5% | GO: 0015698 | inorganic anion transport |
| 5% | GO: 0016079 | synaptic vesicle exocytosis |
| 5% | GO: 0016192 | vesicle-mediated transport |
| 5% | GO: 0016331 | morphogenesis of embryonic epithelium |
| 5% | GO: 0016339 | calcium-dependent cell-cell adhesion |
| 5% | GO: 0017156 | calcium ion-dependent exocytosis |
| 5% | GO: 0017157 | regulation of exocytosis |
| 5% | GO: 0021529 | spinal cord oligodendrocyte cell differentiation |
| 5% | GO: 0021530 | spinal cord oligodendrocyte cell fate specification |
| 5% | GO: 0021779 | oligodendrocyte cell fate commitment |
| 5% | GO: 0021915 | neural tube development |
| 5% | GO: 0021952 | central nervous system projection neuron axonogenesis |
| 5% | GO: 0021955 | central nervous system neuron axonogenesis |
| 5% | GO: 0022010 | central nervous system myelination |
| 5% | GO: 0022900 | electron transport chain |
| 5% | GO: 0022904 | respiratory electron transport chain |
| 5% | GO: 0023052 | signaling |
| 5% | GO: 0023056 | positive regulation of signaling |
| 5% | GO: 0030097 | hemopoiesis |
| 5% | GO: 0030155 | regulation of cell adhesion |
| 5% | GO: 0030198 | extracellular matrix organization |
| 5% | GO: 0030335 | positive regulation of cell migration |
| 5% | GO: 0030593 | neutrophil chemotaxis |
| 5% | GO: 0031099 | regeneration |
| 5% | GO: 0031294 | lymphocyte costimulation |
| 5% | GO: 0031295 | T cell costimulation |
| 5% | GO: 0031579 | membrane raft organization |
| 5% | GO: 0031589 | cell-substrate adhesion |
| 5% | GO: 0031646 | positive regulation of neurological system process |
| 5% | GO: 0031667 | response to nutrient levels |
| 5% | GO: 0032103 | positive regulation of response to external stimulus |
| 5% | GO: 0032291 | axon ensheathment in central nervous system |
| 5% | GO: 0032502 | developmental process |
| 5% | GO: 0032879 | regulation of localization |
| 5% | GO: 0032930 | positive regulation of superoxide anion generation |
| 5% | GO: 0033273 | response to vitamin |
| 5% | GO: 0034382 | chylomicron remnant clearance |
| 5% | GO: 0035282 | segmentation |
| 5% | GO: 0035850 | epithelial cell differentiation involved in kidney development |
| 5% | GO: 0040012 | regulation of locomotion |
| 5% | GO: 0040017 | positive regulation of locomotion |
| 5% | GO: 0042326 | negative regulation of phosphorylation |
| 5% | GO: 0042330 | taxis |
| 5% | GO: 0042493 | response to drug |
| 5% | GO: 0042773 | ATP synthesis coupled electron transport |
| 5% | GO: 0042775 | mitochondrial ATP synthesis coupled electron transport |
| 5% | GO: 0043062 | extracellular structure organization |
| 5% | GO: 0043270 | positive regulation of ion transport |
| 5% | GO: 0043299 | leukocyte degranulation |
| 5% | GO: 0045598 | regulation of fat cell differentiation |
| 5% | GO: 0045599 | negative regulation of fat cell differentiation |
| 5% | GO: 0045607 | regulation of auditory receptor cell differentiation |
| 5% | GO: 0045631 | regulation of mechanoreceptor differentiation |
| 5% | GO: 0045685 | regulation of glial cell differentiation |
| 5% | GO: 0045686 | negative regulation of glial cell differentiation |
| 5% | GO: 0045765 | regulation of angiogenesis |
| 5% | GO: 0045767 | regulation of anti-apoptosis |
| 5% | GO: 0045768 | positive regulation of anti-apoptosis |

TABLE 3-continued

GO term analysis of genes differentially expressed in subgroups

| Proportion of Samples | Biological Process | Biological Process Name |
|---|---|---|
| 5% | GO: 0045936 | negative regulation of phosphate metabolic process |
| 5% | GO: 0046826 | negative regulation of protein export from nucleus |
| 5% | GO: 0046928 | regulation of neurotransmitter secretion |
| 5% | GO: 0048041 | focal adhesion assembly |
| 5% | GO: 0048146 | positive regulation of fibroblast proliferation |
| 5% | GO: 0048520 | positive regulation of behavior |
| 5% | GO: 0048523 | negative regulation of cellular process |
| 5% | GO: 0048534 | hemopoietic or lymphoid organ development |
| 5% | GO: 0048646 | anatomical structure formation involved in morphogenesis |
| 5% | GO: 0048710 | regulation of astrocyte differentiation |
| 5% | GO: 0048754 | branching morphogenesis of a tube |
| 5% | GO: 0048863 | stem cell differentiation |
| 5% | GO: 0050678 | regulation of epithelial cell proliferation |
| 5% | GO: 0050764 | regulation of phagocytosis |
| 5% | GO: 0050776 | regulation of immune response |
| 5% | GO: 0050778 | positive regulation of immune response |
| 5% | GO: 0050795 | regulation of behavior |
| 5% | GO: 0050817 | coagulation |
| 5% | GO: 0050851 | antigen receptor-mediated signaling pathway |
| 5% | GO: 0050863 | regulation of T cell activation |
| 5% | GO: 0050864 | regulation of B cell activation |
| 5% | GO: 0050865 | regulation of cell activation |
| 5% | GO: 0050866 | negative regulation of cell activation |
| 5% | GO: 0050867 | positive regulation of cell activation |
| 5% | GO: 0050870 | positive regulation of T cell activation |
| 5% | GO: 0050921 | positive regulation of chemotaxis |
| 5% | GO: 0050926 | regulation of positive chemotaxis |
| 5% | GO: 0050927 | positive regulation of positive chemotaxis |
| 5% | GO: 0050930 | induction of positive chemotaxis |
| 5% | GO: 0051049 | regulation of transport |
| 5% | GO: 0051249 | regulation of lymphocyte activation |
| 5% | GO: 0051251 | positive regulation of lymphocyte activation |
| 5% | GO: 0051270 | regulation of cellular component movement |
| 5% | GO: 0051272 | positive regulation of cellular component movement |
| 5% | GO: 0051414 | response to cortisol stimulus |
| 5% | GO: 0051823 | regulation of synapse structural plasticity |
| 5% | GO: 0051899 | membrane depolarization |
| 5% | GO: 0051971 | positive regulation of transmission of nerve impulse |
| 5% | GO: 0052031 | modulation by symbiont of host defense response |
| 5% | GO: 0052173 | response to defenses of other organism involved in symbiotic interaction |
| 5% | GO: 0052200 | response to host defenses |
| 5% | GO: 0052255 | modulation by organism of defense response of other organism involved in symbiotic interaction |
| 5% | GO: 0052509 | positive regulation by symbiont of host defense response |
| 5% | GO: 0052510 | positive regulation by organism of defense response of other organism involved in symbiotic interaction |
| 5% | GO: 0052564 | response to immune response of other organism involved in symbiotic interaction |
| 5% | GO: 0052572 | response to host immune response |
| 5% | GO: 0060079 | regulation of excitatory postsynaptic membrane potential |
| 5% | GO: 0060425 | lung morphogenesis |
| 5% | GO: 0060429 | epithelium development |
| 5% | GO: 0060606 | tube closure |
| 5% | GO: 0060688 | regulation of morphogenesis of a branching structure |
| 5% | GO: 0060696 | regulation of phospholipid catabolic process |
| 5% | GO: 0060697 | positive regulation of phospholipid catabolic process |
| 5% | GO: 0060907 | positive regulation of macrophage cytokine production |
| 5% | GO: 0061041 | regulation of wound healing |
| 5% | GO: 0061081 | positive regulation of myeloid leukocyte cytokine production involved in immune response |
| 5% | GO: 0065008 | regulation of biological quality |
| 5% | GO: 0070482 | response to oxygen levels |
| 5% | GO: 0070887 | cellular response to chemical stimulus |
| 5% | GO: 0071216 | cellular response to biotic stimulus |
| 5% | GO: 0071219 | cellular response to molecule of bacterial origin |
| 5% | GO: 0071222 | cellular response to lipopolysaccharide |
| 5% | GO: 0071230 | cellular response to amino acid stimulus |
| 5% | GO: 0071310 | cellular response to organic substance |
| 5% | GO: 0071345 | cellular response to cytokine stimulus |
| 5% | GO: 0071418 | cellular response to amine stimulus |
| 5% | GO: 0071470 | cellular response to osmotic stress |
| 5% | GO: 0071675 | regulation of mononuclear cell migration |
| 5% | GO: 0071830 | triglyceride-rich lipoprotein particle clearance |
| 5% | GO: 0072006 | nephron development |
| 5% | GO: 0072080 | nephron tubule development |

TABLE 3-continued

GO term analysis of genes differentially expressed in subgroups

| Proportion of Samples | Biological Process | Biological Process Name |
|---|---|---|
| 5% | GO: 0072358 | cardiovascular system development |
| 5% | GO: 0072359 | circulatory system development |
| 5% | GO: 0075136 | response to host |
| 5% | GO: 0090072 | positive regulation of sodium ion transport via voltage-gated sodium channel activity |
| 5% | GO: 0090183 | regulation of kidney development |
| 5% | GO: 0097205 | renal filtration |
| 5% | GO: 2000145 | regulation of cell motility |
| 5% | GO: 2000147 | positive regulation of cell motility |
| 5% | GO: 2000980 | regulation of inner ear receptor cell differentiation |
| | | PROLIF (31 Samples) |
| 74% | GO: 0000236 | mitotic prometaphase |
| 71% | GO: 0000087 | M phase of mitotic cell cycle |
| 71% | GO: 0000278 | mitotic cell cycle |
| 71% | GO: 0000280 | nuclear division |
| 71% | GO: 0007067 | mitosis |
| 71% | GO: 0048285 | organelle fission |
| 68% | GO: 0007059 | chromosome segregation |
| 68% | GO: 0022403 | cell cycle phase |
| 65% | GO: 0000279 | M phase |
| 65% | GO: 0022402 | cell cycle process |
| 61% | GO: 0000075 | cell cycle checkpoint |
| 61% | GO: 0007049 | cell cycle |
| 61% | GO: 0051301 | cell division |
| 58% | GO: 0000819 | sister chromatid segregation |
| 58% | GO: 0010564 | regulation of cell cycle process |
| 58% | GO: 0071156 | regulation of cell cycle arrest |
| 52% | GO: 0000070 | mitotic sister chromatid segregation |
| 52% | GO: 0006323 | DNA packaging |
| 52% | GO: 0007051 | spindle organization |
| 48% | GO: 0006260 | DNA replication |
| 48% | GO: 0006336 | DNA replication-independent nucleosome assembly |
| 48% | GO: 0031577 | spindle checkpoint |
| 48% | GO: 0034080 | CenH3-containing nucleosome assembly at centromere |
| 48% | GO: 0034724 | DNA replication-independent nucleosome organization |
| 48% | GO: 0071103 | DNA conformation change |
| 45% | GO: 0031055 | chromatin remodeling at centromere |
| 45% | GO: 0043486 | histone exchange |
| 45% | GO: 0051325 | interphase |
| 45% | GO: 0051329 | interphase of mitotic cell cycle |
| 45% | GO: 0051726 | regulation of cell cycle |
| 42% | GO: 0006261 | DNA-dependent DNA replication |
| 42% | GO: 0006334 | nucleosome assembly |
| **42%** | **GO: 0007399** | **nervous system development** |
| 42% | GO: 0031497 | chromatin assembly |
| **42%** | **GO: 0042063** | **gliogenesis** |
| 42% | GO: 0051276 | chromosome organization |
| 42% | GO: 0065004 | protein-DNA complex assembly |
| 39% | GO: 0006259 | DNA metabolic process |
| 39% | GO: 0006271 | DNA strand elongation involved in DNA replication |
| 39% | GO: 0043044 | ATP-dependent chromatin remodeling |
| 39% | GO: 0051983 | regulation of chromosome segregation |
| 39% | GO: 0071824 | protein-DNA complex subunit organization |
| 35% | GO: 0000226 | microtubule cytoskeleton organization |
| **35%** | **GO: 0007417** | **central nervous system development** |
| 35% | GO: 0022616 | DNA strand elongation |
| 35% | GO: 0034728 | nucleosome organization |
| 32% | GO: 0000082 | G1/S transition of mitotic cell cycle |
| 32% | GO: 0006333 | chromatin assembly or disassembly |
| 32% | GO: 0007017 | microtubule-based process |
| **32%** | **GO: 0022008** | **neurogenesis** |
| 32% | GO: 0030071 | regulation of mitotic metaphase/anaphase transition |
| **32%** | **GO: 0048709** | **oligodendrocyte differentiation** |
| 32% | GO: 0071174 | mitotic cell cycle spindle checkpoint |
| 29% | GO: 0007052 | mitotic spindle organization |
| 29% | GO: 0007093 | mitotic cell cycle checkpoint |
| **29%** | **GO: 0010001** | **glial cell differentiation** |
| 29% | GO: 0032201 | telomere maintenance via semi-conservative replication |
| 29% | GO: 0045841 | negative regulation of mitotic metaphase/anaphase transition |
| 29% | GO: 0048468 | cell development |
| 29% | GO: 0048699 | generation of neurons |
| 26% | GO: 0000216 | M/G1 transition of mitotic cell cycle |
| 26% | GO: 0006270 | DNA-dependent DNA replication initiation |
| 26% | GO: 0006312 | mitotic recombination |

TABLE 3-continued

GO term analysis of genes differentially expressed in subgroups

| Proportion of Samples | Biological Process | Biological Process Name |
|---|---|---|
| 26% | GO: 0006996 | organelle organization |
| 26% | GO: 0007076 | mitotic chromosome condensation |
| 26% | GO: 0007094 | mitotic cell cycle spindle assembly checkpoint |
| 26% | GO: 0007346 | regulation of mitotic cell cycle |
| **26%** | **GO: 0021781** | **glial cell fate commitment** |
| **26%** | **GO: 0045664** | **regulation of neuron differentiation** |
| 26% | GO: 0048015 | phosphatidylinositol-mediated signaling |
| 26% | GO: 0048017 | inositol lipid-mediated signaling |
| 26% | GO: 0071173 | spindle assembly checkpoint |
| 23% | GO: 0000084 | S phase of mitotic cell cycle |
| 23% | GO: 0000722 | telomere maintenance via recombination |
| 23% | GO: 0001944 | vasculature development |
| 23% | GO: 0007088 | regulation of mitosis |
| 23% | GO: 0007155 | cell adhesion |
| 23% | GO: 0022610 | biological adhesion |
| 23% | GO: 0030182 | neuron differentiation |
| 23% | GO: 0045839 | negative regulation of mitosis |
| 23% | GO: 0048812 | neuron projection morphogenesis |
| **23%** | **GO: 0050767** | **regulation of neurogenesis** |
| 23% | GO: 0050793 | regulation of developmental process |
| 23% | GO: 0051093 | negative regulation of developmental process |
| 23% | GO: 0051320 | S phase |
| 23% | GO: 0051783 | regulation of nuclear division |
| 23% | GO: 0051784 | negative regulation of nuclear division |
| 19% | GO: 0001568 | blood vessel development |
| 19% | GO: 0006281 | DNA repair |
| 19% | GO: 0006974 | response to DNA damage stimulus |
| **19%** | **GO: 0014013** | **regulation of gliogenesis** |
| 19% | GO: 0030198 | extracellular matrix organization |
| 19% | GO: 0030261 | chromosome condensation |
| 19% | GO: 0043062 | extracellular structure organization |
| **19%** | **GO: 0045665** | **negative regulation of neuron differentiation** |
| 19% | GO: 0048731 | system development |
| 19% | GO: 0051988 | regulation of attachment of spindle microtubules to kinetochore |
| 19% | GO: 0060284 | regulation of cell development |
| 19% | GO: 0071842 | cellular component organization at cellular level |
| 19% | GO: 2000026 | regulation of multicellular organismal development |
| 16% | GO: 0002504 | antigen processing and presentation of peptide or polysaccharide antigen via MHC class II |
| 16% | GO: 0006297 | nucleotide-excision repair, DNA gap filling |
| 16% | GO: 0006310 | DNA recombination |
| 16% | GO: 0006338 | chromatin remodeling |
| 16% | GO: 0007275 | multicellular organismal development |
| 16% | GO: 0010833 | telomere maintenance via telomere lengthening |
| 16% | GO: 0010948 | negative regulation of cell cycle process |
| 16% | GO: 0030154 | cell differentiation |
| 16% | GO: 0030199 | collagen fibril organization |
| 16% | GO: 0031145 | anaphase-promoting complex-dependent proteasomal ubiquitin-dependent protein catabolic process |
| **16%** | **GO: 0048666** | **neuron development** |
| 16% | GO: 0048856 | anatomical structure development |
| 16% | GO: 0051383 | kinetochore organization |
| 16% | GO: 0071841 | cellular component organization or biogenesis at cellular level |
| 16% | GO: 0072358 | cardiovascular system development |
| 16% | GO: 0072359 | circulatory system development |
| 13% | GO: 0000723 | telomere maintenance |
| 13% | GO: 0000904 | cell morphogenesis involved in differentiation |
| 13% | GO: 0001101 | response to acid |
| 13% | GO: 0001501 | skeletal system development |
| 13% | GO: 0007409 | axonogenesis |
| 13% | GO: 0009653 | anatomical structure morphogenesis |
| 13% | GO: 0009887 | organ morphogenesis |
| 13% | GO: 0014014 | negative regulation of gliogenesis |
| 13% | GO: 0021529 | spinal cord oligodendrocyte cell differentiation |
| 13% | GO: 0021530 | spinal cord oligodendrocyte cell fate specification |
| 13% | GO: 0022603 | regulation of anatomical structure morphogenesis |
| 13% | GO: 0032200 | telomere organization |
| 13% | GO: 0034340 | response to type I interferon |
| 13% | GO: 0034341 | response to interferon-gamma |
| 13% | GO: 0045595 | regulation of cell differentiation |
| 13% | GO: 0045685 | regulation of glial cell differentiation |
| 13% | GO: 0045686 | negative regulation of glial cell differentiation |
| 13% | GO: 0048514 | blood vessel morphogenesis |
| 13% | GO: 0048667 | cell morphogenesis involved in neuron differentiation |
| 13% | GO: 0048713 | regulation of oligodendrocyte differentiation |

TABLE 3-continued

GO term analysis of genes differentially expressed in subgroups

| Proportion of Samples | Biological Process | Biological Process Name |
|---|---|---|
| 13% | GO: 0048858 | cell projection morphogenesis |
| 13% | GO: 0048869 | cellular developmental process |
| 13% | GO: 0051960 | regulation of nervous system development |
| 13% | GO: 0071229 | cellular response to acid |
| 13% | GO: 0071346 | cellular response to interferon-gamma |
| 10% | GO: 0000079 | regulation of cyclin-dependent protein kinase activity |
| 10% | GO: 0000089 | mitotic metaphase |
| 10% | GO: 0000902 | cell morphogenesis |
| 10% | GO: 0006415 | translational termination |
| 10% | GO: 0010389 | regulation of G2/M transition of mitotic cell cycle |
| 10% | GO: 0016043 | cellular component organization |
| 10% | GO: 0019080 | viral genome expression |
| 10% | GO: 0019083 | viral transcription |
| 10% | GO: 0021782 | glial cell development |
| 10% | GO: 0030030 | cell projection organization |
| 10% | GO: 0031175 | neuron projection development |
| 10% | GO: 0031397 | negative regulation of protein ubiquitination |
| 10% | GO: 0032989 | cellular component morphogenesis |
| 10% | GO: 0032990 | cell part morphogenesis |
| 10% | GO: 0034508 | centromere complex assembly |
| 10% | GO: 0035295 | tube development |
| 10% | GO: 0043200 | response to amino acid stimulus |
| 10% | GO: 0048706 | embryonic skeletal system development |
| 10% | GO: 0048710 | regulation of astrocyte differentiation |
| 10% | GO: 0051323 | metaphase |
| 10% | GO: 0051436 | negative regulation of ubiquitin-protein ligase activity involved in mitotic cell cycle |
| 10% | GO: 0060337 | type I interferon-mediated signaling pathway |
| 10% | GO: 0071230 | cellular response to amino acid stimulus |
| 10% | GO: 0071276 | cellular response to cadmium ion |
| 10% | GO: 0071277 | cellular response to calcium ion |
| 10% | GO: 0071357 | cellular response to type I interferon |
| 10% | GO: 0071840 | cellular component organization or biogenesis |
| 10% | GO: 0090068 | positive regulation of cell cycle process |
| 6% | GO: 0000083 | regulation of transcription involved in G1/S phase of mitotic cell cycle |
| 6% | GO: 0000085 | G2 phase of mitotic cell cycle |
| 6% | GO: 0000910 | cytokinesis |
| 6% | GO: 0001656 | metanephros development |
| 6% | GO: 0001838 | embryonic epithelial tube formation |
| 6% | GO: 0002495 | antigen processing and presentation of peptide antigen via MHC class II |
| 6% | GO: 0006302 | double-strand break repair |
| 6% | GO: 0006364 | rRNA processing |
| 6% | GO: 0006412 | translation |
| 6% | GO: 0006414 | translational elongation |
| 6% | GO: 0006928 | cellular component movement |
| 6% | GO: 0006952 | defense response |
| 6% | GO: 0006958 | complement activation, classical pathway |
| 6% | GO: 0007091 | mitotic metaphase/anaphase transition |
| 6% | GO: 0007568 | aging |
| 6% | GO: 0008608 | attachment of spindle microtubules to kinetochore |
| 6% | GO: 0009263 | deoxyribonucleotide biosynthetic process |
| 6% | GO: 0009888 | tissue development |
| 6% | GO: 0010639 | negative regulation of organelle organization |
| 6% | GO: 0010720 | positive regulation of cell development |
| 6% | GO: 0010721 | negative regulation of cell development |
| 6% | GO: 0010812 | negative regulation of cell-substrate adhesion |
| 6% | GO: 0014003 | oligodendrocyte development |
| 6% | GO: 0014015 | positive regulation of gliogenesis |
| 6% | GO: 0016072 | rRNA metabolic process |
| 6% | GO: 0016331 | morphogenesis of embryonic epithelium |
| 6% | GO: 0019886 | antigen processing and presentation of exogenous peptide antigen via MHC class II |
| 6% | GO: 0021778 | oligodendrocyte cell fate specification |
| 6% | GO: 0021780 | glial cell fate specification |
| 6% | GO: 0021953 | central nervous system neuron differentiation |
| 6% | GO: 0022613 | ribonucleoprotein complex biogenesis |
| 6% | GO: 0030111 | regulation of Wnt receptor signaling pathway |
| 6% | GO: 0031102 | neuron projection regeneration |
| 6% | GO: 0031400 | negative regulation of protein modification process |
| 6% | GO: 0031960 | response to corticosteroid stimulus |
| 6% | GO: 0032467 | positive regulation of cytokinesis |
| 6% | GO: 0032502 | developmental process |
| 6% | GO: 0032886 | regulation of microtubule-based process |
| 6% | GO: 0032964 | collagen biosynthetic process |
| 6% | GO: 0033043 | regulation of organelle organization |

TABLE 3-continued

GO term analysis of genes differentially expressed in subgroups

| Proportion of Samples | Biological Process | Biological Process Name |
|---|---|---|
| 6% | GO: 0033205 | cell cycle cytokinesis |
| 6% | GO: 0034097 | response to cytokine stimulus |
| 6% | GO: 0034621 | cellular macromolecular complex subunit organization |
| 6% | GO: 0034622 | cellular macromolecular complex assembly |
| 6% | GO: 0035019 | somatic stem cell maintenance |
| 6% | GO: 0035148 | tube formation |
| 6% | GO: 0042127 | regulation of cell proliferation |
| 6% | GO: 0042254 | ribosome biogenesis |
| 6% | GO: 0043624 | cellular protein complex disassembly |
| 6% | GO: 0043933 | macromolecular complex subunit organization |
| 6% | GO: 0044259 | multicellular organismal macromolecule metabolic process |
| 6% | GO: 0045596 | negative regulation of cell differentiation |
| 6% | GO: 0045786 | negative regulation of cell cycle |
| 6% | GO: 0048736 | appendage development |
| 6% | GO: 0048741 | skeletal muscle fiber development |
| 6% | GO: 0048747 | muscle fiber development |
| 6% | GO: 0050000 | chromosome localization |
| 6% | GO: 0050769 | positive regulation of neurogenesis |
| 6% | GO: 0051094 | positive regulation of developmental process |
| 6% | GO: 0051128 | regulation of cellular component organization |
| 6% | GO: 0051129 | negative regulation of cellular component organization |
| 6% | GO: 0051290 | protein heterotetramerization |
| 6% | GO: 0051303 | establishment of chromosome localization |
| 6% | GO: 0051319 | G2 phase |
| 6% | GO: 0051340 | regulation of ligase activity |
| 6% | GO: 0051352 | negative regulation of ligase activity |
| 6% | GO: 0051437 | positive regulation of ubiquitin-protein ligase activity involved in mitotic cell cycle |
| 6% | GO: 0051438 | regulation of ubiquitin-protein ligase activity |
| 6% | GO: 0051439 | regulation of ubiquitin-protein ligase activity involved in mitotic cell cycle |
| 6% | GO: 0051444 | negative regulation of ubiquitin-protein ligase activity |
| 6% | GO: 0051984 | positive regulation of chromosome segregation |
| 6% | GO: 0055002 | striated muscle cell development |
| 6% | GO: 0055093 | response to hyperoxia |
| 6% | GO: 0060173 | limb development |
| 6% | GO: 0060333 | interferon-gamma-mediated signaling pathway |
| 6% | GO: 0060541 | respiratory system development |
| 6% | GO: 0060564 | negative regulation of mitotic anaphase-promoting complex activity |
| 6% | GO: 0070208 | protein heterotrimerization |
| 6% | GO: 0070507 | regulation of microtubule cytoskeleton organization |
| 6% | GO: 0070777 | D-aspartate transport |
| 6% | GO: 0070779 | D-aspartate import |
| 6% | GO: 0071248 | cellular response to metal ion |
| 6% | GO: 0071775 | regulation of cell cycle cytokinesis |
| 6% | GO: 0071777 | positive regulation of cell cycle cytokinesis |
| 6% | GO: 0072001 | renal system development |
| 6% | GO: 0072006 | nephron development |
| 6% | GO: 0072175 | epithelial tube formation |
| 6% | GO: 0090090 | negative regulation of canonical Wnt receptor signaling pathway |
| 6% | GO: 2000736 | regulation of stem cell differentiation |
| 3% | GO: 0000077 | DNA damage checkpoint |
| 3% | GO: 0000086 | G2/M transition of mitotic cell cycle |
| 3% | GO: 0000184 | nuclear-transcribed mRNA catabolic process, nonsense-mediated decay |
| 3% | GO: 0000956 | nuclear-transcribed mRNA catabolic process |
| 3% | GO: 0001503 | ossification |
| 3% | GO: 0001655 | urogenital system development |
| 3% | GO: 0001666 | response to hypoxia |
| 3% | GO: 0001763 | morphogenesis of a branching structure |
| 3% | GO: 0001822 | kidney development |
| 3% | GO: 0001841 | neural tube formation |
| 3% | GO: 0001843 | neural tube closure |
| 3% | GO: 0002455 | humoral immune response mediated by circulating immunoglobulin |
| 3% | GO: 0002480 | antigen processing and presentation of exogenous peptide antigen via MHC class I, TAP-independent |
| 3% | GO: 0002544 | chronic inflammatory response |
| 3% | GO: 0002576 | platelet degranulation |
| 3% | GO: 0002685 | regulation of leukocyte migration |
| 3% | GO: 0002687 | positive regulation of leukocyte migration |
| 3% | GO: 0002688 | regulation of leukocyte chemotaxis |
| 3% | GO: 0002690 | positive regulation of leukocyte chemotaxis |
| 3% | GO: 0003002 | regionalization |
| 3% | GO: 0003105 | negative regulation of glomerular filtration |
| 3% | GO: 0003170 | heart valve development |
| 3% | GO: 0003179 | heart valve morphogenesis |
| 3% | GO: 0003207 | cardiac chamber formation |

TABLE 3-continued

GO term analysis of genes differentially expressed in subgroups

| Proportion of Samples | Biological Process | Biological Process Name |
|---|---|---|
| 3% | GO: 0003211 | cardiac ventricle formation |
| 3% | GO: 0003281 | ventricular septum development |
| 3% | GO: 0006119 | oxidative phosphorylation |
| 3% | GO: 0006120 | mitochondrial electron transport, NADH to ubiquinone |
| 3% | GO: 0006139 | nucleobase-containing compound metabolic process |
| 3% | GO: 0006221 | pyrimidine nucleotide biosynthetic process |
| 3% | GO: 0006325 | chromatin organization |
| 3% | GO: 0006396 | RNA processing |
| 3% | GO: 0006401 | RNA catabolic process |
| 3% | GO: 0006402 | mRNA catabolic process |
| 3% | GO: 0006413 | translational initiation |
| 3% | GO: 0006563 | L-serine metabolic process |
| 3% | GO: 0006564 | L-serine biosynthetic process |
| 3% | GO: 0006612 | protein targeting to membrane |
| 3% | GO: 0006613 | cotranslational protein targeting to membrane |
| 3% | GO: 0006614 | SRP-dependent cotranslational protein targeting to membrane |
| 3% | GO: 0006807 | nitrogen compound metabolic process |
| 3% | GO: 0006935 | chemotaxis |
| 3% | GO: 0006950 | response to stress |
| 3% | GO: 0006955 | immune response |
| 3% | GO: 0006956 | complement activation |
| 3% | GO: 0007010 | cytoskeleton organization |
| 3% | GO: 0007062 | sister chromatid cohesion |
| 3% | GO: 0007126 | meiosis |
| 3% | GO: 0007127 | meiosis I |
| 3% | GO: 0007162 | negative regulation of cell adhesion |
| 3% | GO: 0007219 | Notch signaling pathway |
| 3% | GO: 0007263 | nitric oxide mediated signal transduction |
| 3% | GO: 0007272 | ensheathment of neurons |
| 3% | GO: 0007389 | pattern specification process |
| 3% | GO: 0007411 | axon guidance |
| 3% | GO: 0007420 | brain development |
| 3% | GO: 0008283 | cell proliferation |
| 3% | GO: 0008285 | negative regulation of cell proliferation |
| 3% | GO: 0008344 | adult locomotory behavior |
| 3% | GO: 0008347 | glial cell migration |
| 3% | GO: 0008366 | axon ensheathment |
| 3% | GO: 0009059 | macromolecule biosynthetic process |
| 3% | GO: 0009147 | pyrimidine nucleoside triphosphate metabolic process |
| 3% | GO: 0009148 | pyrimidine nucleoside triphosphate biosynthetic process |
| 3% | GO: 0009186 | deoxyribonucleoside diphosphate metabolic process |
| 3% | GO: 0009262 | deoxyribonucleotide metabolic process |
| 3% | GO: 0009605 | response to external stimulus |
| 3% | GO: 0009607 | response to biotic stimulus |
| 3% | GO: 0009611 | response to wounding |
| 3% | GO: 0009612 | response to mechanical stimulus |
| 3% | GO: 0009615 | response to virus |
| 3% | GO: 0009628 | response to abiotic stimulus |
| 3% | GO: 0009954 | proximal/distal pattern formation |
| 3% | GO: 0010033 | response to organic substance |
| 3% | GO: 0010243 | response to organic nitrogen |
| 3% | GO: 0010467 | gene expression |
| 3% | GO: 0010498 | proteasomal protein catabolic process |
| 3% | GO: 0010594 | regulation of endothelial cell migration |
| 3% | GO: 0010718 | positive regulation of epithelial to mesenchymal transition |
| 3% | GO: 0010759 | positive regulation of macrophage chemotaxis |
| 3% | GO: 0010769 | regulation of cell morphogenesis involved in differentiation |
| 3% | GO: 0010770 | positive regulation of cell morphogenesis involved in differentiation |
| 3% | GO: 0010975 | regulation of neuron projection development |
| 3% | GO: 0010977 | negative regulation of neuron projection development |
| 3% | GO: 0014020 | primary neural tube formation |
| 3% | GO: 0014052 | regulation of gamma-aminobutyric acid secretion |
| 3% | GO: 0014054 | positive regulation of gamma-aminobutyric acid secretion |
| 3% | GO: 0014070 | response to organic cyclic compound |
| 3% | GO: 0014075 | response to amine stimulus |
| 3% | GO: 0014706 | striated muscle tissue development |
| 3% | GO: 0014812 | muscle cell migration |
| 3% | GO: 0015949 | nucleobase-containing small molecule interconversion |
| 3% | GO: 0015980 | energy derivation by oxidation of organic compounds |
| 3% | GO: 0016064 | immunoglobulin mediated immune response |
| 3% | GO: 0016070 | RNA metabolic process |
| 3% | GO: 0016071 | mRNA metabolic process |
| 3% | GO: 0016477 | cell migration |
| 3% | GO: 0016525 | negative regulation of angiogenesis |
| 3% | GO: 0018149 | peptide cross-linking |

TABLE 3-continued

GO term analysis of genes differentially expressed in subgroups

| Proportion of Samples | Biological Process | Biological Process Name |
|---|---|---|
| 3% | GO: 0019058 | viral infectious cycle |
| 3% | GO: 0019221 | cytokine-mediated signaling pathway |
| 3% | GO: 0019228 | regulation of action potential in neuron |
| 3% | GO: 0019724 | B cell mediated immunity |
| 3% | GO: 0019827 | stem cell maintenance |
| 3% | GO: 0019985 | translesion synthesis |
| 3% | GO: 0021510 | spinal cord development |
| 3% | GO: 0021517 | ventral spinal cord development |
| 3% | GO: 0021522 | spinal cord motor neuron differentiation |
| 3% | GO: 0021542 | dentate gyrus development |
| 3% | GO: 0021779 | oligodendrocyte cell fate commitment |
| 3% | GO: 0021915 | neural tube development |
| 3% | GO: 0022411 | cellular component disassembly |
| 3% | GO: 0022415 | viral reproductive process |
| 3% | GO: 0022604 | regulation of cell morphogenesis |
| 3% | GO: 0022900 | electron transport chain |
| 3% | GO: 0022904 | respiratory electron transport chain |
| 3% | GO: 0030178 | negative regulation of Wnt receptor signaling pathway |
| 3% | GO: 0030204 | chondroitin sulfate metabolic process |
| 3% | GO: 0030278 | regulation of ossification |
| 3% | GO: 0030324 | lung development |
| 3% | GO: 0030334 | regulation of cell migration |
| 3% | GO: 0030513 | positive regulation of BMP signaling pathway |
| 3% | GO: 0030514 | negative regulation of BMP signaling pathway |
| 3% | GO: 0031060 | regulation of histone methylation |
| 3% | GO: 0031103 | axon regeneration |
| 3% | GO: 0031109 | microtubule polymerization or depolymerization |
| 3% | GO: 0031115 | negative regulation of microtubule polymerization |
| 3% | GO: 0031338 | regulation of vesicle fusion |
| 3% | GO: 0031340 | positive regulation of vesicle fusion |
| 3% | GO: 0031570 | DNA integrity checkpoint |
| 3% | GO: 0032331 | negative regulation of chondrocyte differentiation |
| 3% | GO: 0032355 | response to estradiol stimulus |
| 3% | GO: 0032387 | negative regulation of intracellular transport |
| 3% | GO: 0032963 | collagen metabolic process |
| 3% | GO: 0032984 | macromolecular complex disassembly |
| 3% | GO: 0034470 | ncRNA processing |
| 3% | GO: 0034599 | cellular response to oxidative stress |
| 3% | GO: 0034614 | cellular response to reactive oxygen species |
| 3% | GO: 0034623 | cellular macromolecular complex disassembly |
| 3% | GO: 0034641 | cellular nitrogen compound metabolic process |
| 3% | GO: 0034644 | cellular response to UV |
| 3% | GO: 0034645 | cellular macromolecule biosynthetic process |
| 3% | GO: 0034660 | ncRNA metabolic process |
| 3% | GO: 0035107 | appendage morphogenesis |
| 3% | GO: 0035108 | limb morphogenesis |
| 3% | GO: 0035457 | cellular response to interferon-alpha |
| 3% | GO: 0035909 | aorta morphogenesis |
| 3% | GO: 0035988 | chondrocyte proliferation |
| 3% | GO: 0040001 | establishment of mitotic spindle localization |
| 3% | GO: 0040011 | locomotion |
| 3% | GO: 0040012 | regulation of locomotion |
| 3% | GO: 0040034 | regulation of development, heterochronic |
| 3% | GO: 0042060 | wound healing |
| 3% | GO: 0042273 | ribosomal large subunit biogenesis |
| 3% | GO: 0042330 | taxis |
| 3% | GO: 0042476 | odontogenesis |
| 3% | GO: 0042493 | response to drug |
| 3% | GO: 0042552 | myelination |
| 3% | GO: 0042692 | muscle cell differentiation |
| 3% | GO: 0042773 | ATP synthesis coupled electron transport |
| 3% | GO: 0042775 | mitochondrial ATP synthesis coupled electron transport |
| 3% | GO: 0043161 | proteasomal ubiquitin-dependent protein catabolic process |
| 3% | GO: 0043241 | protein complex disassembly |
| 3% | GO: 0043407 | negative regulation of MAP kinase activity |
| 3% | GO: 0044236 | multicellular organismal metabolic process |
| 3% | GO: 0045047 | protein targeting to ER |
| 3% | GO: 0045087 | innate immune response |
| 3% | GO: 0045333 | cellular respiration |
| 3% | GO: 0045597 | positive regulation of cell differentiation |
| 3% | GO: 0045667 | regulation of osteoblast differentiation |
| 3% | GO: 0045746 | negative regulation of Notch signaling pathway |
| 3% | GO: 0045765 | regulation of angiogenesis |
| 3% | GO: 0045766 | positive regulation of angiogenesis |
| 3% | GO: 0045768 | positive regulation of anti-apoptosis |

TABLE 3-continued

GO term analysis of genes differentially expressed in subgroups

| Proportion of Samples | Biological Process | Biological Process Name |
|---|---|---|
| 3% | GO: 0045837 | negative regulation of membrane potential |
| 3% | GO: 0045840 | positive regulation of mitosis |
| 3% | GO: 0046622 | positive regulation of organ growth |
| 3% | GO: 0048008 | platelet-derived growth factor receptor signaling pathway |
| 3% | GO: 0048145 | regulation of fibroblast proliferation |
| 3% | GO: 0048505 | regulation of timing of cell differentiation |
| 3% | GO: 0048545 | response to steroid hormone stimulus |
| 3% | GO: 0048562 | embryonic organ morphogenesis |
| 3% | GO: 0048568 | embryonic organ development |
| 3% | GO: 0048598 | embryonic morphogenesis |
| 3% | GO: 0048641 | regulation of skeletal muscle tissue development |
| 3% | GO: 0048678 | response to axon injury |
| 3% | GO: 0048704 | embryonic skeletal system morphogenesis |
| 3% | GO: 0048708 | astrocyte differentiation |
| 3% | GO: 0048714 | positive regulation of oligodendrocyte differentiation |
| 3% | GO: 0048715 | negative regulation of oligodendrocyte differentiation |
| 3% | GO: 0048742 | regulation of skeletal muscle fiber development |
| 3% | GO: 0048771 | tissue remodeling |
| 3% | GO: 0048863 | stem cell differentiation |
| 3% | GO: 0048864 | stem cell development |
| 3% | GO: 0048870 | cell motility |
| 3% | GO: 0050654 | chondroitin sulfate proteoglycan metabolic process |
| 3% | GO: 0050657 | nucleic acid transport |
| 3% | GO: 0050658 | RNA transport |
| 3% | GO: 0050678 | regulation of epithelial cell proliferation |
| 3% | GO: 0050679 | positive regulation of epithelial cell proliferation |
| 3% | GO: 0050768 | negative regulation of neurogenesis |
| 3% | GO: 0050773 | regulation of dendrite development |
| 3% | GO: 0050808 | synapse organization |
| 3% | GO: 0050920 | regulation of chemotaxis |
| 3% | GO: 0051028 | mRNA transport |
| 3% | GO: 0051095 | regulation of helicase activity |
| 3% | GO: 0051099 | positive regulation of binding |
| 3% | GO: 0051100 | negative regulation of binding |
| 3% | GO: 0051146 | striated muscle cell differentiation |
| 3% | GO: 0051153 | regulation of striated muscle cell differentiation |
| 3% | GO: 0051216 | cartilage development |
| 3% | GO: 0051225 | spindle assembly |
| 3% | GO: 0051236 | establishment of RNA localization |
| 3% | GO: 0051239 | regulation of multicellular organismal process |
| 3% | GO: 0051256 | spindle midzone assembly involved in mitosis |
| 3% | GO: 0051270 | regulation of cellular component movement |
| 3% | GO: 0051293 | establishment of spindle localization |
| 3% | GO: 0051305 | chromosome movement towards spindle pole |
| 3% | GO: 0051321 | meiotic cell cycle |
| 3% | GO: 0051327 | M phase of meiotic cell cycle |
| 3% | GO: 0051382 | kinetochore assembly |
| 3% | GO: 0051384 | response to glucocorticoid stimulus |
| 3% | GO: 0051443 | positive regulation of ubiquitin-protein ligase activity |
| 3% | GO: 0051569 | regulation of histone H3-K4 methylation |
| 3% | GO: 0051571 | positive regulation of histone H3-K4 methylation |
| 3% | GO: 0051592 | response to calcium ion |
| 3% | GO: 0051653 | spindle localization |
| 3% | GO: 0051656 | establishment of organelle localization |
| 3% | GO: 0051674 | localization of cell |
| 3% | GO: 0051707 | response to other organism |
| 3% | GO: 0051785 | positive regulation of nuclear division |
| 3% | GO: 0051823 | regulation of synapse structural plasticity |
| 3% | GO: 0051957 | positive regulation of amino acid transport |
| 3% | GO: 0055001 | muscle cell development |
| 3% | GO: 0060056 | mammary gland involution |
| 3% | GO: 0060071 | Wnt receptor signaling pathway, planar cell polarity pathway |
| 3% | GO: 0060174 | limb bud formation |
| 3% | GO: 0060219 | camera-type eye photoreceptor cell differentiation |
| 3% | GO: 0060249 | anatomical structure homeostasis |
| 3% | GO: 0060429 | epithelium development |
| 3% | GO: 0060537 | muscle tissue development |
| 3% | GO: 0060606 | tube closure |
| 3% | GO: 0060828 | regulation of canonical Wnt receptor signaling pathway |
| 3% | GO: 0060900 | embryonic camera-type eye formation |
| 3% | GO: 0060993 | kidney morphogenesis |
| 3% | GO: 0060998 | regulation of dendritic spine development |
| 3% | GO: 0061001 | regulation of dendritic spine morphogenesis |
| 3% | GO: 0061326 | renal tubule development |
| 3% | GO: 0061333 | renal tubule morphogenesis |

TABLE 3-continued

GO term analysis of genes differentially expressed in subgroups

| Proportion of Samples | Biological Process | Biological Process Name |
|---|---|---|
| 3% | GO: 0065003 | macromolecular complex assembly |
| 3% | GO: 0070206 | protein trimerization |
| 3% | GO: 0070482 | response to oxygen levels |
| 3% | GO: 0070972 | protein localization in endoplasmic reticulum |
| 3% | GO: 0071294 | cellular response to zinc ion |
| 3% | GO: 0071310 | cellular response to organic substance |
| 3% | GO: 0071345 | cellular response to cytokine stimulus |
| 3% | GO: 0071417 | cellular response to organic nitrogen |
| 3% | GO: 0071418 | cellular response to amine stimulus |
| 3% | GO: 0071453 | cellular response to oxygen levels |
| 3% | GO: 0071504 | cellular response to heparin |
| 3% | GO: 0071822 | protein complex subunit organization |
| 3% | GO: 0071843 | cellular component biogenesis at cellular level |
| 3% | GO: 0071845 | cellular component disassembly at cellular level |
| 3% | GO: 0071901 | negative regulation of protein serine/threonine kinase activity |
| 3% | GO: 0072009 | nephron epithelium development |
| 3% | GO: 0072028 | nephron morphogenesis |
| 3% | GO: 0072073 | kidney epithelium development |
| 3% | GO: 0072078 | nephron tubule morphogenesis |
| 3% | GO: 0072079 | nephron tubule formation |
| 3% | GO: 0072080 | nephron tubule development |
| 3% | GO: 0072088 | nephron epithelium morphogenesis |
| 3% | GO: 0072170 | metanephric tubule development |
| 3% | GO: 0072207 | metanephric epithelium development |
| 3% | GO: 0072210 | metanephric nephron development |
| 3% | GO: 0072224 | metanephric glomerulus development |
| 3% | GO: 0072234 | metanephric nephron tubule development |
| 3% | GO: 0072243 | metanephric nephron epithelium development |
| 3% | GO: 0072594 | establishment of protein localization to organelle |
| 3% | GO: 0072599 | establishment of protein localization in endoplasmic reticulum |
| 3% | GO: 0090092 | regulation of transmembrane receptor protein serine/threonine kinase signaling pathway |
| 3% | GO: 0090101 | negative regulation of transmembrane receptor protein serine/threonine kinase signaling pathway |
| 3% | GO: 0090175 | regulation of establishment of planar polarity |
| 3% | GO: 0090304 | nucleic acid metabolic process |
| 3% | GO: 0097066 | response to thyroid hormone stimulus |
| 3% | GO: 0097067 | cellular response to thyroid hormone stimulus |
| 3% | GO: 2000097 | regulation of smooth muscle cell-matrix adhesion |
| 3% | GO: 2000145 | regulation of cell motility |
| 3% | GO: 2000177 | regulation of neural precursor cell proliferation |
| 3% | GO: 2000179 | positive regulation of neural precursor cell proliferation |
| 3% | GO: 2000602 | regulation of interphase of mitotic cell cycle |

The % of individual tumors within a subgroup that are enriched for a specific GO term is shown, ordered by decreasing representation. Neurodevelopmental terms are highlighted with bolded text.

Discussion

The major finding is that AKT pathway genes classify GBM into at least five patient subgroups with unique clinical and molecular characteristics. The results were validated in an independent dataset of non-overlapping samples, suggesting AKT classes reflect underlying structure in the data and do not arise from chance or technical artifacts such as batch effects and patient sampling. Taken together these data add to previous results suggesting histopathologically diagnosed GBM is a collection of molecular subgroups with fundamental differences in biology and clinical behavior. This approach advances classification of GBM by splitting out groups not previously identified by other approaches and expands the understanding of molecular aberrations underlying subgroups.

The inventors interpret with caution the finding that SL patients treated with BCNU or CCNU have appreciably longer survival than SL patients receiving other treatments (median survival 5.8 vs. 1.05 years respectively) Inhomogeneity between the cohorts (including treatment protocols and institution providing tumor) could impact survival. However, age and IDH1 mutation status clearly do not contribute since patients in the longer surviving cohort were older and had less IDH1 mutations. These results suggest AKT classification is a predictive marker that identifies a subset of GBM patients with sensitivity to BCNU/CCNU. Interestingly, there is a subset of anaplastic oligodendroglial tumors characterized by 1p19q loss of heterozygosity (LOH) and IDH1 mutations that significantly benefits from procarbazine, CCNU, and vincristine (PCV) chemotherapy [35]. This anaplastic oligodendroglial subtype shares similarities to the AKT SL subgroup (19q loss and IDH1 mutant tumors).

Mutations in IDH1 are a common and early event in low grade glioma, they are present in secondary GBM [36], [37], [38] and may cause the G-CIMP phenotype [36], [37], [38], [39]. One third of SL tumors have IDH1 mutations and CIMP. This subgroup also has other molecular similarities to secondary tumors (enriched for genomic alterations in TP53 and PDGFRA), longer survival and a tendency for less endothelial proliferation and pallisading necrosis (FIGS. 12 and 13). These data suggest tumors in the SL subtype are grade IV secondary tumors or borderline grade III/IV secondary tumors progressing to GBM. If this is true then genomic alterations associated with the SL subtype might be used as markers of progression for grade II/III secondary tumors. These results also indicate there is a population of GBM without IDH1 mutations that share clinical characteristics and a similar pattern of AKT pathway gene expression with the IDH1 mutant tumors. This suggests other paths beside IDH1 mutation give rise to the IDH1 mutant/CIMP phenotype.

The inventors found distinct patterns of expression for PI3K/AKT/mTOR components in subgroups. The inventors' results suggest gene products that inhibit AKT and mTOR are important regulators of PI3K/AKT/mTOR/S6 axis output. In the inventors' model the loss of AKT and mTOR inhibitors (PHLPP, TSC and pAMPK) increases output of the AKT/mTOR/S6 axis in the MES subgroup. Conversely, increased expression of these inhibitors decreases output in the SL subgroup. In an apparent paradox, p-AKT expression is low in the MES subgroup. While not wishing to be bound by any theory, the inventors suggest AKT phosphorylation is held in check in the MES subgroup by (1) heightened activity of an mTOR/S6K/IRS1 negative feedback loop [40], [41], [42], [43] and (2) low TSC1 and 2 expression that decreases mTORC2 activation and AKT phosphorylation [42], [44]. The inventors' model suggests the MES subtype will be sensitive to joint inhibition of mTOR and PI3K, but inhibition of mTOR alone will increase p-AKT. Interestingly, NF1 loss drives mTOR/S6 hyper-activation via AKT [45], [46], [47] and the MES subtype is enriched for NF1 loss. These data suggest subgroups have variations in AKT pathway signaling that will affect sensitivity to pathway inhibitors.

How do these results compare with other approaches that use mRNA to classify GBM? AKT classification is complementary to previous classification methods but divides GBM into more subgroups. It gives patient subgroups with statistically significant differences in survival while Phillips [4] or TCGA [10] methods do not when using the same database. Interestingly, there was higher concordance between AKT classification and classification based on survival-associated mRNA used by Phillips et. al. [4] than most variable mRNA used by Verhaak et. al. [10]. Without wishing to be bound by any particular theory, the inventors believe classification schemes based on mRNA relevant to tumorigenicity, like survival-associated and AKT pathway genes, are more effective at partitioning tumors into clinically and molecularly relevant groups.

Survival differences found in the discovery dataset were diminished in the validation dataset. Inhomogeneity's between datasets that could confound comparisons including (1) age (median age=49 yrs. in discovery vs. 59 yrs. in validation dataset), (2) patient populations (three institutions contributed tumors to the discovery and eighteen to the validation dataset), (3) treatment (there were large variations in treatment regimens in the validation dataset).

One AKT subgroup was not found in the validation dataset (C1). While not wishing to be bound by any theory, morphological heterogeneity can result in inconsistent intra- and interobserver diagnosis of grade and histological type (astrocytoma, oligodendroglioma and mixed oligoastrocytoma) [48], [49], [50]. Therefore C1 may be a histological variant diagnosed as GBM and included in the discovery, but not the validation dataset.

GO term analysis suggests different cells of origin/dominant biological processes for each subgroup (summarized in FIGS. 8A and B). The younger, longer surviving, SL patient subgroup with molecular similarities to secondary GBM had terms associated with both neuro- and glio-genesis suggesting a NSC cell of origin. Indeed, the longer survival of these patients is consistent with the quiescent nature of NSC. PROLIF tumors also contained neuro- and glio-genesis terms in addition to terms related to mitosis, spindle formation and cell cycle checkpoint. Literature suggests the balance between symmetric and asymmetric cell divisions regulates NSC [51] which is influenced by proteins with a role in spindle formation and mitotic progression [52]. Based on this and their aggressive nature, while not wishing to be bound by any theory, the inventors believe that PROLIF tumors are derived from NSC with enforced symmetric cell divisions that rapidly expand the population (FIG. 8B). The ability of AKT classification to group tumors by cell of origin would suggest a major role for the PI3K/AKT pathway in neurodevelopment. This is consistent with reports showing a role for pathway members in NSC maintenance [53], [54].

The inventors show that AKT-based classification can augment drug development on many levels. This work indicates evaluating new drugs using all GBM patients combined with different natural courses and/or response to therapy can confound clinical trials. It suggests incorporating AKT classification can improve clinical trial design, decreasing their cost and maximizing the number of therapeutics that can be evaluated. In addition, AKT based classification can enhance drug discovery since new pathways and drug targets will be easier to find in molecularly homogeneous samples. The inventors demonstrate that robust molecular classification of GBM can ultimately improve patient care by guiding therapeutic planning, sparing patients ineffective treatments, both standard and experimental, and focusing on strategies more likely to work.

Example 3: Mesenchymal Patients Benefit from Temozolomide

The AKT pathway can be a dominant determinant of response to diverse therapeutics including chemotherapy. The chemotherapy Temozolomide (TMZ; 6 cycles), is currently standard of care for newly diagnosed Glioblastoma. Here we show that AKT classification predicts response to TMZ in Glioblastoma.

We plotted Kaplan Meier survival curves for patients treated with more vs. less TMZ in each AKT subgroup (FIG. 17). Since most TCGA patients received some TMZ, it was not possible to plot survival curves for patients treated with and without the drug. Instead, we compared survival in 2 treatment arms, those receiving more (≥3) vs. less (<3) cycles.

We found that patients in the Secondary-Like subtype treated with more TMZ did worse than those receiving less. There was a tendency for patients who received more TMZ to not have received a nitrosourea. We showed evidence that CCNU/BCNU provides a 4.5 year survival advantage to Secondary-Like patients. Without wishing to be bound by any particular theory, this may underlie the worse survival of patients receiving more TMZ in the Secondary-Like subgroup. Also, we found that only Mesenchymal patients had a statistically significant difference in survival between treatment arms.

These results support that AKT classification is a biomarker identifying Glioblastoma patients responsive to TMZ.

Example 4: Generally

As disclosed herein, biomarkers that select patients for therapeutics would benefit clinical trial design and patient care. The Akt pathway is a therapeutic target in Glioblastoma Multiforme (GBM) and an important determinant of patient outcome. However, it is not known whether activity of this pathway varies among GBM tumors. To examine differences in AKT pathway among GBM, the inventors investigated mRNA expression of Akt pathway genes in published GBM expression datasets. It was found at least 6 distinct patterns of Akt pathway gene expression, and the patterns were prognostic. Pathway analysis suggests specific molecular targets within these Akt groups. Therefore Akt subgroups will help select patients for targeted therapies. Since Akt is an important determinant of response to conventional therapies, Akt subgroups will help select patients for conventional therapies.

Discussion

The inventors show there are at least 6 classes of GBM with different survival and patterns of Akt pathway gene expression. Survival differences suggest Akt class predicts either prognosis (tumor aggressiveness independent of therapy) or response to therapy. The Akt pathway is a partial determinant of sensitivity to both conventional and targeted therapies. Therefore the inventors believe that Akt class predicts response to conventional and targeted therapies. Other data supports this. EGFR and PDGFRα are established therapeutic targets in GBM. mRNA for these receptors is differentially expressed in subgroups. This supports Akt class can predict response to therapeutics targeting these receptors.

The inventors perform gene set enrichment analysis (GSE) using all profiled genes to find pathways activated in subgroups. The data showing EGFR and PDGFRα mRNA are subgroup specific and suggest different pathways are activated in subgroups. This supports mining subgroups for pathways will enhance target identification.

Conclusions

There are at least 6 classes of GBM with different patterns of Akt pathway gene expression. Furthermore, it demonstrates that Akt class can be used to match therapy to patient. Additionally, mining of Akt classes will enhance identification of subgroup-specific targets.

Methods and Materials

Analysis of the nucleic acid from an individual, whether amplified or not, may be performed using any of various techniques readily available and apparent to one of skill in the art. Useful techniques include, without limitation, polymerase chain reaction based analysis, sequence analysis and electrophoretic analysis. As used herein, the term “nucleic acid” means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

Similarly, there are many techniques readily available in the field for detecting the presence or absence of polypeptides or other biomarkers, including protein microarrays. For example, some of the detection paradigms that can be employed to this end include optical methods, electrochemical methods (voltammetry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are many techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called “affinity capture mass spectrometry,” or “Surface-Enhanced Affinity Capture” or “SEAC,” which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The PI3K/Akt Pathway is an Important Therapeutic Target in High Grade Glioma (HGG) and Many Other Cancers.

Akt is an oncogenic serine/threonine kinase that is a key effector in the PI3K/Akt pathway. This large and complex pathway regulates many functions important in cancer including migration, angiogenesis, proliferation, epithelial to mesenchyme transition (EMT) stem cell self-renewal and resistance to cytotoxic therapy. It does this by phosphorylating and regulating the activity of a large number of downstream effectors. There are currently>100 suspected Akt substrates and more are being discovered. A simplified schematic representation of this pathway is shown in FIG. 23 herein.

Akt is hyper-activated in the majority of high grade glioma (HGG) tumors and many other human cancers. Many inhibitors of this pathway are under development or are in clinical trial for treatment of cancer patients. It is not known if the pathway is used similarly among patients with a specific cancer. If different "branches" of the pathway are activated in different patients, this might determine how patients respond to targeted therapies. Since Akt is an important determinant of how cancer cells respond to chemotherapy and radiation, this applies to other anti-neoplastic and conventional therapies also.

Tumor Subtypes are Identified Based on Expression of PI3K/Akt Pathway Genes.

To investigate if the pathway is used differently among HGG patients, the inventors used expression of Akt pathway genes and clustering methods. The inventors generated a hand curated list of Akt pathway genes using PubMed literature searches and protein databases. The following categories were included: 1) upstream regulators and activators of Akt, 2) proteins that physically interact with Akt, 3) downstream effectors phosphorylated by Akt and 4) proteins in complexes known to interact with, regulate or be regulated by Akt (for example all proteins in mTORC1 and mTORC2).

The inventors generated a correlation between clustered samples plot (FIGS. 18A-18C) using the list of Akt pathway genes in a published expression profiling dataset containing 185 HGG and 14 non-neoplastic "autopsy" samples (FIG. 18A). This analysis gives information on the similarity of total Akt pathway gene expression between tumors. In FIG. 18A, tumors are plotted on both axis. If PI3K/Akt pathway genes of 2 tumors are positively correlated then the intersection of the 2 tumors is shown in red; intersection of tumors with negatively correlated Akt pathway gene expression are green; and intersections of tumors with little Akt pathway correlation are black.

This data shows that there are 6 patient subgroups that have similar expression of Akt pathway genes (non-clustering/cluster 0, and clusters 1-5, FIG. 18A) and a group of patients (lower left, FIG. 18A) that have gene expression profiles with low similarity to any cluster. Subgroups are associated with different survival curves (FIG. 18B). Difference between survival for patients in clusters 4 and 5 approached statistical significance (p=0.06 log rank test; FIG. 18C). This data shows tumor subgroups exist that regulate Akt pathway genes differently, and these subgroups use different "branches" of the Akt pathway. It follows that patient subgroups will respond to pathway inhibitors differently. They may also respond differently to chemotherapy and radiation.

Each subgroup may be analyzed for functional categories of genes. This may be accomplished by finding genes that are expressed differently between subgroups. The inventors used an unsupervised clustering method that classifies similar objects into groups. In this case tumors with similar expression of Akt pathway genes are clustered (FIGS. 19A-19D). Tumors are listed at the top and genes at the sides. If the expression of a gene is high in a tumor the intersection between gene and tumor is red; if it is low then green. These analyses should demonstrate which Akt pathway genes are important in each subgroup and therefore which inhibitors should work in specific subgroups. For example, a preliminary analysis shows that PDGFRα is overexpressed in subgroup 4 and EGFR is overexpressed in subgroup 3 (FIGS. 19A-19D). The inventors believe that patients in subgroup 4 will respond to PDGFRα inhibitors and patients in subgroup 3 will respond to EGFR inhibitors. Additionally, as readily apparent to one of skill in the art, any number of other analysis maybe used to find which Akt pathway genes are important in each subgroup. These analyses can also be used to find other genes, not necessarily directly associated with the Akt pathway, that are important to the Akt subgroup.

Summary

The inventors demonstrate there are 6 major subgroups of HGG that regulate Akt pathway genes differently. The inventors believe that these subgroups use different "branches" of the Akt pathway and will respond differently to conventional and targeted therapies. Therefore this analysis may be used to match therapy to patient. A potential benefit of this approach over current methods that analyze a single molecule or gene is that this analysis can allow a more comprehensive categorization of patients and selection between multiple therapy options.

Significance

The inventors believe that the described analysis can be used to match therapy to patient. Subgroups may define patients that will respond to specific therapies targeting growth factors or the PI3K/Akt pathway. They can also define patients that will respond to conventional therapies. Since the PI3K/Akt pathway is important in many other cancers these results can apply to other cancers. The same type of analysis performed on other cancer-associated pathways (Ras, Notch etc . . . ) may also yield subgroups defining patients that will respond to targeted therapies against those pathways.

AKT Pathway Gene Expression Divides Human-Rodent GBM Xenografts into Classes.

The inventors used rodent models of human Akt class to test response to human therapies find if Akt class predicts response to therapy. FIG. 24A is an Akt pathway correlation map of gene expression data from replicates of 15 rodent glioma xenografts. The analysis indicates 4 Akt xenograft classes. It is evident that xenograft models are readily classified by Akt gene expression. Distribution of biological replicates indicated by colors next to the axes demonstrates excellent Akt class stability. Similarities between Akt pathway maps demonstrate xenografts mimic gene expression of parental tumors, consistent with published reports of xenograft models of other tumors. The inventors investigate relationships between human and rodent Akt classes by mapping Akt pathway gene expression from xenografts onto human tumors. It is found 15% of genes have different expression in xenografts compared to the human tumors. When these genes are removed 6 of 7 xenografts cluster with parental human tumors. These data demonstrate human-rodent xenografts model human Akt class.

Response to Therapy Depends on Akt Class in Human-Rodent Xenograft Models.

In FIG. 24B, the inventors analyzed whether xenograft drug sensitivity is associated with Akt class. Xenograft group 2 is more sensitive to temozolomide (TMZ) and temozolomide plus radiation (TMZ+RT) than group 4 ($p<0.05$). The data demonstrates TMZ sensitivity is associated with Akt class and that Akt class predicts therapeutic response.

TABLE 4

Possible List of Genes to Distinguish Subgroups
Genetic loci and corresponding ID number

| | | |
|---|---|---|
| SORBS | 8470 | sorbin and SH3 domain containing protein |
| PPP2R2C | 5522 | protein phosphatase 2 regulatory subunit B gamma |

TABLE 4-continued

| Possible List of Genes to Distinguish Subgroups Genetic loci and corresponding ID number | | |
|---|---|---|
| TP53 | 7157 | tumor protein p53 |
| PIK3C3 | 5289 | phosphatidylinositol 3-kinase catalytic subunit type 3 |
| FGFR3 | 2261 | fibroblast growth factor receptor 3 |
| PPP2R5B | 5526 | protein phosphatase 3 regulator subunit B beta |
| Akt1 | 207 | v-akt murine thymoma viral oncogene homolog 1 |
| Akt1S1 | 84335 | akt 1 substrate 1 |
| HIF1A | 3091 | hypoxia inducible factor 1 alpha |
| EIF4EBP1 | 1978 | eukaryotic translation initiation factor 4E binding protein 1 |
| EGFR | 1956 | epidermal growth factor receptor |
| PDGFC | 56034 | platelet derived growth factor C |
| PDGFA | 5154 | platelet derived growth factor alpha |
| PHLPP | 23239 | PH domain and leucine rich repeat protein phosphatase |
| PDGFRA | 5156 | alpha type platelet derived growth factor receptor |
| RICTOR | 253260 | RPTOR independent companion of MTOR, complex 2 |
| AKT1P | 64400 | AKT interacting protein |
| TWIST | 7291 | twist family bHLH transcription factor |
| CCND1 | 595 | cyclin D1 |
| MDM2 | 4193 | mouse double minute 2 |
| GAB2 | 9846 | GRB2-associated-binding protein 2 |
| HSP90B1 | 7184 | heat shock protein 90 kDa beta member 1 |

TABLE 5

Genes that when used in clustering methods, may divide tumors into subgroups

| Entrez Gene ID No. | Gene Name Official Symbol |
|---|---|
| 1026 | CDKN1A |
| 1027 | CDKN1B |
| 1111 | CHEK1 |
| 116986 | AGAP2 |
| 1950 | EGF |
| 1956 | EGFR |
| 1978 | EIF4EBP1 |
| 2034 | EPAS1 |
| 207 | AKT1 |
| 2260 | FGFR1 |
| 2261 | FGFR3 |
| 2263 | FGFR2 |
| 23035 | PHLPPL |
| 2308 | FOXO1 |
| 2309 | FOXO3 |
| 23239 | PHLPP |
| 2475 | FRAP1 |
| 2549 | GAB1 |
| 2887 | GRB10 |
| 2932 | GSK3B |
| 3091 | HIF1A |
| 3164 | NR4A1 |
| 3265 | HRAS |
| 3316 | HSPB2 |
| 3320 | HSP90AA1 |
| 3479 | IGF1 |
| 3481 | IGF2 |
| 3611 | ILK |
| 3635 | INPP5D |
| 3667 | IRS1 |
| 3791 | KDR |
| 3845 | KRAS |
| 4193 | MDM2 |
| 4217 | MAP3K5 |
| 4303 | FOXO4 |
| 4515 | MTCP1 |
| 4893 | NRAS |
| 4904 | YBX1 |

TABLE 5-continued

Genes that when used in clustering methods, may divide tumors into subgroups

| Entrez Gene ID No. | Gene Name Official Symbol |
|---|---|
| 5036 | PA2G4 |
| 5154 | PDGFA |
| 5156 | PDGFRA |
| 5159 | PDGFRB |
| 5287 | PIK3C2B |
| 5289 | PIK3C3 |
| 5290 | PIK3CA |
| 5293 | PIK3CD |
| 5295 | PIK3R1 |
| 5515 | PPP2CA |
| 5518 | PPP2R1A |
| 5520 | PPP2R2A |
| 5521 | PPP2R2B |
| 5524 | PPP2R4 |
| 5525 | PPP2R5A |
| 5526 | PPP2R5B |
| 5527 | PPP2R5C |
| 5529 | PPP2R5E |
| 5586 | PKN2 |
| 5728 | PTEN |
| 572 | BAD |
| 5747 | PTK2 |
| 57761 | TRIB3 |
| 5829 | PXN |
| 5894 | RAF1 |
| 595 | CCND1 |
| 64223 | GBL |
| 65125 | WNK1 |
| 6850 | SYK |
| 7157 | TP53 |
| 7184 | HSP90B1 |
| 7248 | TSC1 |
| 7249 | TSC2 |
| 7291 | TWIST1 |
| 842 | CASP9 |
| 8660 | IRS2 |
| 8915 | BCL10 |
| 9846 | GAB2 |
| 9882 | TBC1D4 |
| 117145 | THEM4 |
| 253260 | RICTOR |
| 53834 | FGFRL1 |
| 5522 | PPP2R2C |
| 57521 | KIAA1303 |
| 84280 | BTBD10 |
| 84335 | AKT1S1 |
| 10000 | AKT3 |
| 26060 | APPL1 |
| 3326 | HSP90AB1 |
| 56034 | PDGFC |
| 6198 | RPS6KB1 |
| 64400 | AKTIP |
| 79109 | MAPKAP1 |
| 80146 | UXS1 |
| 80310 | PDGFD |
| 8470 | SORBS2 |
| 208 | AKT2 |

TABLE 6

The status of increased expression, decreased expression, or expression not changed significantly (minimal expression difference) of AKT pathway genes as shown in FIG. 10

| | TCGA | | | | | GBM195 | | | | | |
|---|---|---|---|---|---|---|---|---|---|---|---|
| | MES | CLAS | PROLIF | SL | PN | MES | CLAS | PROLIF | SL | PN | |
| SYK | INC | DEC | DEC | NC | DEC | INC | DEC | DEC | INC | DEC | SYK |
| CFD | INC | DEC | DEC | DEC | NC | INC | DEC | DEC | DEC | DEC | CFD |
| INPP5D | INC | NC | DEC | NC | NC | INC | NC | DEC | INC | DEC | INPP5D |
| PDGFRB | INC | INC | DEC | DEC | DEC | INC | INC | DEC | DEC | DEC | PDGFRB |
| CDKN1A | INC | INC | DEC | DEC | DEC | INC | INC | DEC | DEC | DEC | CDKN1A |
| KDR | INC | INC | DEC | INC | NC | INC | INC | DEC | DEC | NC | KDR |
| EPAS1 | INC | INC | DEC | INC | NC | INC | INC | DEC | DEC | NC | EPAS1 |
| IRS2 | NC | INC | DEC | INC | INC | INC | INC | DEC | DEC | DEC | IRS2 |
| PDGFD | INC | INC | DEC | INC | DEC | INC | INC | DEC | DEC | DEC | PDGFD |
| PDGFA | DEC | INC | DEC | INC | NC | INC | INC | DEC | DEC | DEC | PDGFA |
| GRB10 | INC | INC | DEC | INC | DEC | INC | INC | INC | DEC | DEC | GRB10 |
| HSP90B1 | INC | NC | INC | INC | DEC | INC | INC | INC | DEC | DEC | HSP90B1 |
| PDK1 | NC | NC | INC | INC | DEC | NC | INC | INC | DEC | DEC | PDK1 |
| CHEK1 | NC | DEC | INC | INC | DEC | DEC | NC | INC | DEC | DEC | CHEK1 |
| EZH2 | DEC | NC | INC | INC | DEC | DEC | DEC | INC | DEC | DEC | EZH2 |
| EIF3E | NC | NC | INC | INC | DEC | DEC | NC | INC | INC | DEC | EIF3E |
| SRSF1 | DEC | NC | INC | INC | DEC | DEC | INC | INC | NC | DEC | SRSF1 |
| NRAS | NC | NC | INC | DEC | DEC | DEC | INC | INC | DEC | DEC | NRAS |
| SSB | DEC | NC | INC | NC | DEC | DEC | NC | NC | DEC | DEC | SSB |
| IRS1 | INC | DEC | NC | INC | NC | DEC | DEC | DEC | DEC | DEC | IRS1 |
| WNK1 | NC | DEC | NC | INC | INC | DEC | DEC | DEC | DEC | DEC | WNK1 |
| PKN2 | DEC | NC | INC | INC | DEC | DEC | NC | DEC | DEC | DEC | PKN2 |
| BCL10 | INC | NC | INC | NC | DEC | DEC | DEC | NC | DEC | DEC | BCL10 |
| TWIST1 | INC | INC | DEC | DEC | DEC | INC | NC | NC | DEC | DEC | TWIST1 |
| PKD2 | INC | INC | DEC | NC | NC | INC | INC | DEC | DEC | DEC | PKD2 |
| PALLD | INC | INC | DEC | DEC | NC | INC | INC | DEC | DEC | DEC | PALLD |
| HIF1A | INC | NC | DEC | INC | DEC | INC | INC | DEC | DEC | DEC | HIF1A |
| PDGFC | INC | INC | DEC | DEC | DEC | NC | INC | DEC | DEC | DEC | PDGFC |
| VIM | INC | INC | DEC | DEC | DEC | INC | INC | INC | NC | DEC | VIM |
| TRIB3 | INC | INC | INC | DEC | DEC | INC | INC | INC | INC | DEC | TRIB3 |
| EIF4EBP1 | NC | NC | INC | DEC | DEC | INC | INC | INC | NC | DEC | EIF4EBP1 |
| ACLY | DEC | INC | INC | INC | DEC | DEC | INC | INC | NC | DEC | ACLY |
| TP53 | NC | INC | INC | NC | DEC | NC | INC | INC | INC | DEC | TP53 |
| EIF3B | NC | NC | INC | NC | DEC | INC | INC | INC | INC | DEC | EIF3B |
| RAF1 | DEC | NC | INC | INC | DEC | NC | INC | INC | INC | DEC | RAF1 |
| CCND1 | NC | DEC | INC | INC | DEC | NC | DEC | INC | INC | DEC | CCND1 |
| EIF3H | NC | DEC | INC | INC | DEC | DEC | DEC | INC | INC | DEC | EIF3H |
| FYN | DEC | NC | DEC | INC | NC | DEC | INC | INC | INC | DEC | FYN |
| PHLPP1 | DEC | INC | DEC | INC | INC | DEC | NC | NC | INC | INC | PHLPP1 |
| GAB1 | DEC | INC | DEC | INC | NC | DEC | INC | NC | INC | NC | GAB1 |
| EGFR | DEC | INC | DEC | NC | NC | DEC | INC | DEC | INC | DEC | EGFR |
| EIF3G | DEC | INC | NC | NC | DEC | INC | INC | INC | INC | DEC | EIF3G |
| AKT1 | NC | INC | NC | NC | DEC | INC | INC | INC | INC | NC | AKT1 |
| CDC37 | NC | NC | INC | DEC | DEC | INC | INC | INC | INC | NC | CDC37 |
| TSC2 | DEC | NC | INC | INC | NC | NC | INC | INC | INC | INC | TSC2 |
| PPP2R1A | DEC | NC | INC | NC | NC | NC | INC | INC | INC | INC | PPP2R1A |
| HSP90AB1 | NC | DEC | INC | INC | NC | DEC | INC | INC | INC | INC | HSP90AB1 |
| MAPK8IP1 | DEC | NC | NC | INC | INC | DEC | INC | DEC | INC | INC | MAPK8IP1 |
| GAB2 | NC | NC | DEC | INC | INC | DEC | DEC | DEC | INC | INC | GAB2 |
| PIK3C2B | DEC | DEC | NC | INC | INC | DEC | DEC | DEC | INC | INC | PIK3C2B |
| TSC1 | DEC | NC | DEC | INC | INC | DEC | DEC | DEC | INC | INC | TSC1 |
| GSK3B | DEC | DEC | INC | INC | INC | DEC | DEC | INC | NC | INC | GSK3B |
| SORBS2 | DEC | DEC | NC | DEC | INC | NC | DEC | DEC | DEC | INC | SORBS2 |
| FGFR2 | DEC | DEC | NC | NC | INC | DEC | DEC | DEC | DEC | INC | FGFR2 |
| FGFR3 | DEC | INC | DEC | DEC | INC | DEC | INC | DEC | DEC | INC | FGFR3 |
| PPP2R2B | DEC | INC | DEC | NC | INC | DEC | INC | DEC | NC | INC | PPP2R2B |
| PIK3R1 | DEC | NC | DEC | INC | INC | DEC | DEC | DEC | INC | INC | PIK3R1 |
| MAP3K5 | INC | NC | DEC | INC | INC | NC | NC | DEC | INC | INC | MAP3K5 |
| ATXN1 | NC | NC | DEC | INC | INC | DEC | NC | DEC | NC | INC | ATXN1 |
| PPARGC1A | DEC | INC | DEC | DEC | INC | DEC | NC | DEC | DEC | INC | PPARGC1A |
| KRAS | DEC | NC | INC | INC | INC | DEC | DEC | NC | DEC | INC | KRAS |
| CDKN1B | DEC | NC | INC | INC | NC | DEC | DEC | INC | INC | DEC | CDKN1B |
| PIK3CA | NC | DEC | INC | INC | DEC | DEC | DEC | DEC | INC | DEC | PIK3CA |
| FOXO3 | DEC | DEC | DEC | INC | INC | DEC | DEC | DEC | INC | DEC | FOXO3 |
| | MES | CLAS | PROLIF | SL | PN | MES | CLAS | PROLIF | SL | PN | |

NOTE:
INC means increased expression; DEC means decreased expression; and NC means expression not changed significantly or minimal expression difference.

In various embodiments, a subgroup or subtype's expression pattern of AKT pathway components may be determined according to the validation dataset (TCGA) and the discovery dataset (GBM195) as shown in FIG. 10 and Table 6. In some embodiments, a subgroup or subtype's expression pattern of AKT pathway components may be determined according to the validation dataset (TCGA) as shown in FIG. 10 and Table 6. In other embodiments, a subgroup or subtype's expression pattern of AKT pathway components may be determined according to the discovery dataset (GBM195) as shown in FIG. 10 and Table 6.

As readily apparent to one of skill in the art, any number of genetic loci and/or biomarkers could be used to subgroup tumors and conditions, and the invention is not in any way limited to those genes listed in Table 2, Table 4, Table 5, or Table 6 herein. For example, other genes related, both directly and indirectly to the Akt pathway, could be clustered and thus used for subgrouping a condition, disease and/or tumor. Or, for example, other methods of identifying Akt subgroups include the use of biomarkers that include nucleic acid(s), protein(s), modified protein(s), mutated or modified nucleic acid(s), epigenetic changes or a change(s) in DNA copy number associated with Akt subgroups. Similarly, this analysis may be generalized to any cancer that has Akt pathway activation, and the invention is in no way limited to GBM.

REFERENCES

1. Ohgaki H, Kleihues P (2007) Genetic pathways to primary and secondary glioblastoma. The American journal of pathology 170: 1445-1453.
2. DeAngelis L M, Mellinghoff I K (2011) Virchow 2011 or how to ID(H) human glioblastoma. Journal of clinical oncology: official journal of the American Society of Clinical Oncology 29: 4473-4474.
3. Nigro J M, Misra A, Zhang L, Smirnov I, Colman H, et al. (2005) Integrated array-comparative genomic hybridization and expression array profiles identify clinically relevant molecular subtypes of glioblastoma. Cancer Res 65: 1678-1686.
4. Phillips H S, Kharbanda S, Chen R, Forrest W F, Soriano R H, et al. (2006) Molecular subclasses of high-grade glioma predict prognosis, delineate a pattern of disease progression, and resemble stages in neurogenesis. Cancer cell 9: 157-173.
5. Atlas TCG (2008) Comprehensive genomic characterization defines human glioblastoma genes and core pathways. Nature 455: 1061-1068.
6. Bredel M, Scholtens D M, Harsh G R, Bredel C, Chandler J P, et al. (2009) A network model of a cooperative genetic landscape in brain tumors. Jama 302: 261-275.
7. Mischel P S, Shai R, Shi T, Horvath S, Lu K V, et al. (2003) Identification of molecular subtypes of glioblastoma by gene expression profiling. Oncogene 22: 2361-2373.
8. Noushmehr H, Weisenberger D J, Diefes K, Phillips H S, Pujara K, et al. (2010) Identification of a CpG island methylator phenotype that defines a distinct subgroup of glioma. Cancer cell 17: 510-522.
9. Shen R, Mo Q, Schultz N, Seshan V E, Olshen A B, et al. (2012) Integrative subtype discovery in glioblastoma using iCluster. PLoS ONE 7: e35236.
10. Verhaak R G, Hoadley K A, Purdom E, Wang V, Qi Y, et al. (2010) Integrated genomic analysis identifies clinically relevant subtypes of glioblastoma characterized by abnormalities in PDGFRA, IDH1, EGFR, and NF1. Cancer Cell 17: 98-110.
11. Brennan C, Momota H, Hambardzumyan D, Ozawa T, Tandon A, et al. (2009) Glioblastoma subclasses can be defined by activity among signal transduction pathways and associated genomic alterations. PLoS ONE 4: e7752.
12. Engelman J A (2009) Targeting PI3K signalling in cancer: opportunities, challenges and limitations. Nature reviews Cancer 9: 550-562.
13. Wen P Y, Lee E Q, Reardon D A, Ligon K L, Alfred Yung W K (2012) Current clinical development of PI3K pathway inhibitors in glioblastoma. Neuro-oncology 14: 819-829.
14. Huang T T, Sarkaria S M, Cloughesy T F, Mischel P S (2009) Targeted therapy for malignant glioma patients: lessons learned and the road ahead. Neurotherapeutics: the journal of the American Society for Experimental NeuroTherapeutics 6: 500-512.
15. Stambolic V, MacPherson D, Sas D, Lin Y, Snow B, et al. (2001) Regulation of PTEN transcription by p53. Molecular cell 8: 317-325.
16. Singh B, Reddy P G, Goberdhan A, Walsh C, Dao S, et al. (2002) p53 regulates cell survival by inhibiting PIK3CA in squamous cell carcinomas. Genes & development 16: 984-993.
17. Moelling K, Schad K, Bosse M, Zimmermann S, Schweneker M (2002) Regulation of Raf-Akt Cross-talk. The Journal of biological chemistry 277: 31099-31106.
18. Wan X, Harkavy B, Shen N, Grohar P, Helman L J (2007) Rapamycin induces feedback activation of Akt signaling through an IGF-1R-dependent mechanism. Oncogene 26: 1932-1940.
19. Han E K, Leverson J D, McGonigal T, Shah O J, Woods K W, et al. (2007) Akt inhibitor A-443654 induces rapid Akt Ser-473 phosphorylation independent of mTORC1 inhibition. Oncogene 26: 5655-5661.
20. Manning B D, Cantley L C (2007) AKT/PKB signaling: navigating downstream. Cell 129: 1261-1274.
21. Freije W A, Castro-Vargas F E, Fang Z, Horvath S, Cloughesy T, et al. (2004) Gene expression profiling of gliomas strongly predicts survival. Cancer research 64: 6503-6510.
22. Yuan T L, Cantley L C (2008) PI3K pathway alterations in cancer: variations on a theme. Oncogene 27: 5497-5510.
23. Alfarano C, Andrade C E, Anthony K, Bahroos N, Bajec M, et al. (2005) The Biomolecular Interaction Network Database and related tools 2005 update. Nucleic Acids Research 33: D418-424.
24. Rafael. A. Irizarry B M B, Collin F, Cope L M, Hobbs B, et al. (2003) Summaries of Affymetrix GeneChip probe level data. Nucleic Acids Research 31: e15.
25. Monti S T P, Mesirov J, Golub T (2003) Consensus clustering: A resampling-based method for class discovery and visualization of gene expression microarray data. Machine Learning 52: 91-118.
26. Rousseeuw P (1987) Silhouettes: A graphical aid to the interpretation and validation of cluster analysis. Journal of Computational and Applied Mathematics 20: 53-65.
27. Beroukhim R, Getz G, Nghiemphu L, Barretina J, Hsueh T, et al. (2007) Assessing the significance of chromosomal aberrations in cancer: methodology and application to glioma. Proc Natl Acad Sci USA 104: 20007-20012.
28. Robinson J T, Thorvaldsdottir H, Winckler W, Guttman M, Lander E S, et al. (2011) Integrative genomics viewer. Nature biotechnology 29: 24-26.
29. Misra A, Pellarin M, Nigro J, Smirnov I, Moore D, et al. (2005) Array comparative genomic hybridization identifies genetic subgroups in grade 4 human astrocytoma. Clin Cancer Res 11: 2907-2918.
30. Dunnett C W (1955) A multiple comparison procedure for comparing several treatments with a control. Journal of the American Statistical Association 50: 1096-1121.

31. Kutner M H, Nachtsheim C, Neter J, Li W (2005) Applied Linear Statistical Models. New York: McGraw-Hill.

32. The Cancer Genome Atlas NCI, National Institutes of Health, Bethesda, Md. Available: cancergenome.nih.gov.

33. West K A, Castillo S S, Dennis P A (2002) Activation of the PI3K/Akt pathway and chemotherapeutic resistance. Drug Resist Update 5: 234-248.

34. Burton E C, Lamborn K R, Feuerstein B G, Prados M, Scott J, et al. (2002) Genetic aberrations defined by comparative genomic hybridization distinguish long-term from typical survivors of glioblastoma. Cancer research 62: 6205-6210.

35. French P E L, Gravendeel L, Rooi J, Eiler P, Idbaih A, et al. (2012) Intrinsic molecular subtypes of glioma are prognostic and predict benefit from adjuvant PCV chemotherapy in anaplastic oligodendroglial brain tumors: A report from the EORTC study 26951Y 26951 Neuro Oncol. 14: OM-21.

36. Balss J, Meyer J, Mueller W, Korshunov A, Hartmann C, et al. (2008) Analysis of the IDH1 codon 132 mutation in brain tumors. Acta neuropathologica 116: 597-602.

37. Ichimura K, Pearson D M, Kocialkowski S, Backlund L M, Chan R, et al. (2009) IDH1 mutations are present in the majority of common adult gliomas but rare in primary glioblastomas. Neuro-oncology 11: 341-347.

38. Parsons D W, Jones S, Zhang X, Lin J C, Leary R J, et al. (2008) An integrated genomic analysis of human glioblastoma multiforme. Science 321: 1807-1812.

39. Turcan S, Rohle D, Goenka A, Walsh L A, Fang F, et al. (2012) IDH1 mutation is sufficient to establish the glioma hypermethylator phenotype. Nature 483: 479-483.

40. Haruta T, Uno T, Kawahara J, Takano A, Egawa K, et al. (2000) A rapamycin-sensitive pathway down-regulates insulin signaling via phosphorylation and proteasomal degradation of insulin receptor substrate-1. Molecular endocrinology 14: 783-794.

41. Harrington L S, Findlay G M, Gray A, Tolkacheva T, Wigfield S, et al. (2004) The TSC1-2 tumor suppressor controls insulin-PI3K signaling via regulation of IRS proteins. The Journal of cell biology 166: 213-223.

42. Efeyan A, Sabatini D M (2010) mTOR and cancer: many loops in one pathway. Current opinion in cell biology 22: 169-176.

43. Hartley D, Cooper G M (2002) Role of mTOR in the degradation of IRS-1: regulation of PP2A activity. Journal of cellular biochemistry 85: 304-314.

44. Huang J, Dibble C C, Matsuzaki M, Manning B D (2008) The TSC1-TSC2 complex is required for proper activation of mTOR complex 2. Molecular and cellular biology 28: 4104-4115.

45. Dasgupta B, Yi Y, Chen D Y, Weber J D, Gutmann D H (2005) Proteomic analysis reveals hyperactivation of the mammalian target of rapamycin pathway in neurofibromatosis 1-associated human and mouse brain tumors. Cancer research 65: 2755-2760.

46. Banerjee S, Crouse N R, Emnett R J, Gianino S M, Gutmann D H (2011) Neurofibromatosis-1 regulates mTOR-mediated astrocyte growth and glioma formation in a TSC/Rheb-independent manner. Proceedings of the National Academy of Sciences of the United States of America 108: 15996-16001.

47. Johannessen C M, Reczek E E, James M F, Brems H, Legius E, et al. (2005) The NF1 tumor suppressor critically regulates TSC2 and mTOR. Proceedings of the National Academy of Sciences of the United States of America 102: 8573-8578.

48. Everitt B (2006) The Cambridge dictionary of statistics. New York: Cambridge University Press.

49. Coons S W, Johnson P C, Scheithauer B W, Yates A J, Pearl D K (1997) Improving diagnostic accuracy and interobserver concordance in the classification and grading of primary gliomas. Cancer 79: 1381-1393.

50. Mittler M A, Walters B C, Stopa E G (1996) Observer reliability in histological grading of astrocytoma stereotactic biopsies. Journal of neurosurgery 85: 1091-1094.

51. Gotz M, Huttner W B (2005) The cell biology of neurogenesis. Nature reviews Molecular cell biology 6: 777-788.

52. Sakai D, Dixon J, Dixon M J, Trainor P A (2012) Mammalian neurogenesis requires Treacle-Plk1 for precise control of spindle orientation, mitotic progression, and maintenance of neural progenitor cells. PLoS genetics 8: e1002566.

53. Groszer M, Erickson R, Scripture-Adams D D, Dougherty J D, Le Belle J, et al. (2006) PTEN negatively regulates neural stem cell self-renewal by modulating G0-G1 cell cycle entry. Proc Natl Acad Sci USA 103: 111-116.

54. Sinor A D, Lillien L (2004) Akt-1 expression level regulates CNS precursors. J Neurosci 24: 8531-8541.

55. Brennan C W, Verhaak R G, McKenna A, Campos B, Noushmehr H, et al. (2013) The somatic genomic landscape of glioblastoma. Cell 155: 462-477.

56. Network TCGAR (2008) Comprehensive genomic characterization defines human glioblastoma genes and core pathways. Nature 455: 1061-1068.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for treating, reducing the severity of and/or slowing the progression of a high grade glioma in a human subject, comprising:

providing carmustine (BCNU) or lomustine (CCNU), or salt of BCNU or CCNU, or a combination thereof; and administering a therapeutically effective amount of BCNU or CCNU, or salt of BCNU or CCNU, or the combination thereof to the human subject, wherein the human subject has been determined to have an increased expression in a high grade glioma sample from the human subject in adenosine triphosphate (ATP) citrate lyase (ACLY), cyclin DI (CCND1), cyclin-dependent kinase inhibitor D3 (CDKN1B), epidermal growth factor receptor (EGFR), eukaryotic translation initiation factor 3 subunit B (EIF3B), eukaryotic translation initiation factor 3 subunit E (EIF3E), eukaryotic translation initiation factor 3 subunit G (EIF3G), eukaryotic translation initiation factor 3 subunit H (EIF3H), Forkhead box 03 (FOXO3), proto-oncogene tyrosine-protein kinase Fyn (FYN), GRB2-associated binding protein 1 (GAB1), GRB2-associated binding protein 2 (GAB2), inositol polyphosphate-5-phosphatase (INPP5D), insulin receptor substrate 1 (IRS1), mitogen-activated protein kinase kinase kinase 5 (MAP3K5), mitogen-activated protein kinase 8 interacting protein 1 (MAPK8IP1), platelet-derived growth factor C (PDGFC), PH domain and leucine rich repeat protein phosphatase 1 (PHLPP1), phosphatidylinositol-4-phosphate 3-kinase catalytic subunit type 2 beta (PIK3C2B), phosphatidylinositol-4,5-bisphosphate 3-kinase catalytic subunit alpha (PIK3CA), phosphoinositide-3-kinase, regulatory subunit 1 (PIK3R1), V-raf-1 murine leukemia viral oncogene homolog 1 (RAF1), spleen tyrosine kinase (SYK), tumor protein p53 (TP53), Tribbles homolog 3 (TRIB3), tuberous sclerosis 1 (TSC1), and tuberous sclerosis 2 (TSC2), relative to non-neoplastic human brain tissue reference samples for each gene, and a decreased expression in the high grade glioma sample from the human subject in V-akt murine thymoma viral oncogene homolog 1 (AKT1), B-cell CLL/lymphoma 10 (BCL10), cyclin-dependent kinase inhibitor 1A (CDKN1A), complement factor D (CFD), checkpoint kinase 1 (CHEK1), eukaryotic translation initiation factor 4E binding protein 1 (EIF4EBP1), endothelial PAS domain protein 1 (EPAS1), enhancer of zeste homolog 2 (EZH2), fibroblast growth factor receptor 2 (FGFR2), fibroblast growth factor receptor 3 (FGFR3), growth factor receptor-bound protein 10 (GRB10), hypoxia inducible factor 1 alpha subunit (HIF1A), heat shock protein 90 alpha (cytosolic) class B member 1 (HSP90AB1), insulin receptor substrate 2 (IRS2), kinase insert domain receptor (KDR), V-Ki-ras2 Kirsten rat sarcoma viral oncogene homolog (KRAS), neuroblastoma RAS viral (v-ras) oncogene homolog (NRAS), Palladin (PALLD), platelet-derived growth factor alpha polypeptide (PDGFA), platelet-derived growth factor D (PDGFD), Platelet-derived growth factor receptor beta polypeptide (PDGFRB), 3-phosphoinositide dependent protein kinase-1 (PDK1), polycystic kidney disease 2 (PKD2), peroxisome proliferator-activated receptor gamma coactivator 1 alpha (PPARGC1A), sorbin and SH3 domain containing 2 (SORBS2), SRSF1, Sjogren syndrome antigen B (SSB), Twist basic helix-loop-helix transcription factor 1 (TWIST1), vimentin (VIM), and WNK lysine deficient protein kinase 1 (WNK1), relative to non-neoplastic human brain tissue reference samples for each gene, wherein the determination of the expression level is performed by assay selected from the group consisting of RNA sequencing, northern blot, in situ hybridization, hybridization array, serial analysis of gene expression (SAGE), reverse transcription polymerase chain reaction (PCR), real-time PCR, real time reverse transcription PCR, quantitative PCR, microarray, mass spectrometry, and combinations thereof, thereby treating, reducing the severity of and/or slowing the progression of the high grade glioma.

2. A method for detecting an expression pattern in a human subject having high grade glioma and treating, reducing the severity of and/or slowing the progression of the high grade glioma, comprising:

obtaining a high grade glioma sample from the human subject; and detecting the presence of secondary-like (SL) expression pattern of Akt pathway components in the high grade glioma sample, wherein SL expression pattern of Akt pathway components comprises:

an increased gene expression in adenosine triphosphate (ATP) citrate lyase (ACLY), cyclin DI (CCND1), cyclin-dependent kinase inhibitor IB (CDKN1B), epidermal growth factor receptor (EGFR), eukaryotic translation initiation factor 3 subunit B (EIF3B), eukaryotic translation initiation factor 3 subunit E (EIF3E), eukaryotic translation initiation factor 3 subunit G (EIF3G), eukaryotic translation initiation factor 3 subunit H (EIF3H), Forkhead box 03 (FOXO3), proto-oncogene tyrosine-protein kinase Fyn (FYN), GRB2-associated binding protein 1 (GAB1), GRB2-associated binding protein 2 (GAB2), inositol polyphosphate-5-phosphatase (INPP5D), insulin receptor substrate 1 (IRS1), mitogen-activated protein kinase kinase kinase 5 (MAP3K5), mitogen-activated protein kinase 8 interacting protein 1 (MAPK8IP1), platelet-derived growth factor C (PDGFC), PH domain and leucine rich repeat protein phosphatase 1 (PHLPP1), phosphatidylinositol-4-phosphate 3-kinase catalytic subunit type 2 beta (PIK3C2B), phosphatidylinositol-4,5-bisphosphate 3-kinase catalytic subunit alpha (PIK3CA), phosphoinositide-3-kinase, regulatory subunit 1 (PIK3R1), V-raf-1 murine leukemia viral oncogene homolog 1 (RAF1), spleen tyrosine kinase (SYK), tumor protein p53 (TP53), Tribbles homolog 3 (TRIB3), tuberous sclerosis 1 (TSC1), tuberous sclerosis 2 (TSC2), and a decreased gene expression in V-akt murine thymoma viral oncogene homolog 1 (AKT1), B-cell CLL/lymphoma 10 (BCL10), cyclin-dependent kinase inhibitor 1A (CDKN1A), complement factor D (CFD), checkpoint kinase 1 (CHEK1), eukaryotic translation initiation factor 4E binding protein 1 (EIF4EBP1), endothelial PAS domain protein 1 (EPAS1), enhancer of zeste homolog 2 (EZH2), fibroblast growth factor receptor 2 (FGFR2), fibroblast growth factor receptor 3 (FGFR3), growth factor receptor-bound protein 10 (GRB10), hypoxia inducible factor 1 alpha subunit (HIF1A), heat shock protein 90 alpha (cytosolic) class B member 1 (HSP90AB1), insulin receptor substrate 2 (IRS2), kinase insert domain receptor (KDR), V-Ki-ras2 Kirsten rat sarcoma viral oncogene homolog (KRAS), neuroblastoma RAS viral (v-ras) oncogene homolog (NRAS), Palladin (PALLD), platelet-derived growth factor alpha polypeptide (PDGFA), platelet-derived growth factor D (PDGFD), Platelet-derived growth factor receptor beta polypeptide (PDGFRB), 3-phosphoinositide dependent protein kinase-1 (PDK1), polycystic kidney disease 2 (PKD2), peroxisome proliferator-activated receptor gamma coactivator 1 alpha (PPARGC1A), sorbin and SH3 domain containing 2 (SORBS2), SRSF1, Sjogren syndrome antigen B (SSB), Twist basic helix-loop-helix transcription factor 1 (TWIST1), vimentin (VIM), and WNK lysine deficient protein kinase 1 (WNK1), wherein the increase and decrease in gene expression levels are relative to non-neoplastic human brain tissue reference sample for each gene; and administering a therapeutically effective amount of carmustine (BCNU) or lomustine (CCNU), or salt of BCNU or CCNU, or a combination thereof to the human subject and thereby treating, reducing the severity of and/or slowing the progression of the high grade glioma.

3. The method of claim 1, wherein the high grade glioma is glioblastoma multiforme (GBM).

4. The method of claim 2, wherein the high grade glioma is glioblastoma multiforme (GBM).

* * * * *